United States Patent
Aissaoui et al.

(10) Patent No.: US 8,063,099 B2
(45) Date of Patent: *Nov. 22, 2011

(54) TRANS-3-AZA-BICYCLO[3.1.0]HEXANE DERIVATIVES

(75) Inventors: Hamed Aissaoui, Pulversheim (FR); Christoph Boss, Allschwil (CH); Markus Gude, Allschwil (CH); Ralf Koberstein, Lorrach (DE); David Lehman, Bern (CH); Thierry Sifferlen, Wentzwiller (FR); Daniel Trachsel, Bubendorf (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/670,809

(22) PCT Filed: Jul. 25, 2008

(86) PCT No.: PCT/IB2008/052985
§ 371 (c)(1), (2), (4) Date: Jan. 26, 2010

(87) PCT Pub. No.: WO2009/016560
PCT Pub. Date: Feb. 5, 2009

(65) Prior Publication Data
US 2010/0204285 A1 Aug. 12, 2010

(30) Foreign Application Priority Data

Jul. 27, 2007 (WO) .................. PCT/IB2007/052987
Mar. 28, 2008 (WO) .................. PCT/IB2008/051167

(51) Int. Cl.
A61K 31/403 (2006.01)
C07D 209/12 (2006.01)

(52) U.S. Cl. ......... 514/443; 548/452; 548/465; 548/467
(58) Field of Classification Search .................. 548/452, 548/465, 467
See application file for complete search history.

(56) References Cited

U.S. PATENT DOCUMENTS
2006/0040937 A1  2/2006  Branch et al.

FOREIGN PATENT DOCUMENTS

| | | |
|---|---|---|
| WO | WO 01/96302 | 12/2001 |
| WO | WO 02/44172 | 6/2002 |
| WO | WO 02/090355 | 11/2002 |
| WO | WO 03/041711 | 5/2003 |
| WO | WO 03/051368 | 6/2003 |
| WO | WO 03051368 | 6/2003 |
| WO | WO 2004/026866 | 4/2004 |
| WO | WO 2006/011042 | 2/2006 |
| WO | WO 2008/038251 | 4/2008 |
| WO | WO 2008038251 | 4/2008 |
| WO | WO 2008/150364 | 12/2008 |

OTHER PUBLICATIONS

Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the Internet, URL; http://www.cnn.com/2003/HEALTH/conditions/O9/24/alzheimers.drug.ap/indexhtml>.*
Dementia [online], [retrieved on May 24, 2007]. Retrieved from the Internet, URL; http:llen.wikipedia.orglwikilDementia>.*
Cai, et al., Antagonists of the Orexin Receptors, Expert Opinion on the Therapeutic Patents, Informa Healthcare, GB, vol. 16, No. 5, May 1, 2006, pp. 631-646.
U.S. Appl. No. 12/521,453, filed Jun. 29, 2009, Aissaoui, et al.
U.S. Appl. No. 12/311,451, filed Mar. 27, 2009, Aissaoul, et al.
Andreani, A., et al., Eur. J. Med. Chem., vol. 17, pp. 271-274, (1982).
Berry, C.R., et al., Cycloaddition Reactions of Thiazolium Azomethine Ylides: Application to Pyrrolo[2,1-b]thiazoles, Organic Letters, vol. 9, No. 21, pp. 4099-4102, (2007).
Cai, J., et al. Antagonists of the Orexin Receptors, Expert Opinion on Therapeutic Patents, Informa Healthcare, GB, vol. 16, No. 5, pp. 631-646, (May 1, 2006).
Chemelli, R.M., Narcolepsy in orexin Knock Out Mice: Molecular Genetics of Sleep Regulation, Cell, Aug. 20, 1999, vol. 98, 437-451, Cell Press.
Eissenstat, M.A., Aminoalkylindoles: Structure-Activity Relationships of Novel Cannabinoid Mimetics, Journal of Medicinal Chemistry, 1995, vol. 38, 3094-3105, American Chemical Society, Washington DC, USA.
Gould, P.L., Salt Selection for Basic Drugs, International Journal of Pharmaceutics, 1986, vol. 33, 201-217.
Madalengoitia, J. S., et al., Cyclopropanation Reactions of Pyroglutamic Acid-Derived Synthons with Akylidene Transfer Reagents, J. Org. Chem. vol. 64, pp. 547-555, (1999).
March, J., et al., Advanced Organic Chemistry, 4th Edition, John Wiley & Sons, pp. 447-449, 491-493, 919-920, 931, and 1167-1171, (1992).

(Continued)

Primary Examiner — Shawquia Young
(74) Attorney, Agent, or Firm — Hoxie & Associates LLC

(57) ABSTRACT

The invention relates to novel trans-3-aza-bicyclo[3.1.0]hexane derivatives of formula (I), wherein A, B, n and $R^1$ are as described in the description, and to the use of such compounds, or of pharmaceutically acceptable salts of such compounds, as medicaments, especially as orexin receptor antagonists.

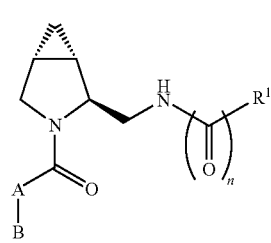

(I)

17 Claims, No Drawings

OTHER PUBLICATIONS

Reisch, J., et al., Synthesis of Daurine and Folidine: Two 2(1H)-Quinolinone Aldaloids from Haplophyllum Species, Monatshefte für Chemie, vol. 119, pp. 1169-1178, (1988).

Remington, The Science and Practice of Pharmacy, 21$^{st}$ Edition (2005), Part 5, "Pharmaceutical Manufacturing", [published by Lippincott Williams & Wilkins].

Sakurai, T. et al., Orexin & Orexin Receptors: A Family of Hypothalamic Neuropeptides and GProtein-Couples Receptors that Regulate Feeding Behavior, Cell, Feb. 20, 1998, vol. 92, 573-585, Cell Press.

Koberstein, R., et al., Tetrahydroisoquinolines as Orexin Receptor Antgonists, Chimia, 2003, vol. 57, No. 5, pp. 270-275.

* cited by examiner

TRANS-3-AZA-BICYCLO[3.1.0]HEXANE DERIVATIVES

CROSS REFERENCE TO RELATED APPLICATIONS

This application is a United States Application under 35 U.S.C. 371 claiming benefit of PCT Application No. PCT/IB2008/052985, filed on Jul. 25, 2008, which claims the benefit of PCT Application No. PCT/IB2008/051167, filed on Mar. 28, 2008 and PCT Application No. PCT/IB2007/052987, filed on Jul. 27, 2007, the contents of each of which are incorporated herein by reference.

The present invention relates to novel trans-3-aza-bicyclo[3.1.0]hexane derivatives of formula (I) and their use as pharmaceuticals. The invention also concerns related aspects including processes for the preparation of the compounds, pharmaceutical compositions containing one or more compounds of formula (I), and especially their use as orexin receptor antagonists.

Orexins (orexin A or OX-A and orexin B or OX-B) are novel neuropeptides found in 1998 by two research groups, orexin A is a 33 amino acid peptide and orexin B is a 28 amino acid peptide (Sakurai T. et al., Cell, 1998, 92, 573-585). Orexins are produced in discrete neurons of the lateral hypothalamus and bind to G-protein-coupled receptors ($OX_1$ and $OX_2$ receptors). The orexin-1 receptor ($OX_1$) is selective for OX-A, and the orexin-2 receptor ($OX_2$) is capable to bind OX-A as well as OX-B. Orexins are found to stimulate food consumption in rats suggesting a physiological role for these peptides as mediators in the central feedback mechanism that regulates feeding behaviour (Sakurai T. et al., Cell, 1998, 92, 573-585). On the other hand, it was also observed that orexins regulate states of sleep and wakefulness opening potentially novel therapeutic approaches to narcolepsy as well as insomnia and other sleep disorders (Chemelli R. M. et al., Cell, 1999, 98, 437-451).

Orexin receptors are found in the mammalian brain and may have numerous implications in pathologies as known from the literature.

The present invention provides trans-3-aza-bicyclo[3.1.0]hexane derivatives, which are non-peptide antagonists of human orexin receptors. These compounds are in particular of potential use in the treatment of e.g. eating disorders, drinking disorders, sleep disorders, or cognitive dysfunctions in psychiatric and neurologic disorders.

Up to now, several low molecular weight compounds are known having a potential to antagonise either specifically $OX_1$ or $OX_2$, or both receptors at the same time. Piperidine derivatives useful as orexin receptor antagonists are disclosed in WO01/096302. N-Aroyl cyclic amine derivatives are disclosed in WO02/090355.

The present invention describes for the first time trans-3-aza-bicyclo[3.1.0]hexane derivatives as orexin receptor antagonists.

i) A first aspect of the invention relates to compounds of formula (I), wherein the stereogenic centers are in a (1S,2S,5R)-configuration

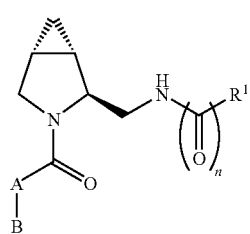

Formula (I)

wherein

A represents aryl or heterocyclyl, wherein the aryl or heterocyclyl is unsubstituted or independently mono- or di-substituted, wherein the substituents are independently selected from the group consisting of $(C_{1-4})$alkyl, $(C_{3-6})$cycloalkyl, $(C_{1-4})$alkoxy, trifluoromethyl, —$NR^2R^3$ and halogen;

B represents a hydrogen atom or an aryl- or heterocyclyl-group, wherein the aryl or heterocyclyl is unsubstituted or independently mono-, di-, or tri-substituted, wherein the substituents are independently selected from the group consisting of $(C_{1-4})$alkyl, $(C_{3-6})$cycloalkyl, $(C_{1-4})$alkoxy, trifluoromethyl, cyano, —$NR^2R^3$, —$NHSO_2$—$(C_{1-4})$alkyl, —$N(R^2)C(O)R^3$ and halogen;

n represents the integer 0 or 1;

$R^1$ represents aryl or heterocyclyl, wherein the aryl or heterocyclyl is unsubstituted or independently mono-, di-, or tri-substituted wherein the substituents are independently selected from the group consisting of $(C_{1-4})$alkyl, $(C_{3-6})$cycloalkyl, $(C_{1-4})$alkoxy, halogen, cyano, trifluoromethyl, trifluoromethoxy and —$NR^2R^3$; or $R^1$ represents a phenyl group which group is mono-substituted with a group selected from morpholin-4-yl and 4-methyl-piperazinyl; or $R^1$ represents a 2,3-dihydro-benzofuranyl-, a 2,3-dihydro-benzo[1,4]dioxinyl-, a 4H-benzo[1,3]dioxinyl-, a 2,3-dihydro-thieno[3,4-b][1,4]dioxinyl-, a 3-oxo-3,4-dihydro-2H-benzo[1,4]oxazinyl-, a 2H-chromenyl-, a 3,4-dihydro-2H-benzo[1,4]oxazinyl- or a chromanyl-group which groups are unsubstituted or independently mono- or di-substituted wherein the substituents are independently selected from the group consisting of $(C_{1-4})$alkyl, $(C_{1-4})$alkoxy and halogen;

$R^2$ represents hydrogen or $(C_{1-4})$alkyl; and $R^3$ represents hydrogen or $(C_{1-4})$alkyl.

Also part of the invention are compounds of formula (I) and pharmaceutically acceptable salts thereof.

The compounds of formula (I) may contain one or more stereogenic or asymmetric centers, such as one or more asymmetric carbon atoms. The compounds of formula (I) may thus be present as mixtures of stereoisomers or preferably as pure stereoisomers. Mixtures of stereoisomers may be separated in a manner known to a person skilled in the art.

The following paragraphs provide definitions of the various chemical moieties for the compounds according to the invention and are intended to apply uniformly throughout the specification and claims, unless an otherwise expressly set out definition provides a broader or narrower definition.

In this patent application, an arrow shows the point of attachment of the radical drawn. For example, the radical drawn below

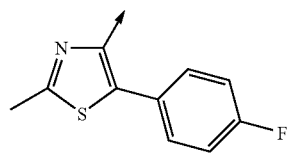

is the 5-(4-fluoro-phenyl)-2-methyl-thiazol-4-yl group.

The term "halogen" means fluorine, chlorine, bromine, or iodine, preferably fluorine or chlorine.

The term "$(C_{1-4})$alkyl", alone or in combination, means a straight-chain or branched-chain alkyl group with 1 to 4 carbon atoms. Examples of $(C_{1-4})$alkyl groups are methyl, ethyl, propyl, isopropyl, n-butyl, isobutyl, sec.-butyl or tert.-butyl. Preferred are methyl and ethyl, especially methyl.

The term "(C$_{3-6}$)cycloalkyl", alone or in combination, means a cycloalkyl group with 3 to 6 carbon atoms. Examples of (C$_{3-6}$)cycloalkyl groups are cyclopropyl, cyclobutyl, cyclopentyl or cyclohexyl. Preferred are cyclopropyl and cyclohexyl. Most preferred is cyclopropyl.

The term "(C$_{1-4}$)alkoxy", alone or in combination, means a group of the formula (C$_{1-4}$)alkyl-O— in which the term "(C$_{1-4}$)alkyl" has the previously given significance, such as methoxy, ethoxy, n-propoxy, isopropoxy, n-butoxy, isobutoxy, sec.-butoxy or tert.-butoxy. Preferred are methoxy and ethoxy, especially methoxy.

The term "aryl", alone or in combination, means a phenyl or a naphthyl group. Preferred is a phenyl group. The aryl group may be unsubstituted or independently mono-, di-, or tri-substituted wherein the substituents are independently selected from the group consisting of (C$_{1-4}$alkyl, (C$_{3-6}$)cycloalkyl, (C$_{1-4}$alkoxy, halogen, cyano, trifluoromethyl, trifluoromethoxy, —NR$^2$R$^3$, —NHSO$_2$—(C$_{1-4}$)alkyl and —N(R$^2$)C(O)R$^3$. In case "A" represents "aryl" the term preferably means the above-mentioned group which is unsubstituted or mono- or di-substituted, wherein the substituents are independently selected from the group consisting of (C$_{1-4}$alkyl, (C$_{3-6}$)cycloalkyl, (C$_{1-4}$)alkoxy, trifluoromethyl, —NR$^2$R$^3$ and halogen. Preferred examples wherein "A" represents "aryl" are unsubstituted or mono- or di-substituted phenyl (preferred unsubstituted or mono-substituted phenyl), wherein the substituents are independently selected from the group consisting of (C$_{1-4}$alkyl, (C$_{3-6}$)cycloalkyl, (C$_{1-4}$alkoxy and trifluoromethyl (preferably from (C$_{1-4}$alkyl, (C$_{1-4}$alkoxy and trifluoromethyl, especially (C$_{1-4}$)alkoxy and trifluoromethyl). Examples are phenyl, 3-trifluoromethylphenyl, and 2-methoxyphenyl. In addition to the above-mentioned examples, further examples are 2-trifluoromethylphenyl and 2-cyclohexylphenyl. In addition to the above-mentioned substituents, the substituent "A" is also substituted by the substituent "B", wherein B is preferably attached in ortho position to the point of attachment of the carbonyl group which links A to the 3-aza-bicyclo[3.1.0]hexane moiety.

In case "B" represents "aryl" the term preferably means the above-mentioned group which is unsubstituted or mono-, di-, or tri-substituted (preferred mono- or di-substituted), wherein the substituents are independently selected from the group consisting of (C$_{1-4}$alkyl, (C$_{3-6}$)cycloalkyl, (C$_{1-4}$alkoxy, trifluoromethyl, cyano, —NR$^2$R$^3$, —NHSO$_2$—(C$_{1-4}$)alkyl, —N(R$^2$)C(O)R$^3$ and halogen. Preferably the substituents are selected from (C$_{1-4}$alkyl, (C$_{1-4}$alkoxy, trifluoromethyl, cyano, —NHSO$_2$—(C$_{1-4}$)alkyl, —N(R$^2$)C(O)R$^3$ and halogen. Preferred examples wherein "B" represents "aryl" are unsubstituted or mono-, di-, or tri-substituted phenyl (preferred mono- or di-substituted, especially mono-substituted phenyl), wherein the substituents are independently selected from the group consisting of (C$_{1-4}$alkyl, (C$_{1-4}$alkoxy, trifluoromethyl, and halogen (especially (C$_{1-4}$)alkyl and halogen). Examples are phenyl, 2-methylphenyl, 3-methylphenyl, 4-methylphenyl, 3,4-dimethylphenyl, 4-ethylphenyl, 2-fluorophenyl, 3-fluorophenyl, 4-fluorophenyl and 3-chlorophenyl. In addition to the above-mentioned examples, further examples are 2,3-dimethylphenyl, 2,4-dimethylphenyl, 3,5-dimethylphenyl, 3-methoxyphenyl, 3-bromophenyl, 4-bromophenyl, 3,4-difluorophenyl, 2-chloro-6-fluorophenyl, 2,3-dichlorophenyl, 3,4-dichlorophenyl, 3-bromo-4-fluorophenyl, 3-fluoro-2-methylphenyl, 3-fluoro-4-methylphenyl, 4-cyanophenyl, 3-trifluoromethylphenyl, 3-fluor-5-trifluoromethylphenyl, 3-acetylamino-phenyl and 3-methanesulfonylamino-phenyl. In addition to the above-mentioned substituents, the substituent "B" is attached to the substituent "A".

In case "A" and "B" both represents "aryl" the combination "A-B" preferably means a biphenyl group which is unsubstituted or independently mono- or di-substituted for "A" and unsubstituted or independently mono-, di- or tri-substituted for "B", wherein the substituents are independently selected from the group consisting of (C$_{1-4}$)alkyl, (C$_{3-6}$)cycloalkyl, (C$_{1-4}$)alkoxy, trifluoromethyl and halogen. Preferred examples wherein "A" and "B" both represent "aryl" are biphenyl groups which are unsubstituted or independently mono- or di-substituted for "A" and unsubstituted or independently mono-, di- or tri-substituted for "B", wherein the substituents are independently selected from the group consisting of (C$_{1-4}$)alkyl and halogen. Examples are:

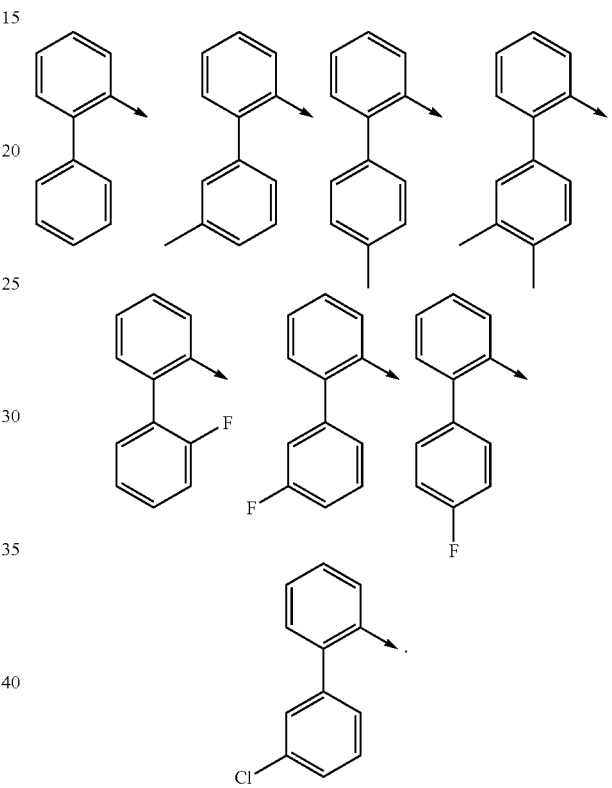

In case R$^1$ represents "aryl" the term preferably means the above-mentioned groups which are unsubstituted or mono-, di-, or tri-substituted wherein the substituents are independently selected from the group consisting of (C$_{1-4}$)alkyl, (C$_{3-6}$)cycloalkyl, (C$_{1-4}$)alkoxy, halogen, cyano, trifluoromethyl, trifluoromethoxy and —NR$^2$R$^3$. In a sub-embodiment, the substituents are preferably selected from (C$_{1-4}$)alkyl, (C$_{3-6}$)cycloalkyl, (C$_{1-4}$)alkoxy, halogen, cyano and trifluoromethyl. In another embodiment, in case R$^1$ represents "aryl", the term preferably means the above-mentioned groups which are unsubstituted or mono-, or di-substituted wherein the substituents are independently selected from the group consisting of (C$_{1-4}$)alkyl, (C$_{1-4}$)alkoxy, halogen, cyano and trifluoromethyl. Preferred examples wherein R$^1$ represents "aryl" are naphthyl, 4-ethylphenyl, 2,5-dimethyl-phenyl, 3,4-dimethylphenyl, 3,5-dimethylphenyl, 4-methoxy-2-methylphenyl, 4-methoxy-3-methylphenyl, 2-fluoro-5-methylphenyl, 3-fluoro-2-methylphenyl, 2-chloro-3-methylphenyl, 3-chloro-2-methylphenyl, 2-bromo-5-methylphenyl, 4-methyl-3-trifluoromethylphenyl, 2-methoxyphenyl, 2,3-dimethoxyphenyl, 2,4-dimethoxyphenyl, 2,5-dimethoxyphenyl, 3,5-dimethoxyphenyl, 5-fluoro-2-methoxy-phenyl, 4-chloro-2-methoxyphenyl, 5-chloro-2-methoxyphenyl, 3-trifluoromethyl-4-methoxyphenyl, 2-chlorophenyl, 3-chlorophenyl, 4-chlorophenyl, 3-bromophenyl, 4-bromophenyl, 3-iodophenyl, 2,4-dichlorophenyl, 3,4-dichlorophenyl, 2-chloro-3-fluorophenyl, 2-chloro-4-fluorophenyl, 5-bromo-2-chlorophenyl, 2-chloro-4,5-difluorophenyl, 3-cyanophenyl, 4-cyanophenyl and 3-trifluoromethylphenyl. In addition to the above-mentioned examples, a further example is 3-methylphenyl.

The term "heterocyclyl", alone or in combination, means a 5- to 10-membered monocyclic or bicyclic aromatic ring containing 1, 2 or 3 heteroatoms independently selected from oxygen, nitrogen and sulfur. Examples of such heterocyclyl groups are furanyl, oxazolyl, isoxazolyl, oxadiazolyl, thienyl, thiazolyl, isothiazolyl, thiadiazolyl, pyrrolyl, imidazolyl, pyrazolyl, triazolyl, pyridyl, pyrimidyl, pyridazinyl, pyrazinyl, indolyl, isoindolyl, benzofuranyl, isobenzofuranyl, benzothiophenyl, indazolyl, benzimidazolyl, benzoxazolyl, benzisoxazolyl, benzothiazolyl, benzotriazolyl, benzoxadiazolyl, benzothiadiazolyl, quinolinyl, isoquinolinyl, naphthyridinyl, cinnolinyl, quinazolinyl, quinoxalinyl, phthalazinyl, pyrazolo[1,5-a]pyridyl, pyrazolo[1,5-a]pyrimidyl, imidazo[1,2-a]pyridyl, pyrrolo[2,1-b]thiazolyl and imidazo[2,1-b]thiazolyl. In addition to the above-mentioned examples, further examples are benzo[2,1,3]thiadiazolyl, benzo[2,1,3]oxadiazolyl and 4H-furo[3,2-b]pyrrolyl. The above-mentioned heterocyclyl groups are unsubstituted or mono-, di-, or tri-substituted wherein the substituents are independently selected from the group consisting of $(C_{1-4})$alkyl, $(C_{3-6})$cycloalkyl, $(C_{1-4})$alkoxy, halogen, trifluoromethyl and $-NR^2R^3$.

In case "A" represents "heterocyclyl" the term preferably means the above-mentioned groups which is unsubstituted or mono- or di-substituted (preferred unsubstituted or mono-substituted) wherein the substituents are independently selected from the group consisting of $(C_{1-4}$alkyl, $(C_{3-6})$cycloalkyl, $(C_{1-4})$alkoxy, trifluoromethyl, $-NR^2R^3$ and halogen. In a further preferred embodiment, in case "A" represents "heterocyclyl" the term means the above-mentioned groups which is unsubstituted or mono-substituted, wherein the substituent is selected from the group consisting of $(C_{1-4})$alkyl, $(C_{3-6})$cycloalkyl, $(C_{1-4})$alkoxy and $-NR^2R^3$ (especially, the substituent is selected from the group consisting of $(C_{1-4})$alkyl, $(C_{1-4})$alkoxy and $-NR^2R^3$). In a further preferred embodiment, in case "A" represents "heterocyclyl" the term means an unsubstituted or mono-substituted group selected from thienyl, oxazolyl, thiazolyl, pyrazolyl, pyrimidyl, pyrazinyl, naphthyridinyl and imidazo[1,2-a]pyridyl (in a sub-embodiment preferably selected from oxazolyl, thiazolyl, pyrazolyl, pyrimidyl, pyrazinyl, naphthyridinyl and imidazo[1,2-a]pyridyl; in another sub-embodiment preferably selected from thienyl, oxazolyl, thiazolyl, pyrazolyl, pyrimidyl, and pyrazinyl (and especially from thienyl and thiazolyl)), wherein the substituent is selected from the group consisting of $(C_{1-4}$alkyl, $(C_{3-6})$cycloalkyl, $(C_{1-4}$alkoxy and $-NR^2R^3$ (especially from $(C_{1-4})$alkyl and $-NR^2R^3$). In addition to the above-mentioned substituents, the substituent "A" is also substituted by the substituent "B", wherein B is preferably attached in ortho position to the point of attachment of the carbonyl group which links A to the 3-aza-bicyclo[3.1.0]hexane moiety.

Particular examples wherein "A" represents "heterocyclyl" are thiophen-2-yl, thiophen-3-yl, thiazol-4-yl, 2-methyl-thiazol-4-yl, 2-amino-thiazol-4-yl, 2-dimethylamino-thiazol-4-yl, 2-bromo-thiazol-4-yl, 2-methoxy-thiazol-4-yl and 2-cyclopropyl-thiazol-4-yl; wherein B is attached in position 5 of the above thiazol-4-yl groups, in position 3 of the above thiophen-2-yl groups, and in position 2 of the above thiophen-3-yl groups. In a sub-embodiment preferred are 2-methyl-thiazol-4-yl, 2-amino-thiazol-4-yl and 2-dimethylamino-thiazol-4-yl. In another sub-embodiment preferred is thiophen-3-yl.

Further examples wherein "A" represents "heterocyclyl" and one of the substituents is represented by "B" are:

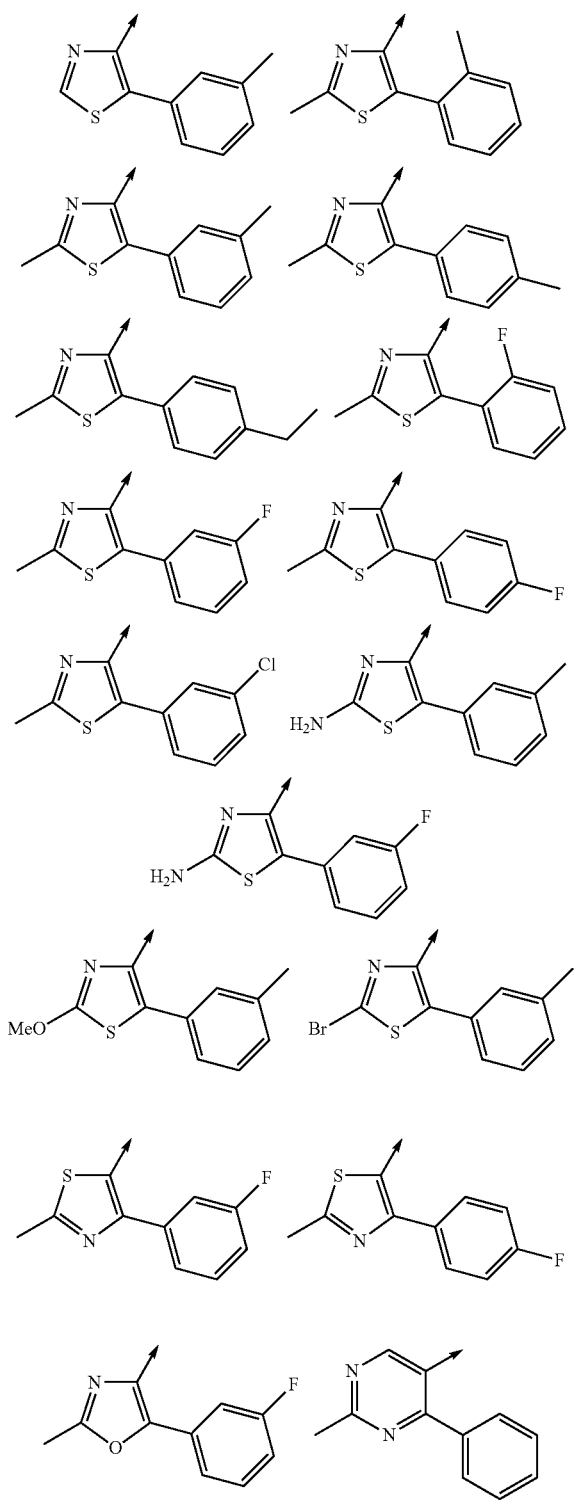

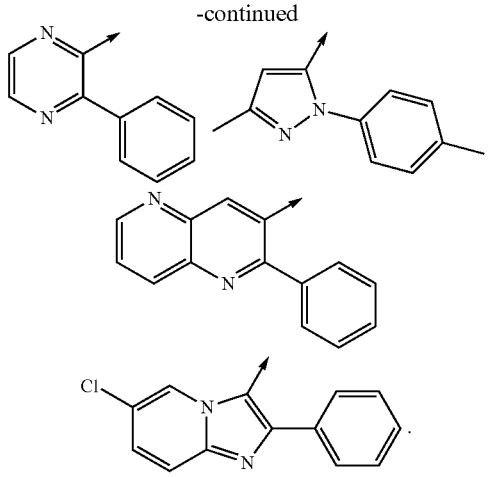
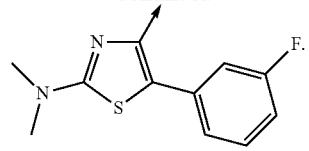

In addition to the above-listed groups, further examples wherein "A" represents "heterocyclyl" and one of the substituents is represented by "B" are:

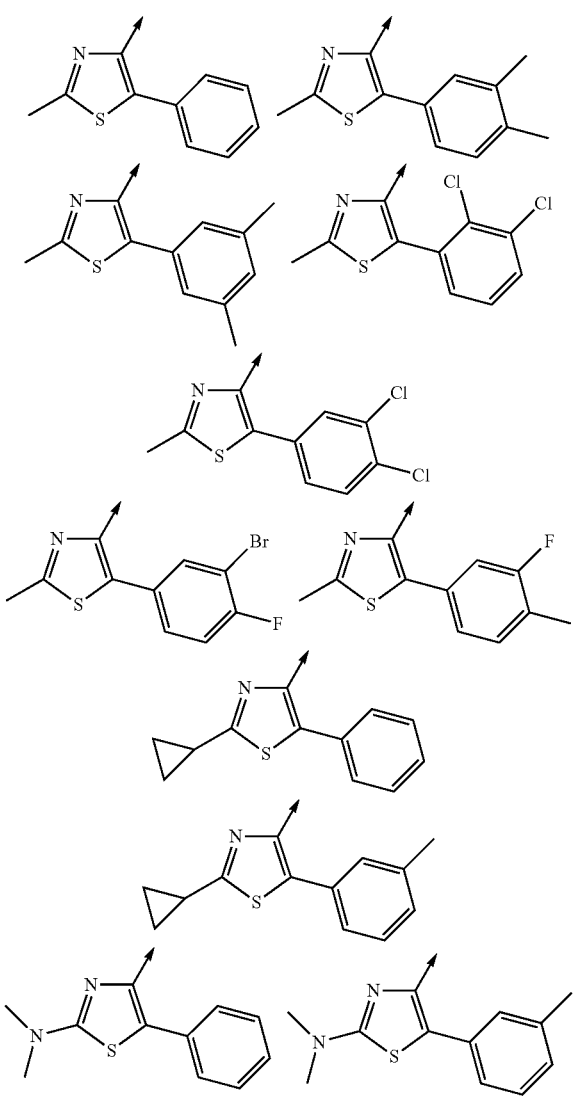

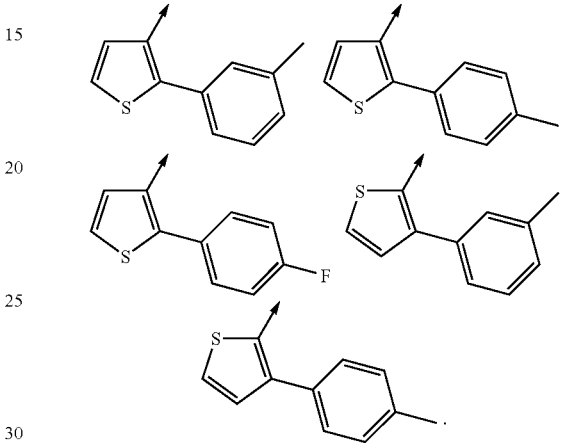

In case "B" represents "heterocyclyl" the term preferably means the above-mentioned groups which is unsubstituted or independently mono-, di-, or tri-substituted (preferred mono- or di-substituted) wherein the substituents are independently selected from the group consisting of $(C_{1-4})$alkyl, trifluoromethyl, —$NR^2R^3$ and halogen. Examples wherein "B" represents "heterocyclyl" are pyrazolyl, thienyl and 2-aminothiazolyl. In addition to the above-mentioned substituents, the substituent "B" is attached to the substituent "A".

In case $R^1$ represents "heterocyclyl" the term preferably means the above-mentioned groups which is unsubstituted or mono-, di-, or tri-substituted (preferred unsubstituted or mono-substituted) wherein the substituents are independently selected from the group consisting of $(C_{1-4})$alkyl, $(C_{3-6})$cycloalkyl, $(C_{1-4})$alkoxy, halogen, cyano, trifluoromethyl, trifluoromethoxy and —$NR^2R^3$. In a sub-embodiment, the substituents are preferably selected from $(C_{1-4})$alkyl, $(C_{3-6})$cycloalkyl, $(C_{1-4})$alkoxy, halogen, trifluoromethyl and —$NR^2R^3$. In a further preferred embodiment, in case $R^1$ represents "heterocyclyl" the term means the above-mentioned groups which are unsubstituted or mono-, di-, or tri-substituted (preferred unsubstituted or mono-substituted) wherein the substituents are independently selected from the group consisting of $(C_{1-4})$alkyl, trifluoromethyl and halogen.

In another embodiment, in case n represents the integer 1, further preferred examples wherein $R^1$ represents "heterocyclyl" are unsubstituted or mono-, di-, or tri-substituted (preferred unsubstituted or mono-substituted) heterocyclyl; wherein the heterocyclyl is selected from the group consisting of isoxazolyl, pyrazolyl, indolyl, benzofuranyl, indazolyl, benzoxazolyl, benzisoxazolyl, benzothiazolyl, quinolinyl, isoquinolinyl, benzo[2,1,3]thiadiazolyl, benzo[2,1,3]oxadiazolyl, 4H-furo[3,2-b]pyrrolyl, pyrazolo[1,5-a]pyridyl, imidazo[1,2-a]pyridyl, pyrrolo[2,1-b]thiazolyl or imidazo[2,1-b]thiazolyl (especially pyrrolo[2, 1-1)]thiazolyl or imidazo

[2, 1-1)]thiazolyl); wherein the substituents are independently selected from the group consisting of (C$_{1-4}$) alkyl, trifluoromethyl and halogen. In a sub-embodiment, the heterocyclyl is selected from the group consisting of isoxazolyl, pyrazolyl, indolyl, benzofuranyl, indazolyl, benzisoxazolyl, quinolinyl, isoquinolinyl, pyrazolo[1,5-a]pyridyl, imidazo[1,2-a]pyridyl or imidazo[2,1-b]thiazolyl (especially imidazo[2,1-b]thiazolyl); wherein the substituents are independently selected from the group consisting of (C$_{1-4}$)alkyl, trifluoromethyl and halogen.

In another embodiment, in case n represents the integer 1, preferred examples are benzo[d] isoxazolyl, benzo[2,1,3]thiadiazolyl, benzo[2,1,3]oxadiazolyl, imidazo[1,2-a]pyridyl, imidazo[2,1-b]thiazolyl, and pyrrolo[2,1-b]thiazolyl. In another embodiment, in case n represents the integer 1, particular examples wherein "R$^1$" represents "heterocyclyl" are pyrazol-3-yl, pyrazol-4-yl, isoxazol-4-yl, indol-2-yl, indol-3-yl, indol-4-yl, benzofuran-4-yl, indazol-3-yl, benzoxazol-4-yl, benzoxazol-7-yl, benzisoxazol-3-yl, benzothiazol-4-yl, benzothiazol-7-yl, quinolin-2-yl, quinolin-8-yl, isoquinolin-1-yl, benzo[2,1,3]thiadiazol-4-yl, benzo[2,1,3]oxadiazol-4-yl, 4H-furo[3,2-b]pyrrol-5-yl, pyrrolo[2,1-b]thiazol-7-yl, imidazo[1,2-a]pyridin-3-yl, pyrazolo[1,5-a]pyridin-3-yl, imidazo[2,1-b]thiazol-2-yl, imidazo[2,1-b]thiazol-5-yl and imidazo[2,1-b]thiazol-6-yl (especially pyrrolo[2,1-b]thiazol-7-yl, imidazo[2,1-b]thiazol-2-yl and imidazo[2,1-b]thiazol-5-yl). The above-mentioned heterocyclyl groups are unsubstituted, mono-, di-, or tri-substituted, wherein the substituents are independently selected from the group consisting of (C$_{1-4}$)alkyl, trifluoromethyl and halogen.

In particular, the above mentioned "heterocyclyl" groups as used for the substituent "R$^1$" are preferably substituted as follows: pyrazolyl groups are di-substituted with (C$_{1-4}$)alkyl; indolyl groups are unsubstituted, or mono- or di-substituted independently with (C$_{1-4}$)alkyl and halogen (especially unsubstituted, or mono- or di-substituted with methyl); benzofuranyl groups are unsubstituted, or mono-substituted with halogen; indazolyl groups are unsubstituted, or mono-substituted with (C$_{1-4}$)alkyl (especially methyl); benzoxazolyl groups are unsubstituted, or mono-substituted with (C$_{1-4}$)alkyl (especially methyl); benzisoxazolyl groups are unsubstituted; benzothiazolyl groups are unsubstituted (preferred), or mono-substituted with halogen (especially chlorine); quinolinyl groups are unsubstituted; isoquinolinyl groups are unsubstituted; benzo[2,1,3]thiadiazolyl groups are unsubstituted; benzo[2,1,3]oxadiazolyl groups are unsubstituted; 4H-furo[3,2-b]pyrrolyl are mono-substituted with (C$_{1-4}$) alkyl (especially methyl); pyrrolo[2,1-b]thiazolyl groups are unsubstituted, or mono-substituted with (C$_{1-4}$)alkyl (especially methyl); imidazo[1,2-a]pyridinyl groups are unsubstituted, or di-substituted with (C$_{1-4}$)alkyl; pyrazolo[1,5-a]pyridinyl groups are unsubstituted; and imidazo[2,1-b]thiazolyl groups are unsubstituted, mono-substituted with (C$_{1-4}$)alkyl, trifluoromethyl or halogen, or di- or tri-substituted with (C$_{1-4}$)alkyl (especially unsubstituted or mono-substituted with methyl).

In another embodiment, in case n represents the integer 0, a preferred example wherein "R$^1$" represents "heterocyclyl" is mono-, or di-substituted heterocyclyl; wherein the heterocyclyl is pyrimidyl (especially pyrimidin-2-yl); wherein the substituents are independently selected from (C$_{1-4}$)alkyl, (C$_{1-4}$)alkoxy, halogen, trifluoromethyl, cyano, and —NR$^2$R$^3$. Especially, said pyrimidinyl is mono-substituted with halogen. A particular example is 5-bromo-pyrimidin-2-yl.

Preferred examples wherein R$^1$ represents "heterocyclyl" are:

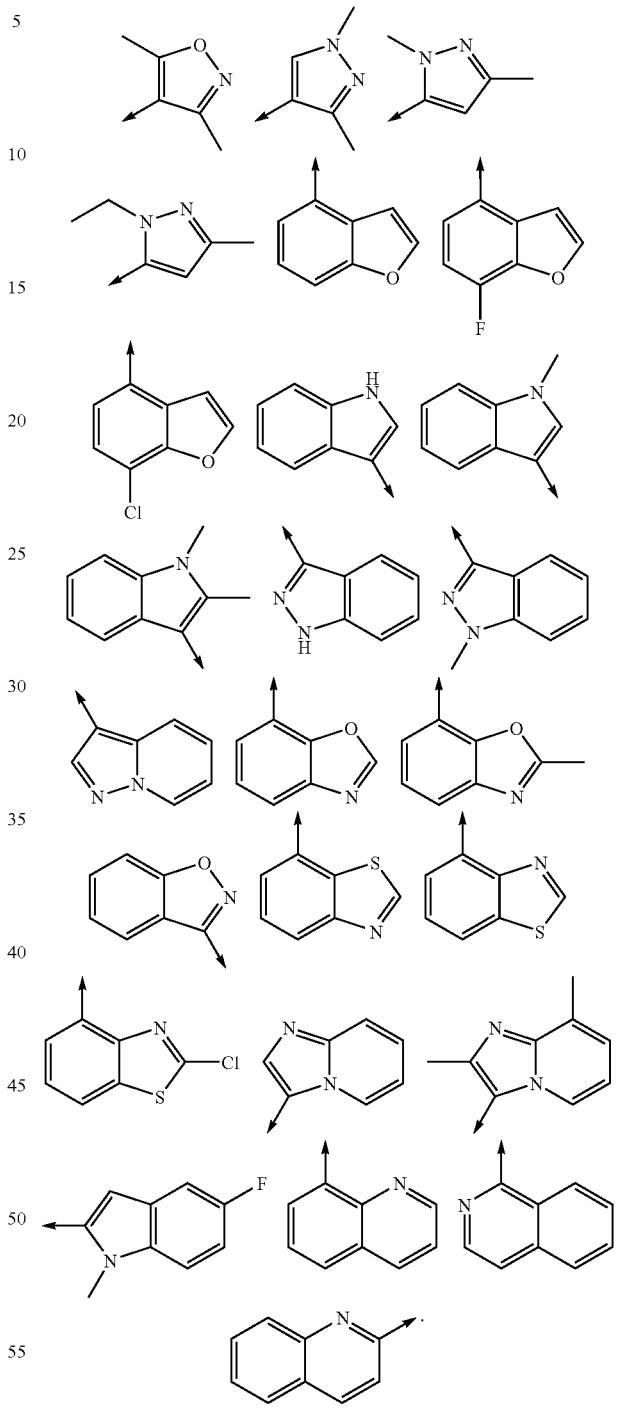

In addition to the above groups, further preferred examples wherein R$^1$ represents "heterocyclyl" are:

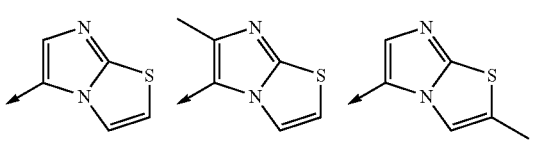

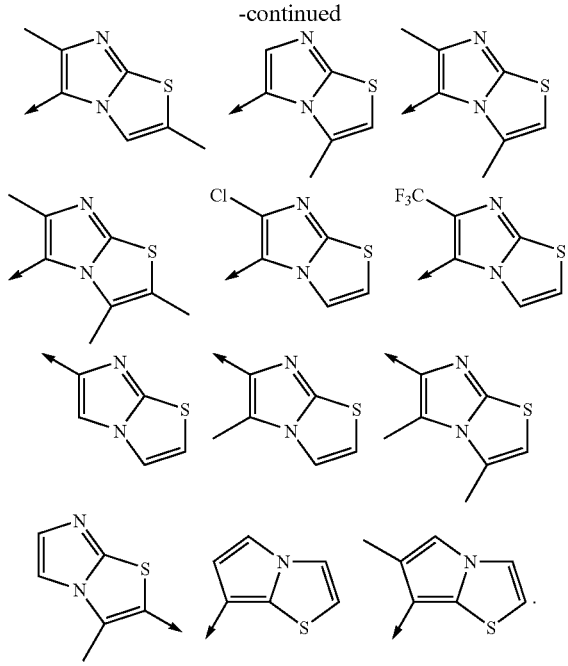

Further preferred examples wherein R¹ represents "heterocyclyl" are the above mentioned pyrrolo[2,1-b]thiazolyl and (especially) imidazo[2,1-b]thiazolyl groups.

In case R¹ represents "a 2,3-dihydro-benzofuranyl-, a 2,3-dihydro-benzo[1,4]dioxinyl-, a 4H-benzo[1,3]dioxinyl-, a 2,3-dihydro-thieno[3,4-b][1,4]dioxinyl-, a 3-oxo-3,4-dihydro-2H-benzo[1,4]oxazinyl-, a 2H-chromenyl-, a 3,4-dihydro-2H-benzo[1,4]oxazinyl- or a chromanyl-group which groups are unsubstituted or independently mono- or di-substituted wherein the substituents are independently selected from the group consisting of ($C_{1-4}$)alkyl, ($C_{1-4}$)alkoxy and halogen", said groups as used for the substituent "R¹" are preferably as follows: 2,3-dihydro-benzofuranyl-groups (especially 2,3-dihydro-benzofuran-4-yl or 2,3-dihydro-benzofuran-7-yl) are unsubstituted or independently di-substituted with ($C_{1-4}$)alkyl, ($C_{1-4}$)alkoxy and halogen (especially unsubstituted, or di-substituted in position 2 with methyl); 4H-benzo[1,3]dioxinyl-groups (especially 4H-benzo[1,3]dioxin-8-yl) are preferably mono-substituted in position 6 with fluorine; 3,4-dihydro-2H-benzo[1,4]oxazinyl-groups (especially 3,4-dihydro-2H-benzo[1,4]oxazin-5-yl or 3,4-dihydro-2H-benzo[1,4]oxazin-8-yl) and 3-oxo-3,4-dihydro-2H-benzo[1,4]oxazinyl-groups (especially 3-oxo-3,4-dihydro-2H-benzo[1,4]oxazin-8-yl) are preferably unsubstituted, or mono-substituted on the nitrogen atom with methyl; 2,3-dihydro-benzo[1,4]dioxinyl-(especially 2,3-dihydro-benzo[1,4]dioxin-5-yl), 2H-chromenyl (especially chromen-5-yl), chromanyl-(especially chroman-5-yl or chroman-8-yl), and 2,3-dihydro-thieno[3,4-b][1,4]dioxinyl-groups (especially 2,3-dihydro-thieno[3,4-b][1,4]dioxine-5-yl) are preferably unsubstituted.

The term "—NR²R³" means for example —NH₂ or —N(CH₃)₂.

The term "—NHSO₂—($C_{1-4}$)alkyl" means for example —NH—SO₂—CH₃.

The term "—N(R²)C(O)R³" means for example the group —NH—C(O)—CH₃.

In the following, further embodiments of the invention are described:

ii) A further embodiment of the invention relates to compounds according to embodiment i), wherein n represents the integer 1.

iii) A further embodiment of the invention relates to compounds according to embodiments i) or ii), wherein at least one, preferably all of the following characteristics are present:

A represents aryl or heterocyclyl, wherein the aryl or heterocyclyl is unsubstituted or independently mono- or di-substituted, wherein the substituents are independently selected from the group consisting of ($C_{1-4}$)alkyl, ($C_{3-6}$)cycloalkyl, ($C_{1-4}$)alkoxy, trifluoromethyl, —NR²R³ and halogen;

B represents a hydrogen atom or an aryl- or heterocyclyl-group, wherein the aryl or heterocyclyl is unsubstituted or independently mono-, di-, or tri-substituted, wherein the substituents are independently selected from the group consisting of ($C_{1-4}$)alkyl, ($C_{3-6}$)cycloalkyl, ($C_{1-4}$)alkoxy, trifluoromethyl, —NR²R³ and halogen;

R¹ represents aryl or heterocyclyl, wherein the aryl or heterocyclyl is unsubstituted or independently mono-, di-, or tri-substituted wherein the substituents are independently selected from the group consisting of ($C_{1-4}$)alkyl, ($C_{3-6}$)cycloalkyl, ($C_{1-4}$)alkoxy, halogen, cyano, trifluoromethyl, trifluoromethoxy and —NR²R³; or R¹ represents a phenyl group which group is mono-substituted with a group selected from morpholin-4-yl and 4-methyl-piperazinyl; or R¹ represents a 2,3-dihydro-benzofuranyl-, a 2,3-dihydro-benzo[1,4]dioxinyl-, a 4H-benzo[1,3]dioxinyl-, a 2,3-dihydro-thieno[3,4-b][1,4]dioxinyl-, a 3-oxo-3,4-dihydro-2H-benzo[1,4]oxazinyl-, a 2H-chromenyl-, a 3,4-dihydro-2H-benzo[1,4]oxazinyl- or a chromanyl-group which groups are unsubstituted or independently mono- or di-substituted wherein the substituents are independently selected from the group consisting of ($C_{1-4}$)alkyl, ($C_{1-4}$)alkoxy and halogen;

R² represents hydrogen or ($C_{1-4}$)alkyl; and

R³ represents hydrogen or ($C_{1-4}$)alkyl.

iv) A further embodiment of the invention relates to compounds according to any one of embodiments i) to iii), wherein A represents aryl or heterocyclyl, wherein the aryl or heterocyclyl is unsubstituted or mono-substituted, wherein the substituent is selected from the group consisting of ($C_{1-4}$)alkyl, ($C_{3-6}$)cycloalkyl, ($C_{1-4}$)alkoxy, —NR²R³ and halogen.

v) A further embodiment of the invention relates to compounds according to any one of embodiments i) to iv), wherein A represents aryl or heterocyclyl, wherein the aryl or heterocyclyl is unsubstituted or mono-substituted, wherein the substituent is selected from the group consisting of ($C_{1-4}$)alkyl, ($C_{1-4}$)alkoxy, —NR²R³ and halogen.

vi) A further embodiment of the invention relates to compounds according to any one of embodiments i) to v), wherein B represents aryl or heterocyclyl, wherein the aryl or heterocyclyl is unsubstituted or independently mono-, di- or tri-substituted, wherein the substituents are independently selected from the group consisting of ($C_{1-4}$)alkyl, —NR²R³ and halogen.

vii) A further embodiment of the invention relates to compounds according to any one of embodiments i) to vi), wherein R¹ represents aryl or heterocyclyl, wherein the aryl or heterocyclyl is unsubstituted or independently mono-, di-, or tri-substituted wherein the substituents are independently selected from the group consisting of ($C_{1-4}$)alkyl, ($C_{1-4}$)alkoxy, halogen, cyano and trifluoromethyl; or R¹ represents a 2,3-dihydro-benzofuranyl-, a 2,3-dihydro-benzo[1,4]dioxinyl-, a 4H-benzo[1,3]dioxinyl-, a 2,3-dihydro-thieno[3,4-b][1,4]dioxinyl-, a 3-oxo-3,4-dihydro-2H-benzo[1,4]oxazinyl-, a 2H-chromenyl-, a 3,4-dihydro-2H-benzo[1,4]oxazinyl- or a chromanyl-group which groups are unsubstituted or independently mono- or di-substituted wherein the substituents are independently selected from the group consisting of $(C_{1-4})$alkyl and halogen.

viii) A further embodiment of the invention relates to compounds according to any one of embodiments i) to iv) or vi) to vii), wherein
A represents a phenyl-, a thienyl-, a thiazolyl-, a pyrimidyl-, a [1,6]naphthyridinyl or a imidazo[1,2-a]pyridyl-group, which group is unsubstituted or mono-substituted, wherein the substituent is selected from the group consisting of $(C_{1-4})$alkyl, $(C_{3-6})$cycloalkyl, $(C_{1-4})$alkoxy, $-NR^2R^3$ and halogen.

ix) A further embodiment of the invention relates to compounds according to any one of embodiments i) to viii), wherein
A represents a phenyl- or a thiazolyl-group, which group is unsubstituted or mono-substituted, wherein the substituent is selected from the group consisting of $(C_{1-4})$alkyl, $(C_{1-4})$alkoxy, $-NR^2R^3$ and halogen.

x) A further embodiment of the invention relates to compounds according to any one of embodiments i) to ix), wherein
A represents a phenyl- or (preferably) a thiazolyl-group, which group is unsubstituted or mono-substituted, wherein the substituent is selected from the group consisting of $(C_{1-4})$alkyl and $-NR^2R^3$.

xi) A further embodiment of the invention relates to compounds according to any one of embodiments i) to x), wherein
B represents a phenyl-group, which group is unsubstituted or mono- or di-substituted, wherein the substituents are independently selected from the group consisting of $(C_{1-4})$alkyl, $(C_{1-4})$alkoxy, trifluoromethyl, and halogen (especially $(C_{1-4})$alkyl and halogen).

xii) A further embodiment of the invention relates to compounds according to any one of embodiments i) to xi), wherein
$R^1$ represents a phenyl-, isoxazolyl-, pyrazolyl-, indolyl-, benzofuranyl-, indazolyl-, benzo[d]isoxazolyl-, quinolinyl-, isoquinolinyl-, benzoxazolyl-, benzothiazolyl-, benzo[2,1,3]thiadiazolyl-, benzo[2,1,3]oxadiazolyl-, 4H-furo[3,2-b]pyrrolyl-, pyrrolo[2,1-b]thiazolyl-, pyrazolo[1,5-a]pyridyl-, imidazo[1,2-a]pyridyl- or imidazo[2,1-b]thiazolyl-group, which group is unsubstituted or independently mono- or di-substituted wherein the substituents are independently selected from the group consisting of $(C_{1-4})$alkyl, $(C_{1-4})$alkoxy, halogen and trifluoromethyl; or $R^1$ represents a 2,3-dihydro-benzofuranyl-, a 2,3-dihydro-benzo[1,4]dioxinyl-, a 4H-benzo[1,3]dioxinyl-, a 2,3-dihydro-thieno[3,4-b][1,4]dioxinyl- or a chromanyl-group which groups are unsubstituted or independently mono- or di-substituted wherein the substituents are independently selected from the group consisting of $(C_{1-4})$alkyl and halogen.

xiii) A further embodiment of the invention relates to compounds according to any one of embodiments i) to xii), wherein
$R^1$ represents a phenyl-, isoxazolyl-, pyrazolyl-, indolyl-, benzofuranyl-, indazolyl-, benzisoxazolyl-, quinolinyl-, isoquinolinyl-, imidazo[1,2-a]pyridyl- or imidazo[2,1-b]thiazolyl-group, which group is unsubstituted or independently mono- or di-substituted wherein the substituents are independently selected from the group consisting of $(C_{1-4})$alkyl, $(C_{1-4})$alkoxy, halogen and trifluoromethyl; or $R^1$ represents a 2,3-dihydro-benzofuranyl-, a 2,3-dihydro-benzo[1,4]dioxinyl-, a 4H-benzo[1,3]dioxinyl-, a 2,3-dihydro-thieno[3,4-b][1,4]dioxinyl- or a chromanyl-group which groups are unsubstituted or independently mono- or di-substituted wherein the substituents are independently selected from the group consisting of $(C_{1-4})$alkyl and halogen.

xiv) A further embodiment of the invention relates to compounds according to any one of embodiments i) to xii), wherein
$R^1$ represents a phenyl-, isoxazolyl-, pyrazolyl-, indolyl-, benzofuranyl-, indazolyl-, benzo[d]isoxazolyl-, quinolinyl-, isoquinolinyl-, benzoxazolyl-, benzothiazolyl-, benzo[2,1,3]thiadiazolyl-, benzo[2,1,3]oxadiazolyl-, 4H-furo[3,2-b]pyrrolyl-, pyrrolo[2,1-b]thiazolyl-, pyrazolo[1,5-a]pyridyl-, imidazo[1,2-a]pyridyl- or imidazo[2,1-b]thiazolyl-group, which group is unsubstituted or independently mono- or di-substituted wherein the substituents are independently selected from the group consisting of $(C_{1-4})$alkyl, $(C_{1-4})$alkoxy, halogen and trifluoromethyl.

xv) A further embodiment of the invention relates to compounds according to any one of embodiments i) to xiv), wherein
$R^1$ represents a phenyl-, isoxazolyl-, pyrazolyl-, indolyl-, benzofuranyl-, indazolyl-, benzisoxazolyl-, quinolinyl-, isoquinolinyl-, imidazo[1,2-a]pyridyl- or imidazo [2,1-b]thiazolyl-group, which group is unsubstituted or independently mono- or di-substituted wherein the substituents are independently selected from the group consisting of $(C_{1-4})$alkyl, $(C_{1-4})$alkoxy, halogen and trifluoromethyl.

xvi) A further embodiment of the invention relates to compounds according to any one of embodiments i) to xiii), wherein
$R^1$ represents a 2,3-dihydro-benzofuranyl-, a 2,3-dihydro-benzo[1,4]dioxinyl-, a 4H-benzo[1,3]dioxinyl-, a 2,3-dihydro-thieno[3,4-b][1,4]dioxinyl- or a chromanyl-group which groups are unsubstituted or independently mono- or di-substituted wherein the substituents are independently selected from the group consisting of $(C_{1-4})$alkyl and halogen.

xvii) A further embodiment of the invention relates to compounds according to any one of embodiments i) to xvi), wherein
A represents a thiazolyl-group, which group is unsubstituted or mono-substituted, wherein the substituent is selected from the group consisting of $(C_{1-4})$alkyl and $-NR^2R^3$.

xviii) A further embodiment of the invention relates to compounds according to any one of embodiments i) to xii) or xiv) or xvii), wherein
$R^1$ represents a pyrrolo[2,1-b]thiazolyl- or a imidazo[2,1-b]thiazolyl-group, which group is unsubstituted or independently mono- or di-substituted wherein the substituents are independently selected from the group consisting of $(C_{1-4})$alkyl, halogen and trifluoromethyl.

xix) A further embodiment of the invention relates to compounds according to any one of embodiments i) or iii) to xi) or xvii), wherein n represents the integer 0.

xx) A further embodiment of the invention relates to compounds according to embodiment xix), wherein
$R^1$ represents a pyrimidyl-group which group is unsubstituted or mono- or di-substituted wherein the substituent is selected from the group consisting of $(C_{1-4})$alkyl, $(C_{1-4})$alkoxy, halogen, trifluoromethyl, cyano, and $-NR^2R^3$.

xxi) A further embodiment of the invention relates to compounds according to embodiments xix) or xx), wherein
$R^1$ represents a pyrimidyl-group which is mono-substituted with halogen.

Preferred compounds of formula (I) according to embodiment i) are selected from the group consisting of:

Benzofuran-4-carboxylic acid[(1S,2S,5R)-3-(biphenyl-2-carbonyl)-3-aza-bicyclo[3.1.0]hex-2-ylmethyl]-amide;

Benzofuran-4-carboxylic acid[(1S,2S,5R)-3-(2-methyl-5-p-tolyl-thiazole-4-carbonyl)-3-aza-bicyclo[3.1.0]hex-2-ylmethyl]-amide;

Benzofuran-4-carboxylic acid{(1S,2S,5R)-3-[5-(4-ethyl-phenyl)-2-methyl-thiazole-4-carbonyl]-3-aza-bicyclo[3.1.0]hex-2-ylmethyl}-amide;

Benzofuran-4-carboxylic acid {(1S,2S,5R)-3-[5-(4-fluoro-phenyl)-2-methyl-thiazole-4-carbonyl]-3-aza-bicyclo[3.1.0]hex-2-ylmethyl}-amide;

Benzofuran-4-carboxylic acid[(1S,2S,5R)-3-(2-methyl-5-m-tolyl-thiazole-4-carbonyl)-3-aza-bicyclo[3.1.0]hex-2-ylmethyl]-amide;

Benzofuran-4-carboxylic acid{(1S,2S,5R)-3-[5-(3-fluoro-phenyl)-2-methyl-thiazole-4-carbonyl]-3-aza-bicyclo[3.1.0]hex-2-ylmethyl}-amide;

6-Methyl-imidazo[2,1-b]thiazole-5-carboxylic acid{(1S,2S,5R)-3-[5-(2-fluoro-phenyl)-2-methyl-thiazole-4-carbonyl]-3-aza-bicyclo[3.1.0]hex-2-ylmethyl}-amide;

6-Methyl-imidazo[2,1-b]thiazole-5-carboxylic acid[(1S,2S,5R)-3-(2-methyl-5-o-tolyl-thiazole-4-carbonyl)-3-aza-bicyclo[3.1.0]hex-2-ylmethyl]-amide;

6-Methyl-imidazo[2,1-b]thiazole-5-carboxylic acid{(1S,2S,5R)-3-[5-(3-fluoro-phenyl)-2-methyl-thiazole-4-carbonyl]-3-aza-bicyclo[3.1.0]hex-2-ylmethyl}-amide;

6-Methyl-imidazo[2,1-b]thiazole-5-carboxylic acid{(1S,2S,5R)-3-[5-(3-chloro-phenyl)-2-methyl-thiazole-4-carbonyl]-3-aza-bicyclo[3.1.0]hex-2-ylmethyl}-amide;

6-Methyl-imidazo[2,1-b]thiazole-5-carboxylic acid{(1S,2S,5R)-3-[5-(4-fluoro-phenyl)-2-methyl-thiazole-4-carbonyl]-3-aza-bicyclo[3.1.0]hex-2-ylmethyl}-amide;

6-Methyl-imidazo[2,1-b]thiazole-5-carboxylic acid{(1S,2S,5R)-3-[5-(4-ethyl-phenyl)-2-methyl-thiazole-4-carbonyl]-3-aza-bicyclo[3.1.0]hex-2-ylmethyl}-amide;

6-Methyl-imidazo[2,1-b]thiazole-5-carboxylic acid[(1S,2S,5R)-3-(2-amino-5-m-tolyl-thiazole-4-carbonyl)-3-aza-bicyclo[3.1.0]hex-2-ylmethyl]-amide;

6-Methyl-imidazo[2,1-b]thiazole-5-carboxylic acid{(1S,2S,5R)-3-[2-amino-5-(3-fluoro-phenyl)-thiazole-4-carbonyl]-3-aza-bicyclo[3.1.0]hex-2-ylmethyl}-amide;

6-Methyl-imidazo[2,1-b]thiazole-5-carboxylic acid[(1S,2S,5R)-3-(biphenyl-2-carbonyl)-3-aza-bicyclo[3.1.0]hex-2-ylmethyl]-amide;

6-Methyl-imidazo[2,1-b]thiazole-5-carboxylic acid[(1S,2S,5R)-3-(2'-fluoro-biphenyl-2-carbonyl)-3-aza-bicyclo[3.1.0]hex-2-ylmethyl]-amide;

6-Methyl-imidazo[2,1-b]thiazole-5-carboxylic acid[(1S,2S,5R)-3-(3'-methyl-biphenyl-2-carbonyl)-3-aza-bicyclo[3.1.0]hex-2-ylmethyl]-amide;

6-Methyl-imidazo[2,1-b]thiazole-5-carboxylic acid[(1S,2S,5R)-3-(3'-chloro-biphenyl-2-carbonyl)-3-aza-bicyclo[3.1.0]hex-2-ylmethyl]-amide;

6-Methyl-imidazo[2,1-b]thiazole-5-carboxylic acid[(1S,2S,5R)-3-(3',4'-dimethyl-biphenyl-2-carbonyl)-3-aza-bicyclo[3.1.0]hex-2-ylmethyl]-amide;

6-Methyl-imidazo[2,1-b]thiazole-5-carboxylic acid[(1S,2S,5R)-3-(2-methyl-4-phenyl-pyrimidine-5-carbonyl)-3-aza-bicyclo[3.1.0]hex-2-ylmethyl]-amide;

6-Methyl-imidazo[2,1-b]thiazole-5-carboxylic acid[(1S,2S,5R)-3-(2-methoxy-5-m-tolyl-thiazole-4-carbonyl)-3-aza-bicyclo[3.1.0]hex-2-ylmethyl]-amide;

6-Methyl-imidazo[2,1-b]thiazole-5-carboxylic acid[(1S,2S,5R)-3-(2-bromo-5-m-tolyl-thiazole-4-carbonyl)-3-aza-bicyclo[3.1.0]hex-2-ylmethyl]-amide;

6-Methyl-imidazo[2,1-b]thiazole-5-carboxylic acid[(1S,2S,5R)-3-(5-m-tolyl-thiazole-4-carbonyl)-3-aza-bicyclo[3.1.0]hex-2-ylmethyl]-amide;

6-Methyl-imidazo[2,1-b]thiazole-5-carboxylic acid[(1S,2S,5R)-3-(2-thiophen-2-yl-benzoyl)-3-aza-bicyclo[3.1.0]hex-2-ylmethyl]-amide;

6-Methyl-imidazo[2,1-b]thiazole-5-carboxylic acid[(1S,2S,5R)-3-(2-phenyl-[1,6]naphthyridine-3-carbonyl)-3-aza-bicyclo[3.1.0]hex-2-ylmethyl]-amide;

6-Methyl-imidazo[2,1-b]thiazole-5-carboxylic acid[(1S,2S,5R)-3-(6-chloro-2-phenyl-imidazo[1,2-a]pyridine-3-carbonyl)-3-aza-bicyclo[3.1.0]hex-2-ylmethyl]-amide;

6-Methyl-imidazo[2,1-b]thiazole-5-carboxylic acid{(1S,2S,5R)-3-[4-(3-fluoro-phenyl)-2-methyl-thiazole-5-carbonyl]-3-aza-bicyclo[3.1.0]hex-2-ylmethyl}-amide;

2,3-Dihydro-benzo[1,4]dioxine-5-carboxylic acid[(1S,2S,5R)-3-(2-methyl-5-m-tolyl-thiazole-4-carbonyl)-3-aza-bicyclo[3.1.0]hex-2-ylmethyl]-amide;

2,3-Dihydro-benzofuran-4-carboxylic acid[(1S,2S,5R)-3-(2-methyl-5-m-tolyl-thiazole-4-carbonyl)-3-aza-bicyclo[3.1.0]hex-2-ylmethyl]-amide;

2,3-Dihydro-benzofuran-7-carboxylic acid[(1S,2S,5R)-3-(2-methyl-5-m-tolyl-thiazole-4-carbonyl)-3-aza-bicyclo[3.1.0]hex-2-ylmethyl]-amide;

6-Fluoro-4H-benzo[1,3]dioxine-8-carboxylic acid[(1S,2S,5R)-3-(2-methyl-5-m-tolyl-thiazole-4-carbonyl)-3-aza-bicyclo[3.1.0]hex-2-ylmethyl]-amide;

2,2-Dimethyl-2,3-dihydro-benzofuran-7-carboxylic acid [(1S,2S,5R)-3-(2-methyl-5-m-tolyl-thiazole-4-carbonyl)-3-aza-bicyclo[3.1.0]hex-2-ylmethyl]-amide;

3-Bromo-N-[(1S,2S,5R)-3-(2-methyl-5-m-tolyl-thiazole-4-carbonyl)-3-aza-bicyclo[3.1.0]hex-2-ylmethyl]-benzamide;

N-[(1S,2S,5R)-3-(2-Methyl-5-m-tolyl-thiazole-4-carbonyl)-3-aza-bicyclo[3.1.0]hex-2-ylmethyl]-3-trifluoromethyl-benzamide;

3-Chloro-N-[(1S,2S,5R)-3-(2-methyl-5-m-tolyl-thiazole-4-carbonyl)-3-aza-bicyclo[3.1.0]hex-2-ylmethyl]-benzamide;

3,5-Dimethoxy-N-[(1S,2S,5R)-3-(2-methyl-5-m-tolyl-thiazole-4-carbonyl)-3-aza-bicyclo[3.1.0]hex-2-ylmethyl]-benzamide;

2,5-Dimethyl-2H-pyrazole-3-carboxylic acid[(1S,2S,5R)-3-(2-methyl-5-m-tolyl-thiazole-4-carbonyl)-3-aza-bicyclo[3.1.0]hex-2-ylmethyl]-amide;

1,3-Dimethyl-1H-pyrazole-4-carboxylic acid[(1S,2S,5R)-3-(2-methyl-5-m-tolyl-thiazole-4-carbonyl)-3-aza-bicyclo[3.1.0]hex-2-ylmethyl]-amide;

2-Ethyl-5-methyl-2H-pyrazole-3-carboxylic acid[(1S,2S,5R)-3-(2-methyl-5-m-tolyl-thiazole-4-carbonyl)-3-aza-bicyclo[3.1.0]hex-2-ylmethyl]-amide;

3,5-Dimethyl-isoxazole-4-carboxylic acid[(1S,2S,5R)-3-(2-methyl-5-m-tolyl-thiazole-4-carbonyl)-3-aza-bicyclo[3.1.0]hex-2-ylmethyl]-amide;

Quinoline-8-carboxylic acid[(1S,2S,5R)-3-(2-methyl-5-m-tolyl-thiazole-4-carbonyl)-3-aza-bicyclo[3.1.0]hex-2-ylmethyl]-amide;

Isoquinoline-1-carboxylic acid[(1S,2S,5R)-3-(2-methyl-5-m-tolyl-thiazole-4-carbonyl)-3-aza-bicyclo[3.1.0]hex-2-ylmethyl]-amide;

Quinoline-2-carboxylic acid[(1S,2S,5R)-3-(2-methyl-5-m-tolyl-thiazole-4-carbonyl)-3-aza-bicyclo[3.1.0]hex-2-ylmethyl]-amide;

1H-Indole-3-carboxylic acid[(1S,2S,5R)-3-(2-methyl-5-m-tolyl-thiazole-4-carbonyl)-3-aza-bicyclo[3.1.0]hex-2-ylmethyl]-amide;

1-Methyl-1H-indole-3-carboxylic acid[(1S,2S,5R)-3-(2-methyl-5-m-tolyl-thiazole-4-carbonyl)-3-aza-bicyclo[3.1.0]hex-2-ylmethyl]-amide;
1H-Indazole-3-carboxylic acid[(1S,2S,5R)-3-(2-methyl-5-m-tolyl-thiazole-4-carbonyl)-3-aza-bicyclo[3.1.0]hex-2-ylmethyl]-amide;
1-Methyl-1H-indazole-3-carboxylic acid[(1S,2S,5R)-3-(2-methyl-5-m-tolyl-thiazole-4-carbonyl)-3-aza-bicyclo[3.1.0]hex-2-ylmethyl]-amide;
1,2-Dimethyl-1H-indole-3-carboxylic acid[(1S,2S,5R)-3-(2-methyl-5-m-tolyl-thiazole-4-carbonyl)-3-aza-bicyclo[3.1.0]hex-2-ylmethyl]-amide;
Benzo[d]isoxazole-3-carboxylic acid[(1S,2S,5R)-3-(2-methyl-5-m-tolyl-thiazole-4-carbonyl)-3-aza-bicyclo[3.1.0]hex-2-ylmethyl]-amide;
Imidazo[1,2-a]pyridine-3-carboxylic acid[(1S,2S,5R)-3-(2-methyl-5-m-tolyl-thiazole-4-carbonyl)-3-aza-bicyclo[3.1.0]hex-2-ylmethyl]-amide;
Pyrazolo[1,5-a]pyridine-3-carboxylic acid[(1S,2S,5R)-3-(2-methyl-5-m-tolyl-thiazole-4-carbonyl)-3-aza-bicyclo[3.1.0]hex-2-ylmethyl]-amide;
2,3-Dihydro-thieno[3,4-b][1,4]dioxine-5-carboxylic acid [(1S,2S,5R)-3-(2-methyl-5-m-tolyl-thiazole-4-carbonyl)-3-aza-bicyclo[3.1.0]hex-2-ylmethyl]-amide;
5-Fluoro-1-methyl-1H-indole-2-carboxylic acid[(1S,2S,5R)-3-(2-methyl-5-m-tolyl-thiazole-4-carbonyl)-3-aza-bicyclo[3.1.0]hex-2-ylmethyl]-amide;
Imidazo[2,1-b]thiazole-5-carboxylic acid[(1S,2S,5R)-3-(2-methyl-5-m-tolyl-thiazole-4-carbonyl)-3-aza-bicyclo[3.1.0]hex-2-ylmethyl]-amide;
3-Methyl-imidazo[2,1-b]thiazole-2-carboxylic acid[(1S,2S,5R)-3-(2-methyl-5-m-tolyl-thiazole-4-carbonyl)-3-aza-bicyclo[3.1.0]hex-2-ylmethyl]-amide;
Imidazo[2,1-b]thiazole-6-carboxylic acid[(1S,2S,5R)-3-(2-methyl-5-m-tolyl-thiazole-4-carbonyl)-3-aza-bicyclo[3.1.0]hex-2-ylmethyl]-amide;
2,3-Dihydro-benzo[1,4]dioxine-5-carboxylic acid{(1S,2S,5R)-3-[5-(3-chloro-phenyl)-2-methyl-thiazole-4-carbonyl]-3-aza-bicyclo[3.1.0]hex-2-ylmethyl}-amide;
2,3-Dihydro-benzofuran-4-carboxylic acid{(1S,2S,5R)-3-[5-(3-chloro-phenyl)-2-methyl-thiazole-4-carbonyl]-3-aza-bicyclo[3.1.0]hex-2-ylmethyl}-amide;
2,3-Dihydro-benzofuran-7-carboxylic acid{(1S,2S,5R)-3-[5-(3-chloro-phenyl)-2-methyl-thiazole-4-carbonyl]-3-aza-bicyclo[3.1.0]hex-2-ylmethyl}-amide;
6-Fluoro-4H-benzo[1,3]dioxine-8-carboxylic acid{(1S,2S,5R)-3-[5-(3-chloro-phenyl)-2-methyl-thiazole-4-carbonyl]-3-aza-bicyclo[3.1.0]hex-2-ylmethyl}-amide;
2,2-Dimethyl-2,3-dihydro-benzofuran-7-carboxylic acid{(1S,2S,5R)-3-[5-(3-chloro-phenyl)-2-methyl-thiazole-4-carbonyl]-3-aza-bicyclo[3.1.0]hex-2-ylmethyl}-amide;
3-Bromo-N-{(1S,2S,5R)-3-[5-(3-chloro-phenyl)-2-methyl-thiazole-4-carbonyl]-3-aza-bicyclo[3.1.0]hex-2-ylmethyl}-benzamide;
N-{(1S,2S,5R)-3-[5-(3-Chloro-phenyl)-2-methyl-thiazole-4-carbonyl]-3-aza-bicyclo[3.1.0]hex-2-ylmethyl}-3-trifluoromethyl-benzamide;
3-Chloro-N-{(1S,2S,5R)-3-[5-(3-chloro-phenyl)-2-methyl-thiazole-4-carbonyl]-3-aza-bicyclo[3.1.0]hex-2-ylmethyl}-benzamide;
N-{(1S,2S,5R)-3-[5-(3-Chloro-phenyl)-2-methyl-thiazole-4-carbonyl]-3-aza-bicyclo[3.1.0]hex-2-ylmethyl}-3,5-dimethoxy-benzamide;
2,5-Dimethyl-2H-pyrazole-3-carboxylic acid{(1S,2S,5R)-3-[5-(3-chloro-phenyl)-2-methyl-thiazole-4-carbonyl]-3-aza-bicyclo[3.1.0]hex-2-ylmethyl}-amide;
1,3-Dimethyl-1H-pyrazole-4-carboxylic acid{(1S,2S,5R)-3-[5-(3-chloro-phenyl)-2-methyl-thiazole-4-carbonyl]-3-aza-bicyclo[3.1.0]hex-2-ylmethyl}-amide;
2-Ethyl-5-methyl-2H-pyrazole-3-carboxylic acid{(1S,2S,5R)-3-[5-(3-chloro-phenyl)-2-methyl-thiazole-4-carbonyl]-3-aza-bicyclo[3.1.0]hex-2-ylmethyl}-amide;
3,5-Dimethyl-isoxazole-4-carboxylic acid{(1S,2S,5R)-3-[5-(3-chloro-phenyl)-2-methyl-thiazole-4-carbonyl]-3-aza-bicyclo[3.1.0]hex-2-ylmethyl}-amide;
Quinoline-8-carboxylic acid{(1S,2S,5R)-3-[5-(3-chloro-phenyl)-2-methyl-thiazole-4-carbonyl]-3-aza-bicyclo[3.1.0]hex-2-ylmethyl}-amide;
Isoquinoline-1-carboxylic acid{(1S,2S,5R)-3-[5-(3-chloro-phenyl)-2-methyl-thiazole-4-carbonyl]-3-aza-bicyclo[3.1.0]hex-2-ylmethyl}-amide;
Quinoline-2-carboxylic acid{(1S,2S,5R)-3-[5-(3-chloro-phenyl)-2-methyl-thiazole-4-carbonyl]-3-aza-bicyclo[3.1.0]hex-2-ylmethyl}-amide;
1H-Indole-3-carboxylic acid{(1S,2S,5R)-3-[5-(3-chloro-phenyl)-2-methyl-thiazole-4-carbonyl]-3-aza-bicyclo[3.1.0]hex-2-ylmethyl}-amide;
1-Methyl-1H-indole-3-carboxylic acid{(1S,2S,5R)-3-[5-(3-chloro-phenyl)-2-methyl-thiazole-4-carbonyl]-3-aza-bicyclo[3.1.0]hex-2-ylmethyl}-amide;
1H-Indazole-3-carboxylic acid{(1S,2S,5R)-3-[5-(3-chloro-phenyl)-2-methyl-thiazole-4-carbonyl]-3-aza-bicyclo[3.1.0]hex-2-ylmethyl}-amide;
1-Methyl-1H-indazole-3-carboxylic acid{(1S,2S,5R)-3-[5-(3-chloro-phenyl)-2-methyl-thiazole-4-carbonyl]-3-aza-bicyclo[3.1.0]hex-2-ylmethyl}-amide;
1,2-Dimethyl-1H-indole-3-carboxylic acid{(1S,2S,5R)-3-[5-(3-chloro-phenyl)-2-methyl-thiazole-4-carbonyl]-3-aza-bicyclo[3.1.0]hex-2-ylmethyl}-amide;
Imidazo[1,2-a]pyridine-3-carboxylic acid{(1S,2S,5R)-3-[5-(3-chloro-phenyl)-2-methyl-thiazole-4-carbonyl]-3-aza-bicyclo[3.1.0]hex-2-ylmethyl}-amide;
Pyrazolo[1,5-a]pyridine-3-carboxylic acid{(1S,2S,5R)-3-[5-(3-chloro-phenyl)-2-methyl-thiazole-4-carbonyl]-3-aza-bicyclo[3.1.0]hex-2-ylmethyl}-amide;
2,3-Dihydro-thieno[3,4-b][1,4]dioxine-5-carboxylic acid{(1S,2S,5R)-3-[5-(3-chloro-phenyl)-2-methyl-thiazole-4-carbonyl]-3-aza-bicyclo[3.1.0]hex-2-ylmethyl}-amide;
5-Fluoro-1-methyl-1H-indole-2-carboxylic acid{(1S,2S,5R)-3-[5-(3-chloro-phenyl)-2-methyl-thiazole-4-carbonyl]-3-aza-bicyclo[3.1.0]hex-2-ylmethyl}-amide;
Imidazo[2,1-b]thiazole-5-carboxylic acid{(1S,2S,5R)-3-[5-(3-chloro-phenyl)-2-methyl-thiazole-4-carbonyl]-3-aza-bicyclo[3.1.0]hex-2-ylmethyl}-amide;
3-Methyl-imidazo[2,1-b]thiazole-2-carboxylic acid{(1S,2S,5R)-3-[5-(3-chloro-phenyl)-2-methyl-thiazole-4-carbonyl]-3-aza-bicyclo[3.1.0]hex-2-ylmethyl}-amide;
2,3-Dihydro-benzo[1,4]dioxine-5-carboxylic acid{(1S,2S,5R)-3-[2-amino-5-(3-fluoro-phenyl)-thiazole-4-carbonyl]-3-aza-bicyclo[3.1.0]hex-2-ylmethyl}-amide;
2,3-Dihydro-benzofuran-4-carboxylic acid{(1S,2S,5R)-3-[2-amino-5-(3-fluoro-phenyl)-thiazole-4-carbonyl]-3-aza-bicyclo[3.1.0]hex-2-ylmethyl}-amide;
2,3-Dihydro-benzofuran-7-carboxylic acid{(1S,2S,5R)-3-[2-amino-5-(3-fluoro-phenyl)-thiazole-4-carbonyl]-3-aza-bicyclo[3.1.0]hex-2-ylmethyl}-amide;
6-Fluoro-4H-benzo[1,3]dioxine-8-carboxylic acid{(1S,2S,5R)-3-[2-amino-5-(3-fluoro-phenyl)-thiazole-4-carbonyl]-3-aza-bicyclo[3.1.0]hex-2-ylmethyl}-amide;
2,2-Dimethyl-2,3-dihydro-benzofuran-7-carboxylic acid{(1S,2S,5R)-3-[2-amino-5-(3-fluoro-phenyl)-thiazole-4-carbonyl]-3-aza-bicyclo[3.1.0]hex-2-ylmethyl}-amide;

N-{(1S,2S,5R)-3-[2-Amino-5-(3-fluoro-phenyl)-thiazole-4-carbonyl]-3-aza-bicyclo[3.1.0]hex-2-ylmethyl}-3-trifluoromethyl-benzamide;

N-{(1S,2S,5R)-3-[2-Amino-5-(3-fluoro-phenyl)-thiazole-4-carbonyl]-3-aza-bicyclo[3.1.0]hex-2-ylmethyl}-3-chloro-benzamide;

N-{(1S,2S,5R)-3-[2-Amino-5-(3-fluoro-phenyl)-thiazole-4-carbonyl]-3-aza-bicyclo[3.1.0]hex-2-ylmethyl}-3,5-dimethoxy-benzamide;

2,5-Dimethyl-2H-pyrazole-3-carboxylic acid{(1S,2S,5R)-3-[2-amino-5-(3-fluoro-phenyl)-thiazole-4-carbonyl]-3-aza-bicyclo[3.1.0]hex-2-ylmethyl}-amide;

2-Ethyl-5-methyl-2H-pyrazole-3-carboxylic acid{(1S,2S,5R)-3-[2-amino-5-(3-fluoro-phenyl)-thiazole-4-carbonyl]-3-aza-bicyclo[3.1.0]hex-2-ylmethyl}-amide;

3,5-Dimethyl-isoxazole-4-carboxylic acid{(1S,2S,5R)-3-[2-amino-5-(3-fluoro-phenyl)-thiazole-4-carbonyl]-3-aza-bicyclo[3.1.0]hex-2-ylmethyl}-amide;

Quinoline-8-carboxylic acid{(1S,2S,5R)-3-[2-amino-5-(3-fluoro-phenyl)-thiazole-4-carbonyl]-3-aza-bicyclo[3.1.0]hex-2-ylmethyl}-amide;

Isoquinoline-1-carboxylic acid{(1S,2S,5R)-3-[2-amino-5-(3-fluoro-phenyl)-thiazole-4-carbonyl]-3-aza-bicyclo[3.1.0]hex-2-ylmethyl}-amide;

1-Methyl-1H-indole-3-carboxylic acid{(1S,2S,5R)-3-[2-amino-5-(3-fluoro-phenyl)-thiazole-4-carbonyl]-3-aza-bicyclo[3.1.0]hex-2-ylmethyl}-amide;

1H-Indazole-3-carboxylic acid{(1S,2S,5R)-3-[2-amino-5-(3-fluoro-phenyl)-thiazole-4-carbonyl]-3-aza-bicyclo[3.1.0]hex-2-ylmethyl}-amide;

1-Methyl-1H-indazole-3-carboxylic acid{(1S,2S,5R)-3-[2-amino-5-(3-fluoro-phenyl)-thiazole-4-carbonyl]-3-aza-bicyclo[3.1.0]hex-2-ylmethyl}-amide;

Imidazo[1,2-a]pyridine-3-carboxylic acid{(1S,2S,5R)-3-[2-amino-5-(3-fluoro-phenyl)-thiazole-4-carbonyl]-3-aza-bicyclo[3.1.0]hex-2-ylmethyl}-amide;

2,3-Dihydro-thieno[3,4-b][1,4]dioxine-5-carboxylic acid{(1S,2S,5R)-3-[2-amino-5-(3-fluoro-phenyl)-thiazole-4-carbonyl]-3-aza-bicyclo[3.1.0]hex-2-ylmethyl}-amide;

5-Fluoro-1-methyl-1H-indole-2-carboxylic acid{(1S,2S,5R)-3-[2-amino-5-(3-fluoro-phenyl)-thiazole-4-carbonyl]-3-aza-bicyclo[3.1.0]hex-2-ylmethyl}-amide;

Imidazo[2,1-b]thiazole-5-carboxylic acid{(1S,2S,5R)-3-[2-amino-5-(3-fluoro-phenyl)-thiazole-4-carbonyl]-3-aza-bicyclo[3.1.0]hex-2-ylmethyl}-amide;

3-Methyl-imidazo[2,1-b]thiazole-2-carboxylic acid{(1S,2S,5R)-3-[2-amino-5-(3-fluoro-phenyl)-thiazole-4-carbonyl]-3-aza-bicyclo[3.1.0]hex-2-ylmethyl}-amide;

1,2-Dimethyl-1H-indole-3-carboxylic acid{(1S,2S,5R)-3-[2-amino-5-(3-fluoro-phenyl)-thiazole-4-carbonyl]-3-aza-bicyclo[3.1.0]hex-2-ylmethyl}-amide;

2-Methoxy-N-[(1S,2S,5R)-3-(2-methyl-5-m-tolyl-thiazole-4-carbonyl)-3-aza-bicyclo[3.1.0]hex-2-ylmethyl]-benzamide;

4-Chloro-2-methoxy-N-[(1S,2S,5R)-3-(2-methyl-5-m-tolyl-thiazole-4-carbonyl)-3-aza-bicyclo[3.1.0]hex-2-ylmethyl]-benzamide;

3,4-Dichloro-N-[(1S,2S,5R)-3-(2-methyl-5-m-tolyl-thiazole-4-carbonyl)-3-aza-bicyclo[3.1.0]hex-2-ylmethyl]-benzamide;

2-Chloro-4,5-difluoro-N-[(1S,2S,5R)-3-(2-methyl-5-m-tolyl-thiazole-4-carbonyl)-3-aza-bicyclo[3.1.0]hex-2-ylmethyl]-benzamide;

3-Fluoro-2-methyl-N-[(1S,2S,5R)-3-(2-methyl-5-m-tolyl-thiazole-4-carbonyl)-3-aza-bicyclo[3.1.0]hex-2-ylmethyl]-benzamide;

5-Fluoro-2-methoxy-N-[(1S,2S,5R)-3-(2-methyl-5-m-tolyl-thiazole-4-carbonyl)-3-aza-bicyclo[3.1.0]hex-2-ylmethyl]-benzamide;

2,5-Dimethyl-N-[(1S,2S,5R)-3-(2-methyl-5-m-tolyl-thiazole-4-carbonyl)-3-aza-bicyclo[3.1.0]hex-2-ylmethyl]-benzamide;

2-Chloro-4-fluoro-N-[(1S,2S,5R)-3-(2-methyl-5-m-tolyl-thiazole-4-carbonyl)-3-aza-bicyclo[3.1.0]hex-2-ylmethyl]-benzamide;

3,5-Dimethyl-N-[(1S,2S,5R)-3-(2-methyl-5-m-tolyl-thiazole-4-carbonyl)-3-aza-bicyclo[3.1.0]hex-2-ylmethyl]-benzamide;

3-Cyano-N-[(1S,2S,5R)-3-(2-methyl-5-m-tolyl-thiazole-4-carbonyl)-3-aza-bicyclo[3.1.0]hex-2-ylmethyl]-benzamide;

N-[(1S,2S,5R)-3-(2-Methyl-5-m-tolyl-thiazole-4-carbonyl)-3-aza-bicyclo[3.1.0]hex-2-ylmethyl]-2-morpholin-4-yl-benzamide;

4-Chloro-N-[(1S,2S,5R)-3-(2-methyl-5-m-tolyl-thiazole-4-carbonyl)-3-aza-bicyclo[3.1.0]hex-2-ylmethyl]-benzamide;

2,3-Dimethoxy-N-[(1S,2S,5R)-3-(2-methyl-5-m-tolyl-thiazole-4-carbonyl)-3-aza-bicyclo[3.1.0]hex-2-ylmethyl]-benzamide;

2-Methyl-imidazo[2,1-b]thiazole-5-carboxylic acid[(1S,2S,5R)-3-(2-methyl-5-m-tolyl-thiazole-4-carbonyl)-3-aza-bicyclo[3.1.0]hex-2-ylmethyl]-amide;

6-Trifluoromethyl-imidazo[2,1-b]thiazole-5-carboxylic acid [(1S,2S,5R)-3-(2-methyl-5-m-tolyl-thiazole-4-carbonyl)-3-aza-bicyclo[3.1.0]hex-2-ylmethyl]-amide;

3,6-Dimethyl-imidazo[2,1-b]thiazole-5-carboxylic acid[(1S,2S,5R)-3-(2-methyl-5-m-tolyl-thiazole-4-carbonyl)-3-aza-bicyclo[3.1.0]hex-2-ylmethyl]-amide;

3-Methyl-imidazo[2,1-b]thiazole-5-carboxylic acid[(1S,2S,5R)-3-(2-methyl-5-m-tolyl-thiazole-4-carbonyl)-3-aza-bicyclo[3.1.0]hex-2-ylmethyl]-amide;

6-Chloro-imidazo[2,1-b]thiazole-5-carboxylic acid[(1S,2S,5R)-3-(2-methyl-5-m-tolyl-thiazole-4-carbonyl)-3-aza-bicyclo[3.1.0]hex-2-ylmethyl]-amide;

3-Oxo-3,4-dihydro-2H-benzo[1,4]oxazine-8-carboxylic acid[(1S,2S,5R)-3-(2-methyl-5-m-tolyl-thiazole-4-carbonyl)-3-aza-bicyclo[3.1.0]hex-2-ylmethyl]-amide;

2H-Chromene-5-carboxylic acid[(1S,2S,5R)-3-(2-methyl-5-m-tolyl-thiazole-4-carbonyl)-3-aza-bicyclo[3.1.0]hex-2-ylmethyl]-amide;

4-Methyl-3,4-dihydro-2H-benzo[1,4]oxazine-8-carboxylic acid[(1S,2S,5R)-3-(2-methyl-5-m-tolyl-thiazole-4-carbonyl)-3-aza-bicyclo[3.1.0]hex-2-ylmethyl]-amide;

Chroman-8-carboxylic acid[(1S,2S,5R)-3-(2-methyl-5-m-tolyl-thiazole-4-carbonyl)-3-aza-bicyclo[3.1.0]hex-2-ylmethyl]-amide;

3,4-Dihydro-2H-benzo[1,4]oxazine-5-carboxylic acid[(1S,2S,5R)-3-(2-methyl-5-m-tolyl-thiazole-4-carbonyl)-3-aza-bicyclo[3.1.0]hex-2-ylmethyl]-amide;

4-Methyl-3-oxo-3,4-dihydro-2H-benzo[1,4]oxazine-8-carboxylic acid[(1S,2S,5R)-3-(2-methyl-5-m-tolyl-thiazole-4-carbonyl)-3-aza-bicyclo[3.1.0]hex-2-ylmethyl]-amide; and 4-Methyl-3,4-dihydro-2H-benzo[1,4]oxazine-5-carboxylic acid[(1S,2S,5R)-3-(2-methyl-5-m-tolyl-thiazole-4-carbonyl)-3-aza-bicyclo[3.1.0]hex-2-ylmethyl]-amide.

In addition to the above-listed compounds, further preferred compounds of formula (I) according to embodiment i) are selected from the group consisting of:

Imidazo[1,2-a]pyridine-3-carboxylic acid{(1S,2S,5R)-3-[5-(2,3-dichloro-phenyl)-2-methyl-thiazole-4-carbonyl]-3-aza-bicyclo[3.1.0]hex-2-ylmethyl}-amide;

2,3-Dihydro-benzofuran-4-carboxylic acid{(1S,2S,5R)-3-[5-(3,4-dichloro-phenyl)-2-methyl-thiazole-4-carbonyl]-3-aza-bicyclo[3.1.0]hex-2-ylmethyl}-amide;
2,3-Dihydro-benzofuran-4-carboxylic acid{(1S,2S,5R)-3-[5-(3,4-dimethyl-phenyl)-2-methyl-thiazole-4-carbonyl]-3-aza-bicyclo[3.1.0]hex-2-ylmethyl}-amide;
2,3-Dihydro-benzofuran-4-carboxylic acid[(1S,2S,5R)-3-(2-methyl-5-phenyl-thiazole-4-carbonyl)-3-aza-bicyclo[3.1.0]hex-2-ylmethyl]-amide;
2,3-Dihydro-benzofuran-4-carboxylic acid[(1S,2S,5R)-3-(2-cyclopropyl-5-phenyl-thiazole-4-carbonyl)-3-aza-bicyclo[3.1.0]hex-2-ylmethyl]-amide;
2,3-Dihydro-benzofuran-4-carboxylic acid[(1S,2S,5R)-3-(2-dimethylamino-5-phenyl-thiazole-4-carbonyl)-3-aza-bicyclo[3.1.0]hex-2-ylmethyl]-amide;
2,3-Dihydro-benzofuran-4-carboxylic acid{(1S,2S,5R)-3-[2-dimethylamino-5-(3-fluoro-phenyl)-thiazole-4-carbonyl]-3-aza-bicyclo[3.1.0]hex-2-ylmethyl}-amide;
2,3-Dihydro-thieno[3,4-b][1,4]dioxine-5-carboxylic acid{(1S,2S,5R)-3-[2-dimethylamino-5-(3-fluoro-phenyl)-thiazole-4-carbonyl]-3-aza-bicyclo[3.1.0]hex-2-ylmethyl}-amide;
6-Methyl-imidazo[2,1-b]thiazole-5-carboxylic acid[(1S,2S,5R)-3-(3-m-tolyl-thiophene-2-carbonyl)-3-aza-bicyclo[3.1.0]hex-2-ylmethyl]-amide;
6-Methyl-imidazo[2,1-b]thiazole-5-carboxylic acid[(1S,2S,5R)-3-(3-p-tolyl-thiophene-2-carbonyl)-3-aza-bicyclo[3.1.0]hex-2-ylmethyl]-amide;
6-Methyl-imidazo[2,1-b]thiazole-5-carboxylic acid[(1S,2S,5R)-3-(2-m-tolyl-thiophene-3-carbonyl)-3-aza-bicyclo[3.1.0]hex-2-ylmethyl]-amide;
6-Methyl-imidazo[2,1-b]thiazole-5-carboxylic acid[(1S,2S,5R)-3-(2-p-tolyl-thiophene-3-carbonyl)-3-aza-bicyclo[3.1.0]hex-2-ylmethyl]-amide;
6-Methyl-imidazo[2,1-b]thiazole-5-carboxylic acid{(1S,2S,5R)-3-[2-(4-fluoro-phenyl)-thiophene-3-carbonyl]-3-aza-bicyclo[3.1.0]hex-2-ylmethyl}-amide;
2-Ethyl-5-methyl-2H-pyrazole-3-carboxylic acid[(1S,2S,5R)-3-(4'-fluoro-biphenyl-2-carbonyl)-3-aza-bicyclo[3.1.0]hex-2-ylmethyl]-amide;
2-Ethyl-5-methyl-2H-pyrazole-3-carboxylic acid[(1S,2S,5R)-3-(3'-fluoro-biphenyl-2-carbonyl)-3-aza-bicyclo[3.1.0]hex-2-ylmethyl]-amide;
2-Ethyl-5-methyl-2H-pyrazole-3-carboxylic acid[(1S,2S,5R)-3-(4'-methyl-biphenyl-2-carbonyl)-3-aza-bicyclo[3.1.0]hex-2-ylmethyl]-amide;
2-Ethyl-5-methyl-2H-pyrazole-3-carboxylic acid[(1S,2S,5R)-3-(3'-methyl-biphenyl-2-carbonyl)-3-aza-bicyclo[3.1.0]hex-2-ylmethyl]-amide;
2-Ethyl-5-methyl-2H-pyrazole-3-carboxylic acid{(1S,2S,5R)-3-[5-(4-fluoro-phenyl)-2-methyl-thiazole-4-carbonyl]-3-aza-bicyclo[3.1.0]hex-2-ylmethyl}-amide;
2-Ethyl-5-methyl-2H-pyrazole-3-carboxylic acid[(1S,2S,5R)-3-(2-methyl-5-p-tolyl-thiazole-4-carbonyl)-3-aza-bicyclo[3.1.0]hex-2-ylmethyl]-amide;
2-Ethyl-5-methyl-2H-pyrazole-3-carboxylic acid{(1S,2S,5R)-3-[5-(3-bromo-4-fluoro-phenyl)-2-methyl-thiazole-4-carbonyl]-3-aza-bicyclo[3.1.0]hex-2-ylmethyl}-amide;
2-Ethyl-5-methyl-2H-pyrazole-3-carboxylic acid[(1S,2S,5R)-3-(5-m-tolyl-thiazole-4-carbonyl)-3-aza-bicyclo[3.1.0]hex-2-ylmethyl]-amide;
2-Ethyl-5-methyl-2H-pyrazole-3-carboxylic acid[(1S,2S,5R)-3-(2-dimethylamino-5-m-tolyl-thiazole-4-carbonyl)-3-aza-bicyclo[3.1.0]hex-2-ylmethyl]-amide;
2-Ethyl-5-methyl-2H-pyrazole-3-carboxylic acid[(1S,2S,5R)-3-(2-amino-5-m-tolyl-thiazole-4-carbonyl)-3-aza-bicyclo[3.1.0]hex-2-ylmethyl]-amide;
2-Ethyl-5-methyl-2H-pyrazole-3-carboxylic acid[(1S,2S,5R)-3-(2-cyclopropyl-5-m-tolyl-thiazole-4-carbonyl)-3-aza-bicyclo[3.1.0]hex-2-ylmethyl]-amide;
2-Ethyl-5-methyl-2H-pyrazole-3-carboxylic acid{(1S,2S,5R)-3-[5-(3,4-dimethyl-phenyl)-2-methyl-thiazole-4-carbonyl]-3-aza-bicyclo[3.1.0]hex-2-ylmethyl}-amide;
2-Ethyl-5-methyl-2H-pyrazole-3-carboxylic acid[(1S,2S,5R)-3-(2-methyl-5-o-tolyl-thiazole-4-carbonyl)-3-aza-bicyclo[3.1.0]hex-2-ylmethyl]-amide;
2-Ethyl-5-methyl-2H-pyrazole-3-carboxylic acid{(1S,2S,5R)-3-[5-(3,5-dimethyl-phenyl)-2-methyl-thiazole-4-carbonyl]-3-aza-bicyclo[3.1.0]hex-2-ylmethyl}-amide;
{(1S,2S,5R)-2-[(5-Bromo-pyrimidin-2-ylamino)-methyl]-3-aza-bicyclo[3.1.0]hex-3-yl}-[5-(3-chloro-phenyl)-2-methyl-thiazol-4-yl]-methanone;
{(1S,2S,5R)-2-[(5-Bromo-pyrimidin-2-ylamino)-methyl]-3-aza-bicyclo[3.1.0]hex-3-yl}-(2-methyl-5-m-tolyl-thiazol-4-yl)-methanone;
{(1S,2S,5R)-2-[(5-Bromo-pyrimidin-2-ylamino)-methyl]-3-aza-bicyclo[3.1.0]hex-3-yl}-[5-(3-fluoro-4-methyl-phenyl)-2-methyl-thiazol-4-yl]-methanone;
Benzoxazole-7-carboxylic acid[(1S,2S,5R)-3-(2-methyl-5-m-tolyl-thiazole-4-carbonyl)-3-aza-bicyclo[3.1.0]hex-2-ylmethyl]-amide;
2-Methyl-benzoxazole-7-carboxylic acid[(1S,2S,5R)-3-(2-methyl-5-m-tolyl-thiazole-4-carbonyl)-3-aza-bicyclo[3.1.0]hex-2-ylmethyl]-amide;
Benzothiazole-7-carboxylic acid[(1S,2S,5R)-3-(2-methyl-5-m-tolyl-thiazole-4-carbonyl)-3-aza-bicyclo[3.1.0]hex-2-ylmethyl]-amide;
7-Chloro-benzofuran-4-carboxylic acid[(1S,2S,5R)-3-(2-methyl-5-m-tolyl-thiazole-4-carbonyl)-3-aza-bicyclo[3.1.0]hex-2-ylmethyl]-amide;
7-Fluoro-benzofuran-4-carboxylic acid[(1S,2S,5R)-3-(2-methyl-5-m-tolyl-thiazole-4-carbonyl)-3-aza-bicyclo[3.1.0]hex-2-ylmethyl]-amide;
Pyrrolo[2,1-b]thiazole-7-carboxylic acid[(1S,2S,5R)-3-(2-methyl-5-m-tolyl-thiazole-4-carbonyl)-3-aza-bicyclo[3.1.0]hex-2-ylmethyl]-amide;
6-Methyl-pyrrolo[2,1-b]thiazole-7-carboxylic acid[(1S,2S,5R)-3-(2-methyl-5-m-tolyl-thiazole-4-carbonyl)-3-aza-bicyclo[3.1.0]hex-2-ylmethyl]-amide;
7-Chloro-2-methoxy-2,3-dihydro-benzofuran-4-carboxylic acid[(1S,2S,5R)-3-(2-methyl-5-m-tolyl-thiazole-4-carbonyl)-3-aza-bicyclo[3.1.0]hex-2-ylmethyl]-amide;
1-Methyl-1H-indole-3-carboxylic acid[(1S,2S,5R)-3-(2-p-tolyl-thiophene-3-carbonyl)-3-aza-bicyclo[3.1.0]hex-2-ylmethyl]-amide;
Quinoline-8-carboxylic acid[(1S,2S,5R)-3-(2-p-tolyl-thiophene-3-carbonyl)-3-aza-bicyclo[3.1.0]hex-2-ylmethyl]-amide;
4-Methyl-4H-furo[3,2-b]pyrrole-5-carboxylic acid[(1S,2S,5R)-3-(2-p-tolyl-thiophene-3-carbonyl)-3-aza-bicyclo[3.1.0]hex-2-ylmethyl]-amide;
3,4-Dihydro-2H-benzo[1,4]oxazine-5-carboxylic acid[(1S,2S,5R)-3-(2-p-tolyl-thiophene-3-carbonyl)-3-aza-bicyclo[3.1.0]hex-2-ylmethyl]-amide;
2,3-Dihydro-thieno[3,4-b][1,4]dioxine-5-carboxylic acid[(1S,2S,5R)-3-(2-p-tolyl-thiophene-3-carbonyl)-3-aza-bicyclo[3.1.0]hex-2-ylmethyl]-amide;
2-Ethyl-5-methyl-2H-pyrazole-3-carboxylic acid[(1S,2S,5R)-3-(2-p-tolyl-thiophene-3-carbonyl)-3-aza-bicyclo[3.1.0]hex-2-ylmethyl]-amide;
2,5-Dimethyl-2H-pyrazole-3-carboxylic acid[(1S,2S,5R)-3-(2-p-tolyl-thiophene-3-carbonyl)-3-aza-bicyclo[3.1.0]hex-2-ylmethyl]-amide;

3-Bromo-N-[(1S,2S,5R)-3-(2-p-tolyl-thiophene-3-carbonyl)-3-aza-bicyclo[3.1.0]hex-2-ylmethyl]-benzamide;
3-Chloro-N-[(1S,2S,5R)-3-(2-p-tolyl-thiophene-3-carbonyl)-3-aza-bicyclo[3.1.0]hex-2-ylmethyl]-benzamide;
3-Methyl-N-[(1S,2S,5R)-3-(2-p-tolyl-thiophene-3-carbonyl)-3-aza-bicyclo[3.1.0]hex-2-ylmethyl]-benzamide;
Benzo[2,1,3]thiadiazole-4-carboxylic acid[(1S,2S,5R)-3-(2-p-tolyl-thiophene-3-carbonyl)-3-aza-bicyclo[3.1.0]hex-2-ylmethyl]-amide;
2,3-Dihydro-benzofuran-4-carboxylic acid[(1S,2S,5R)-3-(2-p-tolyl-thiophene-3-carbonyl)-3-aza-bicyclo[3.1.0]hex-2-ylmethyl]-amide;
Benzoxazole-4-carboxylic acid[(1S,2S,5R)-3-(2-p-tolyl-thiophene-3-carbonyl)-3-aza-bicyclo[3.1.0]hex-2-ylmethyl]-amide;
2-M ethyl-benzoxazole-4-carboxylic acid[(1S,2S,5R)-3-(2-p-tolyl-thiophene-3-carbonyl)-3-aza-bicyclo[3.1.0]hex-2-ylmethyl]-amide;
1-Methyl-1H-indole-3-carboxylic acid[(1S,2S,5R)-3-(2-m-tolyl-thiophene-3-carbonyl)-3-aza-bicyclo[3.1.0]hex-2-ylmethyl]-amide;
Quinoline-8-carboxylic acid[(1S,2S,5R)-3-(2-m-tolyl-thiophene-3-carbonyl)-3-aza-bicyclo[3.1.0]hex-2-ylmethyl]-amide;
4-Methyl-4H-furo[3,2-b]pyrrole-5-carboxylic acid[(1S,2S,5R)-3-(2-m-tolyl-thiophene-3-carbonyl)-3-aza-bicyclo[3.1.0]hex-2-ylmethyl]-amide;
Pyrrolo[2,1-b]thiazole-7-carboxylic acid[(1S,2S,5R)-3-(2-m-tolyl-thiophene-3-carbonyl)-3-aza-bicyclo[3.1.0]hex-2-ylmethyl]-amide;
3,4-Dihydro-2H-benzo[1,4]oxazine-5-carboxylic acid[(1S,2S,5R)-3-(2-m-tolyl-thiophene-3-carbonyl)-3-aza-bicyclo[3.1.0]hex-2-ylmethyl]-amide;
2,3-Dihydro-thieno[3,4-b][1,4]dioxine-5-carboxylic acid [(1S,2S,5R)-3-(2-m-tolyl-thiophene-3-carbonyl)-3-aza-bicyclo[3.1.0]hex-2-ylmethyl]-amide;
2-Ethyl-5-methyl-2H-pyrazole-3-carboxylic acid[(1S,2S,5R)-3-(2-m-tolyl-thiophene-3-carbonyl)-3-aza-bicyclo[3.1.0]hex-2-ylmethyl]-amide;
2,5-Dimethyl-2H-pyrazole-3-carboxylic acid[(1S,2S,5R)-3-(2-m-tolyl-thiophene-3-carbonyl)-3-aza-bicyclo[3.1.0]hex-2-ylmethyl]-amide;
3-Bromo-N-[(1S,2S,5R)-3-(2-m-tolyl-thiophene-3-carbonyl)-3-aza-bicyclo[3.1.0]hex-2-ylmethyl]-benzamide;
3-Chloro-N-[(1S,2S,5R)-3-(2-m-tolyl-thiophene-3-carbonyl)-3-aza-bicyclo[3.1.0]hex-2-ylmethyl]-benzamide;
3-M ethyl-N-[(1S,2S,5R)-3-(2-m-tolyl-thiophene-3-carbonyl)-3-aza-bicyclo[3.1.0]hex-2-ylmethyl]-benzamide;
Benzo[2,1,3]thiadiazole-4-carboxylic acid[(1S,2S,5R)-3-(2-m-tolyl-thiophene-3-carbonyl)-3-aza-bicyclo[3.1.0]hex-2-ylmethyl]-amide;
Benzo[2,1,3]oxadiazole-4-carboxylic acid[(1S,2S,5R)-3-(2-m-tolyl-thiophene-3-carbonyl)-3-aza-bicyclo[3.1.0]hex-2-ylmethyl]-amide;
2,3-Dihydro-benzofuran-4-carboxylic acid[(1S,2S,5R)-3-(2-m-tolyl-thiophene-3-carbonyl)-3-aza-bicyclo[3.1.0]hex-2-ylmethyl]-amide;
Benzothiazole-7-carboxylic acid[(1S,2S,5R)-3-(2-m-tolyl-thiophene-3-carbonyl)-3-aza-bicyclo[3.1.0]hex-2-ylmethyl]-amide;
2-M ethyl-benzoxazole-4-carboxylic acid[(1S,2S,5R)-3-(2-m-tolyl-thiophene-3-carbonyl)-3-aza-bicyclo[3.1.0]hex-2-ylmethyl]-amide;
2-M ethyl-benzoxazole-7-carboxylic acid[(1S,2S,5R)-3-(2-m-tolyl-thiophene-3-carbonyl)-3-aza-bicyclo[3.1.0]hex-2-ylmethyl]-amide;
2-Chloro-benzothiazole-4-carboxylic acid[(1S,2S,5R)-3-(2-methyl-5-m-tolyl-thiazole-4-carbonyl)-3-aza-bicyclo[3.1.0]hex-2-ylmethyl]-amide; and
Benzothiazole-4-carboxylic acid[(1S,2S,5R)-3-(2-methyl-5-m-tolyl-thiazole-4-carbonyl)-3-aza-bicyclo[3.1.0]hex-2-ylmethyl]-amide.

Any reference to a compound of formula (I) is to be understood as referring also to the salts (and especially the pharmaceutically acceptable salts) of such a compound, as appropriate and expedient.

The term "pharmaceutically acceptable salts" refers to non-toxic, inorganic or organic acid and/or base addition salts. Reference can be made to "Salt selection for basic drugs", *Int. J. Pharm.* 1986, 33, 201-217.

A further aspect of the invention is a pharmaceutical composition containing at least one compound according to formula (I), or a pharmaceutically acceptable salt thereof, and a pharmaceutically acceptable carrier material.

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The compounds of formula (I) and their pharmaceutically acceptable salts can be used as medicaments, e.g. in the form of pharmaceutical compositions for enteral or parenteral administration.

The compounds according to formula (I) may be used for the preparation of a medicament, and are suitable, for the prevention or treatment of diseases selected from the group consisting of dysthymic disorders including major depression and cyclothymia, affective neurosis, all types of manic depressive disorders, delirium, psychotic disorders, schizophrenia, catatonic schizophrenia, delusional paranoia, adjustment disorders and all clusters of personality disorders; schizoaffective disorders; anxiety disorders including generalized anxiety, obsessive compulsive disorder, posttraumatic stress disorder, panic attacks, all types of phobic anxiety and avoidance; separation anxiety; all psychoactive substance use, abuse, seeking and reinstatement; all types of psychological or physical addictions, dissociative disorders including multiple personality syndromes and psychogenic amnesias; sexual and reproductive dysfunction; psychosexual dysfunction and addiction; tolerance to narcotics or withdrawal from narcotics; increased anaesthetic risk, anaesthetic responsiveness; hypothalamic-adrenal dysfunctions; disturbed biological and circadian rhythms; sleep disturbances associated with diseases such as neurological disorders including neuropathic pain and restless leg syndrome; sleep apnea; narcolepsy; chronic fatigue syndrome; insomnias related to psychiatric disorders; all types of idiopathic insomnias and parasomnias; sleep-wake schedule disorders including jet-lag; all dementias and cognitive dysfunctions in the healthy population and in psychiatric and neurological disorders; mental dysfunctions of aging; all types of amnesia; severe mental retardation; dyskinesias and muscular diseases; muscle spasticity, tremors, movement disorders; spontaneous and medication-induced dyskinesias; neurodegenerative disorders including Huntington's, Creutzfeld-Jacob's, Alzheimer's diseases and Tourette syndrome;

Amyotrophic lateral sclerosis; Parkinson's disease; Cushing's syndrome; traumatic lesions; spinal cord trauma; head trauma; perinatal hypoxia; hearing loss; tinnitus; demyelinating diseases; spinal and cranial nerve diseases; ocular damage; retinopathy; epilepsy; seizure disorders; absence seizures, complex partial and generalized seizures; Lennox-Gastaut syndrome; migraine and headache; pain disorders; anaesthesia and analgesia; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; dental pain; pain related to infection e.g. by HIV; post-chemotherapy pain; post-stroke pain; post-operative pain; neuralgia; osteoarthritis; conditions associated with visceral pain such as irritable bowel syndrome; eating disorders; diabetes; toxic and dysmetabolic disorders including cerebral anoxia, diabetic neuropathies and alcoholism; appetite, taste, eating, or drinking disorders; somatoform disorders including hypochondriasis; vomiting/nausea; emesis; gastric dyskinesia; gastric ulcers; Kallman's syndrome (anosmia); impaired glucose tolerance; intestinal motility dyskinesias; hypothalamic diseases; hypophysis diseases; hyperthermia syndromes, pyrexia, febrile seizures, idiopathic growth deficiency; dwarfism; gigantism; acromegaly; basophil adenoma; prolactinoma; hyperprolactinemia; brain tumors, adenomas; benign prostatic hypertrophy, prostate cancer; endometrial, breast, colon cancer; all types of testicular dysfunctions, fertility control; reproductive hormone abnormalities; hot flashes; hypothalamic hypogonadism, functional or psychogenic amenorrhea; urinary bladder incontinence; asthma; allergies; all types of dermatitis, acne and cysts, sebaceous gland dysfunctions; cardiovascular disorders; heart and lung diseases, acute and congestive heart failure; hypotension; hypertension; dyslipidemias, hyperlipidemias, insulin resistance; urinary retention; osteoporosis; angina pectoris; myocardial infarction; arrhythmias, coronary diseases, left ventricular hypertrophy; ischemic or haemorrhagic stroke; all types of cerebrovascular disorders including subarachnoid haemorrhage, ischemic and hemorrhagic stroke and vascular dementia; chronic renal failure and other renal diseases; gout; kidney cancer; urinary incontinence; and other diseases related to general orexin system dysfunctions.

In a preferred embodiment, the compounds according to formula (I) may be used for the preparation of a medicament, and are suitable, for the prevention or treatment of diseases selected from the group consisting of all types of sleep disorders, of stress-related syndromes, of psychoactive substance use, abuse, seeking and reinstatement, of cognitive dysfunctions in the healthy population and in psychiatric and neurologic disorders, of eating or drinking disorders.

Eating disorders may be defined as comprising metabolic dysfunction; dysregulated appetite control; compulsive obesities; emeto-bulimia or anorexia nervosa. Pathologically modified food intake may result from disturbed appetite (attraction or aversion for food); altered energy balance (intake vs. expenditure); disturbed perception of food quality (high fat or carbohydrates, high palatability); disturbed food availability (unrestricted diet or deprivation) or disrupted water balance. Drinking disorders include polydipsias in psychiatric disorders and all other types of excessive fluid intake. Sleep disorders include all types of parasomnias, insomnias, narcolepsy and other disorders of excessive sleepiness, sleep-related dystonias; restless leg syndrome; sleep apneas; jet-lag syndrome; shift-work syndrome, delayed or advanced sleep phase syndrome or insomnias related to psychiatric disorders. Insomnias are defined as comprising sleep disorders associated with aging; intermittent treatment of chronic insomnia; situational transient insomnia (new environment, noise) or short-term insomnia due to stress; grief; pain or illness. Insomnia also include stress-related syndromes including post-traumatic stress disorders as well as other types and subtypes of anxiety disorders such as generalized anxiety, obsessive compulsive disorder, panic attacks and all types of phobic anxiety and avoidance. Psychoactive substance use, abuse, seeking and reinstatement are defined as all types of psychological or physical addictions and their related tolerance and dependence components. Cognitive dysfunctions include deficits in all types of attention, learning and memory functions occurring transiently or chronically in the normal, healthy, young, adult or aging population, and also occurring transiently or chronically in psychiatric, neurologic, cardiovascular and immune disorders.

In a further preferred embodiment of the invention, the compounds according to formula (I) may be used for the preparation of a medicament, and are suitable, for the prevention or treatment of diseases selected from the group consisting of sleep disorders that comprises all types of insomnias, narcolepsy and other disorders of excessive sleepiness, sleep-related dystonias, restless leg syndrome, sleep apneas, jet-lag syndrome, shift-work syndrome, delayed or advanced sleep phase syndrome or insomnias related to psychiatric disorders.

In another preferred embodiment of the invention, the compounds according to formula (I) may be used for the preparation of a medicament, and are suitable, for the prevention or treatment of diseases selected from the group consisting of cognitive dysfunctions that comprise deficits in all types of attention, learning and memory functions occurring transiently or chronically in the normal, healthy, young, adult or aging population, and also occurring transiently or chronically in psychiatric, neurologic, cardiovascular and immune disorders.

In another preferred embodiment of the invention, the compounds according to formula (I) may be used for the preparation of a medicament, and are suitable, for the prevention or treatment of diseases selected from the group consisting of eating disorders that comprise metabolic dysfunction; dysregulated appetite control; compulsive obesities; emeto-bulimia or anorexia nervosa.

In another preferred embodiment of the invention, the compounds according to formula (I) may be used for the preparation of a medicament, and are suitable, for the prevention or treatment of diseases selected from the group consisting of psychoactive substance use, abuse, seeking and reinstatement that comprise all types of psychological or physical addictions and their related tolerance and dependence components.

The present invention also relates to a method for the prevention or treatment of a disease or disorder mentioned herein comprising administering to a subject a pharmaceutically active amount of a compound of formula (I).

Where the plural form is used for compounds, salts, pharmaceutical compositions, diseases or the like, this is intended to mean also a single compound, salt, disease or the like.

A further aspect of the invention is a process for the preparation of compounds of formula (I). Compounds of formula (I) of the present invention can be prepared according to the general sequence of reactions outlined in the schemes below wherein A, B, n and $R^1$ are as defined for formula (I). The compounds obtained may also be converted into pharmaceutically acceptable salts thereof in a manner known per se.

In general, all chemical transformations can be performed according to well-known standard methodologies as described in the literature or as described in the procedures below or in the experimental part.

Preparation of Compounds of Formula (I):

The first step in the synthesis of trans-3-aza-bicyclo[3.1.0] hexane derivatives of formula (I) as outlined in scheme 1 was the cyclopropanation of (2R,5S)-2-Phenyl-3-oxa-1-azabicyclo[3.3.0]oct-6-en-8-on (J. S. Madalengoitia et al. *J. Org. Chem.* 1999, 64, 547-555) with trimethylsulfoxonium iodide in the presence of NaH as base. The obtained tricyclic intermediate (2) was reduced with LAH to give the benzyl-protected alcohol (3). The protecting group was exchanged to tert-butoxycarbonyl by hydrogenation of (3) in the presence of Boc-anhydride and the respective alcohol (4) was oxidized to the corresponding aldehyde (5) with e.g. Dess-Martin periodinane. After reductive amination of (5) with benzylamine in the presence of a reducing agent like sodium triacetoxyborohydride the benzyl group was removed by hydrogenolysis to yield the primary amine (7). The acylation of (7) with a carboxylic acid $R^1COOH$ in the presence of a coupling reagent like TBTU resulted in the formation of amides (8) which after removal of the Boc-group were transferred to compounds of formula (I) by amide coupling (e.g. B-A-COOH, TBTU).

Scheme 1: Synthesis of compounds of formula (I), wherein n represents 1

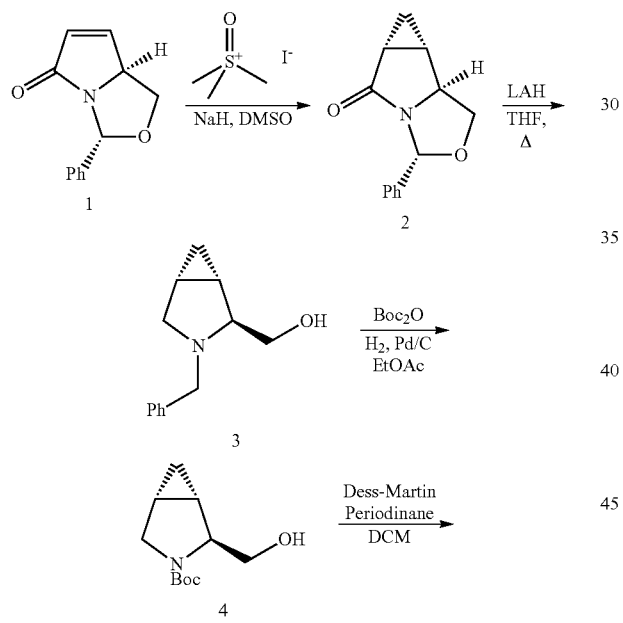

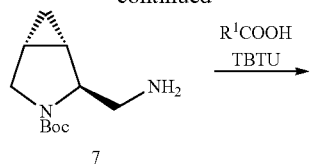

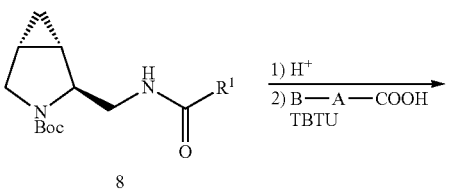

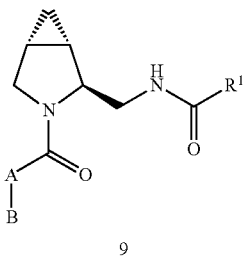

An alternative approach to compounds of formula (I) (scheme 2) started with the protection of amine (7) with ethyl trifluoroacetate to give amides (10) which were Boc-deprotected with an acid like HCl in a solvent like dioxane. The obtained amine (11) was coupled with a carboxylic acid B-A-COOH in the presence of a coupling reagent like TBTU. After removal of the trifluoroacetyl-group with a base like $K_2CO_3$ or NaOH in a solvent or a mixture of solvents like water, MeOH and/or isopropanol amines (12) were obtained which were coupled with a carboxylic acid $R^1COOH$ in the presence of a coupling reagent like TBTU or with an acid chloride $R^1COCl$ in the presence of a base like DIPEA to compounds (9) of formula (I).

Scheme 2: Alternative synthesis of compounds of formula (I), wherein n represents 1

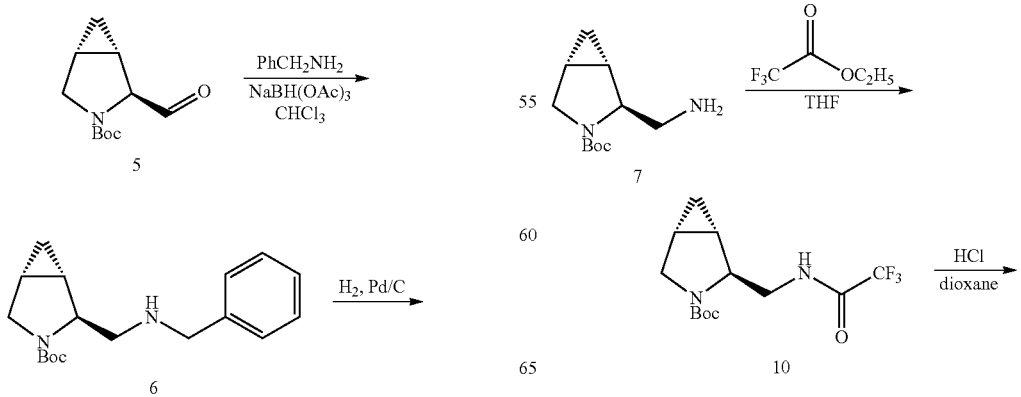

-continued

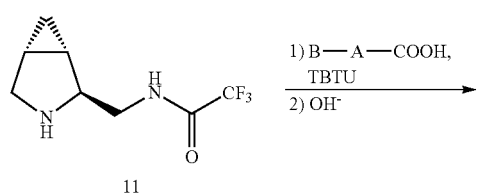
11

1) B—A—COOH, TBTU
2) OH⁻

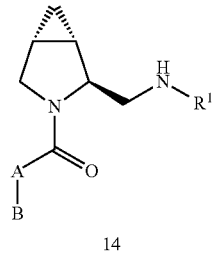
14

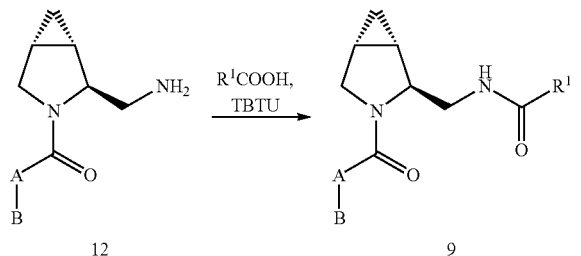
12 → 9

R¹COOH, TBTU

Compounds of formula (I), wherein n represents the integer 0, may be synthesized according to scheme 3.

Scheme 3: Alternative synthesis of compounds of formula (I), wherein n represents 0; X represents Cl, Br, or OTf.

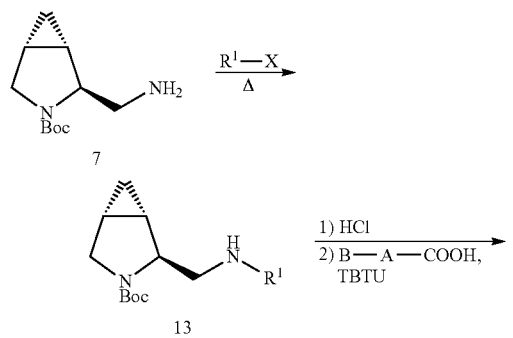
7 → 13

R¹—X, Δ

1) HCl
2) B—A—COOH, TBTU

Starting from building block (7) amines (13) may be obtained by reaction with commercially available or well known compounds R¹—X wherein X represents Cl, Br, or OTf (especially heterocyclyl chlorides or bromides such as chloro-pyrimidine derivatives) in the presence of a base like K₂CO₃ and/or DIPEA under heating, optionally in presence of a suitable metal catalyst (Buchwald-Hartwig conditions). After removal of the Boc-protecting group with an acid like HCl in a solvent like dioxane compounds (14) of formula (I) may be synthesized by amide coupling with an acid B-A-COOH in the presence of a coupling reagent like TBTU.

Thiophene-3-carboxylic acid derivatives of formula B-A-COOH were for instance synthesised according to scheme 4.

Scheme 4: Synthesis of thiophene-3-carboxylic acid derivatives

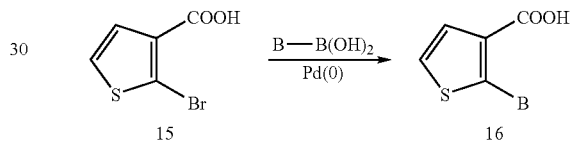
15 → 16

B—B(OH)₂, Pd(0)

Thiophene-3-carboxylic acid derivatives (16) were for instance synthesized in a Suzuki coupling reaction of 2-bromo-thiophene-3-carboxylic acid (15) (or a corresponding ester) with a commercially available arylboronic acid in the presence of a palladium catalyst like Pd(PPh₃)₄ and a base like K₂CO₃ in a solvent like isopropanol or toluene or a mixture thereof. In analogy thiophene-2-carboxylic acid derivatives were synthesized starting from 3-bromo-thiophene-2-carboxylic acid.

Thiazole-4-carboxylic acid derivatives of formula B-A-COOH were for instance synthesised according to scheme 5.

Scheme 5: Synthesis of thiazole-4-carboxylic acid derivatives, wherein R is (C₁₋₄)alkyl, (C₃₋₆)cycloalkyl or ——NR²R³ and R' is (C₁₋₄)alkyl

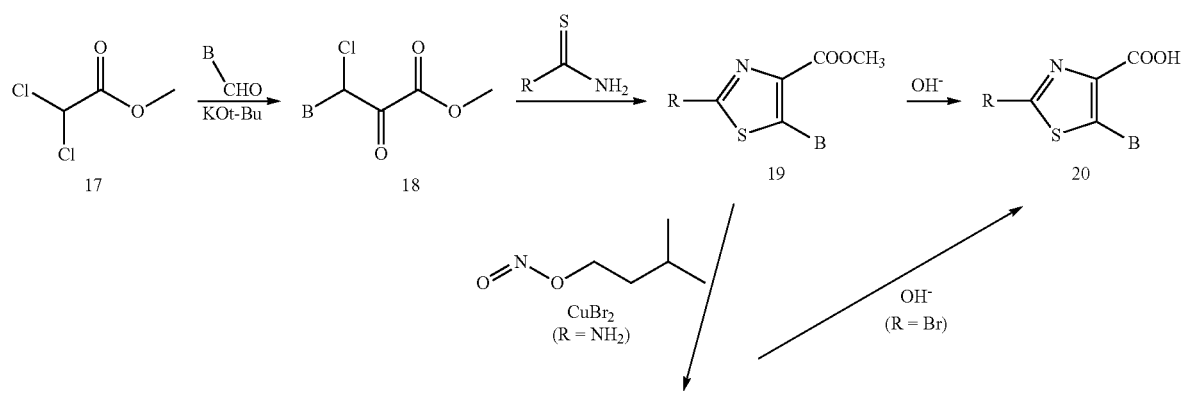

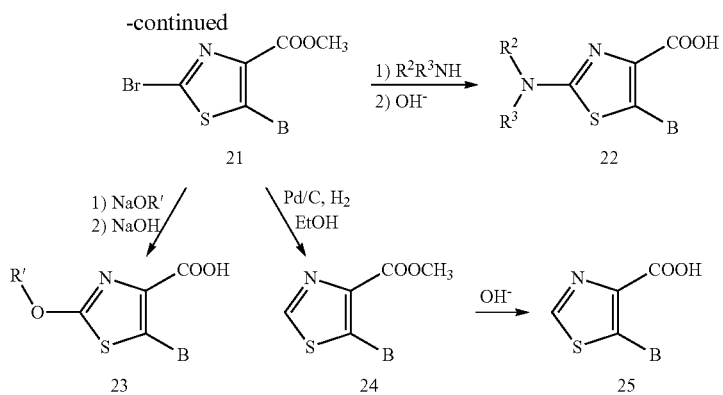

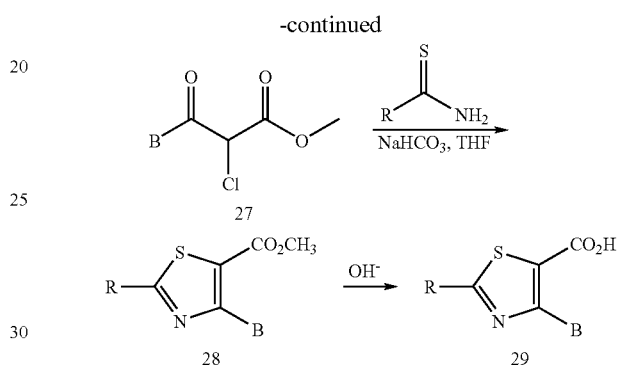

By reaction of methyl dichloroacetate (17; commercially available) with an aldehyde B—CHO in the presence of a base like KOtBu in a solvent like THF the 3-chloro-2-oxo-propionic ester derivatives (18) were obtained which were transformed in a reaction with thioamides [R=(C$_{1-4}$)alkyl or (C$_{3-6}$)cycloalkyl] to 2-alkyl- or 2-cycloalkyl-substituted thiazole derivatives (19) or in a reaction with thioureas (R=—NR$^2$R$^3$) to 2-amino-substituted thiazole derivatives (19). Saponification of the ester function with an aq. solution of e.g. NaOH in a solvent like MeOH resulted in the formation of the desired carboxylic acids (20, R=(C$_{1-4}$)alkyl, (C$_{3-6}$)cycloalkyl or —NR$^2$R$^3$). 2-Bromo-thiazole derivatives (21) were for instance obtained by reaction of the respective 2-amino-thiazole derivative (19, R=NH$_2$) with isoamylnitrite in the presence of CuBr$_2$ in a solvent such as MeCN. The ester derivatives (21) were either transferred to 2-amino-substituted thiazole derivatives (22) by reaction of (21) with amines HNR$^2$R$^3$ and subsequent saponification or to 2-alkoxy substituted analogues (23) by reaction with a sodium alkoxide and subsequent saponification with NaOH solution. Saponification of ester (21) as described above resulted in the formation of carboxylic acids (20, R=Br). In addition compounds (25) which are unsubstituted in 2-position were synthesized by hydrogenation of (21) in the presence of palladium on charcoal and subsequent saponification of the intermediate ester (24).

Aldehydes B—CHO are commercially available or may be synthesized by procedures known from the literature like for instance reduction of the respective carboxylic acid or their different derivatives with a reducing agent, by reduction of the respective nitrile or by oxidation of benzylic alcohols and their heterocyclic analogues with oxidating agents (e.g.: J. March, *Advanced Organic Chemistry*, 4$^{th}$ edition, John Wiley & Sons, p. 447-449, 919-920 and 1167-1171).

(C$_{3-6}$)Cycloalkyl-thioamides may be synthesized by treatment of (C$_{3-6}$)cycloalkyl-carboxamides with Lawesson's reagent.

Thiazole-5-carboxylic acid derivatives of formula B-A-COOH were for instance synthesised according to scheme 6.

Scheme 6: Synthesis of thiazole-5-carboxylic acid derivatives, wherein R is (C$_{1-4}$)alkyl or (C$_{3-6}$)cycloalkyl

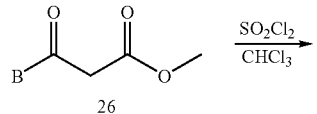

By chlorination of β-keto ester derivatives (26) with sulfuryl chloride in chloroform α-chloro ester derivatives (27) were obtained which by reaction with thioamides in a solvent like THF gave the respective thiazole-5-carboxylic acid esters (28). These were transferred to the desired acids (29) by saponification with for instance KOH in a solvent mixture like water and EtOH.

Oxazole-4-carboxylic acid derivatives of formula B-A-COOH were for instance synthesised according to scheme 7.

Scheme 7: Synthesis of oxazole-4-carboxylic acid derivatives

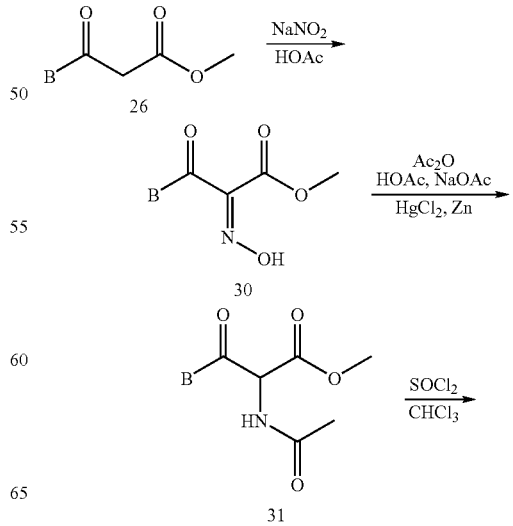

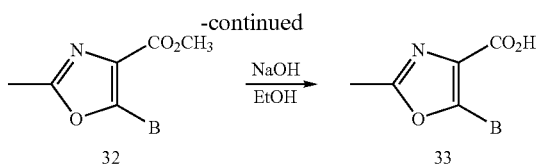

By reaction of β-keto ester derivatives (26) with NaNO$_2$ in the presence of acetic acid α-hydroxyimino ester derivatives (30) were obtained which were transformed to α-acetylamino ester derivatives (31) in a reaction with Ac$_2$O in the presence of HgCl$_2$ and zinc. By cyclisation of these intermediates with SOCl$_2$ in a solvent like CHCl$_3$ the respective oxazole-4-carboxylic ester derivatives (32) were synthesized which were saponified as described above to give the desired acids (33).

β-Keto ester derivatives (26) are commercially available or may be synthesized by procedures known in the literature like for instance Claisen condensation, reaction of aromatic and heteroaromatic ester derivatives with acetic ester derivatives in the presence of strong bases, reaction of acetophenones and their heterocyclic analogues with methyl cyanoformate or diethyl dicarbonate in the presence of bases or a Reformatsky-type reraction (e.g.: J. March, *Advanced Organic Chemistry*, 4$^{th}$ edition, John Wiley & Sons, p. 491-493 and 931).

Benzo[1,4]oxazine-carboxylic acid derivatives of formula R$^1$—COOH were for instance synthesised according to scheme 8.

Scheme 8: Synthesis of benzo[1,4]oxazine-carboxylic acid derivatives

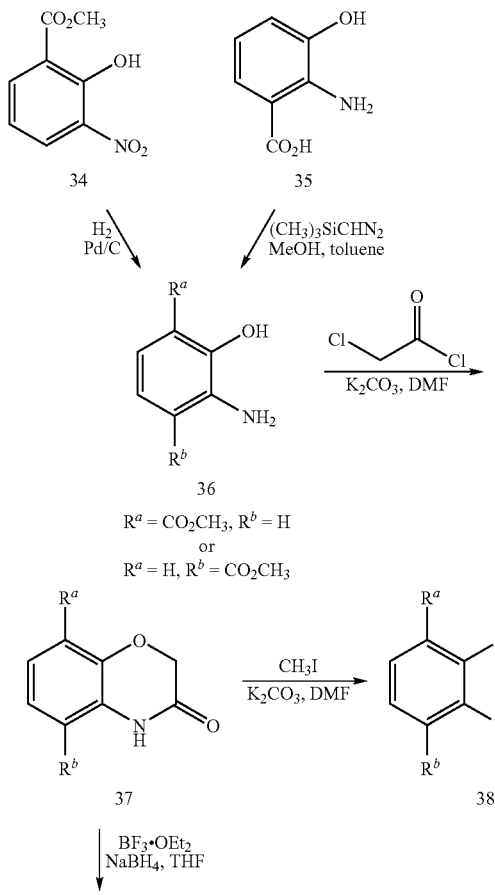

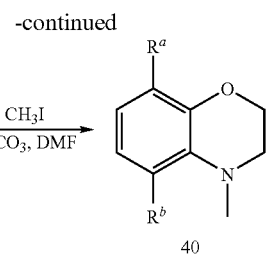

Ester cleavage:

41: R = H, R$^c$ = COOH, R$^d$ = H
42: R = H, R$^c$ = H, R$^d$ = COOH
43: R = Me, R$^c$ = COOH, R$^d$ = H
44: R = Me, R$^c$ = H, R$^d$ = COOH

45: R = H, R$^c$ = COOH, R$^d$ = H
46: R = H, R$^c$ = H, R$^d$ = COOH
47: R = Me, R$^c$ = COOH, R$^d$ = H
48: R = Me, R$^c$ = H, R$^d$ = COOH

By hydrogenation of 3-nitrosalicylate (commercially available) in MeOH 3-amino-2-hydroxy-benzoic acid methyl ester (36, R$^a$=COOMe, R$^b$=H) was obtained. The regioisomer (36, R$^a$=H, R$^b$=COOMe) was synthesized by esterification of commercially available 3-hydroxyanthranilic acid with (trimethylsilyl)diazomethane. Cyclization of one or the other amino-hydroxy-benzoic acid (36) with chloroacetyl chloride in the presence of a base like K$_2$CO$_3$ lead to 3-oxo-3,4-dihydro-2H-benzo[1,4]oxazine derivatives (37) which were reduced to 3,4-dihydro-2H-benzo[1,4]oxazine derivatives (39) with NaBH$_4$ in the presence of boron trifluoride diethyl etherate. Compounds (37) as well as (39) may be alkylated at the nitrogen atom with methyl iodide in the presence of a base like K$_2$CO$_3$ in a solvent like DMF to give the respective analogues (38) or (40). By saponification of the respective ester derivatives (37, 38, 39 or 40) as described above, the desired acids (41, 42, 43, 44, 45, 46, 47 or 48) could be obtained.

Chroman-carboxylic acid derivatives of formula R$^1$—COOH were for instance synthesised according to scheme 9.

Scheme 9: Synthesis of chroman-carboxylic acid derivatives

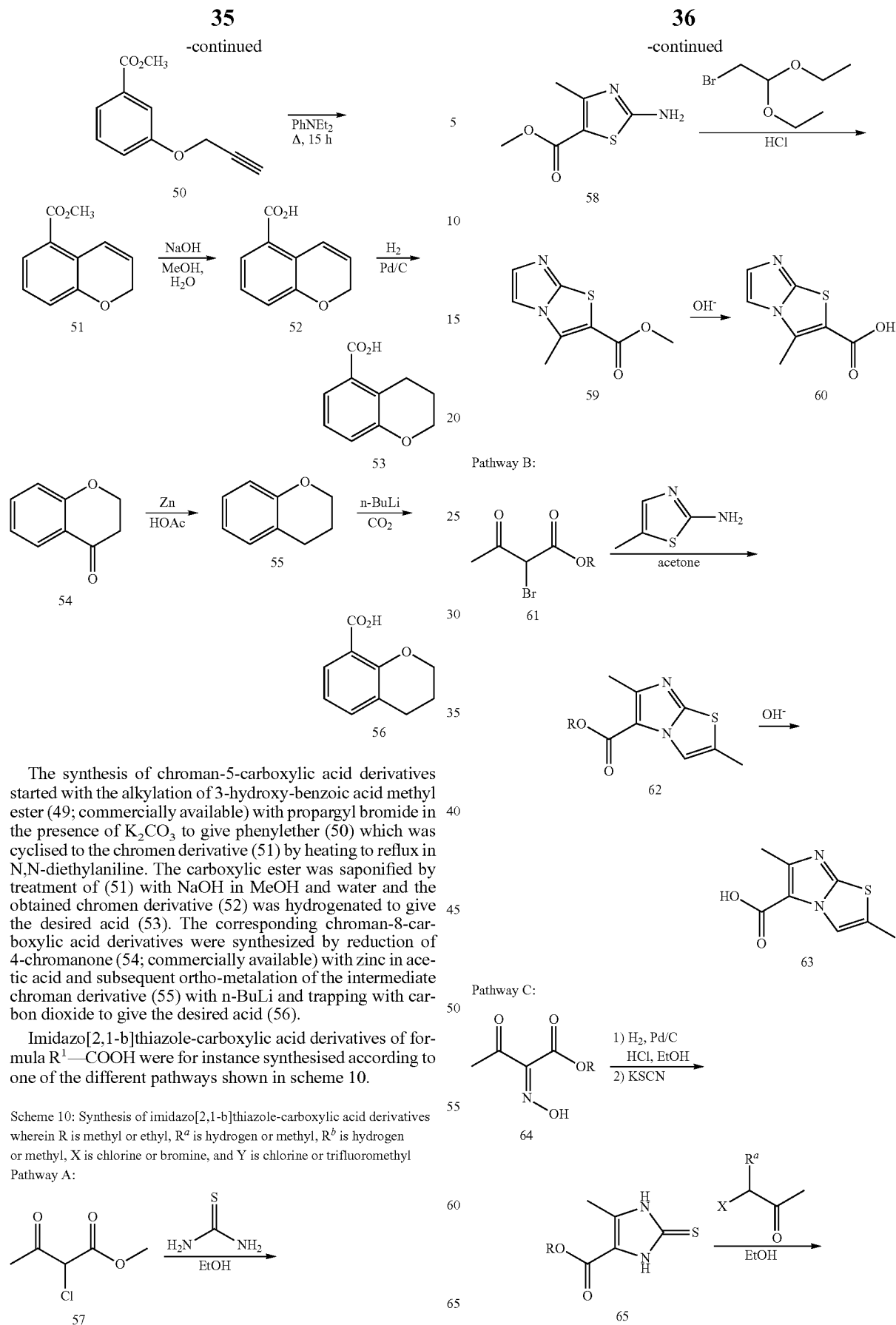

The synthesis of chroman-5-carboxylic acid derivatives started with the alkylation of 3-hydroxy-benzoic acid methyl ester (49; commercially available) with propargyl bromide in the presence of $K_2CO_3$ to give phenylether (50) which was cyclised to the chromen derivative (51) by heating to reflux in N,N-diethylaniline. The carboxylic ester was saponified by treatment of (51) with NaOH in MeOH and water and the obtained chromen derivative (52) was hydrogenated to give the desired acid (53). The corresponding chroman-8-carboxylic acid derivatives were synthesized by reduction of 4-chromanone (54; commercially available) with zinc in acetic acid and subsequent ortho-metalation of the intermediate chroman derivative (55) with n-BuLi and trapping with carbon dioxide to give the desired acid (56).

Imidazo[2,1-b]thiazole-carboxylic acid derivatives of formula $R^1$—COOH were for instance synthesised according to one of the different pathways shown in scheme 10.

Scheme 10: Synthesis of imidazo[2,1-b]thiazole-carboxylic acid derivatives wherein R is methyl or ethyl, $R^a$ is hydrogen or methyl, $R^b$ is hydrogen or methyl, X is chlorine or bromine, and Y is chlorine or trifluoromethyl
Pathway A:

Pathway B:

Pathway C:

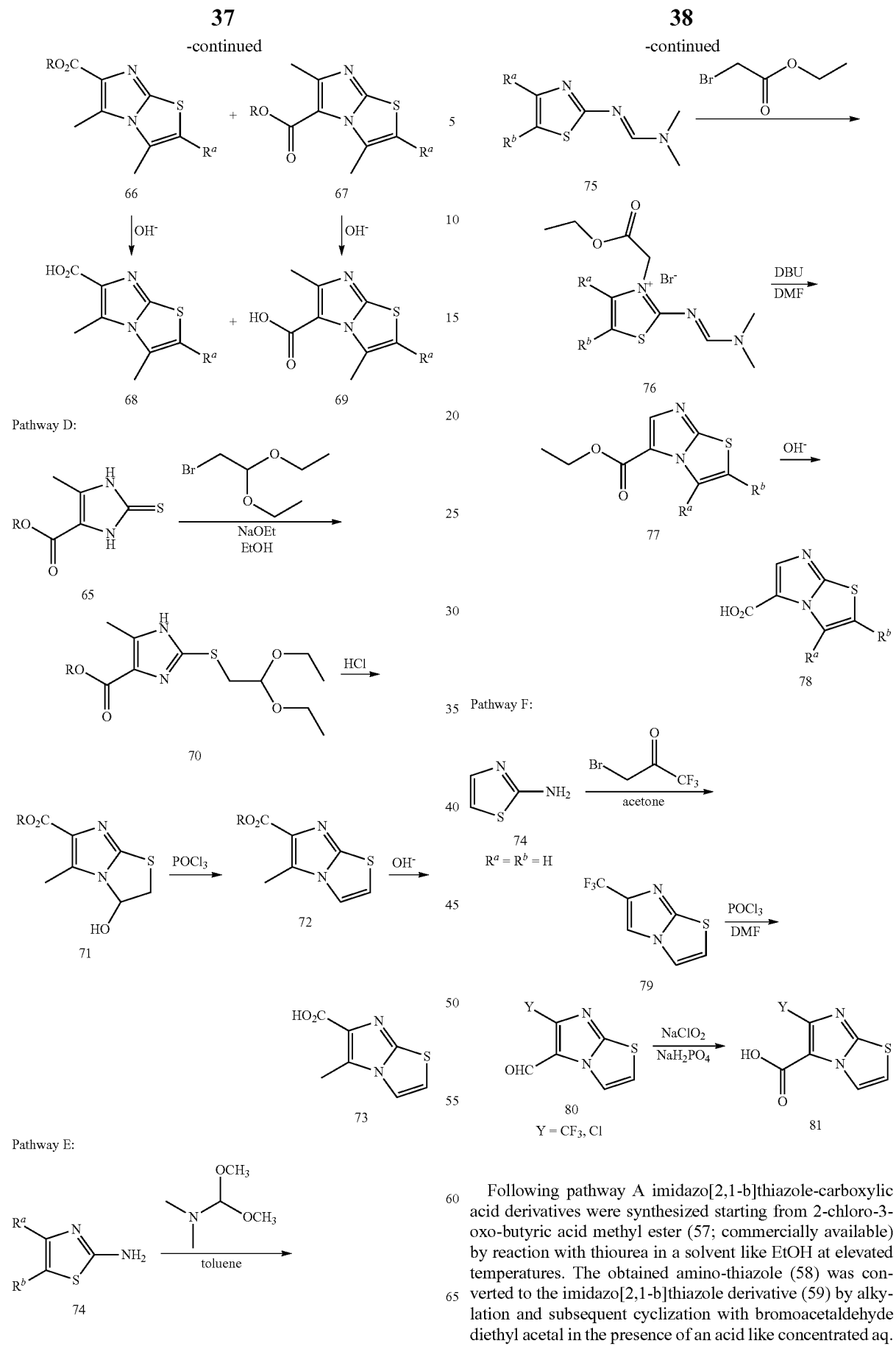

Following pathway A imidazo[2,1-b]thiazole-carboxylic acid derivatives were synthesized starting from 2-chloro-3-oxo-butyric acid methyl ester (57; commercially available) by reaction with thiourea in a solvent like EtOH at elevated temperatures. The obtained amino-thiazole (58) was converted to the imidazo[2,1-b]thiazole derivative (59) by alkylation and subsequent cyclization with bromoacetaldehyde diethyl acetal in the presence of an acid like concentrated aq.

HCl. By saponification of (59) with for instance NaOH in solvents like THF and MeOH the desired acids (60) were obtained.

An alternative approach (pathway B) started with the reaction of 2-bromo-3-oxo-butyric acid ester (61; commercially available) with 2-amino-5-methyl-thiazole in a solvent like acetone to give the imidazo[2,1-b]thiazole derivative (62) which was transformed to the desired acid (63) by saponification with for instance NaOH in solvents like THF and MeOH.

By hydrogenation of 2-hydroxyimino-3-oxo-butyric acid ester (64; commercially available) in the presence of palladium on charcoal under acidic conditions (e.g. HCl in EtOH) and subsequent reaction with KSCN the imidazole derivative (65) was obtained which was transferred to a mixture of the two possible isomers (66) and (67) by reaction with the respective α-halogenated propanone or butanone derivative (pathway C). After separation of the isomers (66) and (67) by chromatography the desired imidazo[2,1-b]thiazole-carboxylic acid derivatives (68) and (69) were obtained by saponification with for instance NaOH in solvents like THF and MeOH. Alternatively (pathway D) the imidazole derivative (65) may be transferred to the acetal (70) by alkylation with bromoacetaldehyde diethyl acetal in the presence of a base like sodium ethoxide. Cyclization under acidic conditions (e.g. aq. HCl) and dehydration of the intermediate (71) with for instance phosphorus oxychloride led to ester (72) which was transformed to the desired acid (73) by saponification with for instance NaOH in solvents like THF and MeOH.

In still an alternative procedure (pathway E) the respective amino-thiazole (74; commercially available) was converted to the formamidine derivative (75) by heating (74) with N,N-dimethylformamide dimethylacetale in a solvent like toluene. After alkylation with ethyl bromoacetate the respective thiazolium bromide (76) was cyclised with DBU to yield the ester (77) which was saponified to the desired acid (78) with for instance NaOH in solvents like THF and MeOH.

Finally pathway F started with the alkylation of 2-aminothiazole with 3-bromo-1,1,1-trifluoroacetone to yield the trifluoromethyl-substituted imidazo[2,1-b]thiazole derivative (79) which was formylated to the aldehyde (80) by reaction with phosphorus oxychloride in a solvent like DMF. By oxidation of aldehyde (79) with sodium chlorite the desired imidazo[2,1-b]thiazole-carboxylic acid (81, Y=CF₃) was obtained. In analogy the commercially available chlorinated aldehyde (80, Y=Cl) was oxidized to the acid (81, Y=Cl).

Derivatives of formula $R^1$—COOH wherein $R^1$ is pyrrolo[2,1-b]thiazole were for instance synthesised according to the pathway shown in scheme 11.

Scheme 11: Synthesis of pyrrolo[2,1-b]thiazole-carboxylic acid derivatives

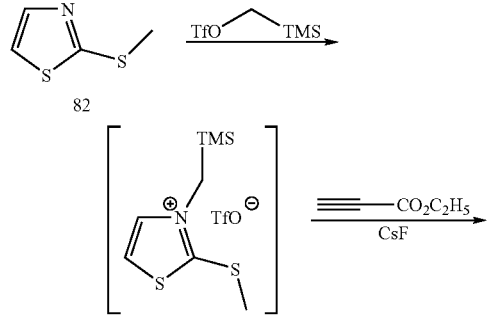

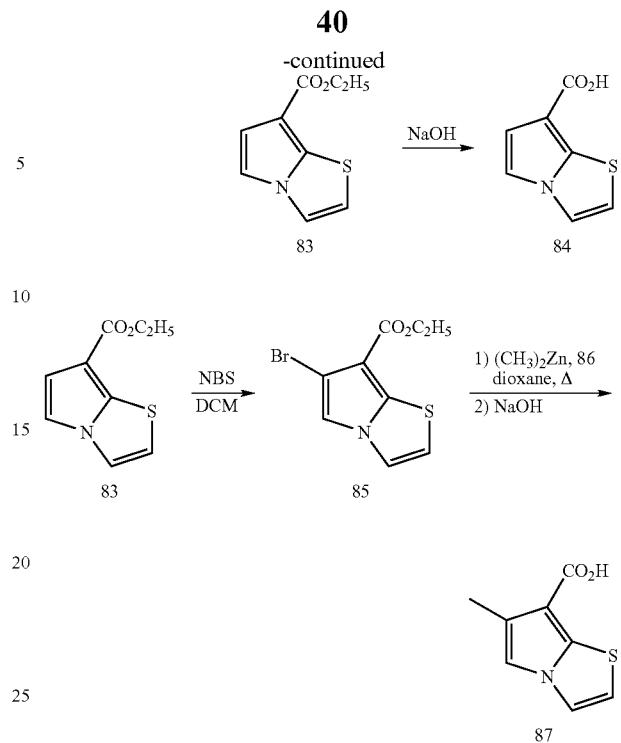

By reaction of 2-methylsulfanylthiazole (82, commercially available) with trimethylsilylmethyl trifluoro-methanesulfonate followed by cyclisation of the resulting thiazolinium salt by reaction with ethyl propiolate in the presence of CsF, the pyrrolo[2,1-b]thiazole (83) can be obtained (Berry C. R. et al., *Organic Letters* 2007, 9, 21, 4099-4102). The ester may be either saponified with NaOH solution to the respective acid (84) or brominated with NBS to the ethyl ester derivative (85). In a Negishi-type coupling of (85) with dimethylzinc in the presence of catalytic amounts of [1,1'-bis(diphenylphosphino)ferrocene]dichloropalladium(II) (86) the bromine atom can be replaced by a methyl group to give after saponification with a base like NaOH in a solvent mixture like EtOH/water the acid derivative (87).

Derivatives of formula $R^1$—COOH wherein $R^1$ is benzothiazole were for instance synthesised according to the pathway shown in scheme 12.

By reaction of 3-amino-benzoic acid methyl ester (88) with KSCN the respective thiourea derivative (89) was obtained which could be cyclised by treatment with an oxidizing reagent like bromine in an acid like acetic acid to 2-amino-benzothiazole derivatives (90). The amino group could be removed with, for instance, isoamyl nitrite to give ester derivatives (91) which were saponified to acid derivatives (92) with a base like NaOH in solvents like water, MeOH and THF.

Scheme 12: Synthesis of benzothiazole-carboxylic acid derivatives

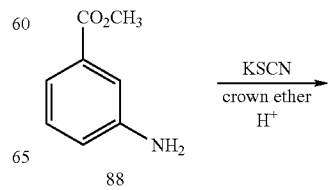

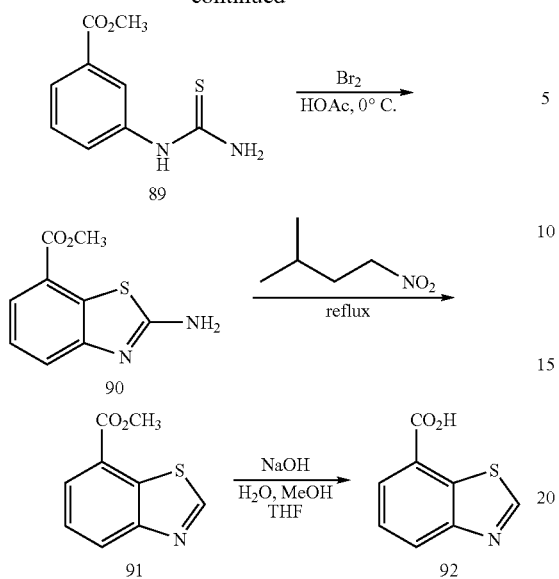

Derivatives of formula R¹—COOH wherein R¹ is benzoxazole were for instance synthesised according to one of the pathways shown in scheme 13.

Scheme 13: Synthesis of benzoxazole-carboxylic acid derivatives wherein R is methyl or ethyl and $R^a$ is hydrogen or methyl

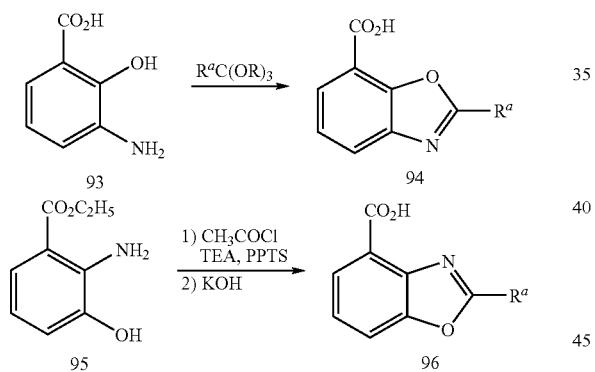

By reaction of 3-aminosalicylic acid (93) with the respective ortho-ester derivative the desired benzoxazole-7-carboxylic acid derivatives (94) could be obtained. The reaction may be catalyzed by addition of an acid like PTSA. The respective benzoxazole-4-carboxylic acid derivatives (96) could be synthesized in analogy by reaction of 2-amino-3-hydroxy-benzoic acid with an ortho-ester derivative. In an alternative procedure benzoxazole-4-carboxylic acid derivatives (96) could be synthesized by reaction of 2-amino-3-hydroxy-benzoic acid ethyl ester [(95), J. Reisch, G. M. K. B. Gunaherath *Monatshefte für Chemie*, 1988, 119, 1169-1178] with acetyl chloride in the presence of TEA and PPTS at elevated temperatures and subsequent saponification of the obtained ester with a base like KOH in a solvent mixture like MeOH/water.

Derivatives of formula R¹—COOH wherein R¹ is benzofurane were for instance synthesised according to one of the pathways shown in scheme 14.

Scheme 14: Synthesis of benzofuran-carboxylic acid derivatives wherein X is fluorine or chlorine

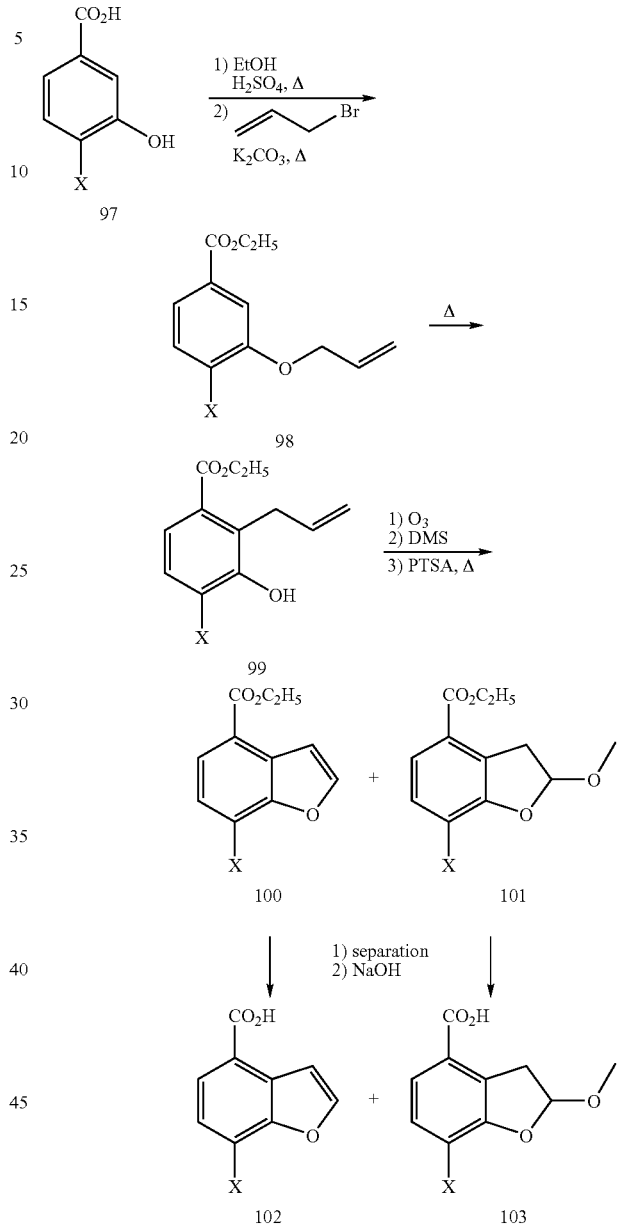

The respective 3-hydroxy-benzoic acid (97) was transferred to ester derivatives (98) by treatment with an alcohol like EtOH under acid-catalyzed conditions (e.g. sulfuric acid) and subsequent allylation of the phenol with allyl bromide in the presence of a base like $K_2CO_3$ in a solvent like acetone. In a Claisen rearrangement (98) was transferred to the allyl-substituted ester (99) by heating which was cyclized by ozonolysis at low temperatures (e.g. −78° C.) in a solvent mixture like DCM and MeOH and subsequent reductive work-up with for instance dimethyl-sulfide. After acid catalyzed elimination of water with for instance PTSA the benzofuran derivative (100) was obtained which was contaminated with side-product (101). After separation of both compounds by, for instance, chromatography the pure ester derivatives was saponified with a base like NaOH in a solvent or solvent mixture like MeOH and/or water to give the respective carboxylic acids (102) and (103).

EXPERIMENTAL SECTION

Abbrevations (as Used Herein and in the Description Above)

| | |
|---|---|
| Ac | Acetyl (e.g. in HOAc = acetic acid or Ac$_2$O = acetic acid anhydride) |
| aq | Aqueous |
| Boc | tert-Butoxycarbonyl |
| BSA | Bovine serum albumine |
| CHO | Chinese hamster ovary |
| conc | Concentrated |
| d | Day(s) |
| DBU | 1,8-Diazabicyclo[5.4.0]undec-7-ene |
| DCM | Dichloromethane |
| DIPEA | Diisopropylethylamine |
| DMAP | 4-Dimethylaminopyridine |
| DMF | N,N-Dimethylformamide |
| DMS | Dimethylsulfide |
| DMSO | Dimethylsulfoxide |
| eq | Equivalent(s) |
| ES | Electron spray |
| Et | Ethyl (e.g. in NaOEt = sodium ethoxide) |
| Ether | Diethylether |
| EtOAc | Ethyl acetate |
| EtOH | Ethanol |
| FC | flash column chromatography on silica gel |
| FCS | Foatal calf serum |
| FLIPR | Fluorescent imaging plate reader |
| h | Hour(s) |
| HBSS | Hank's balanced salt solution |
| HEPES | 4-(2-hydroxyethyl)-piperazine-1-ethanesulfonic acid |
| HPLC | High performance liquid chromatography |
| KOtBu | Potassium tert. butoxide |
| LAH | Lithium aluminum hydride |
| LC | Liquid chromatography |
| M | Molar(ity) |
| Me | Methyl |
| MeCN | Acetonitrile |
| MeOH | Methanol |
| min | Minute(s) |
| MS | Mass spectroscopy |
| NBS | N-Bromosuccinimide |
| Ph | Phenyl |
| PPTS | Pyridinium-para-toluenesulfonate |
| prep | Preparative |
| PTSA | para-Toluenesulfonic acid monohydrate |
| RT | Room temperature |
| sat | Saturated |
| $t_R$ | Retention time |
| TBME | tert-Butyl methyl ether |
| TBTU | O-Benzotriazol-1-yl-N,N,N',N'-tetramethyluronium tetrafluoroborate |
| TEA | Triethylamine |
| Tf | trifluoromethanesulfonyl (e.g. in TfO = trifluoromethanesulfonyloxy) |
| TFA | Trifluoroacetic acid |
| THF | Tetrahydrofuran |
| TMS | Trimethylsilyl |

I-Chemistry

The following examples illustrate the preparation of pharmacologically active compounds of the invention but do not at all limit the scope thereof.

All temperatures are stated in ° C.

Compounds are characterized by:

$^1$H-NMR: 300 MHz Varian Oxford or 400 MHz Bruker Advance; chemical shifts are given in ppm relative to the solvent used; multiplicities: s=singlet, d=doublet, t=triplet, m=multiplet, b=broad, coupling constants are given in Hz;

LC-MS: Agilent 1100 series with DAD and MS detection (MS Finnigan single quadrupole);

columns (4.6×50 mm, 5 μm): Zorbax SB-AQ, Zorbax Extend C18 or Waters XBridge C18;

conditions (if not otherwise stated the acidic gradient is used):

basic: eluent A: MeCN, eluent B: conc. NH$_3$ in water (1.0 mL/L), 5% to 95% CH$_3$CN, flow rate 4.5 mL/min;

acidic: eluent A: MeCN, eluent B: TFA in water (0.4 mL/L), 5% to 95% CH$_3$CN, flow rate 4.5 mL/min;

$t_R$ is given in min;

In case of a partial separation of rotamers, as seen for several examples of compounds of formula (I), two retention times are given.

Compounds are purified by FC or by prep HPLC using RP—C$_{18}$ based columns with MeCN/water gradients and formic acid or ammonia additives.

A. Preparation of Precursors and Intermediates

A.1 Synthesis of thiazole-4-carboxylic acid derivatives

A.1.1 Synthesis of 3-chloro-2-oxo-propionic Ester Derivatives (General Procedure)

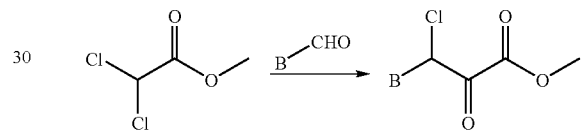

A solution of the respective aldehyde (338 mmol, 1.0 eq) and methyl dichloroacetate (338 mmol, 1.0 eq) in THF (100 mL) is added dropwise to a cold (−60° C.) suspension of KOtBu (335 mmol, 1.0 eq) in THF (420 mL). After 4 h the mixture is allowed to reach RT, stirred over night and concentrated in vacuo. DCM and ice-cold water are added, the layers are separated and the aq. layer is extracted twice with DCM. The combined organic layers are washed with ice-cold water and brine, dried over MgSO$_4$ and concentrated in vacuo to give the desired 3-chloro-2-oxo-propionic ester derivative which is used without further purification.

3-Chloro-2-oxo-3-o-tolyl-propionic Acid Methyl Ester prepared by reaction of 2-methyl-benzaldehyde with methyl dichloro-acetate.

3-Chloro-2-oxo-3-m-tolyl-propionic Acid Methyl Ester prepared by reaction of 3-methyl-benzaldehyde with methyl dichloroacetate.

3-Chloro-2-oxo-3-p-tolyl-propionic Acid Methyl Ester prepared by reaction of 4-methyl-benzaldehyde with methyl dichloroacetate.

3-Chloro-3-(4-ethyl-phenyl)-2-oxo-propionic Acid Methyl Ester prepared by reaction of 4-ethyl-benzaldehyde with methyl dichloroacetate.

3-Chloro-3-(3-methoxy-phenyl)-2-oxo-propionic Acid Methyl Ester prepared by reaction of 3-methoxy-benzaldehyde with methyl dichloro-acetate.

3-Chloro-3-(2-fluoro-phenyl)-2-oxo-propionic Acid Methyl Ester prepared by reaction of 2-fluoro-benzaldehyde with methyl dichloro-acetate.

3-Chloro-3-(3-fluoro-phenyl)-2-oxo-propionic Acid Methyl Ester prepared by reaction of 3-fluoro-benzaldehyde with methyl dichloroacetate.

3-Chloro-3-(4-fluoro-phenyl)-2-oxo-propionic Acid Methyl Ester prepared by reaction of 4-fluoro-benzaldehyde with methyl dichloroacetate.

3-Chloro-3-(3-chloro-phenyl)-2-oxo-propionic Acid Methyl Ester prepared by reaction of 3-chloro-benzaldehyde with methyl dichloro-acetate.

3-Chloro-2-oxo-3-(3-trifluoromethyl-phenyl)-propionic Acid Methyl Ester prepared by reaction of 3-trifluoromethyl-benzaldehyde with methyl dichloro-acetate.

3-Chloro-3-(3,4-dimethyl-phenyl)-2-oxo-propionic Acid Methyl Ester prepared by reaction of 3,4-dimethyl-benzaldehyde with methyl dichloro-acetate.

3-Chloro-3-(2,3-dimethyl-phenyl)-2-oxo-propionic Acid Methyl Ester prepared by reaction of 2,3-dimethyl-benzaldehyde with methyl dichloro-acetate.

3-Chloro-3-(2,4-dimethyl-phenyl)-2-oxo-propionic Acid Methyl Ester prepared by reaction of 2,4-dimethyl-benzaldehyde with methyl dichloro-acetate.

3-Chloro-3-(3,5-dimethyl-phenyl)-2-oxo-propionic Acid Methyl Ester prepared by reaction of 3,5-dimethyl-benzaldehyde with methyl dichloro-acetate.

3-(3-Bromo-4-fluoro-phenyl)-3-chloro-2-oxo-propionic Acid Methyl ester prepared by reaction of 3-bromo-4-fluoro-benzaldehyde with methyl dichloro-acetate.

3-Chloro-3-(3,4-dichloro-phenyl)-2-oxo-propionic Acid Methyl Ester prepared by reaction of 3,4-dichloro-benzaldehyde with methyl dichloro-acetate.

3-Chloro-3-(3,4-difluoro-phenyl)-2-oxo-propionic Acid Methyl Ester prepared by reaction of 3,4-difluoro-benzaldehyde with methyl dichloro-acetate.

3-Chloro-3-(3-fluoro-4-methyl-phenyl)-2-oxo-propionic Acid Methyl Ester prepared by reaction of 3-fluoro-4-methyl-benzaldehyde with methyl dichloro-acetate.

3-Chloro-3-(3-fluoro-5-trifluoromethyl-phenyl)-2-oxo-propionic Acid Methyl Ester prepared by reaction of 3-fluoro-5-trifluoromethyl-benzaldehyde with methyl dichloro-acetate.

3-Chloro-3-(3-fluoro-2-methyl-phenyl)-2-oxo-propionic Acid Methyl Ester prepared by reaction of 3-fluoro-2-methyl-benzaldehyde with methyl dichloro-acetate.

3-Chloro-2-oxo-3-phenyl-propionic Acid Methyl Ester prepared by reaction of benzaldehyde with methyl dichloro-acetate.

3-(3-Bromo-phenyl)-3-chloro-2-oxo-propionic Acid Methyl Ester prepared by reaction of 3-bromo-benzaldehyde with methyl dichloro-acetate.

3-(4-Bromo-phenyl)-3-chloro-2-oxo-propionic Acid Methyl Ester prepared by reaction of 4-bromo-benzaldehyde with methyl dichloro-acetate.

3-Chloro-3-(4-cyano-phenyl)-2-oxo-propionic Acid Methyl Ester prepared by reaction of 4-cyano-benzaldehyde with methyl dichloro-acetate.

3-Chloro-3-(2,3-dichloro-phenyl)-2-oxo-propionic Acid Methyl Ester prepared by reaction of 2,3-dichloro-benzaldehyde with methyl dichloro-acetate.

3-Chloro-3-(3-nitro-phenyl)-2-oxo-propionic Acid Methyl Ester prepared by reaction of 3-nitro-benzaldehyde with methyl dichloro-acetate.

3-Chloro-3-(2-chloro-6-fluoro-phenyl)-2-oxo-propionic Acid Methyl Ester prepared by reaction of 2-chloro-6-fluoro-benzaldehyde with methyl dichloro-acetate.

A.1.2 Synthesis of thiazole-4-carboxylic Acid Methyl Ester Derivatives (General Procedure)

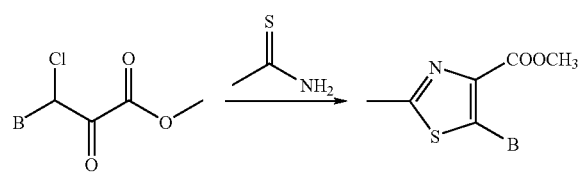

A solution of thioacetamide (132 mmol, 1.0 eq) in MeCN (250 mL) is added to a mixture of the respective 3-chloro-2-oxo-propionic ester derivative (132 mmol, 1.0 eq) and molecular sieves (4 Å, 12 g) in MeCN (60 mL). After stirring for 5 h the mixture is cooled in an ice-bath and the obtained precipitate is filtered off. The residue is washed with cold MeCN, dried, dissolved in MeOH (280 mL) and stirred at 50° C. for 6 h. The solvents are removed in vacuo to give the desired thiazole derivative as a white solid. The presence of molecular sieve is often not necessary for successful reactions.

2-Methyl-5-o-tolyl-thiazole-4-carboxylic Acid Methyl Ester prepared by reaction of 3-chloro-2-oxo-3-o-tolyl-propionic acid methyl ester with thioacetamide. LC-MS: $t_R$=0.92 min; [M+H]$^+$=248.1.

2-Methyl-5-m-tolyl-thiazole-4-carboxylic Acid Methyl Ester prepared by reaction of 3-chloro-2-oxo-3-m-tolyl-propionic acid methyl ester with thioacetamide. LC-MS: $t_R$=0.94 min; [M+H]$^+$=248.0.

2-Methyl-5-p-tolyl-thiazole-4-carboxylic Acid Methyl Ester prepared by reaction of 3-chloro-2-oxo-3-p-tolyl-propionic acid methyl ester with thioacetamide. LC-MS: $t_R$=0.92 min; [M+H]$^+$=248.2.

5-(4-Ethyl-phenyl)-2-methyl-thiazole-4-carboxylic Acid Methyl Ester prepared by reaction of 3-chloro-3-(4-ethyl-phenyl)-2-oxo-propionic acid methyl ester with thioacetamide. LC-MS: $t_R$=0.98 min; [M+H]$^+$=262.1.

5-(2-Fluoro-phenyl)-2-methyl-thiazole-4-carboxylic Acid Methyl Ester prepared by reaction of 3-chloro-3-(2-fluoro-phenyl)-2-oxo-propionic acid methyl ester with thioacetamide. LC-MS: $t_R$=0.89 min; [M+H]$^+$=252.0.

5-(3-Fluoro-phenyl)-2-methyl-thiazole-4-carboxylic Acid Methyl Ester prepared by reaction of 3-chloro-3-(3-fluoro-phenyl)-2-oxo-propionic acid methyl ester with thioacetamide. LC-MS: $t_R$=0.91 min; [M+H]$^+$=252.1.

5-(4-Fluoro-phenyl)-2-methyl-thiazole-4-carboxylic Acid Methyl Ester prepared by reaction of 3-chloro-3-(4-fluoro-phenyl)-2-oxo-propionic acid methyl ester with thioacetamide. $^1$H-NMR (CDCl$_3$): δ=2.75 (s, 3H); 3.84 (s, 3H); 7.10 (m, 2H); 7.47 (m, 2H).

2-Methyl-5-(3-trifluoromethyl-phenyl)-thiazole-4-carboxylic Acid Methyl Ester prepared by reaction of 3-chloro-3-(3-trifluoromethyl-phenyl)-2-oxo-propionic acid methyl ester with thioacetamide. LC-MS: $t_R$=0.98 min; [M+H]$^+$=302.2.

5-(3-Chloro-phenyl)-2-methyl-thiazole-4-carboxylic Acid Methyl Ester prepared by reaction of 3-chloro-3-(3-chloro-phenyl)-2-oxo-propionic acid methyl ester with thioacetamide. LC-MS: $t_R$=0.95 min; [M+H]$^+$=268.0.

5-(3,4-Dimethyl-phenyl)-2-methyl-thiazole-4-carboxylic Acid Methyl Ester prepared by reaction of 3-chloro-3-(3,4-dimethyl-phenyl)-2-oxo-propionic acid methyl ester with thioacetamide. LC-MS: $t_R$=0.96 min; [M+H]$^+$=262.3.

2-Methyl-5-phenyl-thiazole-4-carboxylic Acid Methyl Ester prepared by reaction of 3-chloro-2-oxo-3-phenyl-propionic acid methyl ester with thioacetamide. LC-MS: $t_R$=0.87 min; [M+H]$^+$=234.3.

5-(3-Bromo-phenyl)-2-methyl-thiazole-4-carboxylic Acid Methyl Ester prepared by reaction of 3-(3-bromo-phenyl)-3-chloro-2-oxo-propionic acid methyl ester with thioacetamide. LC-MS: $t_R$=1.00 min; [M+H]$^+$=312.0.

5-(4-Bromo-phenyl)-2-methyl-thiazole-4-carboxylic Acid Methyl Ester prepared by reaction of 3-(4-bromo-phenyl)-3-chloro-2-oxo-propionic acid methyl ester with thioacetamide. LC-MS: $t_R$=0.95 min; [M+H]$^+$=312.1.

5-(4-Cyano-phenyl)-2-methyl-thiazole-4-carboxylic Acid Methyl Ester prepared by reaction of 3-chloro-3-(4-cyano-phenyl)-2-oxo-propionic acid methyl ester with thioacetamide. LC-MS: $t_R$=0.92 min; [M+H]$^+$=259.0.

5-(2,3-Dichloro-phenyl)-2-methyl-thiazole-4-carboxylic Acid Methyl Ester prepared by reaction of 3-chloro-3-(2,3-dichloro-phenyl)-2-oxo-propionic acid methyl ester with thioacetamide. LC-MS: $t_R$=0.97 min; $[M+H]^+$=302.2.

5-(2,3-Dimethyl-phenyl)-2-methyl-thiazole-4-carboxylic Acid Methyl Ester prepared by reaction of 3-chloro-3-(2,3-dimethyl-phenyl)-2-oxo-propionic acid methyl ester with thioacetamide. LC-MS: $t_R$=0.95 min; $[M+H]^+$=262.3.

5-(3-Fluoro-2-methyl-phenyl)-2-methyl-thiazole-4-carboxylic Acid Methyl Ester prepared by reaction of 3-chloro-3-(3-fluoro-2-methyl-phenyl)-2-oxo-propionic acid methyl ester with thioacetamide. LC-MS: $t_R$=0.93 min; $[M+H]^+$=266.3.

5-(3-Bromo-4-fluoro-phenyl)-2-methyl-thiazole-4-carboxylic acid methyl ester prepared by reaction of 3-(3-bromo-4-fluoro-phenyl)-3-chloro-2-oxo-propionic acid methyl ester with thioacetamide. LC-MS: $t_R$=0.95 min; $[M+H]^+$=330.2.

5-(3,4-Dichloro-phenyl)-2-methyl-thiazole-4-carboxylic Acid Methyl Ester prepared by reaction of 3-chloro-3-(3,4-dichloro-phenyl)-2-oxo-propionic acid methyl ester with thioacetamide. LC-MS: $t_R$=0.99 min; $[M+H]^+$=302.2.

5-(3,4-Difluoro-phenyl)-2-methyl-thiazole-4-carboxylic Acid Methyl Ester prepared by reaction of 3-chloro-3-(3,4-difluoro-phenyl)-2-oxo-propionic acid methyl ester with thioacetamide. LC-MS: $t_R$=0.92 min; $[M+H]^+$=270.3.

5-(3-Fluoro-4-methyl-phenyl)-2-methyl-thiazole-4-carboxylic Acid Methyl Ester prepared by reaction of 3-chloro-3-(3-fluoro-4-methyl-phenyl)-2-oxo-propionic acid methyl ester with thioacetamide. LC-MS: $t_R$=1.00 min; $[M+H]^+$=266.0.

5-(3,5-Dimethyl-phenyl)-2-methyl-thiazole-4-carboxylic Acid Methyl Ester prepared by reaction of 3-chloro-3-(3,5-dimethyl-phenyl)-2-oxo-propionic acid methyl ester with thioacetamide. LC-MS: $t_R$=0.97 min; $[M+H]^+$=262.3.

5-(3-Fluoro-5-trifluoromethyl-phenyl)-2-methyl-thiazole-4-carboxylic Acid Methyl Ester prepared by reaction of 3-chloro-3-(3-fluoro-5-trifluoromethyl-phenyl)-2-oxo-propionic acid methyl ester with thioacetamide. LC-MS: $t_R$=1.03 min; $[M+H]^+$=319.8.

5-(2,4-Dimethyl-phenyl)-2-methyl-thiazole-4-carboxylic Acid Methyl Ester prepared by reaction of 3-chloro-3-(2,4-dimethyl-phenyl)-2-oxo-propionic acid methyl ester with thioacetamide. LC-MS: $t_R$=0.96 min; $[M+H]^+$=262.3.

5-(2-Chloro-6-fluoro-phenyl)-2-methyl-thiazole-4-carboxylic Acid Methyl Ester prepared by reaction of 3-chloro-3-(2-chloro-6-fluoro-phenyl)-2-oxo-propionic acid methyl ester with thioacetamide. LC-MS: $t_R$=0.92 min; $[M+H]^+$=286.2.

2-Methyl-5-(3-nitro-phenyl)-thiazole-4-carboxylic Acid Methyl Ester prepared by reaction of 3-chloro-3-(3-nitro-phenyl)-2-oxo-propionic acid methyl ester with thioacetamide. LC-MS: $t_R$=0.94 min; $[M+H]^+$=279.3.

A.1.3 Synthesis of 2-cyclopropyl-thiazole-4-carboxylic Acid Methyl Ester Derivatives Synthesis of Cyclopropanecarbothioic Acid Amide 2,4-Bis-(4-methoxyphenyl)-1,3-dithia-2,4-diphosphetane 2,4-disulfide (Lawesson reagent, 173 mmol) is added to a mixture of cyclopropanecarboxamide (173 mmol) and $Na_2CO_3$ (173 mmol) in THF (750 mL). The reaction mixture is stirred at reflux for 3 h, concentrated in vacuo and diluted with ether (500 mL) and water (500 mL). The layers are separated and the aq. layer is extracted with ether (250 mL). The combined organic layers are washed with brine (100 mL), dried over $MgSO_4$ and concentrated in vacuo to give a crude product which is used without further purification. $^1$H-NMR (DMSO-$d_6$): δ=0.81-0.88 (m, 2H); 0.96-1.00 (m, 2H); 2.00 (tt, J=8.0 Hz, J=4.3 Hz, 1H); 9.23 (bs, 1H); 9.33 (bs, 1H).

Synthesis of 2-cyclopropyl-thiazole-4-carboxylic Acid Methyl Ester Derivatives (General Procedure)

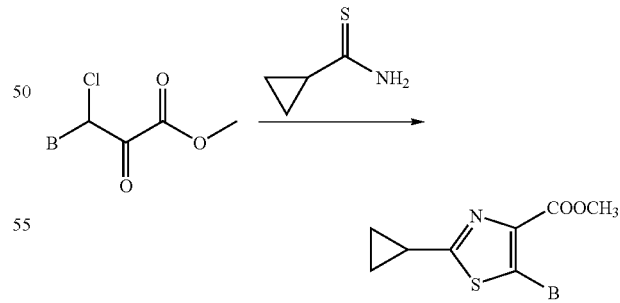

A solution of cyclopropanecarbothioic acid amide (33.9 mmol, 1.0 eq) in MeCN (45 mL) is added to a mixture of the respective 3-chloro-2-oxo-propionic ester derivative (33.9 mmol, 1.0 eq) and $NaHCO_3$ (102 mmol, 3.0 eq) in MeCN (45 mL). After stirring for 2 d at RT the mixture is concentrated in vacuo and the residue is diluted with EtOAc (150 mL) and water (150 mL). The layers are separated and the aq. layer is extracted with EtOAc (100 mL). The combined organic layers are washed with brine (100 mL), dried over $MgSO_4$ and concentrated in vacuo. The residue is dissolved in MeOH (70 mL) and treated with concentrated $H_2SO_4$ (0.18 mL). The mixture is stirred at 60° C. for 16 h and concentrated in vacuo to give the respective crude product which is used without further purification.

2-Cyclopropyl-5-phenyl-thiazole-4-carboxylic Acid Methyl Ester prepared by reaction of 3-chloro-2-oxo-3-phenyl-propionic acid methyl ester with cyclopropanecarbothioic acid amide. LC-MS: $t_R$=0.99 min; $[M+H]^+$=260.5.

2-Cyclopropyl-5-m-tolyl-thiazole-4-carboxylic Acid Methyl Ester prepared by reaction of 3-chloro-2-oxo-3-m-tolyl-propionic acid methyl ester with cyclopropanecarbothioic acid amide. LC-MS: $t_R$=0.99 min; $[M+H]^+$=274.3.

5-(4-Cyano-phenyl)-2-cyclopropyl-thiazole-4-carboxylic Acid Methyl Ester prepared by reaction of 3-chloro-3-(4-cyano-phenyl)-2-oxo-propionic acid methyl ester with cyclopropanecarbothioic acid amide.
LC-MS: $t_R$=1.00 min; $[M+H]^+$=285.0.

2-Cyclopropyl-5-(3-fluoro-phenyl)-thiazole-4-carboxylic Acid Methyl Ester prepared by reaction of 3-chloro-3-(3-fluoro-phenyl)-2-oxo-propionic acid methyl ester with cyclopropanecarbothioic acid amide.
LC-MS: $t_R$=1.02 min; $[M+H]^+$=278.0.

2-Cyclopropyl-5-(3-fluoro-4-methyl-phenyl)-thiazole-4-carboxylic Acid Methyl Ester prepared by reaction of 3-chloro-3-(3-fluoro-4-methyl-phenyl)-2-oxo-propionic acid methyl ester with cyclopropanecarbothioic acid amide.
LC-MS: $t_R$=1.06 min; $[M+H]^+$=292.1.

A.1.4 Synthesis of 2-amino-thiazole-4-carboxylic Acid Methyl Ester Derivatives (General Procedure)

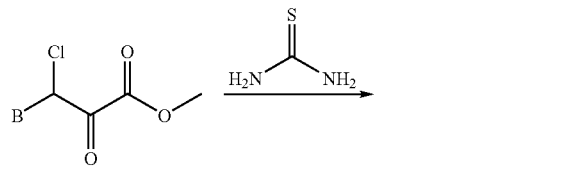

A solution of the respective 3-chloro-2-oxo-propionic ester derivative (22.1 mmol, 1.0 eq) in acetone (25 mL) is added to a suspension of thiourea (22.1 mmol, 1.0 eq) in acetone (45 mL). The mixture is heated to 57° C. (bath temperature), stirred for 24 h and concentrated to half of the volume. The obtained suspension is filtered and the residue is washed with acetone. After drying the desired amino-thiazole derivative is obtained as a solid.

2-Amino-5-m-tolyl-thiazole-4-carboxylic Acid Methyl Ester prepared by reaction of 3-chloro-2-oxo-3-m-tolyl-propionic acid methyl ester with thiourea. LC-MS: $t_R$=0.78 min; $[M+H]^+$=249.0.

2-Amino-5-(3-fluoro-phenyl)-thiazole-4-carboxylic Acid Methyl Ester prepared by reaction of 3-chloro-3-(3-fluoro-phenyl)-2-oxo-propionic acid methyl ester with thiourea. LC-MS: $t_R$=0.78 min; $[M+H]^+$=252.9.

2-Amino-5-(2-fluoro-phenyl)-thiazole-4-carboxylic Acid Methyl Ester prepared by reaction of 3-chloro-3-(2-fluoro-phenyl)-2-oxo-propionic acid methyl ester with thiourea. LC-MS: $t_R$=0.76 min; $[M+H]^+$=253.2.

2-Amino-5-(3-methoxy-phenyl)-thiazole-4-carboxylic Acid Methyl Ester prepared by reaction of 3-chloro-3-(3-methoxy-phenyl)-2-oxo-propionic acid methyl ester with thiourea. LC-MS: $t_R$=0.75 min; $[M+H]^+$=265.3.

2-Amino-5-(3-chloro-phenyl)-thiazole-4-carboxylic Acid Methyl Ester prepared by reaction of 3-chloro-3-(3-chloro-phenyl)-2-oxo-propionic acid methyl ester with thiourea. LC-MS: $t_R$=0.82 min; $[M+H]^+$=269.2.

2-Amino-5-(3-trifluoromethyl-phenyl)-thiazole-4-carboxylic Acid Methyl Ester prepared by reaction of 3-chloro-3-(3-trifluoromethyl-phenyl)-2-oxo-propionic acid methyl ester with thiourea. LC-MS: $t_R$=0.86 min; $[M+H]^+$=303.3.

2-Amino-5-phenyl-thiazole-4-carboxylic Acid Methyl Ester prepared by reaction of 3-chloro-2-oxo-3-phenyl-propionic acid methyl ester with thiourea. LC-MS: $t_R$=0.77 min; $[M+H]^+$=235.1.

A.1.5 Synthesis of 2-bromo-thiazole-4-carboxylic Acid Methyl Ester Derivatives (General Procedure)

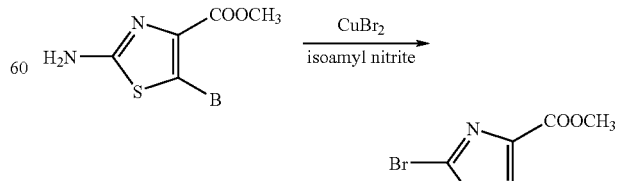

At 15° C. under an atmosphere of nitrogen the respective 2-amino-thiazole-4-carboxylic acid methyl ester (7.10 mmol) is added portionwise to a mixture of CuBr$_2$ (7.10 mmol) and isoamyl nitrite (10.6 mmol) in MeCN (30 mL). The mixture is stirred for 20 min at 15° C., for 30 min at 40° C. and for 90 min at 65° C. The solvents are removed in vacuo and the crude product is either purified by FC (DCM/MeOH or EtOAc/heptane) or used without further purification.

2-Bromo-5-m-tolyl-thiazole-4-carboxylic Acid Methyl Ester prepared by reaction of 2-amino-5-m-tolyl-thiazole-4-carboxylic acid methyl ester with CuBr$_2$ and isoamyl nitrite. LC-MS: $t_R$=1.01 min; [M+H]$^+$=311.8.

2-Bromo-5-(2-fluoro-phenyl)-thiazole-4-carboxylic Acid Methyl Ester prepared by reaction of 2-amino-5-(2-fluoro-phenyl)-thiazole-4-carboxylic acid methyl ester with CuBr$_2$ and isoamyl nitrite. LC-MS: $t_R$=0.96 min; [M+H]$^+$=316.1.

2-Bromo-5-(3-fluoro-phenyl)-thiazole-4-carboxylic Acid Methyl Ester prepared by reaction of 2-amino-5-(3-fluoro-phenyl)-thiazole-4-carboxylic acid methyl ester with CuBr$_2$ and isoamyl nitrite. LC-MS: $t_R$=1.08 min; [M+H]$^+$=316.0.

2-Bromo-5-(3-methoxy-phenyl)-thiazole-4-carboxylic Acid Methyl Ester prepared by reaction of 2-amino-5-(3-methoxy-phenyl)-thiazole-4-carboxylic acid methyl ester with CuBr$_2$ and isoamyl nitrite. LC-MS: $t_R$=0.97 min; [M+H]$^+$=328.2.

2-Bromo-5-(3-chloro-phenyl)-thiazole-4-carboxylic Acid Methyl Ester prepared by reaction of 2-amino-5-(3-chloro-phenyl)-thiazole-4-carboxylic acid methyl ester with CuBr$_2$ and isoamyl nitrite. LC-MS: $t_R$=1.00 min; [M+H]$^+$=332.2.

2-Bromo-5-(3-trifluoromethyl-phenyl)-thiazole-4-carboxylic Acid Methyl Ester prepared by reaction of 2-amino-5-(3-trifluoromethyl-phenyl)-thiazole-4-carboxylic acid methyl ester with CuBr$_2$ and isoamyl nitrite.
LC-MS: $t_R$=1.03 min; [M+H]$^+$=366.2.

2-Bromo-5-phenyl-thiazole-4-carboxylic Acid Methyl Ester prepared by reaction of 2-amino-5-phenyl-thiazole-4-carboxylic acid methyl ester with CuBr$_2$ and isoamyl nitrite. LC-MS: $t_R$=1.07 min; [M+H]$^+$=297.9.

A.1.6 Synthesis of thiazole-4-carboxylic Acid Methyl Ester Derivatives Lacking a Substituent in 2-position (General Procedure)

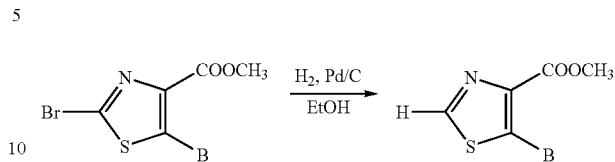

A solution/suspension of the respective 2-bromo-thiazole-4-carboxylic acid methyl ester (3.17 mmol) in EtOH (20 mL) is added to a suspension of Pd/C (600 mg, 10%) in EtOH (20 mL) and stirred under a hydrogen atmosphere (1 bar) for 18 h. After filtration through celite and removal of the solvents the desired product is obtained which is used without further purification.

5-m-Tolyl-thiazole-4-carboxylic Acid Methyl Ester prepared by hydrogenation of 2-bromo-5-m-tolyl-thiazole-4-carboxylic acid methyl ester. LC-MS: $t_R$=0.90 min; [M+H]$^+$=233.9.

5-(2-Fluoro-phenyl)-thiazole-4-carboxylic Acid Methyl Ester prepared by hydrogenation of 2-bromo-5-(2-fluoro-phenyl)-thiazole-4-carboxylic acid methyl ester. LC-MS: $t_R$=0.91 min; [M+H]$^+$=238.0.

5-(3-Fluoro-phenyl)-thiazole-4-carboxylic Acid Methyl Ester prepared by hydrogenation of 2-bromo-5-(3-fluoro-phenyl)-thiazole-4-carboxylic acid methyl ester. LC-MS: $t_R$=0.92 min; [M+H]$^+$=238.1.

5-Phenyl-thiazole-4-carboxylic Acid Methyl Ester prepared by hydrogenation of 2-bromo-5-phenyl-thiazole-4-carboxylic acid methyl ester. LC-MS: $t_R$=0.89 min; [M+H]$^+$=220.1.

5-(3-Methoxy-phenyl)-thiazole-4-carboxylic Acid Methyl Ester prepared by hydrogenation of 2-bromo-5-(3-methoxy-phenyl)-thiazole-4-carboxylic acid methyl ester. LC-MS: $t_R$=0.92 min; [M+H]$^+$=250.1.

5-(3-Chloro-phenyl)-thiazole-4-carboxylic Acid Methyl Ester prepared by hydrogenation of 2-bromo-5-(3-chloro-phenyl)-thiazole-4-carboxylic acid methyl ester. LC-MS: $t_R$=0.91 min; [M+H]$^+$=253.9.

5-(3-Trifluoromethyl-phenyl)-thiazole-4-carboxylic Acid Methyl Ester prepared by hydrogenation of 2-bromo-5-(3-trifluoromethyl-phenyl)-thiazole-4-carboxylic acid methyl ester. LC-MS: $t_R$=0.99 min; [M+H]$^+$=288.0.

A.1.7 Synthesis of 5-(3-amino-phenyl)-2-methyl-thiazole-4-carboxylic Acid Methyl Ester Iron powder (53.7 mmol) is added to a suspension of 2-methyl-5-(3-nitro-phenyl)-thiazole-4-carboxylic acid methyl ester (44.1 mmol) and ammonium chloride (221 mmol) in a mixture of EtOH (100 mL) and water (50 mL). The mixture is stirred at 80° C. for 4 h, iron powder (53.7 mmol) is added and heating is continued for additional 3 h. After addition of a third portion of iron powder (26.8 mmol) the mixture is heated at 80° C. for additional 3 h, cooled to RT, diluted with DCM and filtered through Celite. The residue is washed with DCM and water and the filtrate is concentrated in vacuo. A sat. aq. NaHCO$_3$ solution and DCM are added and the layers are separated. The organic layer is washed with water, dried over MgSO$_4$ and concentrated in vacuo to give a crude product which is used without further purification. LC-MS: $t_R$=0.67 min; [M+H]$^+$=249.4.

A.1.8 Synthesis of 5-(3-methanesulfonylamino-phenyl)-2-methyl-thiazole-4-carboxylic Acid Methyl Ester Methanesulfonyl chloride (5.27 mmol) and 4-methylmorpholine (4.86 mmol) are added successively to a solution of 5-(3-amino-phenyl)-2-methyl-thiazole-4-carboxylic acid methyl ester (4.05 mmol) in DCM (50 mL). After stirring for 2 h water is added, the layers are separated and the aq. layer is extracted once with DCM. The combined organic layers are washed with citric acid (10% solution in water), dried over MgSO$_4$ and concentrated in vacuo to give a crude product which is used without further purification. LC-MS: $t_R$=0.84 min; [M+H]$^+$=327.2.

A.1.9 Synthesis of 5-(3-acetylamino-phenyl)-2-methyl-thiazole-4-carboxylic Acid Methyl Ester TEA (14.2 mmol) and DMAP (4.05 mmol) are added successively to a solution of 5-(3-amino-phenyl)-2-methyl-thiazole-4-carboxylic acid methyl ester (4.05 mmol) in acetic anhydride (25 mL). After stirring for 30 min EtOAc and water are added, the layers are separated and the aq. layer is extracted once with EtOAc. The combined organic layers are washed with sat. aq. NH$_4$Cl solution, sat. aq. NaHCO$_3$ solution and water, dried over MgSO$_4$ and concentrated in vacuo to give a crude product which is diluted with ether. The obtained suspension is filtered. The residue is washed with ether and dried in vacuo to give the desired product which is used without further purification. LC-MS: $t_R$=0.81 min; [M+H]$^+$=291.3.

A.1.10 Synthesis of thiazole-4-carboxylic Acid Derivatives (General Procedure)

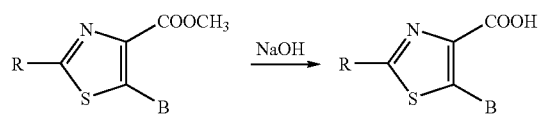

A solution of the respective thiazole-4-carboxylic acid ester (96.2 mmol) in a mixture of THF (150 mL) and either MeOH or isopropanol (50 mL) is treated with an aq. NaOH solution (1.0 M, 192 mL). After stirring for 3 h a white suspension is formed and the organic volatiles are removed in vacuo. The remaining mixture is diluted with water (100 mL), cooled in an ice-bath and made acidic (pH=3-4) by addition of aq. HCl solution (1.0 M). The suspension is filtered and the residue is washed with cold water. After drying the desired acid is obtained as a white solid.

2-Methyl-5-o-tolyl-thiazole-4-carboxylic Acid prepared by saponification of 2-methyl-5-o-tolyl-thiazole-4-carboxylic acid methyl ester. LC-MS: $t_R$=0.80 min; [M+H]$^+$=234.3.

2-Methyl-5-m-tolyl-thiazole-4-carboxylic Acid prepared by saponification of 2-methyl-5-m-tolyl-thiazole-4-carboxylic acid methyl ester. LC-MS: $t_R$=0.83 min; [M+H]$^+$=234.0.

2-Methyl-5-p-tolyl-thiazole-4-carboxylic Acid prepared by saponification of 2-methyl-5-p-tolyl-thiazole-4-carboxylic acid methyl ester. LC-MS: $t_R$=0.83 min; [M+H]$^+$=234.0.

5-(4-Ethyl-phenyl)-2-methyl-thiazole-4-carboxylic Acid prepared by saponification of 5-(4-ethyl-phenyl)-2-methyl-thiazole-4-carboxylic acid methyl ester. LC-MS: $t_R$=0.88 min; [M+H]$^+$=248.0.

5-(2-Fluoro-phenyl)-2-methyl-thiazole-4-carboxylic Acid prepared by saponification of 5-(2-fluoro-phenyl)-2-methyl-thiazole-4-carboxylic acid methyl ester. LC-MS: $t_R$=0.78 min; [M+H]$^+$=238.3.

5-(3-Fluoro-phenyl)-2-methyl-thiazole-4-carboxylic Acid prepared by saponification of 5-(3-fluoro-phenyl)-2-methyl-thiazole-4-carboxylic acid methyl ester. LC-MS: $t_R$=0.82 min; [M+H]$^+$=238.1.

5-(4-Fluoro-phenyl)-2-methyl-thiazole-4-carboxylic Acid prepared by saponification of 5-(4-fluoro-phenyl)-2-methyl-thiazole-4-carboxylic acid methyl ester. $^1$H-NMR (DMSO-d$_6$): δ=2.67 (s, 3H); 7.27 (m, 2H); 7.53 (m, 2H); 12.89 (br.s, 1H).

2-Methyl-5-(3-trifluoromethyl-phenyl)-thiazole-4-carboxylic Acid prepared by saponification of 2-methyl-5-(3-trifluoromethyl-phenyl)-thiazole-4-carboxylic acid methyl ester. LC-MS: $t_R$=0.88 min; [M+H]$^+$=288.0.

5-(3-Chloro-phenyl)-2-methyl-thiazole-4-carboxylic Acid prepared by saponification of 5-(3-chloro-phenyl)-2-methyl-thiazole-4-carboxylic acid methyl ester. LC-MS: $t_R$=0.84 min; [M+H]$^+$=254.0.

5-(3,4-Dimethyl-phenyl)-2-methyl-thiazole-4-carboxylic Acid prepared by saponification of 5-(3,4-dimethyl-phenyl)-2-methyl-thiazole-4-carboxylic acid methyl ester. LC-MS: $t_R$=0.86 min; $[M+H]^+$=248.3.

2-Amino-5-m-tolyl-thiazole-4-carboxylic Acid prepared by saponification of 2-amino-5-m-tolyl-thiazole-4-carboxylic acid methyl ester. LC-MS: $t_R$=0.65 min; $[M+H]^+$=235.0.

2-Amino-5-(3-fluoro-phenyl)-thiazole-4-carboxylic Acid prepared by saponification of 2-amino-5-(3-fluoro-phenyl)-thiazole-4-carboxylic acid methyl ester. LC-MS: $t_R$=0.62 min; $[M+H]^+$=239.1.

2-Bromo-5-m-tolyl-thiazole-4-carboxylic Acid prepared by saponification of 2-Bromo-5-m-tolyl-thiazole-4-carboxylic acid methyl ester. LC-MS (basic): $t_R$=0.57 min; $[M+H]^+$=297.8.

2-Methyl-5-phenyl-thiazole-4-carboxylic Acid prepared by saponification of 2-methyl-5-phenyl-thiazole-4-carboxylic acid methyl ester. LC-MS: $t_R$=0.77 min; $[M+H]^+$=220.3.

5-(3-Bromo-phenyl)-2-methyl-thiazole-4-carboxylic Acid prepared by saponification of 5-(3-bromo-phenyl)-2-methyl-thiazole-4-carboxylic acid methyl ester. LC-MS: $t_R$=0.90 min; $[M+H]^+$=297.8.

5-(4-Bromo-phenyl)-2-methyl-thiazole-4-carboxylic Acid prepared by saponification of 5-(4-bromo-phenyl)-2-methyl-thiazole-4-carboxylic acid methyl ester. LC-MS: $t_R$=0.85 min; $[M+H]^+$=298.2.

5-(4-Cyano-phenyl)-2-methyl-thiazole-4-carboxylic Acid prepared by saponification of 5-(4-cyano-phenyl)-2-methyl-thiazole-4-carboxylic acid methyl ester. LC-MS: $t_R$=0.82 min; $[M+H]^+$=245.1.

5-(2,3-Dichloro-phenyl)-2-methyl-thiazole-4-carboxylic Acid prepared by saponification of 5-(2,3-dichloro-phenyl)-2-methyl-thiazole-4-carboxylic acid methyl ester. LC-MS: $t_R$=0.86 min; $[M+H]^+$=288.2.

5-(2,3-Dimethyl-phenyl)-2-methyl-thiazole-4-carboxylic Acid prepared by saponification of 5-(2,3-dimethyl-phenyl)-2-methyl-thiazole-4-carboxylic acid methyl ester. LC-MS: $t_R$=0.84 min; $[M+H]^+$=248.3.

5-(3-Fluoro-2-methyl-phenyl)-2-methyl-thiazole-4-carboxylic Acid prepared by saponification of 5-(3-fluoro-2-methyl-phenyl)-2-methyl-thiazole-4-carboxylic acid methyl ester. LC-MS: $t_R$=0.83 min; $[M+H]^+$=252.2.

5-(3-Bromo-4-fluoro-phenyl)-2-methyl-thiazole-4-carboxylic Acid prepared by saponification of 5-(3-bromo-4-fluoro-phenyl)-2-methyl-thiazole-4-carboxylic acid methyl ester. LC-MS: $t_R$=0.86 min; $[M+H]^+$=316.2.

5-(3,4-Dichloro-phenyl)-2-methyl-thiazole-4-carboxylic Acid prepared by saponification of 5-(3,4-dichloro-phenyl)-2-methyl-thiazole-4-carboxylic acid methyl ester. LC-MS: $t_R$=0.88 min; $[M+H]^+$=288.2.

5-(3,4-Difluoro-phenyl)-2-methyl-thiazole-4-carboxylic Acid prepared by saponification of 5-(3,4-difluoro-phenyl)-2-methyl-thiazole-4-carboxylic acid methyl ester. LC-MS: $t_R$=0.82 min; $[M+H]^+$=256.3.

5-(3-Fluoro-4-methyl-phenyl)-2-methyl-thiazole-4-carboxylic Acid prepared by saponification of 5-(3-fluoro-4-methyl-phenyl)-2-methyl-thiazole-4-carboxylic acid methyl ester. LC-MS: $t_R$=0.89 min; $[M+H]^+$=252.0.

5-(3,5-Dimethyl-phenyl)-2-methyl-thiazole-4-carboxylic Acid prepared by saponification of 5-(3,5-dimethyl-phenyl)-2-methyl-thiazole-4-carboxylic acid methyl ester. LC-MS: $t_R$=0.86 min; $[M+H]^+$=248.3.

5-(3-Fluoro-5-trifluoromethyl-phenyl)-2-methyl-thiazole-4-carboxylic Acid prepared by saponification of 5-(3-fluoro-5-trifluoromethyl-phenyl)-2-methyl-thiazole-4-carboxylic acid methyl ester. LC-MS: $t_R$=0.94 min; $[M+H]^+$=306.0.

5-(2,4-Dimethyl-phenyl)-2-methyl-thiazole-4-carboxylic Acid prepared by saponification of 5-(2,4-dimethyl-phenyl)-2-methyl-thiazole-4-carboxylic acid methyl ester. LC-MS: $t_R$=0.85 min; $[M+H]^+$=248.3.

5-(2-Chloro-6-fluoro-phenyl)-2-methyl-thiazole-4-carboxylic Acid prepared by saponification of 5-(2-chloro-6-fluoro-phenyl)-2-methyl-thiazole-4-carboxylic acid methyl ester. LC-MS: $t_R$=0.82 min; $[M+H]^+$=272.2.

5-m-tolyl-thiazole-4-carboxylic Acid prepared by saponification of 5-m-tolyl-thiazole-4-carboxylic acid methyl ester.
LC-MS (basic): $t_R$=0.54 min; $[M+H]^+$=218.3.

5-(2-Fluoro-phenyl)-thiazole-4-carboxylic Acid prepared by saponification of 5-(2-fluoro-phenyl)-thiazole-4-carboxylic acid methyl ester. LC-MS: $t_R$=0.80 min; [M+H]$^+$=224.1.

5-(3-Fluoro-phenyl)-thiazole-4-carboxylic Acid prepared by saponification of 5-(3-fluoro-phenyl)-thiazole-4-carboxylic acid methyl ester. LC-MS: $t_R$=0.80 min; [M+H]$^+$=224.0.

5-Phenyl-thiazole-4-carboxylic Acid prepared by saponification of 5-phenyl-thiazole-4-carboxylic acid methyl ester.
LC-MS: $t_R$=0.78 min; [M+H]$^+$=206.2.

5-(3-Methoxy-phenyl)-thiazole-4-carboxylic Acid prepared by saponification of 5-(3-methoxy-phenyl)-thiazole-4-carboxylic acid methyl ester. LC-MS: $t_R$=0.81 min; [M+H]$^+$=236.1.

5-(3-Chloro-phenyl)-thiazole-4-carboxylic Acid prepared by saponification of 5-(3-chloro-phenyl)-thiazole-4-carboxylic acid methyl ester. LC-MS: $t_R$=0.85 min; [M+H]$^+$=240.0.

5-(3-Trifluoromethyl-phenyl)-thiazole-4-carboxylic Acid prepared by saponification of 5-(3-trifluoromethyl-phenyl)-thiazole-4-carboxylic acid methyl ester. LC-MS: $t_R$=0.89 min; [M+H]$^+$=274.0.

5-(4-Fluoro-phenyl)-thiazole-4-carboxylic Acid prepared by saponification of 5-(4-fluoro-phenyl)-thiazole-4-carboxylic acid methyl ester. LC-MS: $t_R$=0.80 min; [M+H]$^+$=224.1.

5-(3-Methanesulfonylamino-phenyl)-2-methyl-thiazole-4-carboxylic Acid prepared by saponification of 5-(3-methanesulfonylamino-phenyl)-2-methyl-thiazole-4-carboxylic acid methyl ester. LC-MS: $t_R$=0.77 min; [M+H]$^+$=313.2.

5-(3-Acetylamino-phenyl)-2-methyl-thiazole-4-carboxylic Acid prepared by saponification of 5-(3-acetylamino-phenyl)-2-methyl-thiazole-4-carboxylic acid methyl ester. LC-MS: $t_R$=0.74 min; [M+H]$^+$=277.2.

2-Cyclopropyl-5-phenyl-thiazole-4-carboxylic Acid prepared by saponification of 2-cyclopropyl-5-phenyl-thiazole-4-carboxylic acid methyl ester. LC-MS: $t_R$=0.91 min; [M+H]$^+$=246.4.

2-Cyclopropyl-5-m-tolyl-thiazole-4-carboxylic Acid prepared by saponification of 2-cyclopropyl-5-m-tolyl-thiazole-4-carboxylic acid methyl ester. LC-MS: $t_R$=0.90 min; [M+H]$^+$=260.2.

5-(4-Cyano-phenyl)-2-cyclopropyl-thiazole-4-carboxylic Acid prepared by saponification of 5-(4-Cyano-phenyl)-2-cyclopropyl-thiazole-4-carboxylic acid methyl ester. LC-MS: $t_R$=0.90 min; [M+H]$^+$=271.0.

2-Cyclopropyl-5-(3-fluoro-phenyl)-thiazole-4-carboxylic Acid prepared by saponification of 2-cyclopropyl-5-(3-fluoro-phenyl)-thiazole-4-carboxylic acid methyl ester. LC-MS: $t_R$=0.92 min; [M+H]$^+$=264.0.

2-Cyclopropyl-5-(3-fluoro-4-methyl-phenyl)-thiazole-4-carboxylic Acid prepared by saponification of 2-cyclopropyl-5-(3-fluoro-4-methyl-phenyl)-thiazole-4-carboxylic acid methyl ester. LC-MS: $t_R$=0.97 min; [M+H]$^+$=278.1.

A.1.11 Synthesis of 2-dimethylamino-thiazole-4-carboxylic Acid Derivatives (General Procedure)

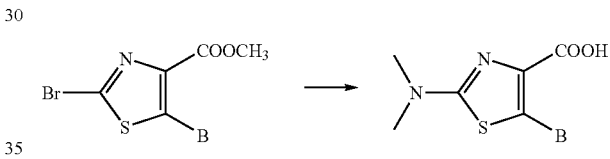

An aq. solution of dimethylamine (40%, 13 mL) is added to a solution of the respective 2-bromo-thiazole-4-carboxylic acid methyl ester derivative (6.71 mmol) in MeCN (38 mL). After 2 h an additional portion of an aq. dimethylamine solution (40%, 13 mL) is added. After stirring at RT for 2 d THF (13.6 mL), MeOH (6.8 mL) and aq. NaOH solution (1.0 M, 13.4 mL) are added successively and the mixture is stirred for 16 h. The solvents are removed in vacuo and the residue is diluted with water (30 mL). The suspension is made acidic (pH 3) by addition of aq. citric acid (10%) and extracted three times with EtOAc. The combined organic layers are washed twice with brine, dried over MgSO$_4$ and concentrated in vacuo to give the desired acid which is used without further purification.

2-Dimethylamino-5-(3-fluoro-phenyl)-thiazole-4-carboxylic Acid prepared by reaction of 2-bromo-5-(3-fluoro-phenyl)-thiazole-4-carboxylic acid methyl ester with dimethylamine. LC-MS: $t_R$=0.87 min; [M+H]$^+$=267.0.

2-Dimethylamino-5-phenyl-thiazole-4-carboxylic Acid prepared by reaction of 2-bromo-5-phenyl-thiazole-4-carboxylic acid methyl ester with dimethylamine. LC-MS: $t_R$=0.81 min; [M+H]$^+$=249.1.

2-Dimethylamino-5-m-tolyl-thiazole-4-carboxylic Acid prepared by reaction of 2-bromo-5-m-tolyl-thiazole-4-carboxylic acid methyl ester with dimethylamine. LC-MS: $t_R$=0.85 min; $[M+H]^+$=263.1.

A.1.12 Synthesis of 2-alkoxy-thiazole-4-carboxylic Acid Derivatives (General Procedure)

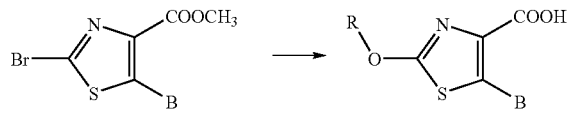

At 0° C. under an atmosphere of nitrogen the respective alcohol (0.96 mmol) is added to a suspension of sodium hydride (0.96 mmol) in THF (2.0 mL). After 5 min a solution of the respective 2-bromo-thiazole-4-carboxylic acid methyl ester (0.48 mmol) in DMF (0.2 mL) and THF (1.0 mL) is added dropwise. The mixture is stirred for 16 h at RT, cooled to 0° C. and treated with water (0.5 mL) and aq. NaOH solution (1.0 M, 0.5 mL). After 2 h the solvents are removed in vacuo and the residue is dissolved in warm water (1.0 mL). Ether is added, the layers are separated and the aq. layer is concentrated partially in vacuo to remove traces of ether. The mixture is cooled to 0° C. and made acidic (pH 4) by addition of aq. HCl (2.0 M). The precipitate is filtered off, washed with water and dried in vacuo to give the desired product.

2-Methoxy-5-m-tolyl-thiazole-4-carboxylic Acid prepared by reaction of 2-bromo-5-m-tolyl-thiazole-4-carboxylic acid methyl ester with MeOH. LC-MS: $t_R$=0.88 min; $[M+H]^+$=250.3.

A.2 Synthesis of thiazole-5-carboxylic Acid Derivatives

A.2.1 Synthesis of 2-chloro-3-oxo-propionic Ester Derivatives (General Procedure)

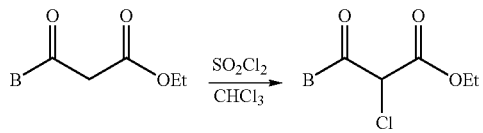

A mixture of the respective β-keto ester (5.52 mmol) and sulfuryl chloride (5.52 mmol) in chloroform (3.3 mL) is heated at reflux for 14 h, cooled to RT and washed with water. The solution is dried over MgSO4 and concentrated in vacuo to give the desired product which is used immediately in the next step without further purification.

2-Chloro-3-(3-fluoro-phenyl)-3-oxo-propionic Acid Ethyl Ester prepared by chlorination of 3-(3-fluoro-phenyl)-3-oxo-propionic acid ethyl ester.

2-Chloro-3-(4-fluoro-phenyl)-3-oxo-propionic Acid Ethyl Ester prepared by chlorination of 3-(4-fluoro-phenyl)-3-oxo-propionic acid ethyl ester.

A.2.2 Synthesis of thiazole-5-carboxylic Acid Ethyl Ester Derivatives (General Procedure)

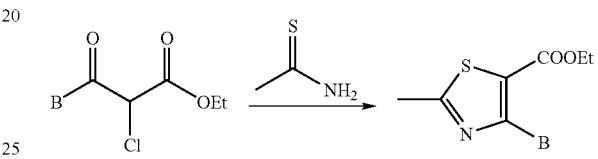

A mixture of the respective 2-chloro-3-oxo-propionic ester derivatives (5.52 mmol), thioacetamide (6.75 mmol) and NaHCO3 (6.07 mmol) in THF (12 mL) is heated at reflux for 6 h, filtered and concentrated in vacuo to give a crude product which is purified by FC (heptane to heptane/EtOAc 6/4).

4-(3-Fluoro-phenyl)-2-methyl-thiazole-5-carboxylic Acid Ethyl Ester prepared by reaction of 2-chloro-3-(3-fluoro-phenyl)-3-oxo-propionic acid ethyl ester with thioacetamide. LC-MS: $t_R$=0.95 min; $[M+H]^+$=266.1.

4-(4-Fluoro-phenyl)-2-methyl-thiazole-5-carboxylic Acid Ethyl Ester prepared by reaction of 2-chloro-3-(4-fluoro-phenyl)-3-oxo-propionic acid ethyl ester with thioacetamide. LC-MS: $t_R$=0.95 min; $[M+H]^+$=266.1.

A.2.3 Synthesis of thiazole-5-carboxylic Acid Derivatives (General Procedure)

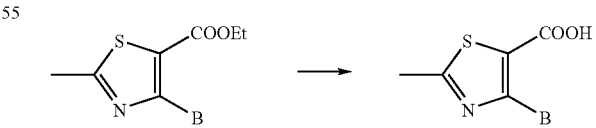

A mixture of the respective thiazole-5-carboxylic acid ethyl ester derivatives (3.38 mmol) and KOH (6.76 mmol) in EtOH (8.5 mL) and water (2.1 mL) is heated to reflux for 3 h, cooled to RT and concentrated in vacuo. Ice-cold water and hexane is added, the layers are separated and the aq. layer is made acidic by addition of aq. HCl (1.0 M). The obtained precipitate is filtered off, washed with water and dried in vacuo to give the desired acid.

4-(3-Fluoro-phenyl)-2-methyl-thiazole-5-carboxylic Acid prepared by saponification of 4-(3-fluoro-phenyl)-2-methyl-thiazole-5-carboxylic acid ethyl ester. LC-MS: $t_R$=0.80 min; [M+H]$^+$=238.3.

4-(4-Fluoro-phenyl)-2-methyl-thiazole-5-carboxylic Acid prepared by saponification of 4-(4-fluoro-phenyl)-2-methyl-thiazole-5-carboxylic acid ethyl ester. LC-MS: $t_R$=0.81 min; [M+H]$^+$=238.0.

A.3 Synthesis of oxazole-4-carboxylic Acid Derivatives

A.3.1 Synthesis of 2-acetylamino-3-(3-fluoro-phenyl)-3-oxo-propionic Acid Ethyl Ester A solution of 3-(3-fluoro-phenyl)-3-oxo-propionic acid ethyl ester (4.85 mmol) in acetic acid (1.90 mmol) is cooled to 10° C. and a solution of sodium nitrite (5.63 mmol) in water (0.68 mL) is added dropwise. The mixture is allowed to reach RT, stirred for 2 h, poured into water (10 mL) and cooled to 0° C. The precipitate is filtered off and dried by azeotropic removal of water with toluene to give crude 3-(3-fluoro-phenyl)-2-hydroxyimino-3-oxo-propionic acid ethyl ester which is dissolved in a mixture of acetic anhydride (1.38 mL) and acetic acid (1.80 mL). Sodium acetate (0.30 mmol), HgCl$_2$ (0.01 mmol) and zinc powder (14.6 mmol) are added successively. The mixture is stirred under reflux for 1 h, cooled to RT and filtered and the residue is washed with ether. The filtrate is washed three times with water and once with aq. K$_2$CO$_3$ solution (1.0 M). The organic layer is dried over MgSO$_4$ and concentrated in vacuo to give the desired crude product which is purified by FC (heptane to heptane/EtOAc 3/7). LC-MS: $t_R$=0.82 min; [M+H]$^+$=268.1.

A.3.2 Synthesis of 5-(3-fluoro-phenyl)-2-methyl-oxazole-4-carboxylic Acid Ethyl Ester At 0° C. SOCl$_2$ (0.88 mmol) is added to a stirred solution of 2-acetylamino-3-(3-fluoro-phenyl)-3-oxo-propionic acid ethyl ester (0.63 mmol) in CHCl$_3$ (0.38 mL). After 30 min the mixture is heated to reflux for 60 min. An additional portion of SOCl$_2$ (0.16 mmol) is added and the mixture is heated to reflux for further 60 min. An aq. K$_2$CO$_3$ solution (1.0 M) is added, the layers are separated and the aq. layer is extracted twice with ether. The combined organic layers are washed with water, dried over MgSO$_4$, filtered and concentrated in vacuo to give the desired ester which is used without further purification. LC-MS: $t_R$=0.93 min; [M+H]$^+$=250.3.

A.3.3 Synthesis of 5-(3-fluoro-phenyl)-2-methyl-oxazole-4-carboxylic Acid

A mixture of 5-(3-fluoro-phenyl)-2-methyl-oxazole-4-carboxylic acid ethyl ester (0.56 mmol), EtOH (0.63 mL) and aq. NaOH solution (2.0 M, 0.63 mL) is stirred for 2 h at RT and washed once with ether. The aq. layer is made acidic by addition of conc HCl and extracted twice with ether. The combined organic layers are dried over MgSO$_4$ and concentrated in vacuo to give the desired acid as a pure yellow solid. LC-MS (basic): $t_R$=0.49 min; [M–H]$^-$=220.3.

A.4 Synthesis of benzo[1,4]oxazine-carboxylic Acid Derivatives

A.4.1 Synthesis of 3-amino-2-hydroxy-benzoic Acid Methyl Ester

A solution of methyl 3-nitrosalicylate (26.6 mmol) in MeOH (50 mL) is treated with Pd/C (10%, 500 mg) and stirred at RT under a hydrogen atmosphere (1 bar) for 16 h. After filtration through celite and removal of the solvents the desired product is obtained which is used without further purification.
LC-MS: $t_R$=0.51 min; [M+H]$^+$=168.0.

A.4.2 Synthesis of 3-oxo-3,4-dihydro-2H-benzo[1,4]oxazine-8-carboxylic Acid Methyl Ester At RT chloro-acetyl chloride (29.0 mmol) is added dropwise to a solution of 3-amino-2-hydroxy-benzoic acid methyl ester (26.4 mmol) in DMF (100 mL). After 20 min K$_2$CO$_3$ (126 mmol) is added portionwise, the mixture is stirred for 16 h at RT and the solvents are removed in vacuo. Water and DCM are added, the layers are separated and the organic layer is washed with brine and dried over Na$_2$SO$_4$. The solvents are removed in vacuo to give a crude product which is used without further purification. LC-MS: $t_R$=0.68 min; [M+H]$^+$=208.0.

A.4.3 Synthesis of 4-methyl-3-oxo-3,4-dihydro-2H-benzo[1,4]oxazine-8-carboxylic Acid Methyl Ester K$_2$CO$_3$ (6.66 mmol) is added to a solution of 3-oxo-3,4-dihydro-2H-benzo[1,4]oxazine-8-carboxylic acid methyl ester (2.90 mmol) in DMF (10 mL). After 30 min methyl iodide (5.79 mmol) is added and the mixture is stirred for 2 h at 75° C. Cold water and EtOAc are added, the layers are separated and the aq. layer is extracted with EtOAc. The combined organic layers are washed with water and brine, dried over MgSO$_4$ and concentrated in vacuo to give a crude product which is used without further purification. LC-MS: $t_R$=0.76 min; [M+H]$^+$=222.2.

A.4.4 Synthesis of 3,4-dihydro-2H-benzo[1,4]oxazine-8-carboxylic Acid Methyl Ester Boron trifluoride diethyl etherate (10.1 mmol) is added dropwise to a mixture of 3-oxo-3,4-dihydro-2H-benzo[1,4]oxazine-8-carboxylic acid methyl ester (4.83 mmol) in THF (12 mL) to keep the temperature below 5° C. After 20 min sodium borohydride (10.1 mmol) is added and the mixture is stirred at 5° C. for 60 min. EtOAc (6.0 mL) and aq. HCl (1.0 M, 6.0 mL) are added dropwise. The mixture is made basic by addition of sat. aq. NaHCO$_3$ solution, the layers are separated and the aq. layer is extracted with EtOAc. The combined organic layers are dried over MgSO$_4$ and concentrated in vacuo to give a crude product which is purified by FC (heptane to heptane/EtOAc 3/7). LC-MS: $t_R$=0.69 min; [M+H]$^+$=194.0.

A.4.5 Synthesis of 4-methyl-3,4-dihydro-2H-benzo[1,4]oxazine-8-carboxylic Acid Methyl Ester K$_2$CO$_3$ (4.76 mmol) is added to a solution of 3,4-dihydro-2H-benzo[1,4]oxazine-8-carboxylic acid methyl ester (2.07 mmol) in DMF (3.0 mL). After 30 min methyl iodide (4.14 mmol) is added and the mixture is stirred for 2 h at 75° C. Cold water and EtOAc are added, the layers are separated and the aq. layer is extracted with EtOAc. The combined organic layers are washed with water and brine, dried over $MgSO_4$ and concentrated in vacuo to give a crude product which is used without further purification. LC-MS: $t_R$=0.83 min; $[M+H]^+$=208.1.

A.4.6 Synthesis of 2-amino-3-hydroxy-benzoic Acid Methyl Ester

A solution of (trimethylsilyl)diazomethane in hexane (2.0 M, 10.9 mmol) is added dropwise (10 min) to a mixture of 3-hydroxyanthranilic acid (9.93 mmol) in MeOH (10.5 mL) and toluene (42 mL). The mixture is stirred for 16 h, concentrated in vacuo, diluted with ether and EtOAc and washed several times with water. The organic layer is dried over $MgSO_4$ and concentrated under reduced pressure. The residue is purified by FC (heptane to heptane/EtOAc 7/3) to give the desired ester as a brown solid.
LC-MS: $t_R$=0.70 min; $[M+H]^+$=168.0.

A.4.7 Synthesis of 3-oxo-3,4-dihydro-2H-benzo[1,4]oxazine-5-carboxylic Acid Methyl Ester At RT chloro-acetyl chloride (8.06 mmol) is added dropwise to a solution of 2-amino-3-hydroxy-benzoic acid methyl ester (7.33 mmol) in DMF (50 mL). After 20 min $K_2CO_3$ (34.9 mmol) is added portionwise, the mixture is stirred for 16 h at RT and the solvents are removed in vacuo. Water and DCM are added, the layers are separated and the organic layer is washed with brine and dried over $Na_2SO_4$. The solvents are removed in vacuo to give a crude product which is purified by FC (heptane to heptane/EtOAc 6/4). LC-MS: $t_R$=0.82 min; $[M+CH_3CN+H]^+$=249.0.

A.4.8 Synthesis of 3,4-dihydro-2H-benzo[1,4]oxazine-5-carboxylic Acid Methyl Ester Boron trifluoride diethyl etherate (7.10 mmol) is added dropwise to a mixture of 3-oxo-3,4-dihydro-2H-benzo[1,4]oxazine-5-carboxylic acid methyl ester (3.38 mmol) in THF (10 mL) to keep the temperature below 5° C. After 20 min sodium borohydride (7.10 mmol) is added and the mixture is stirred at 5° C. for 90 min. EtOAc (6.0 mL) and aq. HCl (1.0 M, 6.0 mL) are added dropwise. The mixture is made basic by addition of aq. $Na_2CO_3$ solution, the layers are separated and the aq. layer is extracted with EtOAc. The combined organic layers are dried over $MgSO_4$ and concentrated in vacuo to give a crude product which is purified by FC (heptane to heptane/EtOAc 3/7). LC-MS: $t_R$=0.90 min; $[M+CH_3CN+H]^+$=235.3.

A.4.9 Synthesis of 4-methyl-3,4-dihydro-2H-benzo[1,4]oxazine-5-carboxylic Acid Methyl Ester $K_2CO_3$ (1.79 mmol) is added to a solution of 3,4-dihydro-2H-benzo[1,4]oxazine-5-carboxylic acid methyl ester (0.78 mmol) in DMF (1.0 mL). After 30 min methyl iodide (1.55 mmol) is added and the mixture is stirred for 2 h at 75° C. Cold water and EtOAc are added, the layers are separated and the aq. layer is extracted with EtOAc. The combined organic layers are washed with water and brine, dried over $MgSO_4$ and concentrated in vacuo to give a crude product which is used without further purification. LC-MS: $t_R$=0.71 min; $[M+H]^+$=208.1.

A.4.10 Synthesis of benzo[1,4]oxazine-carboxylic Acid Derivatives by Ester Hydrolysis (General Procedure)

A solution of NaOH (4.00 mmol) in a mixture of MeOH (3.0 mL) and water (6.8 mL) is added to the respective ester derivative (2.00 mmol). The mixture is stirred at 55° C. for 16 h, partially concentrated in vacuo to remove MeOH and made acidic by addition of aq. HCl (1.0M). The respective carboxylic acid precipitates and is collected by filtration.

3,4-Dihydro-2H-benzo[1,4]oxazine-8-carboxylic Acid prepared by saponification of 3,4-dihydro-2H-benzo[1,4]oxazine-8-carboxylic acid methyl ester. LC-MS: $t_R$=0.55 min; $[M+H]^+$=180.0.

4-Methyl-3,4-dihydro-2H-benzo[1,4]oxazine-8-carboxylic Acid prepared by saponification of 4-methyl-3,4-dihydro-2H-benzo[1,4]oxazine-8-carboxylic acid methyl ester. LC-MS: $t_R$=0.72 min; $[M+H]^+$=194.1.

3,4-Dihydro-2H-benzo[1,4]oxazine-5-carboxylic Acid prepared by saponification of 3,4-dihydro-2H-benzo[1,4]oxazine-5-carboxylic acid methyl ester. LC-MS: $t_R$=0.76 min; $[M+H]^+$=180.2.

4-Methyl-3,4-dihydro-2H-benzo[1,4]oxazine-5-carboxylic Acid prepared by saponification of 4-methyl-3,4-dihydro-2H-benzo[1,4]oxazine-5-carboxylic acid methyl ester. LC-MS: $t_R$=0.55 min; $[M+H]^+$=194.1.

3-Oxo-3,4-dihydro-2H-benzo[1,4]oxazine-8-carboxylic Acid prepared by saponification of 3-oxo-3,4-dihydro-2H-benzo[1,4]oxazine-8-carboxylic acid methyl ester. LC-MS: $t_R$=0.56 min; $[M+CH_3CN+H]^+$=235.0.

4-Methyl-3-oxo-3,4-dihydro-2H-benzo[1,4]oxazine-8-carboxylic Acid prepared by saponification of 4-methyl-3-oxo-3,4-dihydro-2H-benzo[1,4]oxazine-8-carboxylic acid methyl ester. LC-MS: $t_R$=0.64 min; $[M+CH_3CN+H]^+$=249.3.

A.5 Synthesis of Chroman-Carboxylic Acid Derivatives

A.5.1 Synthesis of 3-prop-2-ynyloxy-benzoic Acid Methyl Ester

A solution of propargyl bromide in toluene (80%, 68.7 mmol, 7.40 mL) is added to a solution of 3-hydroxy-benzoic acid methyl ester (48.6 mmol) in DMF (45 mL). $K_2CO_3$ is added and the mixture is stirred at RT for 4 h. Water and ether are added, the layers are separated and the organic layer is washed with aq. NaOH solution (5%) and brine. The solvents are removed in vacuo to give the desired ester as a pale yellow solid. $^1$H-NMR (CDCl$_3$): δ=2.56 (s, 1H); 3.94 (s, 3H); 4.76 (s, 2H); 7.20 (d, J=8.04 Hz, 1H); 7.39 (t, J=8.16 Hz, 1H); 7.66 (bs, 1H); 7.71 (d, J=7.78 Hz, 1H).

A.5.2 Synthesis of 2H-chromene-5-carboxylic Acid Methyl Ester

A solution of 3-prop-2-ynyloxy-benzoic acid methyl ester (10.5 mmol) in N,N-diethylaniline (20 mL) is heated to reflux for 15 h. The mixture is cooled to RT, diluted with ether and washed with aq. HCl (5%) and brine. The solvents are removed in vacuo and the residue is purified by FC (heptane to heptane/EtOAc 95/5) to give the desired chromene derivative. $^1$H-NMR (CDCl$_3$): δ=3.91 (s, 3H); 4.80 (bs, 2H); 5.93-5.98 (m, 1H); 6.99 (d, J=8.03 Hz, 1H); 7.16 (t, J=7.66 Hz, 1H); 7.34 (d, J=10.3 Hz, 1H); 7.50 (d, J=7.28 Hz, 1H).

A.5.3 Synthesis of 2H-chromene-5-carboxylic Acid

A solution of NaOH (7.26 mmol) in a mixture of MeOH (5.4 mL) and water (12.1 mL) is added to 2H-chromene-5-carboxylic acid methyl ester (4.84 mmol). The mixture is stirred at 55° C. for 3 h, partially concentrated in vacuo to remove MeOH and made acidic by addition of aq. HCl (1.0M). The desired carboxylic acid precipitates and is collected by filtration. $^1$H-NMR (DMSO-d$_6$): δ=4.75 (bs, 2H); 5.99-6.05 (m, 1H); 6.98 (d, J=7.78 Hz, 1H); 7.19 (t, J=7.78 Hz, 1H); 7.25 (d, J=10.3 Hz, 1H); 7.40 (d, J=7.78 Hz, 1H); 13.0 (bs, 1H).

A.5.4 Synthesis of chroman-5-carboxylic Acid

A solution of 2H-chromene-5-carboxylic acid (1.42 mmol) in MeOH (5.0 mL) is treated with Pd/C (10%, 50 mg) and stirred at RT under a hydrogen atmosphere (1 bar) for 16 h. After filtration through celite and removal of the solvents the desired product is obtained which is used without further purification. $^1$H-NMR (DMSO-d$_6$): δ=1.90 (m, 2H); 2.98 (m, 2H); 4.13 (m, 2H); 6.89-6.94 (m, 1H); 7.11-7.17 (m, 1H); 7.31-7.36 (m, 1H); 12.8 (bs, 1H).

A.5.5 Synthesis of Chroman

A solution of 4-chromanone (19.6 mmol) in HOAc (30 mL) is added to a suspension of zinc powder (445 mmol) in HOAc (60 mL). The mixture is stirred at 100° C. for 4 h, cooled to RT, filtered through celite and concentrated in vacuo. EtOAc and aq. NaOH solution (1.0 M) are added, the layers are separated and the aq. layer is extracted twice with EtOAc. The combined organic layers are dried over MgSO$_4$ and concentrated in vacuo to give the desired product which is used without further purification.
$^1$H-NMR (CDCl$_3$): δ=2.04 (m, 2H); 2.82 (m, 2H); 4.21 (m, 2H); 6.80-6.89 (m, 2H); 7.04-7.14 (m, 2H).

A.5.6 Synthesis of chroman-8-carboxylic Acid

At RT a solution of chroman (17.7 mmol) in ether (15 mL) is added over 10 min to a solution of n-BuLi (19.5 mmol) in a mixture of hexane (12.2 mL) and ether (15 mL). The mixture is stirred at reflux for 150 min, allowed to reach RT and poured into a mixture of dry ice and ether. Ice water is added and the layers are separated. The aq. layer is made acidic and extracted with a mixture of ether and EtOAc. The combined organic layers are washed with water, dried over Na$_2$SO$_4$ and concentrated in vacuo to give a crude product which is purified by FC (heptane/EtOAc 9/1 to EtOAc).
LC-MS: t$_R$=0.76 min; [M+CH$_3$CN+H]$^+$=220.1.

A.6 Synthesis of 2,3-dihydro-benzofuran-4-carboxylic Acid

Benzofuran-4-carboxylic acid (30.8 mmol, M. A. Eissenstat et al. *J. Med. Chem.* 1995, 38, 3094-3105) is added to a suspension of Pd/C (10%, 2.00 g) in EtOH (25 mL). Additional EtOH (75 mL) is added and the mixture is stirred at RT under a hydrogen atmosphere (4 bar) for 16 h. After filtration through celite and removal of the solvents the desired product is obtained which is used without further purification.
$^1$H-NMR (DMSO-d$_6$): δ=3.45 (t, J=8.79 Hz, 2H); 4.55 (t, J=8.79 Hz, 2H); 6.99 (d, J=7.78 Hz, 1H); 7.21 (t, J=7.91 Hz, 1H); 7.39 (d, J=7.78 Hz, 1H); 12.9 (bs, 1H).

A.7 Synthesis of imidazo[2,1-b]thiazole Derivatives

A.7.1 Synthesis of 2-amino-4-methyl-thiazole-5-carboxylic Acid Methyl Ester A mixture of thiourea (59.8 mmol) and 2-chloro-3-oxo-butyric acid methyl ester (59.8 mmol) in EtOH (140 mL) is heated at reflux for 14 h and concentrated in vacuo. Water and aq. NaHCO$_3$ are added and the mixture is extracted several times with EtOAc. The combined organic layers are dried and concentrated in vacuo to give the desired amino-thiazole derivative. LC-MS: t$_R$=0.51 min; [M+H]$^+$=173.0.

A.7.2 Synthesis of 3-methyl-imidazo[2,1-b]thiazole-2-carboxylic Acid Methyl Ester A mixture of bromoacetaldehyde diethyl acetal (29.3 mmol, 1.26 eq) in water (200 mL) is treated dropwise with conc. HCl (3.0 mL), stirred for 14 h at RT and heated for additional 30 min at 80° C. After cooling to RT NaHCO$_3$ (37.9 mmol) is added carefully and the mixture is stirred for 2 h and treated with 2-Amino-4-methyl-thiazole-5-carboxylic acid methyl ester (23.2 mmol, 1.00 eq). After 1 h dioxane (130 mL) is added and the mixture is stirred at RT for 30 min and at 100° C. for 48 h. The organic solvents are removed in vacuo and the mixture is extracted several times with DCM and chloroform. The combined organic layers are dried over Na$_2$SO$_4$ and concentrated in vacuo to give the desired ester which is used without further purification. LC-MS: t$_R$=0.55 min; [M+H]$^+$=197.0.

A.7.3 Synthesis of 2-bromo-3-oxo-butyric Acid Ethyl Ester

At −5° C. trimethylsilyl trifluoromethanesulfonate (36.9 mmol) is added dropwise to a solution of ethyl acetoacetate (30.7 mmol) and TEA (36.9 mmol) in DCM (50 mL). The solution is stirred for 90 min at 0° C. and treated over 30 min with a solution of bromine (30.7 mmol) in DCM (20 mL). After 60 min water (100 mL) is added, the layers are separated and the aq. layer is extracted three times with water (100 mL each). The organic layer is dried over MgSO$_4$ and concentrated under reduced pressure to give the desired product which is used without further purification. $^1$H-NMR (CDCl$_3$): δ=1.34 (t, J=7.16 Hz, 3H); 2.46 (s, 3H); 4.31 (q, J=7.20 Hz, 2H); 4.77 (s, 1H).

A.7.4 Synthesis of 2,6-dimethyl-imidazo[2,1-b]thiazole-5-carboxylic Acid Ethyl Ester A mixture of 5-methyl-2-aminothiazole (7.09 mmol) and 2-bromo-3-oxo-butyric acid ethyl ester (8.51 mmol) in acetone (17 mL) is stirred for 16 h at RT and for additional 7 h at reflux. The solvents are removed in vacuo, chloroform and sat aq. NaHCO$_3$ solution are added, the layers are separated and the aq. layer is extracted with chloroform. The combined organic layers are dried over MgSO$_4$ and concentrated in vacuo to give a crude product which is purified by FC (heptane to heptane/EtOAc 6/4). LC-MS: $t_R$=0.80 min; [M+H]$^+$=225.3.

A.7.5 Synthesis of 5-methyl-2-thioxo-2,3-dihydro-1H-imidazole-4-carboxylic Acid Ethyl Ester Pd/C (10%, 1.00 g) is added to a solution of 2-hydroxy-imino-3-oxo-butyric acid ethyl ester (62.8 mmol) in HCl (1.25 M in EtOH, 75 mL) and the mixture is stirred at RT under a hydrogen atmosphere (4 bar) for 48 h. After filtration through celite and removal of the solvents crude 2-amino-3-oxo-butyric acid ethyl ester hydrochloride is obtained which is dissolved in a mixture of water (220 mL), EtOH (30 mL) and conc HCl (37%, 2.5 mL). A solution of KSCN (49.9 mmol) in water (25 mL) is added and the mixture is stirred for 2 h at reflux. By cooling in an ice bath the desired product precipitates and is collected by filtration.
LC-MS: $t_R$=0.59 min; [M+H]$^+$=187.2.

A.7.6 Synthesis of 3,5-dimethyl-imidazo[2,1-b]thiazole-6-carboxylic Acid Ethyl Ester A mixture of 5-methyl-2-thioxo-2,3-dihydro-1H-imidazole-4-carboxylic acid ethyl ester (5.37 mmol) and chloroacetone (6.44 mmol) in EtOH (10 mL) is heated at reflux for 150 min. The solvents are removed in vacuo and a solution of POCl$_3$ (16.1 mmol) in MeCN (10 mL) is added. The mixture is stirred at reflux for 60 h, concentrated in vacuo and diluted with chloroform. Ice water is added and the mixture is neutralized by addition of Na$_2$CO$_3$. The layers are separated and the aq. layer is extracted with chloroform. The combined organic layers are dried over Na$_2$SO$_4$ and concentrated in vacuo to give a mixture of two regioisomers (see A.7.7) which are separated by FC (heptane to heptane/EtOAc 3/7). LC-MS: $t_R$=0.71 min; [M+H]$^+$=225.0.

A.7.7 Synthesis of 3,6-dimethyl-imidazo[2,1-b]thiazole-5-carboxylic Acid Ethyl Ester 3,6-dimethyl-imidazo[2,1-b]thiazole-5-carboxylic acid ethyl ester is obtained as a side-product in the synthesis of 3,5-dimethyl-imidazo[2,1-b]thiazole-6-carboxylic acid ethyl ester (see A.7.6). LC-MS: $t_R$=0.81 min; [M+H]$^+$=225.0.

A.7.8 Synthesis of 2,3,6-trimethyl-imidazo[2,1-b]thiazole-5-carboxylic Acid Ethyl Ester A mixture of 5-methyl-2-thioxo-2,3-dihydro-1H-imidazole-4-carboxylic acid ethyl ester (10.7 mmol) and 3-bromo-2-butanone (10.7 mmol) in EtOH (16 mL) is heated at reflux for 3 h. The solvents are removed in vacuo and POCl$_3$ (161 mmol) is added. The mixture is stirred at reflux for 3 h, concentrated in vacuo and diluted with chloroform. Ice water is added and the mixture is neutralized by addition of Na$_2$CO$_3$. The layers are separated and the aq. layer is extracted with chloroform. The combined organic layers are dried over Na$_2$SO$_4$ and concentrated in vacuo to give a mixture of two regioisomers which are separated by FC (heptane/EtOAc 9/1 to EtOAc). 2,3,6-trimethyl-imidazo[2,1-b]thiazole-5-carboxylic acid ethyl ester is obtained as minor isomer. LC-MS: $t_R$=0.84 min; [M+H]$^+$=239.0.

A.7.9 Synthesis of 2-(2,2-diethoxy-ethylsulfanyl)-5-methyl-1H-imidazole-4-carboxylic Acid Ethyl Ester A solution of sodium ethoxide (5.37 mmol) in EtOH (3.3 mL) is added to a solution of 5-methyl-2-thioxo-2,3-dihydro-1H-imidazole-4-carboxylic acid ethyl ester (5.37 mmol) in EtOH (7.0 mL). Bromoacetaldehyde diethyl acetal (5.37 mmol) is added and the mixture is stirred at reflux for 12 h. After cooling to RT the mixture is filtered and concentrated in vacuo to give the desired product which is used without further purification. LC-MS: $t_R$=0.70 min; [M+H]$^+$=303.4.

A.7.10 Synthesis of 3-hydroxy-5-methyl-2,3-dihydro-imidazo[2,1-b]thiazole-6-carboxylic Acid Ethyl Ester A mixture of 2-(2,2-diethoxy-ethylsulfanyl)-5-methyl-1H-imidazole-4-carboxylic acid ethyl ester (10.0 mmol) in aq. HCl (15%, 8.0 mL) is stirred for 1 h at RT and neutralized by addition of aq. Na$_2$CO$_3$ solution. The obtained precipitate is filtered off to give the desired product which is used without further purification.
LC-MS: $t_R$=0.55 min; [M+H]$^+$=229.3.

A.7.11 Synthesis of 5-methyl-imidazo[2,1-b]thiazole-6-carboxylic Acid Ethyl Ester 3-hydroxy-5-methyl-2,3-dihydro-imidazo[2,1-b]thiazole-6-carboxylic acid ethyl ester (4.00 mmol) is added to POCl$_3$ (9.3 mL), stirred at reflux for 3 h and concentrated in vacuo. Chloroform and ice-water are added successively and the mixture is neutralized by addition of Na$_2$CO$_3$. The layers are separated and the aq. layer is extracted with chloroform. The combined organic layers are dried over Na$_2$SO$_4$ and concentrated in vacuo to give the desired product which is purified by FC (heptane/EtOAc 1/1 to EtOAc). LC-MS: $t_R$=0.66 min; [M+H]$^+$=211.0.

A.7.12 Synthesis of N,N-dimethyl-N'-thiazol-2-yl-formamidine Derivatives (General Procedure)

N,N-Dimethylformamide dimethyl acetate (89.9 mmol, 2.0 eq) is added dropwise to a solution of the respective 2-aminothiazole (44.9 mmol, 1.0 eq) in toluene (30 mL). The mixture is heated at reflux for 22 h, cooled to RT and concentrated in vacuo. A small amount of hexane is added and the obtained precipitate is filtered off to give the respective formamidine derivative.

N,N-Dimethyl-N'-thiazol-2-yl-formamidine prepared by reaction of 2-aminothiazole with N,N-dimethylformamide dimethyl acetate. LC-MS: $t_R$=0.40 min; [M+H]$^+$=156.0.

N,N-Dimethyl-N'-(5-methyl-thiazol-2-yl)-formamidine prepared by reaction of 5-methyl-thiazol-2-ylamine with N,N-dimethylformamide dimethyl acetate. LC-MS: $t_R$=0.52 min; $[M+H]^+$=170.2.

N,N-Dimethyl-N'-(4-methyl-thiazol-2-yl)-formamidine prepared by reaction of 4-methyl-thiazol-2-ylamine with N,N-dimethylformamide dimethyl acetate. LC-MS: $t_R$=0.51 min; $[M+H]^+$=170.1.

A.7.13 Synthesis of 3-ethoxycarbonylmethyl-thiazol-3-ium Bromide Derivatives (General Procedure)

The respective N,N-dimethyl-N'-thiazol-2-yl-formamidine derivative (45.1 mmol, 1.00 eq) is added portionwise to vigorously stirred ethyl bromoacetate (225 mmol, 5.0 eq). After 2 h toluene (12 mL) is added and the mixture is stirred for 24 h. The obtained precipitate is filtered off and the residue is recrystallized from MeCN to give the respective thiazolium bromide.

2-(Dimethylamino-methyleneamino)-3-ethoxycarbonylmethyl-thiazol-3-ium Bromide prepared by reaction of ethyl bromoacetate with N,N-dimethyl-N'-thiazol-2-yl-formamidine. LC-MS: $t_R$=0.58 min; $[M+H]^+$=242.1.

2-(Dimethylamino-methyleneamino)-3-ethoxycarbonylmethyl-5-methyl-thiazol-3-ium Bromide prepared by reaction of ethyl bromoacetate with N,N-dimethyl-N'-(5-methyl-thiazol-2-yl)-formamidine. LC-MS: $t_R$=0.63 min; $[M+H]^+$=256.2.

2-(Dimethylamino-methyleneamino)-3-ethoxycarbonylmethyl-4-methyl-thiazol-3-ium Bromide prepared by reaction of ethyl bromoacetate with N,N-dimethyl-N'-(4-methyl-thiazol-2-yl)-formamidine. LC-MS: $t_R$=0.61 min; $[M+H]^+$=256.0.

A.7.14 Synthesis of imidazo[2,1-b]thiazole-5-carboxylic Acid Ethyl Ester Derivatives (General Procedure)

DBU (68.9 mmol, 1.58 eq) is added to a suspension of the respective thiazolium bromide derivative (43.6 mmol, 1.00 eq) in DMF (50 mL). The solution is stirred for 24 h and diluted with ice-cold water. The obtained precipitate is filtered off to give the respective imidazo-thiazole derivative.

Imidazo[2,1-b]thiazole-5-carboxylic Acid Ethyl Ester prepared by cyclisation of 2-(dimethylamino-methyleneamino)-3-ethoxycarbonyl-methyl-thiazol-3-ium bromide. LC-MS: $t_R$=0.76 min; $[M+H]^+$=197.0.

2-Methyl-imidazo[2,1-b]thiazole-5-carboxylic acid ethyl ester prepared by cyclisation of 2-(dimethylamino-methyleneamino)-3-ethoxycarbonyl-methyl-5-methyl-thiazol-3-ium bromide. LC-MS: $t_R$=0.83 min; $[M+H]^+$=211.0.

3-Methyl-imidazo[2,1-b]thiazole-5-carboxylic Acid Ethyl Ester prepared by cyclisation of 2-(dimethylamino-methyleneamino)-3-ethoxycarbonyl-methyl-4-methyl-thiazol-3-ium bromide. LC-MS: $t_R$=0.83 min; $[M+H]^+$=211.0.

A.7.15 Synthesis of imidazo[2,1-b]thiazole-carboxylic Acid Derivatives (General Procedure)

An aq. NaOH solution (1.0M, 23 mL) is added to a solution of the respective carboxylic ester derivative (11.3 mmol) in THF (12 mL) and MeOH (4.0 mL). The mixture is stirred for 16 h, the organic volatiles are removed in vacuo and water (10 mL) is added. The mixture is cooled to 0° C. and made acidic (pH=3-4) by addition of aq. HCl (1.0 M). The obtained precipitate is filtered off, washed with cold water and dried in vacuo to give the desired acid which is used without further purification.

3-Methyl-imidazo[2,1-b]thiazole-2-carboxylic Acid prepared by saponification of 3-methyl-imidazo[2,1-b]thiazole-2-carboxylic acid methyl ester. LC-MS: $t_R$=0.24 min; $[M+H]^+$=183.0.

2,6-Dimethyl-imidazo[2,1-b]thiazole-5-carboxylic Acid prepared by saponification of 2,6-dimethyl-imidazo[2,1-b]thiazole-5-carboxylic acid ethyl ester. LC-MS: $t_R$=0.55 min; $[M+H]^+$=197.3.

3,5-Dimethyl-imidazo[2,1-b]thiazole-6-carboxylic Acid prepared by saponification of 3,5-dimethyl-imidazo[2,1-b]thiazole-6-carboxylic acid ethyl ester. LC-MS: $t_R$=0.50 min; $[M+H]^+$=197.0.

3,6-Dimethyl-imidazo[2,1-b]thiazole-5-carboxylic Acid prepared by saponification of 3,6-dimethyl-imidazo[2,1-b]thiazole-5-carboxylic acid ethyl ester. LC-MS: $t_R$=0.51 min; $[M+H]^+$=197.0.

2,3,6-Trimethyl-imidazo[2,1-b]thiazole-5-carboxylic Acid prepared by saponification of 2,3,6-trimethyl-imidazo[2,1-b]thiazole-5-carboxylic acid ethyl ester. LC-MS: $t_R$=0.56 min; $[M+H]^+$=211.0.

5-Methyl-imidazo[2,1-b]thiazole-6-carboxylic Acid prepared by saponification of 5-methyl-imidazo[2,1-b]thiazole-6-carboxylic acid ethyl ester. LC-MS: $t_R$=0.39 min; $[M+H]^+$=183.0.

Imidazo[2,1-b]thiazole-5-carboxylic Acid prepared by saponification of imidazo[2,1-b]thiazole-5-carboxylic acid ethyl ester. LC-MS: $t_R$=0.39 min; $[M+H]^+$=169.0.

2-Methyl-imidazo[2,1-b]thiazole-5-carboxylic Acid prepared by saponification of 2-methyl-imidazo[2,1-b]thiazole-5-carboxylic acid ethyl ester. LC-MS: $t_R$=0.51 min; $[M+H]^+$=183.0.

3-Methyl-imidazo[2,1-b]thiazole-5-carboxylic Acid prepared by saponification of 3-methyl-imidazo[2,1-b]thiazole-5-carboxylic acid ethyl ester. LC-MS: $t_R$=0.53 min; $[M+H]^+$=183.0.

A.7.16 Synthesis of 6-trifluoromethyl-imidazo[2,1-b]thiazole

3-Bromo-1,1,1-trifluoroacetone (11.0 mmol) is added to a solution of 2-aminothiazole (10.0 mmol) in acetone (20 mL) and the mixture is stirred at reflux for 20 h. The obtained precipitate is filtered off, treated with hydrobromic acid (2.0 M, 40 mL), stirred at reflux for 1 h and cooled to RT. The mixture is made basic by addition of ammonium hydroxide solution (15%) and the resulting free base is crystallized from EtOH to give the desired product. LC-MS: $t_R$=0.78 min; $[M+H]^+$=192.95.

A.7.17 Synthesis of 6-trifluoromethyl-imidazo[2,1-b]thiazole-5-carboxylic Acid

At 0° C. POCl$_3$ (17.1 mmol) is added dropwise to a solution of DMF (20.6 mmol) in chloroform (5.0 mL). A solution of 6-trifluoromethyl-imidazo[2,1-b]thiazole (3.17 mmol) in chloroform (15 mL) is added dropwise at 0° C. and the mixture is stirred for 3 h at RT. After heating for 2.5 d to reflux the mixture is poured into ice, extracted three times with DCM, dried over MgSO$_4$ and concentrated under reduced pressure. DCM is added, the obtained precipitate is filtered off and the filtrate is concentrated in vacuo to give a crude product which is dissolved in tert.-butanol (19.5 mL). A solution of sodium chlorite (23.0 mmol) and sodium dihydrogen phosphate dihydrate (17.6 mmol) in water (19.5 mL) is added dropwise and the mixture is stirred for 90 min at RT. The solvents are partially removed in vacuo and the obtained precipitate is filtered off to give the desired product as a white solid. LC-MS: $t_R$=0.73 min; $[M+H]^+$=237.2.

A.7.18 Synthesis of 6-chloro-imidazo[2,1-b]thiazole-5-carboxylic Acid

A solution of sodium chlorite (230 mmol) and sodium dihydrogen phosphate dihydrate (176 mmol) in water (195 mL) is added dropwise to a solution of 6-chloro-imidazo[2,1-b]thiazole-5-carbaldehyde (26.8 mmol) in tert.-butanol (195 mL) and the mixture is stirred for 8 h at RT. The solvents are partially removed in vacuo and the obtained precipitate is filtered off. The filtrate is made acidic and the obtained precipitate is filtered off to give the desired product as a white solid.
LC-MS: $t_R$=0.67 min; $[M+H]^+$=202.9.

A.8 Synthesis of benzoxazole-7-carboxylic Acid

A solution of 3-amino-2-hydroxy-benzoic acid (12.5 mmol) in trimethyl orthoformate (19.2 mL) is heated to reflux for 20 h and concentrated in vacuo. The residue is washed three times with hot MeOH, the filtrates are combined and the solvent is removed in vacuo to give the desired product which is used without further purification. $^1$H-NMR (DMSO-d$_6$): δ=13.4 (bs, 1H); 8.87 (s, 1H); 8.08 (d, J=8.0 Hz, 1H); 7.96 (d, J=7.5 Hz, 1H); 7.52 (t, J=7.9 Hz, 1H).

A.9 Synthesis of 2-methyl-benzoxazole-7-carboxylic Acid

A solution of 3-amino-2-hydroxy-benzoic acid (9.40 mmol) and p-toluenesulfonic acid monohydrate (0.34 mmol) in triethyl orthoacetate (5.77 mL) is heated to reflux for 5 h and concentrated in vacuo. The residue is washed with ether and dried in vacuo to give the desired product which is used without further purification.
LC-MS: $t_R$=0.67 min; $[M+H]^+$=178.0.

A.10 Synthesis of benzoxazole-4-carboxylic Acid

A solution of 2-amino-3-hydroxy-benzoic acid (13.1 mmol) in trimethyl orthoformate (20.0 mL) is refluxed for 4 h, cooled to RT and concentrated in vacuo to give a crude product which is used without further purification.
LC-MS: $t_R$=0.66 min; $[M+H]^+$=164.1.

A.11 Synthesis of 2-Methyl-benzoxazole-4-carboxylic Acid

A.11.1 Synthesis of 2-Methyl-benzoxazole-4-carboxylic Acid Ethyl Ester

A mixture of 2-amino-3-hydroxy-benzoic acid ethyl ester (5.52 mmol; J. Reisch, G. M. K. B. Gunaherath Monatshefte für Chemie, 1988, 119, 1169-1178), acetyl chloride (6.07 mmol), NEt$_3$ (6.07 mmol) and pyridinium p-toluenesulfonate (1.47 mmol) in xylene (60 mL) is heated at reflux for 16 h, cooled to RT, diluted with EtOAc and washed with water. The organic layer is dried over MgSO$_4$ and concentrated in vacuo to give a crude product which is purified by FC (gradient: heptane to heptane/EtOAc 6/4). LC-MS: $t_R$=0.81 min; $[M+H]^+$=206.0.

A.11.2 Synthesis of 2-Methyl-benzoxazole-4-carboxylic Acid

At 0° C. an aq. KOH solution (1.0 M, 2.40 mL) is added to a solution of 2-methyl-benzoxazole-4-carboxylic acid ethyl ester (0.98 mmol) in MeOH (5.0 mL) and stirred for 30 min. The mixture is allowed to reach RT, stirred for additional 60 min and made acidic by addition of aq. HCl (2.0 M). After removal of MeOH under reduced pressure the obtained precipitate is filtered off to give the desired product which is dried in vacuo. $^1$H-NMR (DMSO-d$_6$): δ=2.64 (s, 3H); 7.41 (t, J=8.0 Hz, 1H); 7.83 (d, J=7.8 Hz, 1H); 7.88 (d, J=8.0 Hz, 1H); 12.8 (bs, 1H).

A.12 Synthesis of benzothiazole-7-carboxylic Acid

A.12.1 Synthesis of 3-thioureido-benzoic Acid Methyl Ester

At −10° C. sulfuric acid (0.46 mL) is added dropwise to a solution of methyl 3-aminobenzoate (17.2 mmol) in chlorobenzene (19 mL). After 15 min KSCN (18.2 mmol) is added portionwise over 30 min. The mixture is treated with 18-crown-6, heated to 100° C. for 16 h and allowed to cool to RT. After 4 h the obtained precipitate is filtered off and washed successively with chlorobenzene (33 mL) and hexane (three times 130 mL). The residue is diluted with water (390 mL) and the suspension is stirred for 30 min. After filtration the residue is washed twice with water (130 ml, each), concentrated in vacuo and dried additionally by azeotropic removal of water with toluene. The obtained product is used without further purification.

LC-MS: $t_R$=0.66 min; [M+H]$^+$=211.0.

A.12.2 Synthesis of 2-amino-benzothiazole-7-carboxylic Acid Methyl Ester

At 0° C. a solution of bromine (13.4 mmol) in acetic acid (9.4 mL) is added dropwise to a vigorously stirred solution of 3-thioureido-benzoic acid methyl ester (12.5 ml) in acetic acid (37 mL). The mixture is allowed to reach RT, stirred at 70° C. for 4 h and cooled to RT. Ether is added and the precipitate is filtered off. The residue is stirred vigorously in a sat aq. NaHCO$_3$ solution, filtered off and washed with water. The obtained solid is dried in vacuo to give the desired product which is used without further purification. LC-MS: $t_R$=0.62 min; [M+H]$^+$=209.0.

A.12.3 Synthesis of benzothiazole-7-carboxylic Acid Methyl Ester

Isoamyl nitrite (22.0 mmol) is added to a solution of 2-amino-benzothiazole-7-carboxylic acid methyl ester (10.1 mmol) in THF (29 mL). The mixture is heated to reflux for 4 h, the solvents are removed in vacuo and the residue is purified by FC (gradient: heptane to EtOAc/heptane 4/6) to give the desired product.

LC-MS: $t_R$=0.85 min; [M+H]$^+$=194.0.

A.12.4 Synthesis of benzothiazole-7-carboxylic Acid

At 0° C. an aq. NaOH solution (50%, 6.0 mL) is added to a solution of benzothiazole-7-carboxylic acid methyl ester in a mixture of MeOH (39 mL), THF (11.7 mL) and water (3.0 mL). The mixture is stirred for 4 h and concentrated in vacuo. At 0° C. water (60 mL) is added and the mixture is made acidic (pH 5) by addition of conc. HCl. After 30 min the precipitate is filtered off, washed with water and dried in vacuo to give the desired product.

LC-MS: $t_R$=0.77 min; [M+CH$_3$CN+H]$^+$=221.1.

A.13 Synthesis of 7-fluoro-benzofuran-4-carboxylic Acid

A.13.1 Synthesis of 4-fluoro-3-hydroxy-benzoic Acid Ethyl Ester

A solution of 4-fluoro-3-hydroxy-benzoic acid (32.0 mmol) in EtOH (120 mL) is treated with conc. sulfuric acid (25.7 mL) and heated to reflux for 16 h. Water (600 mL), sodium bicarbonate (100 g) and ether (300 mL) are added successively, the layers are separated and the aq. layer is extracted twice with ether. The combined organic layers are washed twice with brine, dried over MgSO$_4$ and concentrated in vacuo to give the desired product which is used without further purification. $^1$H-NMR (DMSO-d$_6$): δ=7.75 (d, J=8.5 Hz, 1H); 7.58-7.63 (m, 1H); 7.12 (t, J=9.3 Hz, 1H); 6.21 (bs, 1H); 4.39 (q, J=7.0 Hz, 2H); 1.40 (t, J=7.0 Hz, 3H).

A.13.2 Synthesis of 3-allyloxy-4-fluoro-benzoic Acid Ethyl Ester

K$_2$CO$_3$ (96.9 mmol) and 3-bromo-1-propen (64.6 mmol) are added to a solution of 4-fluoro-3-hydroxy-benzoic acid ethyl ester (32.3 mmol) in acetone (50 mL). The mixture is heated to reflux for 16 h, filtered and cooled to RT. The solvents are removed in vacuo to give the desired product which is used without further purification. LC-MS: $t_R$=1.01 min; [M+CH$_3$CN+H]$^+$=266.0.

A.13.3 Synthesis of 2-allyl-4-fluoro-3-hydroxy-benzoic Acid Ethyl Ester

3-Allyloxy-4-fluoro-benzoic acid ethyl ester (30.4 mmol) is heated to 190° C. for 19 h, cooled to RT and purified by FC (gradient: heptane to heptane/EtOAc 9/1) to give the desired product as an orange oil. LC-MS: $t_R$=0.93 min; [M+H]$^+$=225.0.

A.13.4 Synthesis of 7-fluoro-2-hydroxy-2,3-dihydro-benzofuran-4-carboxylic Acid Ethyl Ester At −78° C. ozone is passed through a solution of 2-allyl-4-fluoro-3-hydroxy-benzoic acid ethyl ester (9.68 mmol) in a mixture of DCM (37 mL) and MeOH (4 mL) for 40 min. After further 20 min nitrogen gas is passed through the mixture. DMS (25.7 mmol) is added and the mixture is allowed to reach RT during 3 h. DCM and water are added, the layers are separated and the aq. layer is extracted twice with DCM. The combined organic layers are washed with brine, dried over Na$_2$SO$_4$ and concentrated in vacuo to give a mixture of 7-fluoro-2-hydroxy-2,3-dihydro-benzofuran-4-carboxylic acid ethyl ester and 7-fluoro-2-methoxy-2,3-dihydro-benzofuran-4-carboxylic acid ethyl ester which is used without purification in the next step.

LC-MS: $t_R$=0.85 min; [M+H]$^+$=227.0.

A.13.5 Synthesis of 7-fluoro-benzofuran-4-carboxylic Acid Ethyl Ester

A mixture of 7-fluoro-2-hydroxy-2,3-dihydro-benzofuran-4-carboxylic acid ethyl ester and 7-fluoro-2-methoxy-2,3-dihydro-benzofuran-4-carboxylic acid ethyl ester (1.15 g, see above) in toluene (6.0 mL) is added dropwise to a solution of PTSA (0.25 mmol) in toluene (5.0 mL) which is heated to reflux. Heating is continued for 5 h, an additional portion of PTSA (0.25 mmol) is added and the mixture is again heated to reflux for 7 h. The solvents are removed in vacuo and the residue is purified by FC (gradient: heptane to heptane/EtOAc 95/5) to give the desired product.

$^1$H-NMR (CDCl$_3$): δ=7.99 (dd, J=8.3 Hz, J=4.3 Hz, 1H); 7.78 (s, 1H); 7.44 (bs, 1H); 7.10 (t, J=9.3 Hz, 1H); 4.46 (q, J=7.0 Hz, 2H); 1.47 (t, J=7.0 Hz, 3H).

A.13.6 Synthesis of 7-fluoro-benzofuran-4-carboxylic Acid

A mixture of 7-fluoro-benzofuran-4-carboxylic acid ethyl ester (1.54 mmol) and NaOH (2.31 mmol) in MeOH (1.7 mL) and water (1.7 mL) is heated to 55° C. for 90 min. The mixture is concentrated vacuo and made acidic by addition of aq. HCl (1.0 M). The obtained precipitate is filtered off and dried in vacuo to give the desired product. $^1$H NMR (DMSO-d$_6$): δ=13.19 (bs, 1H); 8.25 (s, 1H); 7.89-7.94 (m, 1H); 7.41 (s, 1H); 7.36 (t, J=9.5 Hz, 1H).

A.14 Synthesis of 7-chloro-benzofuran-4-carboxylic Acid

A.14.1 Synthesis of 4-chloro-3-hydroxy-benzoic Acid Ethyl Ester

A solution of 4-chloro-3-hydroxy-benzoic acid (29.3 mmol) in EtOH (110 mL) is treated with conc. sulfuric acid (23.6 mL) and heated to reflux for 16 h. Water (600 mL), NaHCO$_3$ (100 g) and ether (300 mL) are added successively, the layers are separated and the aq. layer is extracted twice with ether. The combined organic layers are washed twice with brine, dried over MgSO$_4$ and concentrated in vacuo to give the desired product which is used without further purification.

$^1$H-NMR (CDCl$_3$): δ=7.73 (s, 1H); 7.58 (d, J=8.3 Hz, 1H); 7.40 (d, J=8.3 Hz, 1H); 5.87 (s, 1H); 4.39 (q, J=7.0 Hz, 2H); 1.41 (t, J=7.0 Hz, 3H).

A.14.2 Synthesis of 3-allyloxy-4-chloro-benzoic acid ethyl ester

K$_2$CO$_3$ (78.5 mmol) and 3-bromo-1-propen (52.3 mmol) are added to a solution of 4-chloro-3-hydroxy-benzoic acid ethyl ester (26.2 mmol) in acetone (50 mL). The mixture is heated to reflux for 16 h and cooled to RT. The solvents are removed in vacuo to give the desired product which is used without further purification. LC-MS: t$_R$=1.05 min; [M+H]$^+$=240.9.

A.14.3 Synthesis of 2-allyl-4-chloro-3-hydroxy-benzoic Acid Ethyl Ester

3-Allyloxy-4-chloro-benzoic acid ethyl ester (26.2 mmol) is heated to 190° C. for 19 h, cooled to RT and purified by FC (gradient: heptane to heptane/EtOAc 9/1) to give the desired product as a white solid. LC-MS: t$_R$=0.98 min; [M+H]$^+$=241.0.

A.14.4 Synthesis of a mixture of 7-chloro-2-hydroxy-2,3-dihydro-benzofuran-4-carboxylic Acid Ethyl Ester and 7-chloro-2-methoxy-2,3-dihydro-benzofuran-4-carboxylic Acid Ethyl Ester At −78° C. ozone is passed through a solution of 2-allyl-4-chloro-3-hydroxy-benzoic acid ethyl ester (13.6 mmol) in a mixture of DCM (52 mL) and MeOH (5.5 mL) for 40 min. After further 20 min nitrogen gas is passed through the mixture. DMS (36.1 mmol) is added and the mixture is allowed to reach RT during 3 h. DCM and water are added, the layers are separated and the aq. layer is extracted twice with DCM. The combined organic layers are washed with brine, dried over Na$_2$SO$_4$ and concentrated in vacuo to give a mixture of 7-chloro-2-hydroxy-2,3-dihydro-benzofuran-4-carboxylic acid ethyl ester and 7-chloro-2-methoxy-2,3-dihydro-benzofuran-4-carboxylic acid ethyl ester which is used without purification in the next step. LC-MS: t$_R$=0.89 min; [M+H]$^+$=243.0 (hydroxy) and t$_R$=0.95 min; [M+H]$^+$=257.0 (methoxy).

A.14.5 Synthesis of 7-chloro-benzofuran-4-carboxylic Acid Ethyl Ester

A mixture of 7-chloro-2-hydroxy-2,3-dihydro-benzofuran-4-carboxylic acid ethyl ester and 7-chloro-2-methoxy-2,3-dihydro-benzofuran-4-carboxylic acid ethyl ester (3.36 g, see above) in toluene (20 mL) is added dropwise to a solution of PTSA (0.69 mmol) in toluene (14 mL) which is heated to reflux. Heating is continued for 5 h, an additional portion of PTSA (0.69 mmol) is added and the mixture is again heated to reflux for 150 min. The solvents are removed in vacuo and the residue is purified by FC (gradient: heptane to heptane/EtOAc 95/5) to give the desired product.

$^1$H-NMR (CDCl$_3$): δ=7.95 (d, J=8.3 Hz, 1H); 7.81 (s, 1H); 7.45 (s, 1H); 7.38 (d, J=8.0 Hz, 1H); 4.47 (q, J=7.0 Hz, 2H); 1.48 (t, J=7.0 Hz, 3H).

7-chloro-2-methoxy-2,3-dihydro-benzofuran-4-carboxylic Acid Ethyl Ester is isolated as pure by-product after FC. $^1$H-NMR (CDCl$_3$): δ=7.54 (d, J=8.5 Hz, 1H); 7.25 (d, J=8.5 Hz, 1H); 5.79 (d, J=5.5 Hz, 1H); 4.37 (q, J=7.0 Hz, 2H); 3.67 (dd, J=18.3 Hz, J=6.5 Hz, 1H); 3.60 (s, 3H); 3.53 (d, J=18.1 Hz, 1H); 1.41 (t, J=7.0 Hz, 3H).

A.14.6 Synthesis of 7-chloro-benzofuran-4-carboxylic Acid

A mixture of 7-chloro-benzofuran-4-carboxylic acid ethyl ester (3.90 mmol) and NaOH (5.85 mmol) in MeOH (4.4 mL) and water (4.4 mL) is heated to 55° C. for 90 min. The mixture is concentrated in vacuo and made acidic by addition of aq. HCl (1.0 M). The obtained precipitate is filtered off and dried in vacuo to give the desired product. $^1$H-NMR (DMSO-d$_6$): δ=13.3 (bs, 1H); 8.27 (s, 1H); 7.89 (d, J=8.3 Hz, 1H); 7.56 (d, J=8.3 Hz, 1H); 7.42 (s, 1H).

A.15 Synthesis of 7-chloro-2-methoxy-2,3-dihydro-benzofuran-4-carboxylic Acid A mixture of 7-chloro-2-methoxy-2,3-dihydro-benzofuran-4-carboxylic acid ethyl ester (1.17 mmol) and NaOH (1.75 mmol) in MeOH (1.3 mL) and water (1.3 mL) is heated to 55° C. for 90 min. The mixture is concentrated in vacuo and made acidic by addition of aq. HCl (1.0 M). The obtained precipitate is filtered off and dried in vacuo to give the desired product. $^1$H-NMR (DMSO-d$_6$): δ=13.1 (bs, 1H); 7.45 (d, J=8.3 Hz, 1H); 7.38 (d, J=8.5 Hz, 1H); 5.87 (d, J=6.3 Hz, 1H); 3.67 (dd, J=18.1 Hz, J=6.0 Hz, 1H); 3.47 (s, 3H); 3.30 (d, 1H).

A.16 Synthesis of pyrrolo[2,1-b]thiazole-7-carboxylic Acid

A.16.1 Synthesis of pyrrolo[2,1-b]thiazole-7-carboxylic Acid Ethyl Ester

Under nitrogen atmosphere (trimethylsilyl)methyl trifluoromethanesulfonate (16.3 mmol) is added dropwise to a mixture of 2-methylthio-1,3-thiazole (15.5 mmol) in MeCN (75 mL). The mixture is treated with propynoic acid ethyl ester (23.2 mmol), kept with occasional shaking for 30 min at RT and added dropwise to a vigorously stirred solution of CsF (21.7 mmol) and propynoic acid ethyl ester (23.2 mmol) in MeCN (75 mL). After stirring for 1 h the mixture is concentrated in vacuo, diluted with DCM (100 mL), washed twice with water and twice with brine and dried over Na$_2$SO$_4$. The solvents are removed in vacuo and the residue is purified by FC (gradient: heptane to heptane/EtOAc 8/2) to give the desired product.

LC-MS: t$_R$=0.87 min; [M+H]$^+$=196.0.

A.16.2 Synthesis of pyrrolo[2,1-b]thiazole-7-carboxylic Acid

A mixture of pyrrolo[2,1-b]thiazole-7-carboxylic acid ethyl ester (5.12 mmol) and NaOH (7.68 mmol) in MeOH (5.8 mL) and water (5.8 mL) is heated to 55° C. for 23 h. The mixture is concentrated in vacuo and made acidic by addition of aq. HCl (1.0 M). The obtained precipitate is filtered off and dried in vacuo to give the desired product.
LC-MS: $t_R$=0.87 min; [M+H]$^+$=168.0.

A.17 Synthesis of 6-methyl-pyrrolo[2,1-b]thiazole-7-carboxylic acid

A.17.1 Synthesis of 6-bromo-pyrrolo[2,1-b]thiazole-7-carboxylic acid ethyl ester N-Bromosuccinimide (0.56 mmol) is added to a solution of pyrrolo[2,1-b]thiazole-7-carboxylic acid ethyl ester (0.56 mmol) in DCM (6.0 mL). After 30 min water (5.0 mL) is added, the layers are separated and the aq. layer is extracted with DCM (5.0 mL). The combined organic layers are dried over Na$_2$SO$_4$ and the solvents are removed in vacuo to give the desired product which is used without further purification.
LC-MS: $t_R$=1.02 min; [M+H]$^+$=273.9.

A.17.2 Synthesis of 6-methyl-pyrrolo[2,1-b]thiazole-7-carboxylic Acid Ethyl Ester Under nitrogen atmosphere a solution of dimethylzinc in toluene (1.2 M, 19.1 mL) is added to a mixture of 6-bromo-pyrrolo[2,1-b]thiazole-7-carboxylic acid ethyl ester (11.4 mmol) and [1,1'-bis(diphenylphosphino)ferrocene]dichloropalladium(II) (0.23 mmol, complex with CH$_2$Cl$_2$) in dioxane (35 mL). The mixture is heated to reflux for 2 h, stirred at RT for 12 h and diluted by addition of MeOH (2.3 mL) and TBME. The mixture is washed with aq. HCl (1.0 M) and water, dried over MgSO$_4$, concentrated in vacuo and purified by FC (gradient: heptane to heptane/EtOAc 8/2) to give the desired product. LC-MS: $t_R$=0.91 min; [M+H]$^+$=210.0.

A.17.3 Synthesis of 6-methyl-pyrrolo[2,1-b]thiazole-7-carboxylic Acid

A mixture of 6-methyl-pyrrolo[2,1-b]thiazole-7-carboxylic acid ethyl ester (7.29 mmol) and NaOH (10.9 mmol) in EtOH (11.8 mL) and water (11.8 mL) is heated to 75° C. for 3 d. The mixture is concentrated in vacuo and made acidic by addition of aq. HCl (1.0 M). The obtained precipitate is filtered off and dried in vacuo to give the desired product. LC-MS: $t_R$=0.73 min; [M+H]$^+$=182.0.

A.18 Synthesis of 2-Aryl-thiophene-3-carboxylic acid and 3-Aryl-thiophene-2-carboxylic Acid Derivatives (General Procedure)

A mixture of the respective bromo-thiophenecarboxylic acid (4.69 mmol), the respective arylboronic acid (4.69 mmol), isopropanol (10 mL), toluene (10 mL) and aq. K$_2$CO$_3$ solution (2.0 M, 11.7 mL) is degassed for 3 min with nitrogen. After addition of tetrakis(triphenylphosphine)palladium (0.14 mmol) the mixture is heated to 80° C., stirred until LC-MS indicated complete conversion (5 h to 3 d) and cooled to RT. Ether and aq. NaOH solution (2.0 M) are added, the layers are separated and the aq. layer is made acidic (pH 1) by addition of aq. HCl (2.0 M). The obtained precipitate is filtered off, washed with water (10 mL) and dried in vacuo to give the respective acid which is used without further purification.

2-m-Tolyl-thiophene-3-carboxylic Acid prepared by reaction of 2-bromo-thiophene-3-carboxylic acid with m-tolylboronic acid. LC-MS (basic): $t_R$=0.51 min; [M−H]$^-$=217.3.

2-p-Tolyl-thiophene-3-carboxylic Acid prepared by reaction of 2-bromo-thiophene-3-carboxylic acid with p-tolylboronic acid. LC-MS (basic): $t_R$=0.53 min; [M−H]$^-$=217.1.

2-(4-Fluoro-phenyl)-thiophene-3-carboxylic acid
prepared by reaction of 2-bromo-thiophene-3-carboxylic acid with 4-fluorophenyl-boronic acid. LC-MS (basic): $t_R$=0.50 min; [M−H]$^-$=221.1.

3-m-Tolyl-thiophene-2-carboxylic Acid prepared by reaction of 3-bromo-thiophene-2-carboxylic acid with m-tolylboronic acid. LC-MS (basic): $t_R$=0.49 min; [M−H]$^-$=217.2.

3-p-Tolyl-thiophene-2-carboxylic Acid prepared by reaction of 3-bromo-thiophene-2-carboxylic acid with p-tolylboronic acid. LC-MS (basic): $t_R$=0.50 min; [M−H]$^-$=217.2.

3-(4-Fluoro-phenyl)-thiophene-2-carboxylic Acid prepared by reaction of 3-bromo-thiophene-2-carboxylic acid with 4-fluorophenyl-boronic acid. LC-MS (basic): $t_R$=0.47 min; [M−H]$^-$=221.1.

A.19 Synthesis of (1S,2S,5R)-2-Aminomethyl-3-aza-bicyclo[3.1.0]hexane-3-carboxylic Acid Tert-butyl Ester

A.19.1 Synthesis of (1aS,1bS,4R,5aR)-4-Phenyl-tetrahydro-3-oxa-4a-aza-cyclopropa[a]pentalen-5-one

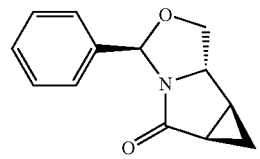

At RT NaH (oil free, 12.5 mmol) is added to DMSO (15 mL). The mixture is treated portionwise with trimethylsulfoxonium iodide (12.7 mmol) and stirred for 30 min. A solution of (2R,5S)-2-Phenyl-3-oxa-1-azabicyclo[3.3.0]oct-6-en-8-on (4.97 mmol, J. Org. Chem. 1999, 64, 547-555) in DMSO (3.0 mL) is added and the mixture is stirred for 16 h. After cooling to 4° C. water and TBME (100 mL) are added, the layers are separated and the aq. layer is extracted with TBME (100 mL). The combined organic layers are concentrated in vacuo and the residue is purified by FC (heptane/EtOAc 1/1) to give the desired product as a pale yellow oil. LC-MS (basic): $t_R$=0.77 min; [M+H]$^+$=216.3.

A.19.2 Synthesis of ((1S,2S,5R)-3-Benzyl-3-aza-bicyclo[3.1.0]hex-2-yl)-methanol At 0° C. a solution of (1aS,1bS,4R,5aR)-4-Phenyl-tetrahydro-3-oxa-4a-aza-cyclopropa[a]pentalen-5-one (13.9 mmol)

in THF (15 mL) is added dropwise to a suspension of lithium aluminum hydride (20.9 mmol) in THF (14 mL) and the mixture is stirred at reflux for 1 h. After cooling to 0° C. water (0.80 mL), aq. NaOH solution (15%, 0.80 mL), THF (15 mL) and additional water (2.0 mL) are added with caution and the mixture is stirred vigorously for 2 h. $Na_2SO_4$ is added, the suspension is filtered through celite and the solvents are removed in vacuo to give the desired product. LC-MS (basic): $t_R$=0.84 min; $[M+H]^+$=204.4.

A.19.3 Synthesis of (1S,2S,5R)-2-Hydroxymethyl-3-aza-bicyclo[3.1.0]hexane-3-carboxylic Acid Tert-butyl Ester A solution of ((1S,2S,5R)-3-Benzyl-3-aza-bicyclo[3.1.0] hex-2-yl)-methanol (4.27 mmol) and di-tent-butyl dicarbonate (6.41 mmol) in EtOAc (40 mL) is treated with Pd/C (850 mg, 50% $H_2O$) and stirred under a hydrogen atmosphere (1 bar) for 16 h. After filtration through celite and removal of the solvents the residue is purified by FC (cyclohexane to cyclohexane/EtOAc 2/1) to give the desired product.
LC-MS (basic): $t_R$=0.84 min; $[M+H]^+$=214.3.

A.19.4 Synthesis of (1S,2S,5R)-2-Formyl-3-aza-bicyclo[3.1.0]hexane-3-carboxylic Acid Tert-butyl Ester Dess-Martin periodinane (3.18 mmol) is added to a solution of (1S,2S,5R)-2-Hydroxymethyl-3-aza-bicyclo[3.1.0] hexane-3-carboxylic acid tert-butyl ester (3.24 mmol) in DCM (45 mL, saturated with water). Additional periodinane (0.80 mmol) is added after 2 h. After additional 2.5 h a sat. $NaHCO_3$ solution is added, the layers are separated and the organic layer is washed with aq. $Na_2S_2O_3$ solution. The aq. layer is extracted twice with DCM, the combined organic layers are concentrated in vacuo and the residue is purified by FC (pentane to pentane/ether 4/1) to give the desired product.
$^1$H-NMR ($CDCl_3$, two rotamers): rotamer A (major): δ=0.33-0.40 (m, 1H); 0.82-0.90 (m, 1H); 1.43 (s, 9H); 1.53-1.57 (m, 2H); 3.57 (dd, J=10.7 and 4.1 Hz, 1H); 3.70 (d, J=10.8 Hz, 1H); 4.21 (d, J=1.8 Hz, 1H); 9.59 (d, J=2.0 Hz, 1H); rotamer B (minor): δ=0.33-0.40 (m, 1H); 0.82-0.90 (m, 1H); 1.48 (s, 9H); 1.53-1.57 (m, 2H); 3.50 (dd, J=10.7 and 4.1 Hz, 1H); 3.61 (d, J=10.5 Hz, 1H); 4.40 (bs, 1H); 9.66 (bs, 1H).

A.19.5 Synthesis of (1S,2S,5R)-2-(Benzylamino-methyl)-3-aza-bicyclo[3.1.0]hexane-3-carboxylic Acid Tert-butyl Ester Benzylamine (2.95 mmol, 1.2 eq) is added to a solution of (1S,2S,5R)-2-Formyl-3-aza-bicyclo[3.1.0]hexane-3-carboxylic acid tert-butyl ester (2.46 mmol, 1.0 eq) in chloroform (6.0 mL). After 10 min the mixture is treated with sodium triacetoxyborohydride (2.95 mmol), stirred for additional 15 h and poured into a sat. aq. $NaHCO_3$ solution. The layers are separated and the aq. layer is extracted once with chloroform. The combined organic layers are washed twice with sat. $NaHCO_3$ solution and water. The solvents are removed in vacuo and the residue is dissolved in ether (30 mL). Aq. HCl (0.1 M, 40 mL) is added, the layers are separated and the organic layer is extracted twice with aq. HCl (0.1 M, 30 mL each). The combined aq. layers are washed with ether (20 mL), made alkaline by addition of NaOH solution (1.0 M, 20 mL) and extracted three times with ether (40 mL each). The combined organic layers are dried over $MgSO_4$ and concentrated in vacuo to give a crude product which is used without further purification. LC-MS (basic): $t_R$=0.96 min; $[M+H]^+$=303.3.

A.19.6 Synthesis of (1S,2S,5R)-2-Aminomethyl-3-aza-bicyclo[3.1.0]hexane-3-carboxylic acid tert-butyl ester A solution of (1S,2S,5R)-2-(Benzylamino-methyl)-3-aza-bicyclo[3.1.0]hexane-3-carboxylic acid tert-butyl ester (2.32 mmol) in EtOH (40 mL) is treated with Pd/C (5%, 460 mg) and stirred under a hydrogen atmosphere (1 bar) for 3 h. An additional amount of Pd/C (150 mg) is added and the mixture is stirred for further 2 h. After filtration through celite and removal of the solvents the desired product is obtained which is used without further purification.
LC-MS (basic): $t_R$=0.73 min; $[M+H]^+$=213.4.

A.20 Synthesis of N-substituted (1S,2S,5R)-2-(amino-methyl)-3-aza-bicyclo[3.1.0]-hexane Derivatives

A.20.1 Synthesis of (1S,2S,5R)-2-(amino-methyl)-3-aza-bicyclo[3.1.0]-hexane-3-carboxylic Acid Tert-butyl Ester Derivatives (General Procedure)

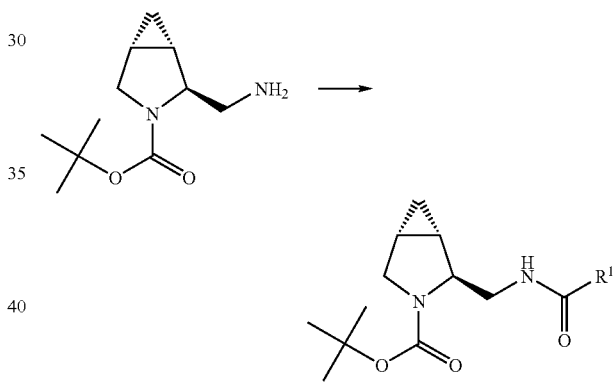

Method A:
To a solution of the respective carboxylic acid (0.85 mmol) in DMF (4.0 mL) is added successively DIPEA (2.40 mmol) and TBTU (0.97 mmol). The obtained mixture is stirred for 10 min and treated with a solution of (1S,2S,5R)-2-Aminomethyl-3-aza-bicyclo[3.1.0]hexane-3-carboxylic acid tert-butyl ester (0.84 mmol) in DMF (1.5 mL). After LC-MS indicated complete conversion (10 min-16 h) sat. aq. $NaHCO_3$ solution and ether (50 mL) are added, the layers are separated and the aq. layer is extracted twice with ether. The combined organic layers are washed twice with sat. $NaHCO_3$ solution, twice with citric acid (5% in water) and once with brine. After drying over $MgSO_4$ and removal of solvents in vacuo the respective amide is obtained which is either purified by FC (EtOAc/heptane) or used without further purification.
Method B:
To a solution of the respective carboxylic acid (9.42 mmol) in DCM or MeCN (60 mL) is added successively TBTU (10.4 mmol) and DIPEA (47.1 mmol). The obtained mixture is stirred for 10 min, treated with (1S,2S,5R)-2-Aminomethyl-3-aza-bicyclo[3.1.0]hexane-3-carboxylic acid tert-butyl ester (9.42 mmol) and stirred for additional 6 h. DCM is removed in vacuo, EtOAc and water are added, the layers are separated and the organic layer is washed four times with water and once with brine. After drying over MgSO$_4$ the solvents are removed in vacuo to give the respective amide which is either purified by FC (EtOAc/heptane) or used without further purification.

(1S,2S,5R)-2-{[(Benzofuran-4-carbonyl)-amino]-methyl}-3-aza-bicyclo[3.1.0]hexane-3-carboxylic Acid Tert-butyl Ester (Method A)

prepared by reaction of (1S,2S,5R)-2-Aminomethyl-3-aza-bicyclo[3.1.0]hexane-3-carboxylic acid tert-butyl ester with benzofuran-4-carboxylic acid (M. A. Eissenstat et al. *J. Med. Chem.* 1995, 38, 3094-3105).

LC-MS (basic): $t_R$=0.91 min; [M+H]$^+$=357.2.

(1S,2S,5R)-2-{[(6-Methyl-imidazo[2,1-b]thiazole-5-carbonyl)-amino]methyl}-3-aza-bicyclo[3.1.0]hexane-3-carboxylic Acid tert-butyl Ester (method A)

prepared by reaction of (1S,2S,5R)-2-Aminomethyl-3-aza-bicyclo[3.1.0]hexane-3-carboxylic acid tert-butyl ester with 6-methyl-imidazo[2,1-b]thiazole-5-carboxylic acid (A. Andreani et al. *Eur. J. Med. Chem.* 1982, 17, 271-274).

LC-MS: $t_R$=0.79 min; [M+H]$^+$=377.5.

(1S,2S,5R)-2-[(3-Chloro-benzoylamino)-methyl]-3-aza-bicyclo[3.1.0]hexane-3-carboxylic Acid Tert-butyl Ester (Method B)

prepared by reaction of (1S,2S,5R)-2-Aminomethyl-3-aza-bicyclo[3.1.0]hexane-3-carboxylic acid tert-butyl ester with 3-Chloro-benzoic acid.

LC-MS: $t_R$=1.04 min; [M+H]$^+$=351.0.

(1S,2S,5R)-2-{[(Imidazo[1,2-a]pyridine-3-carbonyl)-amino]-methyl}-3-aza-bicyclo[3.1.0]hexane-3-carboxylic Acid Tert-butyl Ester (Method A)

prepared by reaction of (1S,2S,5R)-2-Aminomethyl-3-aza-bicyclo[3.1.0]hexane-3-carboxylic acid tert-butyl ester with Imidazo[1,2-a]pyridine-3-carboxylic acid.

LC-MS: $t_R$=0.77 min; [M+H]$^+$=357.2.

(1S,2S,5R)-2-{[(2,3-Dihydro-benzofuran-4-carbonyl)-amino]-methyl}-3-aza-bicyclo[3.1.0]hexane-3-carboxylic Acid Tert-butyl Ester (Method A)

prepared by reaction of (1S,2S,5R)-2-Aminomethyl-3-aza-bicyclo[3.1.0]hexane-3-carboxylic acid tert-butyl ester with 2,3-Dihydro-benzofuran-4-carboxylic acid.

LC-MS: $t_R$=0.99 min; [M+H]$^+$=359.1.

(1S,2S,5R)-2-{[(2,3-Dihydro-thieno[3,4-b][1,4]dioxine-5-carbonyl)-amino]-methyl}-3-aza-bicyclo[3.1.0]hexane-3-carboxylic Acid Tert-butyl Ester (Method B)

prepared by reaction of (1S,2S,5R)-2-Aminomethyl-3-aza-bicyclo[3.1.0]hexane-3-carboxylic acid tert-butyl ester with 2,3-Dihydro-thieno[3,4-b][1,4]dioxine-5-carboxylic acid. LC-MS: $t_R$=0.96 min; [M+H]$^+$=381.1.

(1S,2S,5R)-2-{[(2-Ethyl-5-methyl-2H-pyrazole-3-carbonyl)-amino]-methyl}-3-aza-bicyclo[3.1.0]hexane-3-carboxylic Acid Tert-butyl Ester (Method B)

prepared by reaction of (1S,2S,5R)-2-Aminomethyl-3-aza-bicyclo[3.1.0]hexane-3-carboxylic acid tert-butyl ester with 2-Ethyl-5-methyl-2H-pyrazole-3-carboxylic acid.

$^1$H-NMR (CDCl$_3$): δ=0.19 (q, J=4.3 Hz, 1H); 0.73 (dt, J=7.7 Hz, J=5.5 Hz, 1H); 1.30-1.36 (m, 1H); 1.38-1.43 (m, 3H); 1.45 (s, 9H); 1.46-1.53 (m, 1H); 2.24 (s, 3H); 3.34-3.42 (m, 2H); 3.55-3.64 (m, 2H); 4.18 (dd, J=10.8 Hz, J=3.0 Hz, 1H); 4.47-4.62 (m, 2H); 6.36 (s, 1H); 7.76 (bs, 1H).

A.20.2 Synthesis of (1S,2S,5R)-2-(amino-methyl)-3-aza-bicyclo[3.1.0]-hexane Derivatives Substituted at the Side-Chain Nitrogen Atom (General Procedure)

A solution of HCl in dioxane (4.0 M, 4.0 mL) is added to a solution of the respective Boc-protected 3-aza-bicyclo [3.1.0]-hexane derivative (0.80 mmol) in isopropanol (1.0 mL) or dioxane (4.0 mL). After LC-MS indicated complete conversion (one to several hours) the mixture is concentrated in vacuo. The remaining residue is again dissolved in isopropanol (1.0 mL) and concentrated to dryness to give the respective deprotected product as a hydrochloride salt which is used without further purification.

Benzofuran-4-carboxylic Acid[(1S,2S,5R)-1-(3-aza-bicyclo[3.1.0]hex-2-yl)methyl]-amide prepared by deprotection of (1S,2S,5R)-2-{[(Benzofuran-4-carbonyl)-amino]-methyl}-3-aza-bicyclo[3.1.0]hexane-3-carboxylic acid tert-butyl ester.

LC-MS (basic): $t_R$=0.72 min; [M+H]$^+$=257.2.

6-Methyl-imidazo[2,1-b]thiazole-5-carboxylic Acid [(1S,2S,5R)-3-aza-bicyclo[3.1.0]hex-2-ylmethyl]-amide prepared by deprotection of (1S,2S,5R)-2-{[(6-Methyl-imidazo[2,1-b]thiazole-5-carbonyl)-amino]-methyl}-3-aza-bicyclo[3.1.0]hexane-3-carboxylic acid tert-butyl ester. LC-MS: $t_R$=0.51 min; [M+H]$^+$=277.0.

N-[(1S,2S,5R)-1-(3-Aza-bicyclo[3.1.0]hex-2-yl) methyl]-3-chloro-benzamide prepared by deprotection of (1S,2S,5R)-2-[(3-Chloro-benzoylamino)-methyl]-3-aza-bicyclo[3.1.0]hexane-3-carboxylic acid tert-butyl ester.

LC-MS: $t_R$=0.69 min; [M+H]$^+$=251.1.

Imidazo[1,2-a]pyridine-3-carboxylic acid[(1S,2S,5R)-1-(3-aza-bicyclo[3.1.0]hex-2-yl)methyl]-amide prepared by deprotection of (1S,2S,5R)-2-{[(Imidazo[1,2-a]pyridine-3-carbonyl)-amino]-methyl}-3-aza-bicyclo [3.1.0]hexane-3-carboxylic acid tert-butyl ester.

LC-MS: $t_R$=0.47 min; [M+H]$^+$=257.1.

2,3-Dihydro-benzofuran-4-carboxylic acid[(1S,2S, 5R)-1-(3-aza-bicyclo[3.1.0]hex-2-yl)methyl]-amide prepared by deprotection of (1S,2S,5R)-2-{[(2,3-Dihydro-benzofuran-4-carbonyl)-amino]-methyl}-3-aza-bicyclo[3.1.0]hexane-3-carboxylic acid tert-butyl ester.
LC-MS: $t_R$=0.64 min; [M+H]$^+$=259.2.

2,3-Dihydro-thieno[3,4-b][1,4]dioxine-5-carboxylic Acid[(1S,2S,5R)-1-(3-aza-bicyclo[3.1.0]hex-2-yl)methyl]-amide prepared by deprotection of (1S,2S,5R)-2-{[(2,3-Dihydro-thieno[3,4-b][1,4]dioxine-5-carbonyl)-amino]-methyl}-3-aza-bicyclo[3.1.0]hexane-3-carboxylic acid tert-butyl ester.
LC-MS: $t_R$=0.66 min; [M+H]$^+$=281.1.

2-Ethyl-5-methyl-2H-pyrazole-3-carboxylic Acid [(1S,2S,5R)-1-(3-aza-bicyclo[3.1.0]hex-2-yl)methyl]-amide prepared by deprotection of (1S,2S,5R)-2-{[(2-Ethyl-5-methyl-2H-pyrazole-3-carbonyl)-amino]-methyl}-3-aza-bicyclo[3.1.0]hexane-3-carboxylic acid tert-butyl ester.
$^1$H-NMR (CDCl$_3$): δ=0.88 (q, J=7.9 Hz, 1H); 0.93-1.00 (m, 1H); 1.48 (t, J=7.0 Hz, 3H); 1.61-1.68 (m, 1H); 1.75-1.83 (m, 1H); 2.47 (s, 3H); 3.29-3.40 (m, 1H); 3.42-3.49 (m, 1H); 3.52-3.61 (m, 1H); 3.91-4.03 (m, 2H); 4.67-4.84 (m, 2H); 7.19 (s, 1H); 9.36 (m, 1H); 9.58 (bs, 1H); 10.02 (bs, 1H).

A.21 Synthesis of 3-substituted (1S,2S,5R)-2-(amino-methyl)-3-aza-bicyclo[3.1.0]-hexane Derivatives A.21.1 Synthesis of (1S,2S,5R)-2-[(2,2,2-Trifluoro-acetylamino)-methyl]-3-aza-bicyclo[3.1.0]hexane-3-carboxylic Acid Tert-butyl Ester At 0° C. ethyl trifluoroacetate (41.9 mmol, 1.3 eq) is added to a solution of (1S,2S,5R)-2-Aminomethyl-3-aza-bicyclo[3.1.0]hexane-3-carboxylic acid tert-butyl ester (32.0 mmol, 1.00 eq) in THF (80 mL). The mixture is stirred at RT for 90 min and the solvents are removed in vacuo to give the desired product which is used without further purification in the next step. LC-MS: $t_R$=0.94 min; [M+H]$^+$=309.1.

A.21.2 Synthesis of N-[(1S,2S,5R)-1-(3-Aza-bicyclo[3.1.0]hex-2-yl)methyl]-2,2,2-trifluoro-acetamide A solution of HCl in dioxane (4 M, 30 mL) is added to a solution of (1S,2S,5R)-2-[(2,2,2-Trifluoro-acetylamino)-methyl]-3-aza-bicyclo[3.1.0]hexane-3-carboxylic acid tert-butyl ester (31.6 mmol) in dioxane (30 mL) and the mixture is stirred for 60 min at RT and for 30 min at 45° C. The solvents are removed in vacuo and the obtained solid is washed twice with a small volume of dioxane to give the desired product which is used without further purification in the next step.
LC-MS (basic): $t_R$=0.63 min; [M+H]$^+$=209.4.

A.21.3 Synthesis of 3-substituted N-[(1S,2S,5R)-1-(3-Aza-bicyclo[3.1.0]hex-2-yl)methyl]-2,2,2-trifluoro-acetamide Derivatives (General Procedure)

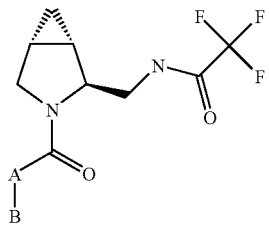

DIPEA (19.1 mmol) and TBTU (7.79 mmol) are added successively to a solution of the respective carboxylic acid (6.43 mmol) in DMF or MeCN (20 mL). A solution of N-[(1S,2S,5R)-1-(3-Aza-bicyclo[3.1.0]hex-2-yl)methyl]-2,2,2-trifluoro-acetamide (6.37 mmol) in DMF or DCM (20 mL) is added. The mixture is stirred until LC-MS indicated completion of reaction (60 min to 2 d) and poured into a mixture of ice, aq. HCl (0.5 M) and TBME. The layers are separated and the aq. layer is extracted with TBME. The combined organic layers are washed successively twice with sat aq. NaHCO$_3$ solution and once with brine. The solvents are removed in vacuo to give the respective product which is used without further purification in the next step.

2,2,2-Trifluoro-N-[(1S,2S,5R)-3-(2-methyl-5-m-tolyl-thiazole-4-carbonyl)-3-aza-bicyclo[3.1.0]hex-2-ylmethyl]-acetamide prepared by reaction of N-[(1S,2S,5R)-1-(3-Aza-bicyclo[3.1.0]hex-2-yl)methyl]-2,2,2-trifluoro-acetamide with 2-Methyl-5-m-tolyl-thiazole-4-carboxylic acid.
LC-MS (basic): $t_R$=0.91 min; [M+H]$^+$=424.3.

N-{(1S,2S,5R)-3-[5-(3-Chloro-phenyl)-2-methyl-thiazole-4-carbonyl]-3-aza-bicyclo[3.1.0]hex-2-ylmethyl}-2,2,2-trifluoro-acetamide prepared by reaction of N-[(1S,2S,5R)-1-(3-Aza-bicyclo[3.1.0]hex-2-yl)methyl]-2,2,2-trifluoro-acetamide with 5-(3-Chloro-phenyl)-2-methyl-thiazole-4-carboxylic acid.
LC-MS (basic): $t_R$=0.92 min; [M+H]$^+$=444.2.

N-{(1S,2S,5R)-3-[2-Amino-5-(3-fluoro-phenyl)-thiazole-4-carbonyl]-3-aza-bicyclo[3.1.0]hex-2-ylmethyl}-2,2,2-trifluoro-acetamide prepared by reaction of N-[(1S,2S,5R)-1-(3-Aza-bicyclo[3.1.0]hex-2-yl)methyl]-2,2,2-trifluoro-acetamide with 2-Amino-5-(3-fluoro-phenyl)-thiazole-4-carboxylic acid.
LC-MS (basic): $t_R$=0.80 min; [M+H]$^+$=429.2.

2,2,2-Trifluoro-N-[(1S,2S,5R)-3-(2-p-tolyl-thiophene-3-carbonyl)-3-aza-bicyclo[3.1.0]hex-2-ylmethyl]-acetamide prepared by reaction of N-[(1S,2S,5R)-1-(3-Aza-bicyclo[3.1.0]hex-2-yl)methyl]-2,2,2-trifluoro-acetamide with 2-p-tolyl-thiophene-3-carboxylic acid.
LC-MS: $t_R$=1.07 min; [M+H]$^+$=409.5.

2,2,2-Trifluoro-N-[(1S,2S,5R)-3-(2-m-tolyl-thiophene-3-carbonyl)-3-aza-bicyclo[3.1.0]hex-2-ylmethyl]-acetamide prepared by reaction of N-[(1S,2S,5R)-1-(3-Aza-bicyclo[3.1.0]hex-2-yl)methyl]-2,2,2-trifluoro-acetamide with 2-m-tolyl-thiophene-3-carboxylic acid.

LC-MS: $t_R$=1.07 min; [M+H]$^+$=409.2.

A.21.4 Synthesis of 3-substituted (1S,2S,5R)-2-(amino-methyl)-3-aza-bicyclo[3.1.0]-hexane Derivatives (General Procedure)

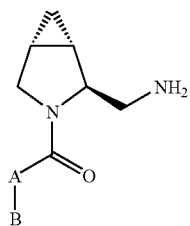

A sat aq. K$_2$CO$_3$ solution (12 mL) is added to a solution of the respective trifluoro-acetamide derivative (2.61 mmol) in MeOH (12 mL). The mixture is stirred for 3 h at 60° C. and partially concentrated in vacuo to remove MeOH. DCM is added, the layers are separated and the aq. layer is extracted three times with DCM. The combined organic extracts are dried over Na$_2$SO$_4$ and concentrated in vacuo to give the desired primary amine which is used without further purification.

((1S,2S,5R)-2-Aminomethyl-3-aza-bicyclo[3.1.0]hex-3-yl)-(2-methyl-5-m-tolyl-thiazol-4-yl)-methanone prepared by deprotection of 2,2,2-Trifluoro-N-[(1S,2S,5R)-3-(2-methyl-5-m-tolyl-thiazole-4-carbonyl)-3-aza-bicyclo[3.1.0]hex-2-ylmethyl]-acetamide.

LC-MS: $t_R$=0.75 min; [M+H]$^+$=328.1.

((1S,2S,5R)-2-Aminomethyl-3-aza-bicyclo[3.1.0]hex-3-yl)-[5-(3-chloro-phenyl)-2-methyl-thiazol-4-yl]-methanone prepared by deprotection of N-{(1S,2S,5R)-3-[5-(3-Chloro-phenyl)-2-methyl-thiazole-4-carbonyl]-3-aza-bicyclo[3.1.0]hex-2-ylmethyl}-2,2,2-trifluoro-acetamide.
LC-MS: $t_R$=0.75 min; [M+H]$^+$=348.0.

[2-Amino-5-(3-fluoro-phenyl)-thiazol-4-yl]-((1S,2S,5R)-2-aminomethyl-3-aza-bicyclo[3.1.0]hex-3-yl)-methanone prepared by deprotection of N-{(1S,2S,5R)-3-[2-Amino-5-(3-fluoro-phenyl)-thiazole-4-carbonyl]-3-aza-bicyclo[3.1.0]hex-2-ylmethyl}-2,2,2-trifluoro-acetamide.

LC-MS: $t_R$=0.69 min; [M+H]$^+$=333.1.

A.21.5 Synthesis of 3-substituted (1S,2S,5R)-2-(amino-methyl)-3-aza-bicyclo[3.1.0]-hexane Derivatives (General Procedure II)

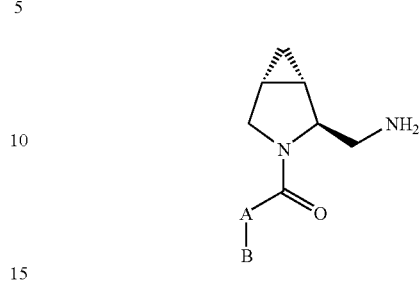

An aq. NaOH solution (1.0 M, 8.5 mL) is added to a solution of the respective trifluoro-acetamide derivative (4.10 mmol) in isopropanol (35 mL). The mixture is stirred for 3 h at RT and diluted with EtOAc and water. The layers are separated and the aq. layer is extracted once with EtOAc. The combined organic extracts are washed with water and brine, dried over MgSO$_4$ and concentrated in vacuo to give the desired primary amine which is used without further purification.

((1S,2S,5R)-2-Aminomethyl-3-aza-bicyclo[3.1.0]hex-3-yl)-(2-p-tolyl-thiophen-3-yl)-methanone prepared by deprotection of 2,2,2-Trifluoro-N-[(1S,2S,5R)-3-(2-p-tolyl-thiophene-3-carbonyl)-3-aza-bicyclo[3.1.0]hex-2-ylmethyl]-acetamide.

LC-MS: $t_R$=0.80 min; [M+H]$^+$=313.3.

((1S,2S,5R)-2-Aminomethyl-3-aza-bicyclo[3.1.0]hex-3-yl)-(2-m-tolyl-thiophen-3-yl)-methanone prepared by deprotection of 2,2,2-Trifluoro-N-[(1S,2S,5R)-3-(2-m-tolyl-thiophene-3-carbonyl)-3-aza-bicyclo[3.1.0]hex-2-ylmethyl]-acetamide.

LC-MS: $t_R$=0.79 min; [M+H]$^+$=313.4.

A.22 Synthesis of [(1S,2S,5R)-1-(3-Aza-bicyclo[3.1.0]hex-2-yl)methyl]-(5-bromo-pyrimidin-2-yl)-amine

A.22.1 Synthesis of (1S,2S,5R)-2-[(5-Bromo-pyrimidin-2-ylamino)-methyl]-3-aza-bicyclo[3.1.0]hexane-3-carboxylic Acid Tert-butyl Ester 5-Bromo-2-chloro-pyrimidine (18.4 mmol) is added to a solution of (1S,2S,5R)-2-aminomethyl-3-aza-bicyclo[3.1.0]hexane-3-carboxylic acid tert-butyl ester (14.1 mmol) in o-xylene (30 mL). K$_2$CO$_3$ (42.4 mmol) and DIPEA (42.4 mmol) are added successively and the mixture is heated to 140° C. for 17 h. The mixture is cooled to RT and diluted with EtOAc (100 mL) and water (100 mL). The layers are separated and the aq. layer is extracted with DCM (100 mL). The combined organic layers are dried over MgSO$_4$ and concentrated in vacuo. The obtained brownish solid is stirred in ether (75 mL). The suspension is filtered and washed with ether (25 mL) and the residue is dried in vacuo to give the desired product.

LC-MS: $t_R$=1.03 min; [M+H]$^+$=369.0.

A.22.2 Synthesis of [(1S,2S,5R)-1-(3-Aza-bicyclo[3.1.0]hex-2-yl)methyl]-(5-bromo-pyrimidin-2-yl)-amine A solution of HCl in dioxane (4.0 M, 22 mL) is added to a solution of (1S,2S,5R)-2-[(5-Bromo-pyrimidin-2-ylamino)-methyl]-3-aza-bicyclo[3.1.0]hexane-3-carboxylic acid tert-butyl ester (8.67 mmol) in dioxane (20 mL). After 90 min the solvents are removed in vacuo to give a crude product which is used without further purification. LC-MS: $t_R$=0.64 min; [M+H]$^+$=269.0.

B. Preparation of Examples

B.1 Synthesis of Carboxylic Amide Derivatives (General Procedure)

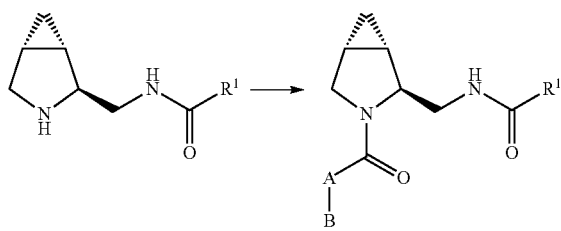

To a solution of the respective carboxylic acid (0.035 mmol, 1.2 eq) in either DMF (0.25 mL) or MeCN (0.35 mL) is added successively a solution of DIPEA (0.058 mmol, 2.0 eq) in DMF (0.15 mL) and a solution of TBTU (0.035 mmol, 1.2 eq) in DMF (0.15 mL). The obtained mixture is treated with a solution of the respective 3-aza-bicyclo[3.1.0]hexane derivative (0.029 mmol, 1.0 eq, free base or hydrochloride salt) and DIPEA (0.073 mmol) in DMF (0.15 mL). The mixture is shaken over night and purified by prep. HPLC (basic gradient) to give the respective amide derivatives.

Example 1

Benzofuran-4-carboxylic Acid[(1S,2S,5R)-3-(2-trifluoromethyl-benzoyl)-3-aza-bicyclo[3.1.0]hex-2-ylmethyl]-amide prepared by reaction of benzofuran-4-carboxylic acid[(1S,2S,5R)-1-(3-aza-bicyclo[3.1.0]hex-2-yl)methyl]-amide with 2-trifluoromethyl-benzoic acid.
LC-MS (basic): $t_R$=0.89 min; [M+H]$^+$=429.0.

Example 2

Benzofuran-4-carboxylic acid[(1S,2S,5R)-3-(biphenyl-2-carbonyl)-3-aza-bicyclo[3.1.0]hex-2-ylmethyl]-amide prepared by reaction of benzofuran-4-carboxylic acid[(1S,2S,5R)-1-(3-aza-bicyclo[3.1.0]hex-2-yl)methyl]-amide with biphenyl-2-carboxylic acid.
LC-MS (basic): $t_R$=0.94 min; [M+H]$^+$=437.1.

Example 3

Benzofuran-4-carboxylic acid[(1S,2S,5R)-3-(3-trifluoromethyl-benzoyl)-3-aza-bicyclo[3.1.0]hex-2-ylmethyl]-amide prepared by reaction of benzofuran-4-carboxylic acid[(1S,2S,5R)-1-(3-aza-bicyclo[3.1.0]hex-2-yl)methyl]-amide with 3-trifluoromethyl-benzoic acid.
LC-MS (basic): $t_R$=0.90 min; [M+H]$^+$=429.1.

Example 4

Benzofuran-4-carboxylic acid[(1S,2S,5R)-3-(2-methoxy-benzoyl)-3-aza-bicyclo[3.1.0]hex-2-ylmethyl]-amide
prepared by reaction of benzofuran-4-carboxylic acid[(1S,2S,5R)-1-(3-aza-bicyclo[3.1.0]hex-2-yl)methyl]-amide with 2-methoxy-benzoic acid.
LC-MS (basic): $t_R$=0.84 min; [M+H]$^+$=391.2.

Example 5

Benzofuran-4-carboxylic acid[(1S,2S,5R)-3-(2-methyl-5-p-tolyl-thiazole-4-carbonyl)-3-aza-bicyclo[3.1.0]hex-2-ylmethyl]-amide prepared by reaction of benzofuran-4-carboxylic acid[(1S,2S,5R)-1-(3-aza-bicyclo[3.1.0]hex-2-yl)methyl]-amide with 2-methyl-5-p-tolyl-thiazole-4-carboxylic acid. LC-MS (basic): $t_R$=0.89 min; [M+H]$^+$=472.1.

Example 6

Benzofuran-4-carboxylic acid{(1S,2S,5R)-3-[5-(4-ethyl-phenyl)-2-methyl-thiazole-4-carbonyl]-3-aza-bicyclo[3.1.0]hex-2-ylmethyl}-amide prepared by reaction of benzofuran-4-carboxylic acid[(1S,2S,5R)-1-(3-aza-bicyclo[3.1.0]hex-2-yl)methyl]-amide with 5-(4-ethyl-phenyl)-2-methyl-thiazole-4-carboxylic acid.
LC-MS (basic): $t_R$=0.93 min; [M+H]$^+$=486.1.

Example 7

Benzofuran-4-carboxylic acid{(1S,2S,5R)-3-[5-(4-fluoro-phenyl)-2-methyl-thiazole-4-carbonyl]-3-aza-bicyclo[3.1.0]hex-2-ylmethyl}-amide prepared by reaction of benzofuran-4-carboxylic acid[(1S,2S,5R)-1-(3-aza-bicyclo[3.1.0]hex-2-yl)methyl]-amide with 5-(4-fluoro-phenyl)-2-methyl-thiazole-4-carboxylic acid.
LC-MS (basic): $t_R$=0.90 min; [M+H]$^+$=476.1.

Example 8

Benzofuran-4-carboxylic acid[(1S,2S,5R)-3-(2-methyl-5-m-tolyl-thiazole-4-carbonyl)-3-aza-bicyclo[3.1.0]hex-2-ylmethyl]-amide prepared by reaction of benzofuran-4-carboxylic acid[(1S,2S,5R)-1-(3-aza-bicyclo[3.1.0]hex-2-yl)methyl]-amide with 2-methyl-5-m-tolyl-thiazole-4-carboxylic acid. LC-MS (basic): $t_R$=0.93 min; [M+H]$^+$=472.2.

Example 9

Benzofuran-4-carboxylic acid{(1S,2S,5R)-3-[5-(3-fluoro-phenyl)-2-methyl-thiazole-4-carbonyl]-3-aza-bicyclo[3.1.0]hex-2-ylmethyl}-amide prepared by reaction of Benzofuran-4-carboxylic acid[(1S,2S,5R)-1-(3-aza-bicyclo[3.1.0]hex-2-yl)methyl]-amide with 5-(3-Fluoro-phenyl)-2-methyl-thiazole-4-carboxylic acid.
LC-MS (basic): $t_R$=0.90 min; [M+H]$^+$=476.0.

Example 10

6-Methyl-imidazo[2,1-b]thiazole-5-carboxylic acid {(1S,2S,5R)-3-[5-(2-fluoro-phenyl)-2-methyl-thiazole-4-carbonyl]-3-aza-bicyclo[3.1.0]hex-2-ylmethyl}-amide prepared by reaction of 6-Methyl-imidazo[2,1-b]thiazole-5-carboxylic acid [(1S,2S,5R)-1-(3-aza-bicyclo[3.1.0]hex-2-yl)methyl]-amide with 5-(2-Fluoro-phenyl)-2-methyl-thiazole-4-carboxylic acid.
LC-MS (basic): $t_R$=1.30 min; [M+H]$^+$=496.1.

Example 11

6-Methyl-imidazo[2,1-b]thiazole-5-carboxylic acid [(1S,2S,5R)-3-(2-methyl-5-o-tolyl-thiazole-4-carbonyl)-3-aza-bicyclo[3.1.0]hex-2-ylmethyl]-amide prepared by reaction of 6-Methyl-imidazo[2,1-b]thiazole-5-carboxylic acid [(1S,2S,5R)-1-(3-aza-bicyclo[3.1.0]hex-2-yl)methyl]-amide with 2-M ethyl-5-o-tolyl-thiazole-4-carboxylic acid. LC-MS (basic): $t_R$=1.31 min; [M+H]$^+$=492.1.

Example 12

6-Methyl-imidazo[2,1-b]thiazole-5-carboxylic acid {(1S,2S,5R)-3-[5-(3-fluoro-phenyl)-2-methyl-thiazole-4-carbonyl]-3-aza-bicyclo[3.1.0]hex-2-ylmethyl}-amide prepared by reaction of 6-Methyl-imidazo[2,1-b]thiazole-5-carboxylic acid [(1S,2S,5R)-1-(3-aza-bicyclo[3.1.0]hex-2-yl)methyl]-amide with 5-(3-Fluoro-phenyl)-2-methyl-thiazole-4-carboxylic acid.
LC-MS (basic): $t_R$=1.30 min; [M+H]$^+$=496.1.

Example 13

6-Methyl-imidazo[2,1-b]thiazole-5-carboxylic acid {(1S,2S,5R)-3-[5-(3-chloro-phenyl)-2-methyl-thiazole-4-carbonyl]-3-aza-bicyclo[3.1.0]hex-2-ylmethyl}-amide prepared by reaction of 6-Methyl-imidazo[2,1-b]thiazole-5-carboxylic acid [(1S,2S,5R)-1-(3-aza-bicyclo[3.1.0]hex-2-yl)methyl]-amide with 5-(3-Chloro-phenyl)-2-methyl-thiazole-4-carboxylic acid.
LC-MS (basic): $t_R$=1.34 min; [M+H]$^+$=512.1.

Example 14

6-Methyl-imidazo[2,1-b]thiazole-5-carboxylic acid {(1S,2S,5R)-3-[5-(4-fluoro-phenyl)-2-methyl-thiazole-4-carbonyl]-3-aza-bicyclo[3.1.0]hex-2-ylmethyl}-amide prepared by reaction of 6-Methyl-imidazo[2,1-b]thiazole-5-carboxylic acid [(1S,2S,5R)-1-(3-aza-bicyclo[3.1.0]hex-2-yl)methyl]-amide with 5-(4-Fluoro-phenyl)-2-methyl-thiazole-4-carboxylic acid.
LC-MS (basic): $t_R$=1.29 min; [M+H]$^+$=496.1.

Example 15

6-Methyl-imidazo[2,1-b]thiazole-5-carboxylic acid {(1S,2S,5R)-3-[5-(4-ethyl-phenyl)-2-methyl-thiazole-4-carbonyl]-3-aza-bicyclo[3.1.0]hex-2-ylmethyl}-amide prepared by reaction of 6-Methyl-imidazo[2,1-b]thiazole-5-carboxylic acid [(1S,2S,5R)-1-(3-aza-bicyclo[3.1.0]hex-2-yl)methyl]-amide with 5-(4-Ethyl-phenyl)-2-methyl-thiazole-4-carboxylic acid. LC-MS (basic): $t_R$=1.37 min; [M+H]$^+$=506.1.

Example 16

6-Methyl-imidazo[2,1-b]thiazole-5-carboxylic acid [(1S,2S,5R)-3-(2-amino-5-m-tolyl-thiazole-4-carbonyl)-3-aza-bicyclo[3.1.0]hex-2-ylmethyl]-amide prepared by reaction of 6-Methyl-imidazo[2,1-b]thiazole-5-carboxylic acid[(1S,2S,5R)-1-(3-aza-bicyclo[3.1.0]hex-2-yl)methyl]-amide with 2-Amino-5-m-tolyl-thiazole-4-carboxylic acid. LC-MS (basic): $t_R$=1.24 min; [M+H]$^+$=493.1.

Example 17

6-Methyl-imidazo[2,1-b]thiazole-5-carboxylic acid {(1S,2S,5R)-3-[2-amino-5-(3-fluoro-phenyl)-thiazole-4-carbonyl]-3-aza-bicyclo[3.1.0]hex-2-ylmethyl}-amide prepared by reaction of 6-Methyl-imidazo[2,1-b]thiazole-5-carboxylic acid [(1S,2S,5R)-1-(3-aza-bicyclo[3.1.0]hex-2-yl)methyl]-amide with 2-Amino-5-(3-fluoro-phenyl)-thiazole-4-carboxylic acid. LC-MS (basic): $t_R$=1.21 min; [M+H]$^+$=497.1.

Example 18

6-Methyl-imidazo[2,1-b]thiazole-5-carboxylic acid [(1S,2S,5R)-3-(biphenyl-2-carbonyl)-3-aza-bicyclo[3.1.0]hex-2-ylmethyl]-amide prepared by reaction of 6-Methyl-imidazo[2,1-b]thiazole-5-carboxylic acid [(1S,2S,5R)-1-(3-aza-bicyclo[3.1.0]hex-2-yl)methyl]-amide with Biphenyl-2-carboxylic acid. LC-MS (basic): $t_R$=1.34 min; [M+H]$^+$=457.0.

Example 19

6-Methyl-imidazo[2,1-b]thiazole-5-carboxylic acid [(1S,2S,5R)-3-(2'-fluoro-biphenyl-2-carbonyl)-3-aza-bicyclo[3.1.0]hex-2-ylmethyl]-amide prepared by reaction of 6-Methyl-imidazo[2,1-b]thiazole-5-carboxylic acid [(1S,2S,5R)-1-(3-aza-bicyclo[3.1.0]hex-2-yl)methyl]-amide with 2'-Fluoro-biphenyl-2-carboxylic acid. LC-MS (basic): $t_R$=1.33 min; [M+H]$^+$=475.1.

Example 20

6-Methyl-imidazo[2,1-b]thiazole-5-carboxylic acid [(1S,2S,5R)-3-(3'-methyl-biphenyl-2-carbonyl)-3-aza-bicyclo[3.1.0]hex-2-ylmethyl]-amide prepared by reaction of 6-Methyl-imidazo[2,1-b]thiazole-5-carboxylic acid [(1S,2S,5R)-1-(3-aza-bicyclo[3.1.0]hex-2- yl)methyl]-amide with 3'-Methyl-biphenyl-2-carboxylic acid. LC-MS (basic): $t_R$=1.38 min; [M+H]$^+$=471.2.

Example 21

6-Methyl-imidazo[2,1-b]thiazole-5-carboxylic acid [(1S,2S,5R)-3-(3'-chloro-biphenyl-2-carbonyl)-3-aza-bicyclo[3.1.0]hex-2-ylmethyl]-amide prepared by reaction of 6-Methyl-imidazo[2,1-b]thiazole-5-carboxylic acid [(1S,2S,5R)-1-(3-aza-bicyclo[3.1.0]hex-2-yl)methyl]-amide with 3'-Chloro-biphenyl-2-carboxylic acid. LC-MS (basic): $t_R$=1.38 min; [M+H]$^+$=490.9.

Example 22

6-Methyl-imidazo[2,1-b]thiazole-5-carboxylic acid [(1S,2S,5R)-3-(3',4'-dimethyl-biphenyl-2-carbonyl)-3-aza-bicyclo[3.1.0]hex-2-ylmethyl]-amide prepared by reaction of 6-Methyl-imidazo[2,1-b]thiazole-5-carboxylic acid [(1S,2S,5R)-1-(3-aza-bicyclo[3.1.0]hex-2-yl)methyl]-amide with 3',4'-Dimethyl-biphenyl-2-carboxylic acid. LC-MS (basic): $t_R$=1.40 min; [M+H]$^+$=485.2.

Example 23

6-Methyl-imidazo[2,1-b]thiazole-5-carboxylic Acid [(1S,2S,5R)-3-(2-methyl-4-phenyl-pyrimidine-5-carbonyl)-3-aza-bicyclo[3.1.0]hex-2-ylmethyl]-amide prepared by reaction of 6-Methyl-imidazo[2,1-b]thiazole-5-carboxylic acid [(1S,2S,5R)-1-(3-aza-bicyclo[3.1.0]hex-2-yl)methyl]-amide with 2-Methyl-4-phenyl-pyrimidine-5-carboxylic acid. LC-MS (basic): $t_R$=1.19 min; [M+H]$^+$=473.1.

Example 24

6-Methyl-imidazo[2,1-b]thiazole-5-carboxylic acid{(1S,2S,5R)-3-[2-(2-amino-thiazol-4-yl)-benzoyl]-3-aza-bicyclo[3.1.0]hex-2-ylmethyl}-amide prepared by reaction of 6-Methyl-imidazo[2,1-b]thiazole-5-carboxylic acid [(1S,2S,5R)-1-(3-aza-bicyclo[3.1.0]hex-2-yl)methyl]-amide with 2-(2-Amino-thiazol-4-yl)-benzoic acid. LC-MS (basic): $t_R$=1.15 min; [M+H]$^+$=479.2.

Example 25

6-Methyl-imidazo[2,1-b]thiazole-5-carboxylic acid [(1S,2S,5R)-3-(3-phenyl-pyrazine-2-carbonyl)-3-aza-bicyclo[3.1.0]hex-2-ylmethyl]-amide prepared by reaction of 6-Methyl-imidazo[2,1-b]thiazole-5-carboxylic acid[(1S,2S,5R)-1-(3-aza-bicyclo[3.1.0]hex-2-yl)methyl]-amide with 3-Phenyl-pyrazine-2-carboxylic acid. LC-MS (basic): $t_R$=1.18 min; [M+H]$^+$=458.9.

Example 26

6-Methyl-imidazo[2,1-b]thiazole-5-carboxylic acid [(1S,2S,5R)-3-(2-pyrazol-1-yl-benzoyl)-3-aza-bicyclo[3.1.0]hex-2-ylmethyl]-amide prepared by reaction of 6-Methyl-imidazo[2,1-b]thiazole-5-carboxylic acid [(1S,2S,5R)-1-(3-aza-bicyclo[3.1.0]hex-2-yl)methyl]-amide with 2-Pyrazol-1-yl-benzoic acid. LC-MS (basic): $t_R$=1.20 min; [M+H]$^+$=447.1.

Example 27

6-Methyl-imidazo[2,1-b]thiazole-5-carboxylic acid [(1S,2S,5R)-3-(3-bromo-thiophene-2-carbonyl)-3-aza-bicyclo[3.1.0]hex-2-ylmethyl]-amide prepared by reaction of 6-Methyl-imidazo[2,1-b]thiazole-5-carboxylic acid [(1S,2S,5R)-1-(3-aza-bicyclo[3.1.0]hex-2-yl)methyl]-amide with 3-Bromo-thiophene-2-carboxylic acid. LC-MS (basic): $t_R$=1.22 min; [M+H]$^+$=465.0.

Example 28

6-Methyl-imidazo[2,1-b]thiazole-5-carboxylic acid [(1S,2S,5R)-3-(2-methoxy-5-m-tolyl-thiazole-4-carbonyl)-3-aza-bicyclo[3.1.0]hex-2-ylmethyl]-amide prepared by reaction of 6-Methyl-imidazo[2,1-b]thiazole-5-carboxylic acid [(1S,2S,5R)-1-(3-aza-bicyclo[3.1.0]hex-2-yl)methyl]-amide with 2-Methoxy-5-m-tolyl-thiazole-4-carboxylic acid. LC-MS (basic): $t_R$=1.38 min; [M+H]$^+$=508.2.

Example 29

6-Methyl-imidazo[2,1-b]thiazole-5-carboxylic acid [(1S,2S,5R)-3-(2-bromo-5-m-tolyl-thiazole-4-carbonyl)-3-aza-bicyclo[3.1.0]hex-2-ylmethyl]-amide prepared by reaction of 6-Methyl-imidazo[2,1-b]thiazole-5-carboxylic acid [(1S,2S,5R)-1-(3-aza-bicyclo[3.1.0]hex-2-yl)methyl]-amide with 2-Bromo-5-m-tolyl-thiazole-4-carboxylic acid. LC-MS (basic): $t_R$=1.41 min; [M+H]$^+$=555.9.

Example 30

6-Methyl-imidazo[2,1-b]thiazole-5-carboxylic Acid [(1S,2S,5R)-3-(5-m-tolyl-thiazole-4-carbonyl)-3-aza-bicyclo[3.1.0]hex-2-ylmethyl]-amide prepared by reaction of 6-Methyl-imidazo[2,1-b]thiazole-5-carboxylic acid[(1S,2S,5R)-1-(3-aza-bicyclo[3.1.0]hex-2-yl)methyl]-amide with 5-m-Tolyl-thiazole-4-carboxylic acid. LC-MS (basic): $t_R$=1.29 min; [M+H]$^+$=478.1.

Example 31

6-Methyl-imidazo[2,1-b]thiazole-5-carboxylic acid [(1S,2S,5R)-3-(2-cyclohexyl-benzoyl)-3-aza-bicyclo[3.1.0]hex-2-ylmethyl]-amide prepared by reaction of 6-Methyl-imidazo[2,1-b]thiazole-5-carboxylic acid[(1S,2S,5R)-1-(3-aza-bicyclo[3.1.0]hex-2-yl)methyl]-amide with 2-Cyclohexyl-benzoic acid. LC-MS (basic): $t_R$=1.42 min; [M+H]$^+$=463.2.

Example 32

6-Methyl-imidazo[2,1-b]thiazole-5-carboxylic acid [(1S,2S,5R)-3-(2-thiophen-2-yl-benzoyl)-3-aza-bicyclo[3.1.0]hex-2-ylmethyl]-amide prepared by reaction of 6-Methyl-imidazo[2,1-b]thiazole-5-carboxylic acid[(1S,2S,5R)-1-(3-aza-bicyclo[3.1.0]hex-2- yl)methyl]-amide with 2-Thiophen-2-yl-benzoic acid. LC-MS (basic): $t_R$=1.33 min; $[M+H]^+$=463.1.

Example 33

6-Methyl-imidazo[2,1-b]thiazole-5-carboxylic acid [(1S,2S,5R)-3-(5-methyl-2-p-tolyl-2H-pyrazole-3-carbonyl)-3-aza-bicyclo[3.1.0]hex-2-ylmethyl]-amide prepared by reaction of 6-Methyl-imidazo[2,1-b]thiazole-5-carboxylic acid[(1S,2S,5R)-1-(3-aza-bicyclo[3.1.0]hex-2-yl)methyl]-amide with 5-Methyl-2-p-tolyl-2H-pyrazole-3-carboxylic acid. LC-MS (basic): $t_R$=1.27 min; $[M+H]^+$=475.2.

Example 34

6-Methyl-imidazo[2,1-b]thiazole-5-carboxylic acid [(1S,2S,5R)-3-(2-phenyl-[1,6]naphthyridine-3-carbonyl)-3-aza-bicyclo[3.1.0]hex-2-ylmethyl]-amide prepared by reaction of 6-Methyl-imidazo[2,1-b]thiazole-5-carboxylic acid[(1S,2S,5R)-1-(3-aza-bicyclo[3.1.0]hex-2-yl)methyl]-amide with 2-Phenyl-[1,6]naphthyridine-3-carboxylic acid. LC-MS (basic): $t_R$=1.20 min; $[M+H]^+$=509.1.

Example 35

6-Methyl-imidazo[2,1-b]thiazole-5-carboxylic acid{(1S,2S,5R)-3-[5-(3-fluoro-phenyl)-2-methyl-oxazole-4-carbonyl]-3-aza-bicyclo[3.1.0]hex-2-ylmethyl}-amide prepared by reaction of 6-Methyl-imidazo[2,1-b]thiazole-5-carboxylic acid[(1S,2S,5R)-1-(3-aza-bicyclo[3.1.0]hex-2-yl)methyl]-amide with 5-(3-Fluoro-phenyl)-2-methyl-oxazole-4-carboxylic acid.
LC-MS (basic): $t_R$=1.30 min; $[M+H]^+$=480.1.

Example 36

6-Methyl-imidazo[2,1-b]thiazole-5-carboxylic acid [(1S,2S,5R)-3-(6-chloro-2-phenyl-imidazo[1,2-a]pyridine-3-carbonyl)-3-aza-bicyclo[3.1.0]hex-2-ylmethyl]-amide prepared by reaction of 6-Methyl-imidazo[2,1-b]thiazole-5-carboxylic acid[(1S,2S,5R)-1-(3-aza-bicyclo[3.1.0]hex-2-yl)methyl]-amide with 6-Chloro-2-phenyl-imidazo[1,2-a]pyridine-3-carboxylic acid.
LC-MS (basic): $t_R$=1.22 min; $[M+H]^+$=531.1.

Example 37

6-Methyl-imidazo[2,1-b]thiazole-5-carboxylic acid{(1S,2S,5R)-3-[4-(3-fluoro-phenyl)-2-methyl-thiazole-5-carbonyl]-3-aza-bicyclo[3.1.0]hex-2-ylmethyl}-amide prepared by reaction of 6-Methyl-imidazo[2,1-b]thiazole-5-carboxylic Acid[(1S,2S,5R)-1-(3-aza-bicyclo[3.1.0]hex-2-yl)methyl]-amide with 4-(3-Fluoro-phenyl)-2-methyl-thiazole-5-carboxylic acid.
LC-MS (basic): $t_R$=1.28 min; $[M+H]^+$=496.0.

Example 38

6-Methyl-imidazo[2,1-b]thiazole-5-carboxylic acid{(1S,2S,5R)-3-[4-(4-fluoro-phenyl)-2-methyl-thiazole-5-carbonyl]-3-aza-bicyclo[3.1.0]hex-2-ylmethyl}-amide prepared by reaction of 6-Methyl-imidazo[2,1-b]thiazole-5-carboxylic Acid[(1S,2S,5R)-1-(3-aza-bicyclo[3.1.0]hex-2-yl)methyl]-amide with 4-(4-Fluoro-phenyl)-2-methyl-thiazole-5-carboxylic acid.
LC-MS (basic): $t_R$=1.26 min; $[M+H]^+$=496.1.

B.2 Synthesis of Carboxylic Amide Derivatives (General Procedure II)

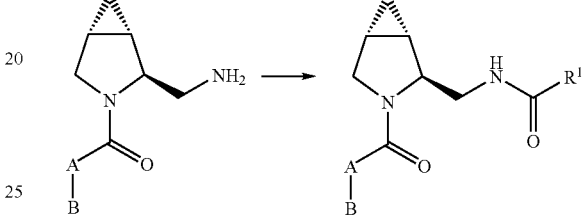

To a solution of the respective carboxylic acid (0.030 mmol, 1.2 eq) in DMF (0.20 mL) is added successively a solution of DIPEA (0.075 mmol, 3.0 eq) in DMF (0.15 mL) and a solution of TBTU (0.030 mmol, 1.2 eq) in DMF (0.15 mL). The obtained mixture is treated with a solution of the respective 3-aza-bicyclo[3.1.0]hexane derivative (0.025 mmol, 1.0 eq) in DMF (0.40 mL). The mixture is shaken over night and purified by prep. HPLC to give the respective amide derivative.

Example 39

2,3-Dihydro-benzo[1,4]dioxine-5-carboxylic acid [(1S,2S,5R)-3-(2-methyl-5-m-tolyl-thiazole-4-carbonyl)-3-aza-bicyclo[3.1.0]hex-2-ylmethyl]-amide prepared by reaction of ((1S,2S,5R)-2-Aminomethyl-3-aza-bicyclo[3.1.0]hex-3-yl)-(2-methyl-5-m-tolyl-thiazol-4-yl)-methanone with 2,3-Dihydro-benzo[1,4]dioxine-5-carboxylic acid. LC-MS (basic): $t_R$=0.88 min; $[M+H]^+$=490.1.

Example 40

2,3-Dihydro-benzofuran-4-carboxylic Acid[(1S,2S,5R)-3-(2-methyl-5-m-tolyl-thiazole-4-carbonyl)-3-aza-bicyclo[3.1.0]hex-2-ylmethyl]-amide prepared by reaction of ((1S,2S,5R)-2-Aminomethyl-3-aza-bicyclo[3.1.0]hex-3-yl)-(2-methyl-5-m-tolyl-thiazol-4-yl)-methanone with 2,3-Dihydro-benzofuran-4-carboxylic acid. LC-MS (basic): $t_R$=0.90 min; $[M+H]^+$=474.4.

Example 41

2,3-Dihydro-benzofuran-7-carboxylic Acid[(1S,2S,5R)-3-(2-methyl-5-m-tolyl-thiazole-4-carbonyl)-3-aza-bicyclo[3.1.0]hex-2-ylmethyl]-amide prepared by reaction of ((1S,2S,5R)-2-Aminomethyl-3-aza-bicyclo[3.1.0]hex-3-yl)-(2-methyl-5-m-tolyl-thiazol-4-yl)-methanone with 2,3-Dihydro-benzofuran-7-carboxylic acid. LC-MS (basic): $t_R$=0.88 min; $[M+H]^+$=474.4.

Example 42

6-Fluoro-4H-benzo[1,3]dioxine-8-carboxylic Acid [(1S,2S,5R)-3-(2-methyl-5-m-tolyl-thiazole-4-carbonyl)-3-aza-bicyclo[3.1.0]hex-2-ylmethyl]-amide prepared by reaction of ((1S,2S,5R)-2-Aminomethyl-3-aza-bicyclo[3.1.0]hex-3-yl)-(2-methyl-5-m-tolyl-thiazol-4-yl)-methanone with 6-Fluoro-4H-benzo[1,3]dioxine-8-carboxylic acid. LC-MS (basic): $t_R$=0.91 min; [M+H]$^+$=508.4.

Example 43

2,2-Dimethyl-2,3-dihydro-benzofuran-7-carboxylic acid[(1S,2S,5R)-3-(2-methyl-5-m-tolyl-thiazole-4-carbonyl)-3-aza-bicyclo[3.1.0]hex-2-ylmethyl]-amide prepared by reaction of ((1S,2S,5R)-2-Aminomethyl-3-aza-bicyclo[3.1.0]hex-3-yl)-(2-methyl-5-m-tolyl-thiazol-4-yl)-methanone with 2,2-Dimethyl-2,3-dihydro-benzofuran-7-carboxylic acid. LC-MS (basic): $t_R$=0.97 min; [M+H]$^+$=502.4.

Example 44

3-Bromo-N-[(1S,2S,5R)-3-(2-methyl-5-m-tolyl-thiazole-4-carbonyl)-3-aza-bicyclo[3.1.0]hex-2-ylmethyl]-benzamide prepared by reaction of ((1S,2S,5R)-2-Aminomethyl-3-aza-bicyclo[3.1.0]hex-3-yl)-(2-methyl-5-m-tolyl-thiazol-4-yl)-methanone with 3-Bromo-benzoic Acid.
LC-MS (basic): $t_R$=0.97 min; [M+H]$^+$=510.3.

Example 45

N-[(1S,2S,5R)-3-(2-Methyl-5-m-tolyl-thiazole-4-carbonyl)-3-aza-bicyclo[3.1.0]hex-2-ylmethyl]-3-trifluoromethyl-benzamide prepared by reaction of ((1S,2S,5R)-2-Aminomethyl-3-aza-bicyclo[3.1.0]hex-3-yl)-(2-methyl-5-m-tolyl-thiazol-4-yl)-methanone with 3-Trifluoromethyl-benzoic acid.
LC-MS (basic): $t_R$=0.97 min; [M+H]$^+$=510.3.

Example 46

3-Chloro-N-[(1S,2S,5R)-3-(2-methyl-5-m-tolyl-thiazole-4-carbonyl)-3-aza-bicyclo[3.1.0]hex-2-ylmethyl]-benzamide prepared by reaction of ((1S,2S,5R)-2-Aminomethyl-3-aza-bicyclo[3.1.0]hex-3-yl)-(2-methyl-5-m-tolyl-thiazol-4-yl)-methanone with 3-Chloro-benzoic acid.
LC-MS (basic): $t_R$=0.95 min; [M+H]$^+$=466.3.

Example 47

3,5-Dimethoxy-N-[(1S,2S,5R)-3-(2-methyl-5-m-tolyl-thiazole-4-carbonyl)-3-aza-bicyclo[3.1.0]hex-2-ylmethyl]-benzamide prepared by reaction of ((1S,2S,5R)-2-Aminomethyl-3-aza-bicyclo[3.1.0]hex-3-yl)-(2-methyl-5-m-tolyl-thiazol-4-yl)-methanone with 3,5-Dimethoxy-benzoic acid.
LC-MS (basic): $t_R$=0.92 min; [M+H]$^+$=492.4.

Example 48

2,5-Dimethyl-2H-pyrazole-3-carboxylic Acid[(1S,2S,5R)-3-(2-methyl-5-m-tolyl-thiazole-4-carbonyl)-3-aza-bicyclo[3.1.0]hex-2-ylmethyl]-amide prepared by reaction of ((1S,2S,5R)-2-Aminomethyl-3-aza-bicyclo[3.1.0]hex-3-yl)-(2-methyl-5-m-tolyl-thiazol-4-yl)-methanone with 2,5-Dimethyl-2H-pyrazole-3-carboxylic acid. LC-MS (basic): $t_R$=0.84 min; [M+H]$^+$=450.3.

Example 49

1,3-Dimethyl-1H-pyrazole-4-carboxylic Acid[(1S,2S,5R)-3-(2-methyl-5-m-tolyl-thiazole-4-carbonyl)-3-aza-bicyclo[3.1.0]hex-2-ylmethyl]-amide prepared by reaction of ((1S,2S,5R)-2-Aminomethyl-3-aza-bicyclo[3.1.0]hex-3-yl)-(2-methyl-5-m-tolyl-thiazol-4-yl)-methanone with 1,3-Dimethyl-1H-pyrazole-4-carboxylic acid. LC-MS (basic): $t_R$=0.77 min; [M+H]$^+$=450.5.

Example 50

2-Ethyl-5-methyl-2H-pyrazole-3-carboxylic acid [(1S,2S,5R)-3-(2-methyl-5-m-tolyl-thiazole-4-carbonyl)-3-aza-bicyclo[3.1.0]hex-2-ylmethyl]-amide prepared by reaction of ((1S,2S,5R)-2-Aminomethyl-3-aza-bicyclo[3.1.0]hex-3-yl)-(2-methyl-5-m-tolyl-thiazol-4-yl)-methanone with 2-Ethyl-5-methyl-2H-pyrazole-3-carboxylic acid. LC-MS (basic): $t_R$=0.88 min; [M+H]$^+$=464.4.

Example 51

3,5-Dimethyl-isoxazole-4-carboxylic Acid[(1S,2S,5R)-3-(2-methyl-5-m-tolyl-thiazole-4-carbonyl)-3-aza-bicyclo[3.1.0]hex-2-ylmethyl]-amide prepared by reaction of ((1S,2S,5R)-2-Aminomethyl-3-aza-bicyclo[3.1.0]hex-3-yl)-(2-methyl-5-m-tolyl-thiazol-4-yl)-methanone with 3,5-Dimethyl-isoxazole-4-carboxylic acid. LC-MS (basic): $t_R$=0.85 min; [M+H]$^+$=451.3.

Example 52

Naphthalene-1-carboxylic acid[(1S,2S,5R)-3-(2-methyl-5-m-tolyl-thiazole-4-carbonyl)-3-aza-bicyclo[3.1.0]hex-2-ylmethyl]-amide prepared by reaction of ((1S,2S,5R)-2-Aminomethyl-3-aza-bicyclo[3.1.0.]hex-3-yl)-(2-methyl-5-m-tolyl-thiazol-4-yl)-methanone with Naphthalene-1-carboxylic acid. LC-MS (basic): $t_R$=0.94 min; [M+H]$^+$=482.4.

Example 53

Quinoline-8-carboxylic acid[(1S,2S,5R)-3-(2-methyl-5-m-tolyl-thiazole-4-carbonyl)-3-aza-bicyclo[3.1.0]hex-2-ylmethyl]-amide prepared by reaction of ((1S,2S,5R)-2-Aminomethyl-3-aza-bicyclo[3.1.0]hex-3-yl)-(2-methyl-5-m-tolyl-thiazol-4-yl)-methanone with Quinoline-8-carboxylic acid.
LC-MS (basic): $t_R$=0.89 min; [M+H]$^+$=483.4.

Example 54

Isoquinoline-1-carboxylic Acid[(1S,2S,5R)-3-(2-methyl-5-m-tolyl-thiazole-4-carbonyl)-3-aza-bicyclo[3.1.0]hex-2-ylmethyl]-amide prepared by reaction of ((1S,2S,5R)-2-Aminomethyl-3-aza-bicyclo[3.1.0]hex-3-yl)-(2-methyl-5-m-tolyl-thiazol-4-yl)-methanone with Isoquinoline-1-carboxylic acid.
LC-MS (basic): $t_R$=0.95 min; [M+H]$^+$=483.4.

Example 55

Quinoline-2-carboxylic Acid[(1S,2S,5R)-3-(2-methyl-5-m-tolyl-thiazole-4-carbonyl)-3-aza-bicyclo[3.1.0]hex-2-ylmethyl]-amide prepared by reaction of ((1S,2S,5R)-2-Aminomethyl-3-aza-bicyclo[3.1.0]hex-3-yl)-(2-methyl-5-m-tolyl-thiazol-4-yl)-methanone with Quinoline-2-carboxylic acid.
LC-MS (basic): $t_R$=0.95 min; [M+H]$^+$=483.4.

Example 56

1H-Indole-3-carboxylic Acid[(1S,2S,5R)-3-(2-methyl-5-m-tolyl-thiazole-4-carbonyl)-3-aza-bicyclo[3.1.0]hex-2-ylmethyl]-amide prepared by reaction of ((1S,2S,5R)-2-Aminomethyl-3-aza-bicyclo[3.1.0]hex-3-yl)-(2-methyl-5-m-tolyl-thiazol-4-yl)-methanone with 1H-Indole-3-carboxylic acid.
LC-MS (basic): $t_R$=0.85 min; [M+H]$^+$=471.4.

Example 57

1-Methyl-1H-indole-3-carboxylic Acid[(1S,2S,5R)-3-(2-methyl-5-m-tolyl-thiazole-4-carbonyl)-3-aza-bicyclo[3.1.0]hex-2-ylmethyl]-amide prepared by reaction of ((1S,2S,5R)-2-Aminomethyl-3-aza-bicyclo[3.1.0]hex-3-yl)-(2-methyl-5-m-tolyl-thiazol-4-yl)-methanone with 1-Methyl-1H-indole-3-carboxylic acid. LC-MS (basic): $t_R$=0.90 min; [M+H]$^+$=485.4.

Example 58

1H-Indazole-3-carboxylic Acid[(1S,2S,5R)-3-(2-methyl-5-m-tolyl-thiazole-4-carbonyl)-3-aza-bicyclo[3.1.0]hex-2-ylmethyl]-amide prepared by reaction of ((1S,2S,5R)-2-Aminomethyl-3-aza-bicyclo[3.1.0]hex-3-yl)-(2-methyl-5-m-tolyl-thiazol-4-yl)-methanone with 1H-Indazole-3-carboxylic acid.
LC-MS (basic): $t_R$=0.86 min; [M+H]$^+$=472.4.

Example 59

1-Methyl-1H-indazole-3-carboxylic Acid[(1S,2S,5R)-3-(2-methyl-5-m-tolyl-thiazole-4-carbonyl)-3-aza-bicyclo[3.1.0]hex-2-ylmethyl]-amide prepared by reaction of ((1S,2S,5R)-2-Aminomethyl-3-aza-bicyclo[3.1.0]hex-3-yl)-(2-methyl-5-m-tolyl-thiazol-4-yl)-methanone with 1-Methyl-1H-indazole-3-carboxylic acid. LC-MS (basic): $t_R$=0.92 min; [M+H]$^+$=486.4.

Example 60

1,2-Dimethyl-1H-indole-3-carboxylic Acid[(1S,2S,5R)-3-(2-methyl-5-m-tolyl-thiazole-4-carbonyl)-3-aza-bicyclo[3.1.0]hex-2-ylmethyl]-amide prepared by reaction of ((1S,2S,5R)-2-Aminomethyl-3-aza-bicyclo[3.1.0]hex-3-yl)-(2-methyl-5-m-tolyl-thiazol-4-yl)-methanone with 1,2-Dimethyl-1H-indole-3-carboxylic acid. LC-MS (basic): $t_R$=0.92 min; [M+H]$^+$=499.4.

Example 61

Benzo[d] isoxazole-3-carboxylic acid[(1S,2S,5R)-3-(2-methyl-5-m-tolyl-thiazole-4-carbonyl)-3-aza-bicyclo[3.1.0]hex-2-ylmethyl]-amide prepared by reaction of ((1S,2S,5R)-2-Aminomethyl-3-aza-bicyclo[3.1.0]hex-3-yl)-(2-methyl-5-m-tolyl-thiazol-4-yl)-methanone with Benzo[d]isoxazole-3-carboxylic acid. LC-MS (basic): $t_R$=0.93 min; [M+H]$^+$=473.3.

Example 62

Imidazo[1,2-a]pyridine-3-carboxylic Acid[(1S,2S,5R)-3-(2-methyl-5-m-tolyl-thiazole-4-carbonyl)-3-aza-bicyclo[3.1.0]hex-2-ylmethyl]-amide prepared by reaction of ((1S,2S,5R)-2-Aminomethyl-3-aza-bicyclo[3.1.0]hex-3-yl)-(2-methyl-5-m-tolyl-thiazol-4-yl)-methanone with Imidazo[1,2-a]pyridine-3-carboxylic acid. LC-MS (basic): $t_R$=0.82 min; [M+H]$^+$=472.3.

Example 63

Pyrazolo[1,5-a]pyridine-3-carboxylic Acid[(1S,2S,5R)-3-(2-methyl-5-m-tolyl-thiazole-4-carbonyl)-3-aza-bicyclo[3.1.0]hex-2-ylmethyl]-amide prepared by reaction of ((1S,2S,5R)-2-Aminomethyl-3-aza-bicyclo[3.1.0]hex-3-yl)-(2-methyl-5-m-tolyl-thiazol-4-yl)-methanone with Pyrazolo[1,5-a]pyridine-3-carboxylic acid. LC-MS (basic): $t_R$=0.83 min; [M+H]$^+$=472.3.

Example 64

2,3-Dihydro-thieno[3,4-b][1,4]dioxine-5-carboxylic Acid[(1S,2S,5R)-3-(2-methyl-5-m-tolyl-thiazole-4-carbonyl)-3-aza-bicyclo[3.1.0]hex-2-ylmethyl]-amide prepared by reaction of ((1S,2S,5R)-2-Aminomethyl-3-aza-bicyclo[3.1.0]hex-3-yl)-(2-methyl-5-m-tolyl-thiazol-4-yl)-methanone with 2,3-Dihydro-thieno[3,4-b][1,4]dioxine-5-carboxylic acid. LC-MS (basic): $t_R$=0.85 min; [M+H]$^+$=496.3.

Example 65

5-Fluoro-1-methyl-1H-indole-2-carboxylic Acid[(1S,2S,5R)-3-(2-methyl-5-m-tolyl-thiazole-4-carbonyl)-3-aza-bicyclo[3.1.0]hex-2-ylmethyl]-amide prepared by reaction of ((1S,2S,5R)-2-Aminomethyl-3-aza-bicyclo[3.1.0]hex-3-yl)-(2-methyl-5-m-tolyl-thiazol-4-yl)-methanone with 5-Fluoro-1-methyl-1H-indole-2-carboxylic acid. LC-MS (basic): $t_R$=0.98 min; [M+H]$^+$=503.4.

Example 66

Imidazo[2,1-b]thiazole-5-carboxylic Acid[(1S,2S,5R)-3-(2-methyl-5-m-tolyl-thiazole-4-carbonyl)-3-aza-bicyclo[3.1.0]hex-2-ylmethyl]-amide prepared by reaction of ((1S,2S,5R)-2-Aminomethyl-3-aza-bicyclo[3.1.0]hex-3-yl)-(2-methyl-5-m-tolyl-thiazol-4-yl)-methanone with Imidazo[2,1-b]thiazole-5-carboxylic acid. LC-MS (basic): $t_R$=0.82 min; [M+H]$^+$=478.3.

Example 67

3-Methyl-imidazo[2,1-b]thiazole-2-carboxylic Acid [(1S,2S,5R)-3-(2-methyl-5-m-tolyl-thiazole-4-carbonyl)-3-aza-bicyclo[3.1.0]hex-2-ylmethyl]-amide prepared by reaction of ((1S,2S,5R)-2-Aminomethyl-3-aza-bicyclo[3.1.0]hex-3-yl)-(2-methyl-5-m-tolyl-thiazol-4-yl)-methanone with 3-Methyl-imidazo[2,1-b]thiazole-2-carboxylic acid. LC-MS (basic): $t_R$=0.82 min; [M+H]$^+$=492.3.

Example 68

Imidazo[2,1-b]thiazole-6-carboxylic Acid[(1S,2S,5R)-3-(2-methyl-5-m-tolyl-thiazole-4-carbonyl)-3-aza-bicyclo[3.1.0]hex-2-ylmethyl]-amide prepared by reaction of ((1S,2S,5R)-2-Aminomethyl-3-aza-bicyclo[3.1.0]hex-3-yl)-(2-methyl-5-m-tolyl-thiazol-4-yl)-methanone with Imidazo[2,1-b]thiazole-6-carboxylic acid. LC-MS (basic): $t_R$=0.81 min; [M+H]$^+$=478.3.

Example 69

2,3-Dihydro-benzo[1,4]dioxine-5-carboxylic Acid{(1S,2S,5R)-3-[5-(3-chloro-phenyl)-2-methyl-thiazole-4-carbonyl]-3-aza-bicyclo[3.1.0]hex-2-ylmethyl}-amide prepared by reaction of ((1S,2S,5R)-2-Aminomethyl-3-aza-bicyclo[3.1.0]hex-3-yl)-[5-(3-chloro-phenyl)-2-methyl-thiazol-4-yl]-methanone with 2,3-Dihydro-benzo[1,4]dioxine-5-carboxylic acid. LC-MS (basic): $t_R$=0.89 min; [M+H]$^+$=510.3.

Example 70

2,3-Dihydro-benzofuran-4-carboxylic Acid{(1S,2S,5R)-3-[5-(3-chloro-phenyl)-2-methyl-thiazole-4-carbonyl]-3-aza-bicyclo[3.1.0]hex-2-ylmethyl}-amide prepared by reaction of ((1S,2S,5R)-2-Aminomethyl-3-aza-bicyclo[3.1.0]hex-3-yl)-[5-(3-chloro-phenyl)-2-methyl-thiazol-4-yl]-methanone with 2,3-Dihydro-benzofuran-4-carboxylic acid. LC-MS (basic): $t_R$=0.91 min; [M+H]$^+$=494.3.

Example 71

2,3-Dihydro-benzofuran-7-carboxylic Acid{(1S,2S,5R)-3-[5-(3-chloro-phenyl)-2-methyl-thiazole-4-carbonyl]-3-aza-bicyclo[3.1.0]hex-2-ylmethyl}-amide prepared by reaction of ((1S,2S,5R)-2-Aminomethyl-3-aza-bicyclo[3.1.0]hex-3-yl)-[5-(3-chloro-phenyl)-2-methyl-thiazol-4-yl]-methanone with 2,3-Dihydro-benzofuran-7-carboxylic acid. LC-MS (basic): $t_R$=0.90 min; [M+H]$^+$=494.3.

Example 72

6-Fluoro-4H-benzo[1,3]dioxine-8-carboxylic Acid{(1S,2S,5R)-3-[5-(3-chloro-phenyl)-2-methyl-thiazole-4-carbonyl]-3-aza-bicyclo[3.1.0]hex-2-ylmethyl}-amide prepared by reaction of ((1S,2S,5R)-2-Aminomethyl-3-aza-bicyclo[3.1.0]hex-3-yl)-[5-(3-chloro-phenyl)-2-methyl-thiazol-4-yl]-methanone with 6-Fluoro-4H-benzo[1,3]dioxine-8-carboxylic acid. LC-MS (basic): $t_R$=0.92 min; [M+H]$^+$=528.3.

Example 73

2,2-Dimethyl-2,3-dihydro-benzofuran-7-carboxylic Acid{(1S,2S,5R)-3-[5-(3-chloro-phenyl)-2-methyl-thiazole-4-carbonyl]-3-aza-bicyclo[3.1.0]hex-2-ylmethyl}-amide prepared by reaction of ((1S,2S,5R)-2-Aminomethyl-3-aza-bicyclo[3.1.0]hex-3-yl)-[5-(3-chloro-phenyl)-2-methyl-thiazol-4-yl]-methanone with 2,2-Dimethyl-2,3-dihydro-benzofuran-7-carboxylic acid.
LC-MS (basic): $t_R$=0.99 min; [M+H]$^+$=522.0.

Example 74

3-Bromo-N-{(1S,2S,5R)-3-[5-(3-chloro-phenyl)-2-methyl-thiazole-4-carbonyl]-3-aza-bicyclo[3.1.0]hex-2-ylmethyl}-benzamide prepared by reaction of ((1S,2S,5R)-2-Aminomethyl-3-aza-bicyclo[3.1.0]hex-3-yl)-[5-(3-chloro-phenyl)-2-methyl-thiazol-4-yl]-methanone with 3-Bromo-benzoic acid.
LC-MS (basic): $t_R$=0.97 min; [M+H]$^+$=530.2.

Example 75

N-{(1S,2S,5R)-3-[5-(3-Chloro-phenyl)-2-methyl-thiazole-4-carbonyl]-3-aza-bicyclo[3.1.0]hex-2-ylmethyl}-3-trifluoromethyl-benzamide prepared by reaction of ((1S,2S,5R)-2-Aminomethyl-3-aza-bicyclo[3.1.0]hex-3-yl)-[5-(3-chloro-phenyl)-2-methyl-thiazol-4-yl]-methanone with 3-Trifluoromethyl-benzoic acid. LC-MS (basic): $t_R$=0.98 min; [M+H]$^+$=520.3.

Example 76

3-Chloro-N-{(1S,2S,5R)-3-[5-(3-chloro-phenyl)-2-methyl-thiazole-4-carbonyl]-3-aza-bicyclo[3.1.0]hex-2-ylmethyl}-benzamide prepared by reaction of ((1S,2S,5R)-2-Aminomethyl-3-aza-bicyclo[3.1.0]hex-3-yl)-[5-(3-chloro-phenyl)-2-methyl-thiazol-4-yl]-methanone with 3-Chloro-benzoic acid.
LC-MS (basic): $t_R$=0.96 min; [M+H]$^+$=486.3.

Example 77

N-{(1S,2S,5R)-3-[5-(3-Chloro-phenyl)-2-methyl-thiazole-4-carbonyl]-3-aza-bicyclo[3.1.0]hex-2-ylmethyl}-3,5-dimethoxy-benzamide prepared by reaction of ((1S,2S,5R)-2-Aminomethyl-3-aza-bicyclo[3.1.0]hex-3-yl)-[5-(3-chloro-phenyl)-2-methyl-thiazol-4-yl]-methanone with 3,5-dimethoxy-benzoic acid. LC-MS (basic): $t_R$=0.92 min; $[M+H]^+$=512.3.

Example 78

2,5-Dimethyl-2H-pyrazole-3-carboxylic Acid{(1S,2S,5R)-3-[5-(3-chloro-phenyl)-2-methyl-thiazole-4-carbonyl]-3-aza-bicyclo[3.1.0]hex-2-ylmethyl}-amide prepared by reaction of ((1S,2S,5R)-2-Aminomethyl-3-aza-bicyclo[3.1.0]hex-3-yl)-[5-(3-chloro-phenyl)-2-methyl-thiazol-4-yl]-methanone with 2,5-Dimethyl-2H-pyrazole-3-carboxylic acid. LC-MS (basic): $t_R$=0.85 min; $[M+H]^+$=470.3.

Example 79

1,3-Dimethyl-1H-pyrazole-4-carboxylic Acid{(1S,2S,5R)-3-[5-(3-chloro-phenyl)-2-methyl-thiazole-4-carbonyl]-3-aza-bicyclo[3.1.0]hex-2-ylmethyl}-amide prepared by reaction of ((1S,2S,5R)-2-Aminomethyl-3-aza-bicyclo[3.1.0]hex-3-yl)-[5-(3-chloro-phenyl)-2-methyl-thiazol-4-yl]-methanone with 1,3-Dimethyl-1H-pyrazole-4-carboxylic acid. LC-MS (basic): $t_R$=0.78 min; $[M+H]^+$=470.3.

Example 80

2-Ethyl-5-methyl-2H-pyrazole-3-carboxylic Acid{(1S,2S,5R)-3-[5-(3-chloro-phenyl)-2-methyl-thiazole-4-carbonyl]-3-aza-bicyclo[3.1.0]hex-2-ylmethyl}-amide prepared by reaction of ((1S,2S,5R)-2-Aminomethyl-3-aza-bicyclo[3.1.0]hex-3-yl)-[5-(3-chloro-phenyl)-2-methyl-thiazol-4-yl]-methanone with 2-Ethyl-5-methyl-2H-pyrazole-3-carboxylic acid. LC-MS (basic): $t_R$=0.89 min; $[M+H]^+$=484.3.

Example 81

3,5-Dimethyl-isoxazole-4-carboxylic Acid{(1S,2S,5R)-3-[5-(3-chloro-phenyl)-2-methyl-thiazole-4-carbonyl]-3-aza-bicyclo[3.1.0]hex-2-ylmethyl}-amide prepared by reaction of ((1S,2S,5R)-2-Aminomethyl-3-aza-bicyclo[3.1.0]hex-3-yl)-[5-(3-chloro-phenyl)-2-methyl-thiazol-4-yl]-methanone with 3,5-Dimethyl-isoxazole-4-carboxylic acid. LC-MS (basic): $t_R$=0.87 min; $[M+H]^+$=471.3.

Example 82

Naphthalene-1-carboxylic Acid{(1S,2S,5R)-3-[5-(3-chloro-phenyl)-2-methyl-thiazole-4-carbonyl]-3-aza-bicyclo[3.1.0]hex-2-ylmethyl}-amide prepared by reaction of ((1S,2S,5R)-2-Aminomethyl-3-aza-bicyclo[3.1.0]hex-3-yl)-[5-(3-chloro-phenyl)-2-methyl-thiazol-4-yl]-methanone with Naphthalene-1-carboxylic acid. LC-MS (basic): $t_R$=0.95 min; $[M+H]^+$=502.3.

Example 83

Quinoline-8-carboxylic Acid{(1S,2S,5R)-3-[5-(3-chloro-phenyl)-2-methyl-thiazole-4-carbonyl]-3-aza-bicyclo[3.1.0]hex-2-ylmethyl}-amide prepared by reaction of ((1S,2S,5R)-2-Aminomethyl-3-aza-bicyclo[3.1.0]hex-3-yl)-[5-(3-chloro-phenyl)-2-methyl-thiazol-4-yl]-methanone with Quinoline-8-carboxylic acid. LC-MS (basic): $t_R$=0.90 min; $[M+H]^+$=503.3.

Example 84

Isoquinoline-1-carboxylic Acid{(1S,2S,5R)-3-[5-(3-chloro-phenyl)-2-methyl-thiazole-4-carbonyl]-3-aza-bicyclo[3.1.0]hex-2-ylmethyl}-amide prepared by reaction of ((1S,2S,5R)-2-Aminomethyl-3-aza-bicyclo[3.1.0]hex-3-yl)-[5-(3-chloro-phenyl)-2-methyl-thiazol-4-yl]-methanone with Isoquinoline-1-carboxylic acid. LC-MS (basic): $t_R$=0.96 min; $[M+H]^+$=503.3.

Example 85

Quinoline-2-carboxylic Acid{(1S,2S,5R)-3-[5-(3-chloro-phenyl)-2-methyl-thiazole-4-carbonyl]-3-aza-bicyclo[3.1.0]hex-2-ylmethyl}-amide prepared by reaction of ((1S,2S,5R)-2-Aminomethyl-3-aza-bicyclo[3.1.0]hex-3-yl)-[5-(3-chloro-phenyl)-2-methyl-thiazol-4-yl]-methanone with Quinoline-2-carboxylic acid. LC-MS (basic): $t_R$=0.96 min; $[M+H]^+$=503.3.

Example 86

1H-Indole-3-carboxylic Acid{(1S,2S,5R)-3-[5-(3-chloro-phenyl)-2-methyl-thiazole-4-carbonyl]-3-aza-bicyclo[3.1.0]hex-2-ylmethyl}-amide prepared by reaction of ((1S,2S,5R)-2-Aminomethyl-3-aza-bicyclo[3.1.0]hex-3-yl)-[5-(3-chloro-phenyl)-2-methyl-thiazol-4-yl]-methanone with 1H-Indole-3-carboxylic acid. LC-MS (basic): $t_R$=0.86 min; $[M+H]^+$=491.2.

Example 87

1-Methyl-1H-indole-3-carboxylic Acid{(1S,2S,5R)-3-[5-(3-chloro-phenyl)-2-methyl-thiazole-4-carbonyl]-3-aza-bicyclo[3.1.0]hex-2-ylmethyl}-amide prepared by reaction of ((1S,2S,5R)-2-Aminomethyl-3-aza-bicyclo[3.1.0]hex-3-yl)-[5-(3-chloro-phenyl)-2-methyl-thiazol-4-yl]-methanone with 1-Methyl-1H-indole-3-carboxylic acid. LC-MS (basic): $t_R$=0.91 min; $[M+H]^+$=505.4.

Example 88

1H-Indazole-3-carboxylic Acid{(1S,2S,5R)-3-[5-(3-chloro-phenyl)-2-methyl-thiazole-4-carbonyl]-3-aza-bicyclo[3.1.0]hex-2-ylmethyl}-amide prepared by reaction of ((1S,2S,5R)-2-Aminomethyl-3-aza-bicyclo[3.1.0]hex-3-yl)-[5-(3-chloro-phenyl)-2-methyl-thiazol-4-yl]-methanone with 1H-Indazole-3-carboxylic acid. LC-MS (basic): $t_R$=0.87 min; [M+H]$^+$=492.3.

Example 89

1-Methyl-1H-indazole-3-carboxylic Acid{(1S,2S,5R)-3-[5-(3-chloro-phenyl)-2-methyl-thiazole-4-carbonyl]-3-aza-bicyclo[3.1.0]hex-2-ylmethyl}-amide prepared by reaction of ((1S,2S,5R)-2-Aminomethyl-3-aza-bicyclo[3.1.0]hex-3-yl)-[5-(3-chloro-phenyl)-2-methyl-thiazol-4-yl]-methanone with 1-Methyl-1H-indazole-3-carboxylic acid. LC-MS (basic): $t_R$=0.93 min; [M+H]$^+$=506.3.

Example 90

1,2-Dimethyl-1H-indole-3-carboxylic Acid{(1S,2S,5R)-3-[5-(3-chloro-phenyl)-2-methyl-thiazole-4-carbonyl]-3-aza-bicyclo[3.1.0]hex-2-ylmethyl}-amide prepared by reaction of ((1S,2S,5R)-2-Aminomethyl-3-aza-bicyclo[3.1.0]hex-3-yl)-[5-(3-chloro-phenyl)-2-methyl-thiazol-4-yl]-methanone with 1,2-Dimethyl-1H-indole-3-carboxylic acid. LC-MS (basic): $t_R$=0.93 min; [M+H]$^+$=519.3.

Example 91

Imidazo[1,2-a]pyridine-3-carboxylic Acid{(1S,2S,5R)-3-[5-(3-chloro-phenyl)-2-methyl-thiazole-4-carbonyl]-3-aza-bicyclo[3.1.0]hex-2-ylmethyl}-amide prepared by reaction of ((1S,2S,5R)-2-Aminomethyl-3-aza-bicyclo[3.1.0]hex-3-yl)-[5-(3-chloro-phenyl)-2-methyl-thiazol-4-yl]-methanone with Imidazo[1,2-a]pyridine-3-carboxylic acid. LC-MS (basic): $t_R$=0.83 min; [M+H]$^+$=492.2.

Example 92

2,8-Dimethyl-imidazo[1,2-a]pyridine-3-carboxylic Acid{(1S,2S,5R)-3-[5-(3-chloro-phenyl)-2-methyl-thiazole-4-carbonyl]-3-aza-bicyclo[3.1.0]hex-2-ylmethyl}-amide prepared by reaction of ((1S,2S,5R)-2-Aminomethyl-3-aza-bicyclo[3.1.0]hex-3-yl)-[5-(3-chloro-phenyl)-2-methyl-thiazol-4-yl]-methanone with 2,8-Dimethyl-imidazo[1,2-a]pyridine-3-carboxylic acid.
LC-MS (basic): $t_R$=0.87 min; [M+H]$^+$=520.4.

Example 93

Pyrazolo[1,5-a]pyridine-3-carboxylic Acid{(1S,2S,5R)-3-[5-(3-chloro-phenyl)-2-methyl-thiazole-4-carbonyl]-3-aza-bicyclo[3.1.0]hex-2-ylmethyl}-amide prepared by reaction of ((1S,2S,5R)-2-Aminomethyl-3-aza-bicyclo[3.1.0]hex-3-yl)-[5-(3-chloro-phenyl)-2-methyl-thiazol-4-yl]-methanone with Pyrazolo[1,5-a]pyridine-3-carboxylic acid. LC-MS (basic): $t_R$=0.84 min; [M+H]$^+$=492.2.

Example 94

2,3-Dihydro-thieno[3,4-b][1,4]dioxine-5-carboxylic acid{(1S,2S,5R)-3-[5-(3-chloro-phenyl)-2-methyl-thiazole-4-carbonyl]-3-aza-bicyclo[3.1.0]hex-2-ylmethyl}-amide prepared by reaction of ((1S,2S,5R)-2-Aminomethyl-3-aza-bicyclo[3.1.0]hex-3-yl)-[5-(3-chloro-phenyl)-2-methyl-thiazol-4-yl]-methanone with 2,3-Dihydro-thieno[3,4-b][1,4]dioxine-5-carboxylic acid. LC-MS (basic): $t_R$=0.86 min; [M+H]$^+$=516.3.

Example 95

5-Fluoro-1-methyl-1H-indole-2-carboxylic Acid{(1S,2S,5R)-3-[5-(3-chloro-phenyl)-2-methyl-thiazole-4-carbonyl]-3-aza-bicyclo[3.1.0]hex-2-ylmethyl}-amide prepared by reaction of ((1S,2S,5R)-2-Aminomethyl-3-aza-bicyclo[3.1.0]hex-3-yl)-[5-(3-chloro-phenyl)-2-methyl-thiazol-4-yl]-methanone with 5-Fluoro-1-methyl-1H-indole-2-carboxylic acid. LC-MS (basic): $t_R$=0.99 min; [M+H]$^+$=523.2.

Example 96

Imidazo[2,1-b]thiazole-5-carboxylic Acid{(1S,2S,5R)-3-[5-(3-chloro-phenyl)-2-methyl-thiazole-4-carbonyl]-3-aza-bicyclo[3.1.0]hex-2-ylmethyl}-amide prepared by reaction of ((1S,2S,5R)-2-Aminomethyl-3-aza-bicyclo[3.1.0]hex-3-yl)-[5-(3-chloro-phenyl)-2-methyl-thiazol-4-yl]-methanone with Imidazo[2,1-b]thiazole-5-carboxylic acid. LC-MS (basic): $t_R$=0.83 min; [M+H]$^+$=498.3.

Example 97

3-Methyl-imidazo[2,1-b]thiazole-2-carboxylic Acid{(1S,2S,5R)-3-[5-(3-chloro-phenyl)-2-methyl-thiazole-4-carbonyl]-3-aza-bicyclo[3.1.0]hex-2-ylmethyl}-amide prepared by reaction of ((1S,2S,5R)-2-Aminomethyl-3-aza-bicyclo[3.1.0]hex-3-yl)-[5-(3-chloro-phenyl)-2-methyl-thiazol-4-yl]-methanone with 3-Methyl-imidazo[2,1-b]thiazole-2-carboxylic acid. LC-MS (basic): $t_R$=0.83 min; [M+H]$^+$=512.3.

Example 98

2,3-Dihydro-benzo[1,4]dioxine-5-carboxylic Acid{(1S,2S,5R)-3-[2-amino-5-(3-fluoro-phenyl)-thiazole-4-carbonyl]-3-aza-bicyclo[3.1.0]hex-2-ylmethyl}-amide prepared by reaction of [2-Amino-5-(3-fluoro-phenyl)-thiazol-4-yl]-((1S,2S,5R)-2-aminomethyl-3-aza-bicyclo[3.1.0]hex-3-yl)-methanone with 2,3-Dihydro-benzo[1,4]dioxine-5-carboxylic acid. LC-MS (basic): $t_R$=0.77 min; [M+H]$^+$=495.3.

Example 99

2,3-Dihydro-benzofuran-4-carboxylic Acid{(1S,2S,5R)-3-[2-amino-5-(3-fluoro-phenyl)-thiazole-4-carbonyl]-3-aza-bicyclo[3.1.0]hex-2-ylmethyl}-amide prepared by reaction of [2-Amino-5-(3-fluoro-phenyl)-thiazol-4-yl]-((1S,2S,5R)-2-aminomethyl-3-aza-bicyclo[3.1.0]hex-3-yl)-methanone with 2,3-Dihydro-benzofuran-4-carboxylic acid. LC-MS (basic): $t_R$=0.79 min; [M+H]$^+$=479.4.

Example 100

2,3-Dihydro-benzofuran-7-carboxylic Acid{(1S,2S,5R)-3-[2-amino-5-(3-fluoro-phenyl)-thiazole-4-carbonyl]-3-aza-bicyclo[3.1.0]hex-2-ylmethyl}-amide prepared by reaction of [2-Amino-5-(3-fluoro-phenyl)-thiazol-4-yl]-((1S,2S,5R)-2-aminomethyl-3-aza-bicyclo[3.1.0]hex-3-yl)-methanone with 2,3-Dihydro-benzofuran-7-carboxylic acid. LC-MS (basic): $t_R$=0.77 min; [M+H]$^+$=479.3.

Example 101

6-Fluoro-4H-benzo[1,3]dioxine-8-carboxylic acid{(1S,2S,5R)-3-[2-amino-5-(3-fluoro-phenyl)-thiazole-4-carbonyl]-3-aza-bicyclo[3.1.0]hex-2-ylmethyl}-amide prepared by reaction of [2-Amino-5-(3-fluoro-phenyl)-thiazol-4-yl]-((1S,2S,5R)-2-aminomethyl-3-aza-bicyclo[3.1.0]hex-3-yl)-methanone with 6-Fluoro-4H-benzo[1,3]dioxine-8-carboxylic acid. LC-MS (basic): $t_R$=0.79 min; [M+H]$^+$=513.3.

Example 102

2,2-Dimethyl-2,3-dihydro-benzofuran-7-carboxylic Acid{(1S,2S,5R)-3-[2-amino-5-(3-fluoro-phenyl)-thiazole-4-carbonyl]-3-aza-bicyclo[3.1.0]hex-2-ylmethyl}-amide prepared by reaction of [2-Amino-5-(3-fluoro-phenyl)-thiazol-4-yl]-((1S,2S,5R)-2-aminomethyl-3-aza-bicyclo[3.1.0]hex-3-yl)-methanone with 2,2-Dimethyl-2,3-dihydro-benzofuran-7-carboxylic acid.
LC-MS (basic): $t_R$=0.84 min; [M+H]$^+$=507.4.

Example 103

N-{(1S,2S,5R)-3-[2-Amino-5-(3-fluoro-phenyl)-thiazole-4-carbonyl]-3-aza-bicyclo[3.1.0]hex-2-ylmethyl}-3-trifluoromethyl-benzamide prepared by reaction of [2-Amino-5-(3-fluoro-phenyl)-thiazol-4-yl]-((1S,2S,5R)-2-aminomethyl-3-aza-bicyclo[3.1.0]hex-3-yl)-methanone with 3-Trifluoromethyl-benzoic acid. LC-MS (basic): $t_R$=0.86 min; [M+H]$^+$=505.3.

Example 104

N-{(1S,2S,5R)-3-[2-Amino-5-(3-fluoro-phenyl)-thiazole-4-carbonyl]-3-aza-bicyclo[3.1.0]hex-2-ylmethyl}-3-chloro-benzamide prepared by reaction of [2-Amino-5-(3-fluoro-phenyl)-thiazol-4-yl]-((1S,2S,5R)-2-aminomethyl-3-aza-bicyclo[3.1.0]hex-3-yl)-methanone with 3-Chloro-benzoic acid. LC-MS (basic): $t_R$=0.83 min; [M+H]$^+$=471.3.

Example 105

N-{(1S,2S,5R)-3-[2-Amino-5-(3-fluoro-phenyl)-thiazole-4-carbonyl]-3-aza-bicyclo[3.1.0]hex-2-ylmethyl}-3,5-dimethoxy-benzamide prepared by reaction of [2-Amino-5-(3-fluoro-phenyl)-thiazol-4-yl]-((1S,2S,5R)-2-aminomethyl-3-aza-bicyclo[3.1.0]hex-3-yl)-methanone with 3,5-dimethoxy-benzoic acid. LC-MS (basic): $t_R$=0.80 min; [M+H]$^+$=497.3.

Example 106

2,5-Dimethyl-2H-pyrazole-3-carboxylic Acid{(1S,2S,5R)-3-[2-amino-5-(3-fluoro-phenyl)-thiazole-4-carbonyl]-3-aza-bicyclo[3.1.0]hex-2-ylmethyl}-amide prepared by reaction of [2-Amino-5-(3-fluoro-phenyl)-thiazol-4-yl]-((1S,2S,5R)-2-aminomethyl-3-aza-bicyclo[3.1.0]hex-3-yl)-methanone with 2,5-Dimethyl-2H-pyrazole-3-carboxylic acid. LC-MS (basic): $t_R$=0.73 min; [M+H]$^+$=455.3.

Example 107

1,3-Dimethyl-1H-pyrazole-4-carboxylic acid{(1S,2S,5R)-3-[2-amino-5-(3-fluoro-phenyl)-thiazole-4-carbonyl]-3-aza-bicyclo[3.1.0]hex-2-ylmethyl}-amide prepared by reaction of [2-Amino-5-(3-fluoro-phenyl)-thiazol-4-yl]-((1S,2S,5R)-2-aminomethyl-3-aza-bicyclo[3.1.0]hex-3-yl)-methanone with 1,3-Dimethyl-1H-pyrazole-4-carboxylic acid. LC-MS (basic): $t_R$=0.69 min; [M+H]$^+$=455.2.

Example 108

2-Ethyl-5-methyl-2H-pyrazole-3-carboxylic Acid{(1S,2S,5R)-3-[2-amino-5-(3-fluoro-phenyl)-thiazole-4-carbonyl]-3-aza-bicyclo[3.1.0]hex-2-ylmethyl}-amide prepared by reaction of [2-Amino-5-(3-fluoro-phenyl)-thiazol-4-yl]-((1S,2S,5R)-2-aminomethyl-3-aza-bicyclo[3.1.0]hex-3-yl)-methanone with 2-Ethyl-5-methyl-2H-pyrazole-3-carboxylic acid. LC-MS (basic): $t_R$=0.76 min; [M+H]$^+$=469.3.

Example 109

3,5-Dimethyl-isoxazole-4-carboxylic Acid{(1S,2S,5R)-3-[2-amino-5-(3-fluoro-phenyl)-thiazole-4-carbonyl]-3-aza-bicyclo[3.1.0]hex-2-ylmethyl}-amide prepared by reaction of [2-Amino-5-(3-fluoro-phenyl)-thiazol-4-yl]-((1S,2S,5R)-2-aminomethyl-3-aza-bicyclo[3.1.0]hex-3-yl)-methanone with 3,5-Dimethyl-isoxazole-4-carboxylic acid. LC-MS (basic): $t_R$=0.75 min; [M+H]$^+$=456.3.

Example 110

Naphthalene-1-carboxylic Acid{(1S,2S,5R)-3-[2-amino-5-(3-fluoro-phenyl)-thiazole-4-carbonyl]-3-aza-bicyclo[3.1.0]hex-2-ylmethyl}-amide prepared by reaction of [2-Amino-5-(3-fluoro-phenyl)-thiazol-4-yl]-((1S,2S,5R)-2-aminomethyl-3-aza-bicyclo[3.1.0]hex-3-yl)-methanone with Naphthalene-1-carboxylic acid. LC-MS (basic): $t_R$=0.83 min; $[M+H]^+$=487.4.

Example 111

Quinoline-8-carboxylic Acid{(1S,2S,5R)-3-[2-amino-5-(3-fluoro-phenyl)-thiazole-4-carbonyl]-3-aza-bicyclo[3.1.0]hex-2-ylmethyl}-amide prepared by reaction of [2-Amino-5-(3-fluoro-phenyl)-thiazol-4-yl]-((1S,2S,5R)-2-aminomethyl-3-aza-bicyclo[3.1.0]hex-3-yl)-methanone with Quinoline-8-carboxylic acid. LC-MS (basic): $t_R$=0.78 min; $[M+H]^+$=488.3.

Example 112

Isoquinoline-1-carboxylic Acid{(1S,2S,5R)-3-[2-amino-5-(3-fluoro-phenyl)-thiazole-4-carbonyl]-3-aza-bicyclo[3.1.0]hex-2-ylmethyl}-amide prepared by reaction of [2-Amino-5-(3-fluoro-phenyl)-thiazol-4-yl]-((1S,2S,5R)-2-aminomethyl-3-aza-bicyclo[3.1.0]hex-3-yl)-methanone with Isoquinoline-1-carboxylic acid. LC-MS (basic): $t_R$=0.83 min; $[M+H]^+$=488.4.

Example 113

Quinoline-2-carboxylic Acid{(1S,2S,5R)-3-[2-amino-5-(3-fluoro-phenyl)-thiazole-4-carbonyl]-3-aza-bicyclo[3.1.0]hex-2-ylmethyl}-amide prepared by reaction of [2-Amino-5-(3-fluoro-phenyl)-thiazol-4-yl]-((1S,2S,5R)-2-aminomethyl-3-aza-bicyclo[3.1.0]hex-3-yl)-methanone with Quinoline-2-carboxylic acid. LC-MS (basic): $t_R$=0.83 min; $[M+H]^+$=488.4.

Example 114

1H-Indole-3-carboxylic Acid{(1S,2S,5R)-3-[2-amino-5-(3-fluoro-phenyl)-thiazole-4-carbonyl]-3-aza-bicyclo[3.1.0]hex-2-ylmethyl}-amide prepared by reaction of [2-Amino-5-(3-fluoro-phenyl)-thiazol-4-yl]-((1S,2S,5R)-2-aminomethyl-3-aza-bicyclo[3.1.0]hex-3-yl)-methanone with 1H-Indole-3-carboxylic acid. LC-MS (basic): $t_R$=0.76 min; $[M+H]^+$=476.3.

Example 115

1-Methyl-1H-indole-3-carboxylic Acid{(1S,2S,5R)-3-[2-amino-5-(3-fluoro-phenyl)-thiazole-4-carbonyl]-3-aza-bicyclo[3.1.0]hex-2-ylmethyl}-amide prepared by reaction of [2-Amino-5-(3-fluoro-phenyl)-thiazol-4-yl]-((1S,2S,5R)-2-aminomethyl-3-aza-bicyclo[3.1.0]hex-3-yl)-methanone with 1-Methyl-1H-indole-3-carboxylic acid. LC-MS (basic): $t_R$=0.80 min; $[M+H]^+$=490.1.

Example 116

1H-Indazole-3-carboxylic Acid{(1S,2S,5R)-3-[2-amino-5-(3-fluoro-phenyl)-thiazole-4-carbonyl]-3-aza-bicyclo[3.1.0]hex-2-ylmethyl}-amide prepared by reaction of [2-Amino-5-(3-fluoro-phenyl)-thiazol-4-yl]-((1S,2S,5R)-2-aminomethyl-3-aza-bicyclo[3.1.0]hex-3-yl)-methanone with 1H-Indazole-3-carboxylic acid. LC-MS (basic): $t_R$=0.77 min; $[M+H]^+$=477.3.

Example 117

1-Methyl-1H-indazole-3-carboxylic Acid{(1S,2S,5R)-3-[2-amino-5-(3-fluoro-phenyl)-thiazole-4-carbonyl]-3-aza-bicyclo[3.1.0]hex-2-ylmethyl}-amide prepared by reaction of [2-Amino-5-(3-fluoro-phenyl)-thiazol-4-yl]-((1S,2S,5R)-2-aminomethyl-3-aza-bicyclo[3.1.0]hex-3-yl)-methanone with 1-Methyl-1H-indazole-3-carboxylic acid. LC-MS (basic): $t_R$=0.81 min; $[M+H]^+$=491.2.

Example 118

Imidazo[1,2-a]pyridine-3-carboxylic Acid{(1S,2S,5R)-3-[2-amino-5-(3-fluoro-phenyl)-thiazole-4-carbonyl]-3-aza-bicyclo[3.1.0]hex-2-ylmethyl}-amide prepared by reaction of [2-Amino-5-(3-fluoro-phenyl)-thiazol-4-yl]-((1S,2S,5R)-2-aminomethyl-3-aza-bicyclo[3.1.0]hex-3-yl)-methanone with Imidazo[1,2-a]pyridine-3-carboxylic acid. LC-MS (basic): $t_R$=0.74 min; $[M+H]^+$=477.3.

Example 119

2,8-Dimethyl-imidazo[1,2-a]pyridine-3-carboxylic Acid{(1S,2S,5R)-3-[2-amino-5-(3-fluoro-phenyl)-thiazole-4-carbonyl]-3-aza-bicyclo[3.1.0]hex-2-ylmethyl}-amide prepared by reaction of [2-Amino-5-(3-fluoro-phenyl)-thiazol-4-yl]-((1S,2S,5R)-2-aminomethyl-3-aza-bicyclo[3.1.0]hex-3-yl)-methanone with 2,8-Dimethyl-imidazo[1,2-a]pyridine-3-carboxylic acid.

LC-MS (basic): $t_R$=0.75 min; $[M+H]^+$=505.4.

Example 120

Pyrazolo[1,5-a]pyridine-3-carboxylic Acid{(1S,2S,5R)-3-[2-amino-5-(3-fluoro-phenyl)-thiazole-4-carbonyl]-3-aza-bicyclo[3.1.0]hex-2-ylmethyl}-amide prepared by reaction of [2-Amino-5-(3-fluoro-phenyl)-thiazol-4-yl]-((1S,2S,5R)-2-aminomethyl-3-aza-bicyclo[3.1.0]hex-3-yl)-methanone with Pyrazolo[1,5-a]pyridine-3-carboxylic acid. LC-MS (basic): $t_R$=0.74 min; $[M+H]^+$=477.4.

Example 121

2,3-Dihydro-thieno[3,4-b][1,4]dioxine-5-carboxylic Acid{(1S,2S,5R)-3-[2-amino-5-(3-fluoro-phenyl)-thiazole-4-carbonyl]-3-aza-bicyclo[3.1.0]hex-2-ylmethyl}-amide prepared by reaction of [2-Amino-5-(3-fluoro-phenyl)-thiazol-4-yl]-((1S,2S,5R)-2-aminomethyl-3-aza-bicyclo[3.1.0]hex-3-yl)-methanone with 2,3-Dihydro-thieno[3,4-b][1,4]dioxine-5-carboxylic acid. LC-MS (basic): $t_R$=0.75 min; $[M+H]^+$=501.3.

Example 122

5-Fluoro-1-methyl-1H-indole-2-carboxylic Acid{(1S,2S,5R)-3-[2-amino-5-(3-fluoro-phenyl)-thiazole-4-carbonyl]-3-aza-bicyclo[3.1.0]hex-2-ylmethyl}-amide prepared by reaction of [2-Amino-5-(3-fluoro-phenyl)-thiazol-4-yl]-((1S,2S,5R)-2-aminomethyl-3-aza-bicyclo[3.1.0]hex-3-yl)-methanone with 5-Fluoro-1-methyl-1H-indole-2-carboxylic acid. LC-MS (basic): $t_R$=0.87 min; [M+H]$^+$=508.3.

Example 123

Imidazo[2,1-b]thiazole-5-carboxylic Acid{(1S,2S,5R)-3-[2-amino-5-(3-fluoro-phenyl)-thiazole-4-carbonyl]-3-aza-bicyclo[3.1.0]hex-2-ylmethyl}-amide prepared by reaction of [2-Amino-5-(3-fluoro-phenyl)-thiazol-4-yl]-((1S,2S,5R)-2-aminomethyl-3-aza-bicyclo[3.1.0]hex-3-yl)-methanone with Imidazo[2,1-b]thiazole-5-carboxylic acid. LC-MS (basic): $t_R$=0.73 min; [M+H]$^+$=483.3.

Example 124

3-Methyl-imidazo[2,1-b]thiazole-2-carboxylic Acid{(1S,2S,5R)-3-[2-amino-5-(3-fluoro-phenyl)-thiazole-4-carbonyl]-3-aza-bicyclo[3.1.0]hex-2-ylmethyl}-amide prepared by reaction of [2-Amino-5-(3-fluoro-phenyl)-thiazol-4-yl]-((1S,2S,5R)-2-aminomethyl-3-aza-bicyclo[3.1.0]hex-3-yl)-methanone with 3-Methyl-imidazo[2,1-b]thiazole-2-carboxylic acid. LC-MS (basic): $t_R$=0.73 min; [M+H]$^+$=497.3.

Example 125

1,2-Dimethyl-1H-indole-3-carboxylic Acid{(1S,2S,5R)-3-[2-amino-5-(3-fluoro-phenyl)-thiazole-4-carbonyl]-3-aza-bicyclo[3.1.0]hex-2-ylmethyl}-amide prepared by reaction of [2-Amino-5-(3-fluoro-phenyl)-thiazol-4-yl]-((1S,2S,5R)-2-aminomethyl-3-aza-bicyclo[3.1.0]hex-3-yl)-methanone with 1,2-Dimethyl-1H-indole-3-carboxylic acid. LC-MS (basic): $t_R$=0.81 min; [M+H]$^+$=504.4.

Example 126

2-Methoxy-N-[(1S,2S,5R)-3-(2-methyl-5-m-tolyl-thiazole-4-carbonyl)-3-aza-bicyclo[3.1.0]hex-2-ylmethyl]-benzamide prepared by reaction of ((1S,2S,5R)-2-Aminomethyl-3-aza-bicyclo[3.1.0]hex-3-yl)-(2-methyl-5-m-tolyl-thiazol-4-yl)-methanone with 2-Methoxy-benzoic acid. LC-MS (basic): $t_R$=0.89 min; [M+H]$^+$=462.1.

Example 127

5-Chloro-2-methoxy-N-[(1S,2S,5R)-3-(2-methyl-5-m-tolyl-thiazole-4-carbonyl)-3-aza-bicyclo[3.1.0]hex-2-ylmethyl]-benzamide prepared by reaction of ((1S,2S,5R)-2-Aminomethyl-3-aza-bicyclo[3.1.0]hex-3-yl)-(2-methyl-5-m-tolyl-thiazol-4-yl)-methanone with 5-Chloro-2-methoxy-benzoic acid. LC-MS (basic): $t_R$=0.96 min; [M+H]$^+$=496.0.

Example 128

4-Bromo-N-[(1S,2S,5R)-3-(2-methyl-5-m-tolyl-thiazole-4-carbonyl)-3-aza-bicyclo[3.1.0]hex-2-ylmethyl]-benzamide prepared by reaction of ((1S,2S,5R)-2-Aminomethyl-3-aza-bicyclo[3.1.0]hex-3-yl)-(2-methyl-5-m-tolyl-thiazol-4-yl)-methanone with 4-Bromo-benzoic acid. LC-MS (basic): $t_R$=0.96 min; [M+H]$^+$=509.9.

Example 129

4-Chloro-2-methoxy-N-[(1S,2S,5R)-3-(2-methyl-5-m-tolyl-thiazole-4-carbonyl)-3-aza-bicyclo[3.1.0]hex-2-ylmethyl]-benzamide prepared by reaction of ((1S,2S,5R)-2-Aminomethyl-3-aza-bicyclo[3.1.0]hex-3-yl)-(2-methyl-5-m-tolyl-thiazol-4-yl)-methanone with 4-Chloro-2-methoxy-benzoic acid. LC-MS (basic): $t_R$=0.96 min; [M+H]$^+$=496.0.

Example 130

3,4-Dichloro-N-[(1S,2S,5R)-3-(2-methyl-5-m-tolyl-thiazole-4-carbonyl)-3-aza-bicyclo[3.1.0]hex-2-ylmethyl]-benzamide prepared by reaction of ((1S,2S,5R)-2-Aminomethyl-3-aza-bicyclo[3.1.0]hex-3-yl)-(2-methyl-5-m-tolyl-thiazol-4-yl)-methanone with 3,4-Dichloro-benzoic acid. LC-MS (basic): $t_R$=1.01 min; [M+H]$^+$=500.0.

Example 131

2-Chloro-4,5-difluoro-N-[(1S,2S,5R)-3-(2-methyl-5-m-tolyl-thiazole-4-carbonyl)-3-aza-bicyclo[3.1.0]hex-2-ylmethyl]-benzamide prepared by reaction of ((1S,2S,5R)-2-Aminomethyl-3-aza-bicyclo[3.1.0]hex-3-yl)-(2-methyl-5-m-tolyl-thiazol-4-yl)-methanone with 2-Chloro-4,5-difluoro-benzoic acid. LC-MS (basic): $t_R$=0.94 min; [M+H]$^+$=502.0.

Example 132

2-Fluoro-5-methyl-N-[(1S,2S,5R)-3-(2-methyl-5-m-tolyl-thiazole-4-carbonyl)-3-aza-bicyclo[3.1.0]hex-2-ylmethyl]-benzamide prepared by reaction of ((1S,2S,5R)-2-Aminomethyl-3-aza-bicyclo[3.1.0]hex-3-yl)-(2-methyl-5-m-tolyl-thiazol-4-yl)-methanone with 2-Fluoro-5-methyl-benzoic acid. LC-MS (basic): $t_R$=0.93 min; [M+H]$^+$=464.1.

Example 133

3-Fluoro-2-methyl-N-[(1S,2S,5R)-3-(2-methyl-5-m-tolyl-thiazole-4-carbonyl)-3-aza-bicyclo[3.1.0]hex-2-ylmethyl]-benzamide prepared by reaction of ((1S,2S,5R)-2-Aminomethyl-3-aza-bicyclo[3.1.0]hex-3-yl)-(2-methyl-5-m-tolyl-thiazol-4-yl)-methanone with 3-Fluoro-2-methyl-benzoic acid. LC-MS (basic): $t_R$=0.92 min; [M+H]$^+$=464.1.

Example 134

5-Fluoro-2-methoxy-N-[(1S,2S,5R)-3-(2-methyl-5-m-tolyl-thiazole-4-carbonyl)-3-aza-bicyclo[3.1.0]hex-2-ylmethyl]-benzamide prepared by reaction of ((1S,2S,5R)-2-Aminomethyl-3-aza-bicyclo[3.1.0]hex-3-yl)-(2-methyl-5-m-tolyl-thiazol-4-yl)-methanone with 5-Fluoro-2-methoxy-benzoic acid. LC-MS (basic): $t_R$=0.92 min; $[M+H]^+$=480.1.

Example 135

3-Chloro-2-methyl-N-[(1S,2S,5R)-3-(2-methyl-5-m-tolyl-thiazole-4-carbonyl)-3-aza-bicyclo[3.1.0]hex-2-ylmethyl]-benzamide prepared by reaction of ((1S,2S,5R)-2-Aminomethyl-3-aza-bicyclo[3.1.0]hex-3-yl)-(2-methyl-5-m-tolyl-thiazol-4-yl)-methanone with 3-Chloro-2-methyl-benzoic acid. LC-MS (basic): $t_R$=0.95 min; $[M+H]^+$=480.0.

Example 136

2-Chloro-3-fluoro-N-[(1S,2S,5R)-3-(2-methyl-5-m-tolyl-thiazole-4-carbonyl)-3-aza-bicyclo[3.1.0]hex-2-ylmethyl]-benzamide prepared by reaction of ((1S,2S,5R)-2-Aminomethyl-3-aza-bicyclo[3.1.0]hex-3-yl)-(2-methyl-5-m-tolyl-thiazol-4-yl)-methanone with 2-Chloro-3-fluoro-benzoic acid.
LC-MS (basic): $t_R$=0.91 min; $[M+H]^+$=484.0.

Example 137

2,5-Dimethyl-N-[(1S,2S,5R)-3-(2-methyl-5-m-tolyl-thiazole-4-carbonyl)-3-aza-bicyclo[3.1.0]hex-2-ylmethyl]-benzamide prepared by reaction of ((1S,2S,5R)-2-Aminomethyl-3-aza-bicyclo[3.1.0]hex-3-yl)-(2-methyl-5-m-tolyl-thiazol-4-yl)-methanone with 2,5-Dimethyl-benzoic acid.
LC-MS (basic): $t_R$=0.93 min; $[M+H]^+$=460.0.

Example 138

3,4-Dimethyl-N-[(1S,2S,5R)-3-(2-methyl-5-m-tolyl-thiazole-4-carbonyl)-3-aza-bicyclo[3.1.0]hex-2-ylmethyl]-benzamide prepared by reaction of ((1S,2S,5R)-2-Aminomethyl-3-aza-bicyclo[3.1.0]hex-3-yl)-(2-methyl-5-m-tolyl-thiazol-4-yl)-methanone with 3,4-Dimethyl-benzoic acid.
LC-MS (basic): $t_R$=0.95 min; $[M+H]^+$=460.0.

Example 139

2,5-Dimethoxy-N-[(1S,2S,5R)-3-(2-methyl-5-m-tolyl-thiazole-4-carbonyl)-3-aza-bicyclo[3.1.0]hex-2-ylmethyl]-benzamide prepared by reaction of ((1S,2S,5R)-2-Aminomethyl-3-aza-bicyclo[3.1.0]hex-3-yl)-(2-methyl-5-m-tolyl-thiazol-4-yl)-methanone with 2,5-Dimethoxy-benzoic acid.
LC-MS (basic): $t_R$=0.90 min; $[M+H]^+$=492.0.

Example 140

2-Chloro-4-fluoro-N-[(1S,2S,5R)-3-(2-methyl-5-m-tolyl-thiazole-4-carbonyl)-3-aza-bicyclo[3.1.0]hex-2-ylmethyl]-benzamide prepared by reaction of ((1S,2S,5R)-2-Aminomethyl-3-aza-bicyclo[3.1.0]hex-3-yl)-(2-methyl-5-m-tolyl-thiazol-4-yl)-methanone with 2-Chloro-4-fluoro-benzoic acid. LC-MS (basic): $t_R$=0.91 min; $[M+H]^+$=484.0.

Example 141

2-Chloro-3-methyl-N-[(1S,2S,5R)-3-(2-methyl-5-m-tolyl-thiazole-4-carbonyl)-3-aza-bicyclo[3.1.0]hex-2-ylmethyl]-benzamide prepared by reaction of ((1S,2S,5R)-2-Aminomethyl-3-aza-bicyclo[3.1.0]hex-3-yl)-(2-methyl-5-m-tolyl-thiazol-4-yl)-methanone with 2-Chloro-3-methyl-benzoic acid.
LC-MS (basic): $t_R$=0.92 min; $[M+H]^+$=480.0.

Example 142

2,4-Dichloro-N-[(1S,2S,5R)-3-(2-methyl-5-m-tolyl-thiazole-4-carbonyl)-3-aza-bicyclo[3.1.0]hex-2-ylmethyl]-benzamide prepared by reaction of ((1S,2S,5R)-2-Aminomethyl-3-aza-bicyclo[3.1.0]hex-3-yl)-(2-methyl-5-m-tolyl-thiazol-4-yl)-methanone with 2,4-Dichloro-benzoic acid.
LC-MS (basic): $t_R$=0.96 min; $[M+H]^+$=500.0.

Example 143

4-Methyl-N-[(1S,2S,5R)-3-(2-methyl-5-m-tolyl-thiazole-4-carbonyl)-3-aza-bicyclo[3.1.0]hex-2-ylmethyl]-3-trifluoromethyl-benzamide prepared by reaction of ((1S,2S,5R)-2-Aminomethyl-3-aza-bicyclo[3.1.0]hex-3-yl)-(2-methyl-5-m-tolyl-thiazol-4-yl)-methanone with 4-Methyl-3-trifluoromethyl-benzoic acid. LC-MS (basic): $t_R$=1.00 min; $[M+H]^+$=514.1.

Example 144

4-Methoxy-2-methyl-N-[(1S,2S,5R)-3-(2-methyl-5-m-tolyl-thiazole-4-carbonyl)-3-aza-bicyclo[3.1.0]hex-2-ylmethyl]-benzamide prepared by reaction of ((1S,2S,5R)-2-Aminomethyl-3-aza-bicyclo[3.1.0]hex-3-yl)-(2-methyl-5-m-tolyl-thiazol-4-yl)-methanone with 4-Methoxy-2-methyl-benzoic acid. LC-MS (basic): $t_R$=0.90 min; $[M+H]^+$=476.2.

Example 145

4-Ethyl-N-[(1S,2S,5R)-3-(2-methyl-5-m-tolyl-thiazole-4-carbonyl)-3-aza-bicyclo[3.1.0]hex-2-ylmethyl]-benzamide prepared by reaction of ((1S,2S,5R)-2-Aminomethyl-3-aza-bicyclo[3.1.0]hex-3-yl)-(2-methyl-5-m-tolyl-thiazol-4-yl)-methanone with 4-Ethyl-benzoic acid.
LC-MS (basic): $t_R$=0.96 min; $[M+H]^+$=460.0.

Example 146

4-Methoxy-3-methyl-N-[(1S,2S,5R)-3-(2-methyl-5-m-tolyl-thiazole-4-carbonyl)-3-aza-bicyclo[3.1.0]hex-2-ylmethyl]-benzamide prepared by reaction of ((1S,2S,5R)-2-Aminomethyl-3-aza-bicyclo[3.1.0]hex-3-yl)-(2-methyl-5-m-tolyl-thiazol-4-yl)-methanone with 4-Methoxy-3-methyl-benzoic acid.
LC-MS (basic): $t_R$=0.93 min; $[M+H]^+$=476.1.

Example 147

3,5-Dimethyl-N-[(1S,2S,5R)-3-(2-methyl-5-m-tolyl-thiazole-4-carbonyl)-3-aza-bicyclo[3.1.0]hex-2-ylmethyl]-benzamide prepared by reaction of ((1S,2S,5R)-2-Aminomethyl-3-aza-bicyclo[3.1.0]hex-3-yl)-(2-methyl-5-m-tolyl-thiazol-4-yl)-methanone with 3,5-Dimethyl-benzoic acid. LC-MS (basic): $t_R$=0.96 min; $[M+H]^+$=460.0.

Example 148

5-Bromo-2-chloro-N-[(1S,2S,5R)-3-(2-methyl-5-m-tolyl-thiazole-4-carbonyl)-3-aza-bicyclo[3.1.0]hex-2-ylmethyl]-benzamide prepared by reaction of ((1S,2S,5R)-2-Aminomethyl-3-aza-bicyclo[3.1.0]hex-3-yl)-(2-methyl-5-m-tolyl-thiazol-4-yl)-methanone with 5-Bromo-2-chloro-benzoic acid.
LC-MS (basic): $t_R$=0.96 min; $[M+H]^+$=543.9.

Example 149

3-Cyano-N-[(1S,2S,5R)-3-(2-methyl-5-m-tolyl-thiazole-4-carbonyl)-3-aza-bicyclo[3.1.0]hex-2-ylmethyl]-benzamide prepared by reaction of ((1S,2S,5R)-2-Aminomethyl-3-aza-bicyclo[3.1.0]hex-3-yl)-(2-methyl-5-m-tolyl-thiazol-4-yl)-methanone with 3-Cyano-benzoic acid.
LC-MS (basic): $t_R$=0.88 min; $[M+H]^+$=456.9.

Example 150

4-Cyano-N-[(1S,2S,5R)-3-(2-methyl-5-m-tolyl-thiazole-4-carbonyl)-3-aza-bicyclo[3.1.0]hex-2-ylmethyl]-benzamide prepared by reaction of ((1S,2S,5R)-2-Aminomethyl-3-aza-bicyclo[3.1.0]hex-3-yl)-(2-methyl-5-m-tolyl-thiazol-4-yl)-methanone with 4-Cyano-benzoic acid.
LC-MS (basic): $t_R$=0.88 min; $[M+H]^+$=457.0.

Example 151

2,4-Dimethoxy-N-[(1S,2S,5R)-3-(2-methyl-5-m-tolyl-thiazole-4-carbonyl)-3-aza-bicyclo[3.1.0]hex-2-ylmethyl]-benzamide prepared by reaction of ((1S,2S,5R)-2-Aminomethyl-3-aza-bicyclo[3.1.0]hex-3-yl)-(2-methyl-5-m-tolyl-thiazol-4-yl)-methanone with 2,4-Dimethoxy-benzoic acid.
LC-MS (basic): $t_R$=0.89 min; $[M+H]^+$=492.0.

Example 152

N-[(1S,2S,5R)-3-(2-Methyl-5-m-tolyl-thiazole-4-carbonyl)-3-aza-bicyclo[3.1.0]hex-2-ylmethyl]-2-morpholin-4-yl-benzamide prepared by reaction of ((1S,2S,5R)-2-Aminomethyl-3-aza-bicyclo[3.1.0]hex-3-yl)-(2-methyl-5-m-tolyl-thiazol-4-yl)-methanone with 2-Morpholin-4-yl-benzoic acid.
LC-MS (basic): $t_R$=0.90 min; $[M+H]^+$=517.1.

Example 153

2-(4-Methyl-piperazin-1-yl)-N-[(1S,2S,5R)-3-(2-methyl-5-m-tolyl-thiazole-4-carbonyl)-3-aza-bicyclo[3.1.0]hex-2-ylmethyl]-benzamide prepared by reaction of ((1S,2S,5R)-2-Aminomethyl-3-aza-bicyclo[3.1.0]hex-3-yl)-(2-methyl-5-m-tolyl-thiazol-4-yl)-methanone with 2-(4-Methyl-piperazin-1-yl)-benzoic acid. LC-MS (basic): $t_R$=0.86 min; $[M+H]^+$=530.1.

Example 154

4-Chloro-N-[(1S,2S,5R)-3-(2-methyl-5-m-tolyl-thiazole-4-carbonyl)-3-aza-bicyclo[3.1.0]hex-2-ylmethyl]-benzamide prepared by reaction of ((1S,2S,5R)-2-Aminomethyl-3-aza-bicyclo[3.1.0]hex-3-yl)-(2-methyl-5-m-tolyl-thiazol-4-yl)-methanone with 4-Chloro-benzoic acid.
LC-MS (basic): $t_R$=0.95 min; $[M+H]^+$=466.0.

Example 155

2,3-Dimethoxy-N-[(1S,2S,5R)-3-(2-methyl-5-m-tolyl-thiazole-4-carbonyl)-3-aza-bicyclo[3.1.0]hex-2-ylmethyl]-benzamide prepared by reaction of ((1S,2S,5R)-2-Aminomethyl-3-aza-bicyclo[3.1.0]hex-3-yl)-(2-methyl-5-m-tolyl-thiazol-4-yl)-methanone with 2,3-Dimethoxy-benzoic acid.
LC-MS (basic): $t_R$=0.89 min; $[M+H]^+$=492.0.

Example 156

3-Iodo-N-[(1S,2S,5R)-3-(2-methyl-5-m-tolyl-thiazole-4-carbonyl)-3-aza-bicyclo[3.1.0]hex-2-ylmethyl]-benzamide prepared by reaction of ((1S,2S,5R)-2-Aminomethyl-3-aza-bicyclo[3.1.0]hex-3-yl)-(2-methyl-5-m-tolyl-thiazol-4-yl)-methanone with 3-Iodo-benzoic acid.
LC-MS (basic): $t_R$=0.98 min; $[M+H]^+$=557.9.

Example 157

4-Methoxy-N-[(1S,2S,5R)-3-(2-methyl-5-m-tolyl-thiazole-4-carbonyl)-3-aza-bicyclo[3.1.0]hex-2-ylmethyl]-3-trifluoromethyl-benzamide prepared by reaction of ((1S,2S,5R)-2-Aminomethyl-3-aza-bicyclo[3.1.0]hex-3-yl)-(2-methyl-5-m-tolyl-thiazol-4-yl)-methanone with 4-Methoxy-3-trifluoromethyl-benzoic acid. LC-MS (basic): $t_R$=0.96 min; $[M+H]^+$=530.0.

Example 158

2-Chloro-N-[(1S,2S,5R)-3-(2-methyl-5-m-tolyl-thiazole-4-carbonyl)-3-aza-bicyclo[3.1.0]hex-2-ylmethyl]-benzamide prepared by reaction of ((1S,2S,5R)-2-Aminomethyl-3-aza-bicyclo[3.1.0]hex-3-yl)-(2-methyl-5-m-tolyl-thiazol-4-yl)-methanone with 2-Chloro-benzoic acid.
LC-MS (basic): $t_R$=0.89 min; [M+H]$^+$=466.1.

Example 159

2-Bromo-5-methyl-N-[(1S,2S,5R)-3-(2-methyl-5-m-tolyl-thiazole-4-carbonyl)-3-aza-bicyclo[3.1.0]hex-2-ylmethyl]-benzamide prepared by reaction of ((1S,2S,5R)-2-Aminomethyl-3-aza-bicyclo[3.1.0]hex-3-yl)-(2-methyl-5-m-tolyl-thiazol-4-yl)-methanone with 2-Bromo-5-methyl-benzoic acid.
LC-MS (basic): $t_R$=0.93 min; [M+H]$^+$=523.9.

Example 160

5-Methyl-imidazo[2,1-b]thiazole-6-carboxylic Acid [(1S,2S,5R)-3-(2-methyl-5-m-tolyl-thiazole-4-carbonyl)-3-aza-bicyclo[3.1.0]hex-2-ylmethyl]-amide prepared by reaction of ((1S,2S,5R)-2-Aminomethyl-3-aza-bicyclo[3.1.0]hex-3-yl)-(2-methyl-5-m-tolyl-thiazol-4-yl)-methanone with 5-Methyl-imidazo[2,1-b]thiazole-6-carboxylic acid. LC-MS (basic): $t_R$=0.84 min; [M+H]$^+$=491.9.

Example 161

3,5-Dimethyl-imidazo[2,1-b]thiazole-6-carboxylic Acid[(1S,2S,5R)-3-(2-methyl-5-m-tolyl-thiazole-4-carbonyl)-3-aza-bicyclo[3.1.0]hex-2-ylmethyl]-amide prepared by reaction of ((1S,2S,5R)-2-Aminomethyl-3-aza-bicyclo[3.1.0]hex-3-yl)-(2-methyl-5-m-tolyl-thiazol-4-yl)-methanone with 3,5-Dimethyl-imidazo[2,1-b]thiazole-6-carboxylic acid. LC-MS (basic): $t_R$=0.88 min; [M+H]$^+$=506.0.

Example 162

2,6-Dimethyl-imidazo[2,1-b]thiazole-5-carboxylic Acid[(1S,2S,5R)-3-(2-methyl-5-m-tolyl-thiazole-4-carbonyl)-3-aza-bicyclo[3.1.0]hex-2-ylmethyl]-amide prepared by reaction of ((1S,2S,5R)-2-Aminomethyl-3-aza-bicyclo[3.1.0]hex-3-yl)-(2-methyl-5-m-tolyl-thiazol-4-yl)-methanone with 2,6-Dimethyl-imidazo[2,1-b]thiazole-5-carboxylic acid. LC-MS (basic): $t_R$=0.87 min; [M+H]$^+$=506.0.

Example 163

2-Methyl-imidazo[2,1-b]thiazole-5-carboxylic Acid [(1S,2S,5R)-3-(2-methyl-5-m-tolyl-thiazole-4-carbonyl)-3-aza-bicyclo[3.1.0]hex-2-ylmethyl]-amide prepared by reaction of ((1S,2S,5R)-2-Aminomethyl-3-aza-bicyclo[3.1.0]hex-3-yl)-(2-methyl-5-m-tolyl-thiazol-4-yl)-methanone with 2-Methyl-imidazo[2,1-b]thiazole-5-carboxylic acid. LC-MS (basic): $t_R$=0.86 min; [M+H]$^+$=491.9.

Example 164

6-Trifluoromethyl-imidazo[2,1-b]thiazole-5-carboxylic Acid[(1S,2S,5R)-3-(2-methyl-5-m-tolyl-thiazole-4-carbonyl)-3-aza-bicyclo[3.1.0]hex-2-ylmethyl]-amide prepared by reaction of ((1S,2S,5R)-2-Aminomethyl-3-aza-bicyclo[3.1.0]hex-3-yl)-(2-methyl-5-m-tolyl-thiazol-4-yl)-methanone with 6-Trifluoromethyl-imidazo[2,1-b]thiazole-5-carboxylic acid. LC-MS (basic): $t_R$=0.92 min; [M+H]$^+$=545.9.

Example 165

3,6-Dimethyl-imidazo[2,1-b]thiazole-5-carboxylic Acid[(1S,2S,5R)-3-(2-methyl-5-m-tolyl-thiazole-4-carbonyl)-3-aza-bicyclo[3.1.0]hex-2-ylmethyl]-amide prepared by reaction of ((1S,2S,5R)-2-Aminomethyl-3-aza-bicyclo[3.1.0]hex-3-yl)-(2-methyl-5-m-tolyl-thiazol-4-yl)-methanone with 3,6-Dimethyl-imidazo[2,1-b]thiazole-5-carboxylic acid. LC-MS (basic): $t_R$=0.83 min; [M+H]$^+$=506.0.

Example 166

3-Methyl-imidazo[2,1-b]thiazole-5-carboxylic Acid [(1S,2S,5R)-3-(2-methyl-5-m-tolyl-thiazole-4-carbonyl)-3-aza-bicyclo[3.1.0]hex-2-ylmethyl]-amide prepared by reaction of ((1S,2S,5R)-2-Aminomethyl-3-aza-bicyclo[3.1.0]hex-3-yl)-(2-methyl-5-m-tolyl-thiazol-4-yl)-methanone with 3-Methyl-imidazo[2,1-b]thiazole-5-carboxylic acid. LC-MS (basic): $t_R$=0.83 min; [M+H]$^+$=492.0.

Example 167

2,3,6-Trimethyl-imidazo[2,1-b]thiazole-5-carboxylic Acid[(1S,2S,5R)-3-(2-methyl-5-m-tolyl-thiazole-4-carbonyl)-3-aza-bicyclo[3.1.0]hex-2-ylmethyl]-amide prepared by reaction of ((1S,2S,5R)-2-Aminomethyl-3-aza-bicyclo[3.1.0]hex-3-yl)-(2-methyl-5-m-tolyl-thiazol-4-yl)-methanone with 2,3,6-Trimethyl-imidazo[2,1-b]thiazole-5-carboxylic acid. LC-MS (basic): $t_R$=0.86 min; [M+H]$^+$=520.0.

Example 168

6-Chloro-imidazo[2,1-b]thiazole-5-carboxylic Acid [(1S,2S,5R)-3-(2-methyl-5-m-tolyl-thiazole-4-carbonyl)-3-aza-bicyclo[3.1.0]hex-2-ylmethyl]-amide prepared by reaction of ((1S,2S,5R)-2-Aminomethyl-3-aza-bicyclo[3.1.0]hex-3-yl)-(2-methyl-5-m-tolyl-thiazol-4-yl)-methanone with 6-Chloro-imidazo[2,1-b]thiazole-5-carboxylic acid. LC-MS (basic): $t_R$=0.90 min; [M+H]$^+$=511.9.

Example 169

3-Oxo-3,4-dihydro-2H-benzo[1,4]oxazine-8-carboxylic Acid[(1S,2S,5R)-3-(2-methyl-5-m-tolyl-thiazole-4-carbonyl)-3-aza-bicyclo[3.1.0]hex-2-ylmethyl]-amide prepared by reaction of ((1S,2S,5R)-2-Aminomethyl-3-aza-bicyclo[3.1.0]hex-3-yl)-(2-methyl-5-m-tolyl-thiazol-4-yl)-methanone with 3-Oxo-3,4-dihydro-2H-benzo[1,4]oxazine-8-carboxylic acid. LC-MS (basic): $t_R$=0.77 min; $[M+H]^+$=503.0.

Example 170

2H-Chromene-5-carboxylic Acid[(1S,2S,5R)-3-(2-methyl-5-m-tolyl-thiazole-4-carbonyl)-3-aza-bicyclo[3.1.0]hex-2-ylmethyl]-amide prepared by reaction of ((1S,2S,5R)-2-Aminomethyl-3-aza-bicyclo[3.1.0]hex-3-yl)-(2-methyl-5-m-tolyl-thiazol-4-yl)-methanone with 2H-Chromene-5-carboxylic acid. LC-MS (basic): $t_R$=0.91 min; $[M+H]^+$=486.1.

Example 171

4-Methyl-3,4-dihydro-2H-benzo[1,4]oxazine-8-carboxylic Acid[(1S,2S,5R)-3-(2-methyl-5-m-tolyl-thiazole-4-carbonyl)-3-aza-bicyclo[3.1.0]hex-2-ylmethyl]-amide prepared by reaction of ((1S,2S,5R)-2-Aminomethyl-3-aza-bicyclo[3.1.0]hex-3-yl)-(2-methyl-5-m-tolyl-thiazol-4-yl)-methanone with 4-Methyl-3,4-dihydro-2H-benzo[1,4]oxazine-8-carboxylic acid. LC-MS (basic): $t_R$=0.90 min; $[M+H]^+$=503.1.

Example 172

Chroman-8-carboxylic Acid[(1S,2S,5R)-3-(2-methyl-5-m-tolyl-thiazole-4-carbonyl)-3-aza-bicyclo[3.1.0]hex-2-ylmethyl]-amide
prepared by reaction of ((1S,2S,5R)-2-Aminomethyl-3-aza-bicyclo[3.1.0]hex-3-yl)-(2-methyl-5-m-tolyl-thiazol-4-yl)-methanone with Chroman-8-carboxylic acid. LC-MS (basic): $t_R$=0.93 min; $[M+H]^+$=488.1.

Example 173

Chroman-5-carboxylic Acid[(1S,2S,5R)-3-(2-methyl-5-m-tolyl-thiazole-4-carbonyl)-3-aza-bicyclo[3.1.0]hex-2-ylmethyl]-amide
prepared by reaction of ((1S,2S,5R)-2-Aminomethyl-3-aza-bicyclo[3.1.0]hex-3-yl)-(2-methyl-5-m-tolyl-thiazol-4-yl)-methanone with Chroman-5-carboxylic acid. LC-MS (basic): $t_R$=0.90 min; $[M+H]^+$=488.1.

Example 174

3,4-Dihydro-2H-benzo[1,4]oxazine-8-carboxylic Acid[(1S,2S,5R)-3-(2-methyl-5-m-tolyl-thiazole-4-carbonyl)-3-aza-bicyclo[3.1.0]hex-2-ylmethyl]-amide prepared by reaction of ((1S,2S,5R)-2-Aminomethyl-3-aza-bicyclo[3.1.0]hex-3-yl)-(2-methyl-5-m-tolyl-thiazol-4-yl)-methanone with 3,4-Dihydro-2H-benzo[1,4]oxazine-8-carboxylic acid. LC-MS (basic): $t_R$=0.82 min; $[M+H]^+$=488.9.

Example 175

3,4-Dihydro-2H-benzo[1,4]oxazine-5-carboxylic Acid[(1S,2S,5R)-3-(2-methyl-5-m-tolyl-thiazole-4-carbonyl)-3-aza-bicyclo[3.1.0]hex-2-ylmethyl]-amide prepared by reaction of ((1S,2S,5R)-2-Aminomethyl-3-aza-bicyclo[3.1.0]hex-3-yl)-(2-methyl-5-m-tolyl-thiazol-4-yl)-methanone with 3,4-Dihydro-2H-benzo[1,4]oxazine-5-carboxylic acid. LC-MS (basic): $t_R$=0.94 min; $[M+H]^+$=488.9.

Example 176

4-Methyl-3-oxo-3,4-dihydro-2H-benzo[1,4]oxazine-8-carboxylic Acid[(1S,2S,5R)-3-(2-methyl-5-m-tolyl-thiazole-4-carbonyl)-3-aza-bicyclo[3.1.0]hex-2-ylmethyl]-amide prepared by reaction of ((1S,2S,5R)-2-Aminomethyl-3-aza-bicyclo[3.1.0]hex-3-yl)-(2-methyl-5-m-tolyl-thiazol-4-yl)-methanone with 4-Methyl-3-oxo-3,4-dihydro-2H-benzo[1,4]oxazine-8-carboxylic acid. LC-MS (basic): $t_R$=0.83 min; $[M+H]^+$=517.1.

Example 177

4-Methyl-3,4-dihydro-2H-benzo[1,4]oxazine-5-carboxylic Acid[(1S,2S,5R)-3-(2-methyl-5-m-tolyl-thiazole-4-carbonyl)-3-aza-bicyclo[3.1.0]hex-2-ylmethyl]-amide prepared by reaction of ((1S,2S,5R)-2-Aminomethyl-3-aza-bicyclo[3.1.0]hex-3-yl)-(2-methyl-5-m-tolyl-thiazol-4-yl)-methanone with 4-Methyl-3,4-dihydro-2H-benzo[1,4]oxazine-5-carboxylic acid. LC-MS (basic): $t_R$=0.89 min; $[M+H]^+$=503.1.

B.3 Synthesis of Carboxylic Amide Derivatives (General Procedure III)

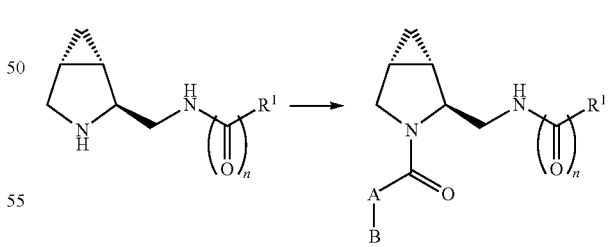

The respective carboxylic acid (0.18 mmol, 1.0 eq) is treated successively with a solution of TBTU (0.20 mmol, 1.1 eq) in DMF or MeCN (0.50 mL) and DIPEA (0.27 mmol, 1.5 eq). After 15 min a solution of the respective 3-aza-bicyclo[3.1.0]hexane derivative (0.18 mmol, 1.0 eq, hydrochloride salt) and DIPEA (0.27 mmol, 1.5 eq) in DMF or MeCN (0.50 mL) is added. The mixture is stirred for 20 h and purified by prep. HPLC (acidic gradient) to give the respective amide derivative.

Starting from N-[(1S,2S,5R)-1-(3-Aza-bicyclo[3.1.0]hex-2-yl)methyl]-3-chloro-benzamide:

| Example | Name | eluent | LC-MS $t_R$ [min] | $[M + H]^+$ |
|---|---|---|---|---|
| 178 | 3-Chloro-N-{(1S,2S,5R)-3-[5-(3-chloro-phenyl)-thiazole-4-carbonyl]-3-aza-bicyclo[3.1.0]hex-2-ylmethyl}-benzamide | acidic | 1.02 1.06 | 471.9 |
| 179 | 3-Chloro-N-[(1S,2S,5R)-3-(5-phenyl-thiazole-4-carbonyl)-3-aza-bicyclo[3.1.0]hex-2-ylmethyl]-benzamide | acidic | 0.98 1.02 | 437.9 |
| 180 | 3-Chloro-N-{(1S,2S,5R)-3-[5-(3-trifluoromethyl-phenyl)-thiazole-4-carbonyl]-3-aza-bicyclo[3.1.0]hex-2-ylmethyl}-benzamide | acidic | 1.05 1.08 | 505.9 |
| 181 | 3-Chloro-N-{(1S,2S,5R)-3-[5-(3-fluoro-phenyl)-thiazole-4-carbonyl]-3-aza-bicyclo[3.1.0]hex-2-ylmethyl}-benzamide | acidic | 0.99 1.03 | 455.9 |
| 182 | 3-Chloro-N-{(1S,2S,5R)-3-[5-(2-fluoro-phenyl)-thiazole-4-carbonyl]-3-aza-bicyclo[3.1.0]hex-2-ylmethyl}-benzamide | acidic | 0.99 1.03 | 455.9 |
| 183 | 3-Chloro-N-{(1S,2S,5R)-3-[2-cyclopropyl-5-(3-fluoro-phenyl)-thiazole-4-carbonyl]-3-aza-bicyclo[3.1.0]hex-2-ylmethyl}-benzamide | acidic | 1.07 1.11 | 495.9 |
| 184 | 3-Chloro-N-{(1S,2S,5R)-3-[2-cyclopropyl-5-(3-fluoro-4-methyl-phenyl)-thiazole-4-carbonyl]-3-aza-bicyclo[3.1.0]hex-2-ylmethyl}-benzamide | acidic | 1.10 1.14 | 509.9 |
| 185 | 3-Chloro-N-{(1S,2S,5R)-3-[5-(3-methoxy-phenyl)-thiazole-4-carbonyl]-3-aza-bicyclo[3.1.0]hex-2-ylmethyl}-benzamide | acidic | 0.99 1.04 | 467.9 |
| 186 | 3-Chloro-N-{(1S,2S,5R)-3-[5-(4-cyano-phenyl)-2-cyclopropyl-thiazole-4-carbonyl]-3-aza-bicyclo[3.1.0]hex-2-ylmethyl}-benzamide | acidic | 1.05 1.09 | 502.9 |
| 187 | 3-Chloro-N-{(1S,2S,5R)-3-[5-(3-fluoro-4-methyl-phenyl)-2-methyl-thiazole-4-carbonyl]-3-aza-bicyclo[3.1.0]hex-2-ylmethyl}-benzamide | acidic | 1.05 1.09 | 483.9 |
| 188 | 3-Chloro-N-{(1S,2S,5R)-3-[5-(3-fluoro-5-trifluoromethyl-phenyl)-2-methyl-thiazole-4-carbonyl]-3-aza-bicyclo[3.1.0]hex-2-ylmethyl}-benzamide | acidic | 1.09 1.11 | 537.9 |
| 189 | N-{(1S,2S,5R)-3-[5-(3-Bromo-phenyl)-2-methyl-thiazole-4-carbonyl]-3-aza-bicyclo[3.1.0]hex-2-ylmethyl}-3-chloro-benzamide | acidic | 1.08 1.09 | 529.8 |
| 190 | 3-Chloro-N-{(1S,2S,5R)-3-[5-(4-cyano-phenyl)-2-methyl-thiazole-4-carbonyl]-3-aza-bicyclo[3.1.0]hex-2-ylmethyl}-benzamide | acidic | 0.99 1.03 | 476.9 |

Starting from Imidazo[1,2-a]pyridine-3-carboxylic acid [(1S,2S,5R)-1-(3-aza-bicyclo[3.1.0]hex-2-yl)methyl]-amide:

| Example | Name | eluent | LC-MS $t_R$ [min] | $[M + H]^+$ |
|---|---|---|---|---|
| 191 | Imidazo[1,2-a]pyridine-3-carboxylic acid {(1S,2S,5R)-3-[2-methyl-5-(3-trifluoromethyl-phenyl)-thiazole-4-carbonyl]-3-aza-bicyclo[3.1.0]hex-2-ylmethyl}-amide | acidic | 0.85 0.89 | 526.0 |
| 192 | Imidazo[1,2-a]pyridine-3-carboxylic acid {(1S,2S,5R)-3-[5-(2,3-dimethyl-phenyl)-2-methyl-thiazole-4-carbonyl]-3-aza-bicyclo[3.1.0]hex-2-ylmethyl}-amide | acidic | 0.85 0.87 | 486.1 |
| 193 | Imidazo[1,2-a]pyridine-3-carboxylic acid {(1S,2S,5R)-3-[5-(2,3-dichloro-phenyl)-2-methyl-thiazole-4-carbonyl]-3-aza-bicyclo[3.1.0]hex-2-ylmethyl}-amide | acidic | 0.86 0.89 | 526.0 |
| 194 | Imidazo[1,2-a]pyridine-3-carboxylic acid {(1S,2S,5R)-3-[5-(3-bromo-4-fluoro-phenyl)-2-methyl-thiazole-4-carbonyl]-3-aza-bicyclo[3.1.0]hex-2-ylmethyl}-amide | acidic | 0.85 0.88 | 553.9 |

-continued

| Example | Name | LC-MS eluent | $t_R$ [min] | $[M + H]^+$ |
|---|---|---|---|---|
| 195 | Imidazo[1,2-a]pyridine-3-carboxylic acid {(1S,2S,5R)-3-[5-(3-fluoro-2-methyl-phenyl)-2-methyl-thiazole-4-carbonyl]-3-aza-bicyclo[3.1.0]hex-2-ylmethyl}-amide | acidic | 0.83 0.84 | 490.0 |
| 196 | Imidazo[1,2-a]pyridine-3-carboxylic acid {(1S,2S,5R)-3-[5-(3,4-dichloro-phenyl)-2-methyl-thiazole-4-carbonyl]-3-aza-bicyclo[3.1.0]hex-2-ylmethyl}-amide | acidic | 0.87 0.91 | 525.1 |
| 197 | Imidazo[1,2-a]pyridine-3-carboxylic acid {(1S,2S,5R)-3-[5-(3,4-dimethyl-phenyl)-2-methyl-thiazole-4-carbonyl]-3-aza-bicyclo[3.1.0]hex-2-ylmethyl}-amide | acidic | 0.85 0.90 | 486.1 |
| 198 | Imidazo[1,2-a]pyridine-3-carboxylic acid {(1S,2S,5R)-3-[5-(2-chloro-6-fluoro-phenyl)-2-methyl-thiazole-4-carbonyl]-3-aza-bicyclo[3.1.0]hex-2-ylmethyl}-amide | acidic | 0.83 0.86 | 510.0 |

Starting from 2,3-Dihydro-benzofuran-4-carboxylic acid [(1S,2S,5R)-1-(3-aza-bicyclo[3.1.0]hex-2-yl)methyl]-amide:

| Example | Name | LC-MS eluent | $t_R$ [min] | $[M + H]^+$ |
|---|---|---|---|---|
| 199 | 2,3-Dihydro-benzofuran-4-carboxylic acid {(1S,2S,5R)-3-[5-(3-fluoro-phenyl)-2-methyl-thiazole-4-carbonyl]-3-aza-bicyclo[3.1.0]hex-2-ylmethyl}-amide | acidic | 0.99 1.03 | 478.0 |
| 200 | 2,3-Dihydro-benzofuran-4-carboxylic acid {(1S,2S,5R)-3-[5-(4-fluoro-phenyl)-2-methyl-thiazole-4-carbonyl]-3-aza-bicyclo[3.1.0]hex-2-ylmethyl}-amide | acidic | 0.98 1.03 | 478.0 |
| 201 | 2,3-Dihydro-benzofuran-4-carboxylic acid {(1S,2S,5R)-3-[2-methyl-5-(3-trifluoromethyl-phenyl)-thiazole-4-carbonyl]-3-aza-bicyclo[3.1.0]hex-2-ylmethyl}-amide | acidic | 1.06 1.09 | 528.0 |
| 202 | 2,3-Dihydro-benzofuran-4-carboxylic acid {(1S,2S,5R)-3-[5-(4-bromo-phenyl)-2-methyl-thiazole-4-carbonyl]-3-aza-bicyclo[3.1.0]hex-2-ylmethyl}-amide | acidic | 1.05 1.10 | 537.9 |
| 203 | 2,3-Dihydro-benzofuran-4-carboxylic acid {(1S,2S,5R)-3-[5-(3,5-dimethyl-phenyl)-2-methyl-thiazole-4-carbonyl]-3-aza-bicyclo[3.1.0]hex-2-ylmethyl}-amide | acidic | 1.06 1.12 | 488.0 |
| 204 | 2,3-Dihydro-benzofuran-4-carboxylic acid {(1S,2S,5R)-3-[5-(2,3-dimethyl-phenyl)-2-methyl-thiazole-4-carbonyl]-3-aza-bicyclo[3.1.0]hex-2-ylmethyl}-amide | acidic | 1.05 1.10 | 488.0 |
| 205 | 2,3-Dihydro-benzofuran-4-carboxylic acid {(1S,2S,5R)-3-[5-(2,3-dichloro-phenyl)-2-methyl-thiazole-4-carbonyl]-3-aza-bicyclo[3.1.0]hex-2-ylmethyl}-amide | acidic | 1.12 | 527.9 |
| 206 | 2,3-Dihydro-benzofuran-4-carboxylic acid {(1S,2S,5R)-3-[5-(3-bromo-4-fluoro-phenyl)-2-methyl-thiazole-4-carbonyl]-3-aza-bicyclo[3.1.0]hex-2-ylmethyl}-amide | acidic | 1.05 1.10 | 555.8 |
| 207 | 2,3-Dihydro-benzofuran-4-carboxylic acid {(1S,2S,5R)-3-[5-(3,4-difluoro-phenyl)-2-methyl-thiazole-4-carbonyl]-3-aza-bicyclo[3.1.0]hex-2-ylmethyl}-amide | acidic | 1.01 1.04 | 496.0 |
| 208 | 2,3-Dihydro-benzofuran-4-carboxylic acid {(1S,2S,5R)-3-[5-(2,4-dimethyl-phenyl)-2-methyl-thiazole-4-carbonyl]-3-aza-bicyclo[3.1.0]hex-2-ylmethyl}-amide | acidic | 1.06 1.11 | 488.0 |
| 209 | 2,3-Dihydro-benzofuran-4-carboxylic acid {(1S,2S,5R)-3-[5-(3-fluoro-2-methyl-phenyl)-2-methyl-thiazole-4-carbonyl]-3-aza-bicyclo[3.1.0]hex-2-ylmethyl}-amide | acidic | 1.03 1.07 | 492.0 |

-continued

| Example | Name | LC-MS eluent | $t_R$ [min] | [M + H]+ |
|---|---|---|---|---|
| 210 | 2,3-Dihydro-benzofuran-4-carboxylic acid {(1S,2S,5R)-3-[5-(3,4-dichloro-phenyl)-2-methyl-thiazole-4-carbonyl]-3-aza-bicyclo[3.1.0]hex-2-ylmethyl}-amide | acidic | 1.03 1.14 | 527.9 |
| 211 | 2,3-Dihydro-benzofuran-4-carboxylic acid {(1S,2S,5R)-3-[5-(3,4-dimethyl-phenyl)-2-methyl-thiazole-4-carbonyl]-3-aza-bicyclo[3.1.0]hex-2-ylmethyl}-amide | acidic | 1.05 1.10 | 488.1 |
| 212 | 2,3-Dihydro-benzofuran-4-carboxylic acid {(1S,2S,5R)-3-[5-(3-methanesulfonylamino-phenyl)-2-methyl-thiazole-4-carbonyl]-3-aza-bicyclo[3.1.0]hex-2-ylmethyl}-amide | acidic | 0.87 0.92 | 552.9 |
| 213 | 2,3-Dihydro-benzofuran-4-carboxylic acid {(1S,2S,5R)-3-[5-(3-acetylamino-phenyl)-2-methyl-thiazole-4-carbonyl]-3-aza-bicyclo[3.1.0]hex-2-ylmethyl}-amide | acidic | 0.84 0.88 | 517.1 |
| 214 | 2,3-Dihydro-benzofuran-4-carboxylic acid {(1S,2S,5R)-3-[5-(2-chloro-6-fluoro-phenyl)-2-methyl-thiazole-4-carbonyl]-3-aza-bicyclo[3.1.0]hex-2-ylmethyl}-amide | acidic | 1.08 | 512.3 |
| 215 | 2,3-Dihydro-benzofuran-4-carboxylic acid [(1S,2S,5R)-3-(2-methyl-5-phenyl-thiazole-4-carbonyl)-3-aza-bicyclo[3.1.0]hex-2-ylmethyl]-amide | acidic | 0.97 1.01 | 460.0 |
| 216 | 2,3-Dihydro-benzofuran-4-carboxylic acid [(1S,2S,5R)-3-(2-cyclopropyl-5-phenyl-thiazole-4-carbonyl)-3-aza-bicyclo[3.1.0]hex-2-ylmethyl]-amide | acidic | 1.04 1.10 | 486.0 |
| 217 | 2,3-Dihydro-benzofuran-4-carboxylic acid [(1S,2S,5R)-3-(2-dimethylamino-5-phenyl-thiazole-4-carbonyl)-3-aza-bicyclo[3.1.0]hex-2-ylmethyl]-amide | acidic | 0.97 1.05 | 489.0 |
| 218 | 2,3-Dihydro-benzofuran-4-carboxylic acid {(1S,2S,5R)-3-[2-dimethylamino-5-(3-fluoro-phenyl)-thiazole-4-carbonyl]-3-aza-bicyclo[3.1.0]hex-2-ylmethyl}-amide | acidic | 1.00 1.06 | 507.0 |

Starting from 2,3-Dihydro-thieno[3,4-b][1,4]dioxine-5-carboxylic acid[(1S,2S,5R)-1-(3-aza-bicyclo[3.1.0]hex-2-yl)methyl]-amide:

| Example | Name | LC-MS eluent | $t_R$ [min] | [M + H]+ |
|---|---|---|---|---|
| 219 | 2,3-Dihydro-thieno[3,4-b][1,4]dioxine-5-carboxylic acid [(1S,2S,5R)-3-(2-dimethylamino-5-phenyl-thiazole-4-carbonyl)-3-aza-bicyclo[3.1.0]hex-2-ylmethyl]-amide | acidic | 0.93 0.98 | 510.8 |
| 220 | 2,3-Dihydro-thieno[3,4-b][1,4]dioxine-5-carboxylic acid {(1S,2S,5R)-3-[2-dimethylamino-5-(3-fluoro-phenyl)-thiazole-4-carbonyl]-3-aza-bicyclo[3.1.0]hex-2-ylmethyl}-amide | acidic | 0.97 1.01 | 528.9 |

Starting from 6-Methyl-imidazo[2,1-b]thiazole-5-carboxylic acid[(1S,2S,5R)-1-(3-aza-bicyclo[3.1.0]hex-2-yl)methyl]-amide:

| Example | Name | LC-MS eluent | $t_R$ [min] | [M + H]+ |
|---|---|---|---|---|
| 221 | 6-Methyl-imidazo[2,1-b]thiazole-5-carboxylic acid [(1S,2S,5R)-3-(3-m-tolyl-thiophene-2-carbonyl)-3-aza-bicyclo[3.1.0]hex-2-ylmethyl]-amide | acidic | 0.93 | 477.4 |

-continued

| Example | Name | LC-MS eluent | $t_R$ [min] | [M + H]+ |
|---|---|---|---|---|
| 222 | 6-Methyl-imidazo[2,1-b]thiazole-5-carboxylic acid [(1S,2S,5R)-3-(3-p-tolyl-thiophene-2-carbonyl)-3-aza-bicyclo[3.1.0]hex-2-ylmethyl]-amide | acidic | 0.93 | 477.4 |
| 223 | 6-Methyl-imidazo[2,1-b]thiazole-5-carboxylic acid {(1S,2S,5R)-3-[3-(4-fluoro-phenyl)-thiophene-2-carbonyl]-3-aza-bicyclo[3.1.0]hex-2-ylmethyl}-amide | acidic | 0.90 | 481.2 |
| 224 | 6-Methyl-imidazo[2,1-b]thiazole-5-carboxylic acid [(1S,2S,5R)-3-(2-m-tolyl-thiophene-3-carbonyl)-3-aza-bicyclo[3.1.0]hex-2-ylmethyl]-amide | acidic | 0.96 | 477.4 |
| 225 | 6-Methyl-imidazo[2,1-b]thiazole-5-carboxylic acid [(1S,2S,5R)-3-(2-p-tolyl-thiophene-3-carbonyl)-3-aza-bicyclo[3.1.0]hex-2-ylmethyl]-amide | acidic | 0.96 | 477.3 |
| 226 | 6-Methyl-imidazo[2,1-b]thiazole-5-carboxylic acid {(1S,2S,5R)-3-[2-(4-fluoro-phenyl)-thiophene-3-carbonyl]-3-aza-bicyclo[3.1.0]hex-2-ylmethyl}-amide | acidic | 0.92 | 481.3 |

Starting from 2-Ethyl-5-methyl-2H-pyrazole-3-carboxylic acid[(1S,2S,5R)-1-(3-aza-bicyclo[3.1.0]hex-2-yl)methyl]-amide:

| Example | Name | LC-MS eluent | $t_R$ [min] | [M + H]+ |
|---|---|---|---|---|
| 227 | 2-Ethyl-5-methyl-2H-pyrazole-3-carboxylic acid [(1S,2S,5R)-3-(4'-fluoro-biphenyl-2-carbonyl)-3-aza-bicyclo[3.1.0]hex-2-ylmethyl]-amide | acidic | 0.94 0.98 | 447.3 |
| 228 | 2-Ethyl-5-methyl-2H-pyrazole-3-carboxylic acid [(1S,2S,5R)-3-(3'-fluoro-biphenyl-2-carbonyl)-3-aza-bicyclo[3.1.0]hex-2-ylmethyl]-amide | acidic | 0.94 0.98 | 447.3 |
| 229 | 2-Ethyl-5-methyl-2H-pyrazole-3-carboxylic acid [(1S,2S,5R)-3-(4'-methyl-biphenyl-2-carbonyl)-3-aza-bicyclo[3.1.0]hex-2-ylmethyl]-amide | acidic | 0.96 1.01 | 443.3 |
| 230 | 2-Ethyl-5-methyl-2H-pyrazole-3-carboxylic acid [(1S,2S,5R)-3-(3'-methyl-biphenyl-2-carbonyl)-3-aza-bicyclo[3.1.0]hex-2-ylmethyl]-amide | acidic | 0.96 1.01 | 443.3 |
| 231 | 2-Ethyl-5-methyl-2H-pyrazole-3-carboxylic acid {(1S,2S,5R)-3-[5-(4-fluoro-phenyl)-2-methyl-thiazole-4-carbonyl]-3-aza-bicyclo[3.1.0]hex-2-ylmethyl}-amide | acidic | 0.90 0.94 | 468.2 |
| 232 | 2-Ethyl-5-methyl-2H-pyrazole-3-carboxylic acid [(1S,2S,5R)-3-(2-methyl-5-p-tolyl-thiazole-4-carbonyl)-3-aza-bicyclo[3.1.0]hex-2-ylmethyl]-amide | acidic | 0.92 0.96 | 464.2 |
| 233 | 2-Ethyl-5-methyl-2H-pyrazole-3-carboxylic acid {(1S,2S,5R)-3-[5-(3-bromo-4-fluoro-phenyl)-2-methyl-thiazole-4-carbonyl]-3-aza-bicyclo[3.1.0]hex-2-ylmethyl}-amide | acidic | 0.95 0.99 | 546.2 |
| 234 | 2-Ethyl-5-methyl-2H-pyrazole-3-carboxylic acid [(1S,2S,5R)-3-(5-m-tolyl-thiazole-4-carbonyl)-3-aza-bicyclo[3.1.0]hex-2-ylmethyl]-amide | acidic | 0.90 0.94 | 450.2 |
| 235 | 2-Ethyl-5-methyl-2H-pyrazole-3-carboxylic acid [(1S,2S,5R)-3-(2-dimethylamino-5-m-tolyl-thiazole-4-carbonyl)-3-aza-bicyclo[3.1.0]hex-2-ylmethyl]-amide | acidic | 0.92 0.99 | 493.3 |
| 236 | 2-Ethyl-5-methyl-2H-pyrazole-3-carboxylic acid [(1S,2S,5R)-3-(2-amino-5-m-tolyl-thiazole-4-carbonyl)-3-aza-bicyclo[3.1.0]hex-2-ylmethyl]-amide | acidic | 0.81 0.86 | 465.2 |

-continued

| Example | Name | LC-MS eluent | t_R [min] | [M + H]+ |
|---|---|---|---|---|
| 237 | 2-Ethyl-5-methyl-2H-pyrazole-3-carboxylic acid [(1S,2S,5R)-3-(2-cyclopropyl-5-m-tolyl-thiazole-4-carbonyl)-3-aza-bicyclo[3.1.0]hex-2-ylmethyl]-amide | acidic | 0.98 1.03 | 490.3 |
| 238 | 2-Ethyl-5-methyl-2H-pyrazole-3-carboxylic acid {(1S,2S,5R)-3-[5-(3,4-dimethyl-phenyl)-2-methyl-thiazole-4-carbonyl]-3-aza-bicyclo[3.1.0]hex-2-ylmethyl}-amide | acidic | 0.95 0.99 | 478.3 |
| 239 | 2-Ethyl-5-methyl-2H-pyrazole-3-carboxylic acid [(1S,2S,5R)-3-(2-methyl-5-o-tolyl-thiazole-4-carbonyl)-3-aza-bicyclo[3.1.0]hex-2-ylmethyl]-amide | acidic | 0.91 0.95 | 464.2 |
| 240 | 2-Ethyl-5-methyl-2H-pyrazole-3-carboxylic acid {(1S,2S,5R)-3-[5-(3,5-dimethyl-phenyl)-2-methyl-thiazole-4-carbonyl]-3-aza-bicyclo[3.1.0]hex-2-ylmethyl}-amide | acidic | 0.95 1.00 | 478.3 |

Starting from [(1S,2S,5R)-1-(3-Aza-bicyclo[3.1.0]hex-2-yl)methyl]-(5-bromo-pyrimidin-2-yl)-amine:

| Example | Name | LC-MS eluent | t_R [min] | [M + H]+ |
|---|---|---|---|---|
| 241 | {(1S,2S,5R)-2-[(5-Bromo-pyrimidin-2-ylamino)-methyl]-3-aza-bicyclo[3.1.0]hex-3-yl}-[5-(3-chloro-phenyl)-2-methyl-thiazol-4-yl]-methanone | acidic | 1.03 1.08 | 503.8 |
| 242 | {(1S,2S,5R)-2-[(5-Bromo-pyrimidin-2-ylamino)-methyl]-3-aza-bicyclo[3.1.0]hex-3-yl}-[5-(3-fluoro-phenyl)-2-methyl-thiazol-4-yl]-methanone | acidic | 1.00 1.05 | 487.9 |
| 243 | {(1S,2S,5R)-2-[(5-Bromo-pyrimidin-2-ylamino)-methyl]-3-aza-bicyclo[3.1.0]hex-3-yl}-[5-(4-fluoro-phenyl)-2-methyl-thiazol-4-yl]-methanone | acidic | 0.99 1.05 | 487.9 |
| 244 | {(1S,2S,5R)-2-[(5-Bromo-pyrimidin-2-ylamino)-methyl]-3-aza-bicyclo[3.1.0]hex-3-yl}-(2-methyl-5-m-tolyl-thiazol-4-yl)-methanone | acidic | 1.01 1.08 | 483.9 |
| 245 | {(1S,2S,5R)-2-[(5-Bromo-pyrimidin-2-ylamino)-methyl]-3-aza-bicyclo[3.1.0]hex-3-yl}-[2-methyl-5-(3-trifluoromethyl-phenyl)-thiazol-4-yl]-methanone | acidic | 1.05 1.10 | 537.8 |
| 246 | [5-(4-Bromo-phenyl)-2-methyl-thiazol-4-yl]-{(1S,2S,5R)-2-[(5-bromo-pyrimidin-2-ylamino)-methyl]-3-aza-bicyclo[3.1.0]hex-3-yl}-methanone | acidic | 1.04 1.09 | 547.8 |
| 247 | {(1S,2S,5R)-2-[(5-Bromo-pyrimidin-2-ylamino)-methyl]-3-aza-bicyclo[3.1.0]hex-3-yl}-[5-(3,5-dimethyl-phenyl)-2-methyl-thiazol-4-yl]-methanone | acidic | 1.04 1.11 | 497.9 |
| 248 | {(1S,2S,5R)-2-[(5-Bromo-pyrimidin-2-ylamino)-methyl]-3-aza-bicyclo[3.1.0]hex-3-yl}-[5-(2,3-dichloro-phenyl)-2-methyl-thiazol-4-yl]-methanone | acidic | 1.04 1.11 | 537.9 |
| 249 | [5-(3-Bromo-4-fluoro-phenyl)-2-methyl-thiazol-4-yl]-{(1S,2S,5R)-2-[(5-bromo-pyrimidin-2-ylamino)-methyl]-3-aza-bicyclo[3.1.0]hex-3-yl}-methanone | acidic | 1.05 1.10 | 565.7 |
| 250 | {(1S,2S,5R)-2-[(5-Bromo-pyrimidin-2-ylamino)-methyl]-3-aza-bicyclo[3.1.0]hex-3-yl}-[5-(3,4-dichloro-phenyl)-2-methyl-thiazol-4-yl]-methanone | acidic | 1.07 1.12 | 537.8 |
| 251 | {(1S,2S,5R)-2-[(5-Bromo-pyrimidin-2-ylamino)-methyl]-3-aza-bicyclo[3.1.0]hex-3-yl}-(2-methyl-5-phenyl-thiazol-4-yl)-methanone | acidic | 0.98 1.04 | 469.9 |
| 252 | {(1S,2S,5R)-2-[(5-Bromo-pyrimidin-2-ylamino)-methyl]-3-aza-bicyclo[3.1.0]hex-3-yl}-[5-(3-fluoro-4-methyl-phenyl)-2-methyl-thiazol-4-yl]-methanone | acidic | 1.03 1.09 | 501.9 |

-continued

| Example | Name | LC-MS eluent | $t_R$ [min] | $[M + H]^+$ |
|---|---|---|---|---|
| 253 | {(1S,2S,5R)-2-[(5-Bromo-pyrimidin-2-ylamino)-methyl]-3-aza-bicyclo[3.1.0]hex-3-yl}-[5-(3-fluoro-5-trifluoromethyl-phenyl)-2-methyl-thiazol-4-yl]-methanone | acidic | 1.08 1.12 | 555.7 |
| 254 | {(1S,2S,5R)-2-[(5-Bromo-pyrimidin-2-ylamino)-methyl]-3-aza-bicyclo[3.1.0]hex-3-yl}-[2-cyclopropyl-5-(3-fluoro-4-methyl-phenyl)-thiazol-4-yl]-methanone | acidic | 1.08 1.14 | 527.8 |

B.4 Synthesis of Carboxylic Amide Derivatives (General Procedure IV)

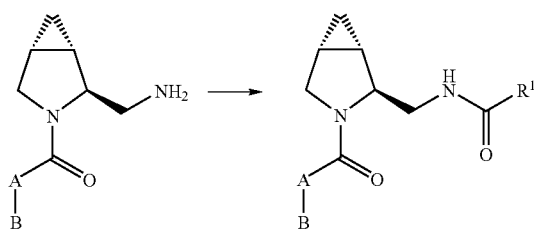

A solution of the respective carboxylic acid (0.09 mmol, 1.0 eq) in DMF (0.5 mL) is treated successively with TBTU (0.09 mmol, 1.0 eq) and DIPEA (0.25 mmol, 2.7 eq). After 30 min a solution of the respective 3-aza-bicyclo[3.1.0]hexane derivative (0.09 mmol, 1.0 eq) in DMF (0.50 mL) is added. The mixture is stirred for 12 h and purified by prep. HPLC (basic gradient) to give the respective amide derivative.

Starting from ((1S,2S,5R)-2-Aminomethyl-3-aza-bicyclo[3.1.0]hex-3-yl)-(2-methyl-5-m-tolyl-thiazol-4-yl)-methanone:

| Example | Name | LC-MS eluent | $t_R$ [min] | $[M + H]^+$ |
|---|---|---|---|---|
| 255 | Benzoxazole-7-carboxylic acid [(1S,2S,5R)-3-(2-methyl-5-m-tolyl-thiazole-4-carbonyl)-3-aza-bicyclo[3.1.0]hex-2-ylmethyl]-amide | acidic | 0.89 0.93 | 473.1 |
| 256 | 2-Methyl-benzoxazole-7-carboxylic acid [(1S,2S,5R)-3-(2-methyl-5-m-tolyl-thiazole-4-carbonyl)-3-aza-bicyclo[3.1.0]hex-2-ylmethyl]-amide | acidic | 0.91 0.95 | 487.2 |
| 257 | Benzothiazole-7-carboxylic acid [(1S,2S,5R)-3-(2-methyl-5-m-tolyl-thiazole-4-carbonyl)-3-aza-bicyclo[3.1.0]hex-2-ylmethyl]-amide | acidic | 0.95 1.01 | 489.1 |
| 258 | 7-Chloro-benzofuran-4-carboxylic acid [(1S,2S,5R)-3-(2-methyl-5-m-tolyl-thiazole-4-carbonyl)-3-aza-bicyclo[3.1.0]hex-2-ylmethyl]-amide | acidic | 1.02 1.05 | 506.0 |
| 259 | 7-Fluoro-benzofuran-4-carboxylic acid [(1S,2S,5R)-3-(2-methyl-5-m-tolyl-thiazole-4-carbonyl)-3-aza-bicyclo[3.1.0]hex-2-ylmethyl]-amide | acidic | 0.99 1.03 | 490.1 |
| 260 | Pyrrolo[2,1-b]thiazole-7-carboxylic acid [(1S,2S,5R)-3-(2-methyl-5-m-tolyl-thiazole-4-carbonyl)-3-aza-bicyclo[3.1.0]hex-2-ylmethyl]-amide | acidic | 0.90 0.96 | 477.1 |
| 261 | 6-Methyl-pyrrolo[2,1-b]thiazole-7-carboxylic acid [(1S,2S,5R)-3-(2-methyl-5-m-tolyl-thiazole-4-carbonyl)-3-aza-bicyclo[3.1.0]hex-2-ylmethyl]-amide | acidic | 0.93 0.98 | 491.0 |
| 262 | 7-Chloro-2-methoxy-2,3-dihydro-benzofuran-4-carboxylic acid [(1S,2S,5R)-3-(2-methyl-5-m-tolyl-thiazole-4-carbonyl)-3-aza-bicyclo[3.1.0]hex-2-ylmethyl]-amide | acidic | 1.01 1.05 | 538.1 |

Starting from ((1S,2S,5R)-2-Aminomethyl-3-aza-bicyclo[3.1.0]hex-3-yl)-(2-p-tolyl-thiophen-3-yl)-methanone:

| Example | Name | eluent | $t_R$ [min] | $[M + H]^+$ |
|---|---|---|---|---|
| 263 | 1-Methyl-1H-indole-3-carboxylic acid [(1S,2S,5R)-3-(2-p-tolyl-thiophene-3-carbonyl)-3-aza-bicyclo[3.1.0]hex-2-ylmethyl]-amide | acidic | 1.03 1.07 | 470.3 |
| 264 | Quinoline-8-carboxylic acid [(1S,2S,5R)-3-(2-p-tolyl-thiophene-3-carbonyl)-3-aza-bicyclo[3.1.0]hex-2-ylmethyl]-amide | acidic | 1.00 1.04 | 468.4 |
| 265 | 4-Methyl-4H-furo[3,2-b]pyrrole-5-carboxylic acid [(1S,2S,5R)-3-(2-p-tolyl-thiophene-3-carbonyl)-3-aza-bicyclo[3.1.0]hex-2-ylmethyl]-amide | acidic | 1.05 1.09 | 460.1 |
| 266 | 3,4-Dihydro-2H-benzo[1,4]oxazine-5-carboxylic acid [(1S,2S,5R)-3-(2-p-tolyl-thiophene-3-carbonyl)-3-aza-bicyclo[3.1.0]hex-2-ylmethyl]-amide | acidic | 1.06 1.10 | 474.4 |
| 267 | 2,3-Dihydro-thieno[3,4-b][1,4]dioxine-5-carboxylic acid [(1S,2S,5R)-3-(2-p-tolyl-thiophene-3-carbonyl)-3-aza-bicyclo[3.1.0]hex-2-ylmethyl]-amide | acidic | 1.01 1.04 | 481.4 |
| 268 | 2-Ethyl-5-methyl-2H-pyrazole-3-carboxylic acid [(1S,2S,5R)-3-(2-p-tolyl-thiophene-3-carbonyl)-3-aza-bicyclo[3.1.0]hex-2-ylmethyl]-amide | acidic | 1.00 1.04 | 448.7 |
| 269 | 2,5-Dimethyl-2H-pyrazole-3-carboxylic acid [(1S,2S,5R)-3-(2-p-tolyl-thiophene-3-carbonyl)-3-aza-bicyclo[3.1.0]hex-2-ylmethyl]-amide | acidic | 0.99 1.04 | 435.3 |
| 270 | 5-Fluoro-1-methyl-1H-indole-carboxylic acid [(1S,2S,5R)-3-(2-p-tolyl-thiophene-3-carbonyl)-3-aza-bicyclo[3.1.0]hex-2-ylmethyl]-amide | acidic | 1.10 1.13 | 488.2 |
| 271 | 3-Bromo-N-[(1S,2S,5R)-3-(2-p-tolyl-thiophene-3-carbonyl)-3-aza-bicyclo[3.1.0]hex-2-ylmethyl]-benzamide | acidic | 1.07 1.11 | 495.3 |
| 272 | 3-Chloro-N-[(1S,2S,5R)-3-(2-p-tolyl-thiophene-3-carbonyl)-3-aza-bicyclo[3.1.0]hex-2-ylmethyl]-benzamide | acidic | 1.06 1.11 | 451.1 |
| 273 | 3-Methyl-N-[(1S,2S,5R)-3-(2-p-tolyl-thiophene-3-carbonyl)-3-aza-bicyclo[3.1.0]hex-2-ylmethyl]-benzamide | acidic | 1.04 1.09 | 431.3 |
| 274 | Benzo[2,1,3]thiadiazole-4-carboxylic acid [(1S,2S,5R)-3-(2-p-tolyl-thiophene-3-carbonyl)-3-aza-bicyclo[3.1.0]hex-2-ylmethyl]-amide | acidic | 1.07 | 475.3 |
| 275 | Benzo[2,1,3]oxadiazole-4-carboxylic acid [(1S,2S,5R)-3-(2-p-tolyl-thiophene-3-carbonyl)-3-aza-bicyclo[3.1.0]hex-2-ylmethyl]-amide | acidic | 1.05 1.08 | 459.2 |
| 276 | 2,3-Dihydro-benzofuran-4-carboxylic acid [(1S,2S,5R)-3-(2-p-tolyl-thiophene-3-carbonyl)-3-aza-bicyclo[3.1.0]hex-2-ylmethyl]-amide | acidic | 1.03 1.07 | 459.2 |
| 277 | Benzoxazole-4-carboxylic acid [(1S,2S,5R)-3-(2-p-tolyl-thiophene-3-carbonyl)-3-aza-bicyclo[3.1.0]hex-2-ylmethyl]-amide | acidic | 1.06 | 458.3 |
| 278 | 2-Methyl-benzoxazole-4-carboxylic acid [(1S,2S,5R)-3-(2-p-tolyl-thiophene-3-carbonyl)-3-aza-bicyclo[3.1.0]hex-2-ylmethyl]-amide | acidic | 1.08 | 472.3 |

Starting from ((1S,2S,5R)-2-Aminomethyl-3-aza-bicyclo[3.1.0]hex-3-yl)-(2-m-tolyl-thiophen-3-yl)-methanone:

| Example | Name | eluent | $t_R$ [min] | $[M + H]^+$ |
|---|---|---|---|---|
| 279 | 1-Methyl-1H-indole-3-carboxylic acid [(1S,2S,5R)-3-(2-m-tolyl-thiophene-3-carbonyl)-3-aza-bicyclo[3.1.0]hex-2-ylmethyl]-amide | acidic | 1.03 1.08 | 470.5 |
| 280 | 1-Methyl-1H-indole-4-carboxylic acid [(1S,2S,5R)-3-(2-m-tolyl-thiophene-3-carbonyl)-3-aza-bicyclo[3.1.0]hex-2-ylmethyl]-amide | acidic | 1.03 1.08 | 470.5 |

-continued

| Example | Name | eluent | LC-MS t$_R$ [min] | [M + H]$^+$ |
|---|---|---|---|---|
| 281 | Quinoline-8-carboxylic acid [(1S,2S,5R)-3-(2-m-tolyl-thiophene-3-carbonyl)-3-aza-bicyclo[3.1.0]hex-2-ylmethyl]-amide | acidic | 0.99 1.03 | 468.6 |
| 282 | 4-Methyl-4H-furo[3,2-b]pyrrole-5-carboxylic acid [(1S,2S,5R)-3-(2-m-tolyl-thiophene-3-carbonyl)-3-aza-bicyclo[3.1.0]hex-2-ylmethyl]-amide | acidic | 1.04 1.08 | 460.4 |
| 283 | 6-Methyl-pyrrolo[2,1-b]thiazole-7-carboxylic acid [(1S,2S,5R)-3-(2-m-tolyl-thiophene-3-carbonyl)-3-aza-bicyclo[3.1.0]hex-2-ylmethyl]-amide | acidic | 1.02 1.06 | 476.4 |
| 284 | Pyrrolo[2,1-b]thiazole-7-carboxylic acid [(1S,2S,5R)-3-(2-m-tolyl-thiophene-3-carbonyl)-3-aza-bicyclo[3.1.0]hex-2-ylmethyl]-amide | acidic | 0.99 1.04 | 462.3 |
| 285 | 3,4-Dihydro-2H-benzo[1,4]oxazine-5-carboxylic acid [(1S,2S,5R)-3-(2-m-tolyl-thiophene-3-carbonyl)-3-aza-bicyclo[3.1.0]hex-2-ylmethyl]-amide | acidic | 1.05 1.10 | 474.6 |
| 286 | 2,3-Dihydro-thieno[3,4-b][1,4]dioxine-5-carboxylic acid [(1S,2S,5R)-3-(2-m-tolyl-thiophene-3-carbonyl)-3-aza-bicyclo[3.1.0]hex-2-ylmethyl]-amide | acidic | 1.01 1.04 | 481.2 |
| 287 | 2-Ethyl-5-methyl-2H-pyrazole-3-carboxylic acid [(1S,2S,5R)-3-(2-m-tolyl-thiophene-3-carbonyl)-3-aza-bicyclo[3.1.0]hex-2-ylmethyl]-amide | acidic | 0.99 1.04 | 449.5 |
| 288 | 2,5-Dimethyl-2H-pyrazole-3-carboxylic acid [(1S,2S,5R)-3-(2-m-tolyl-thiophene-3-carbonyl)-3-aza-bicyclo[3.1.0]hex-2-ylmethyl]-amide | acidic | 0.98 1.04 | 435.3 |
| 289 | 5-Fluoro-1-methyl-1H-indole-2-carboxylic acid [(1S,2S,5R)-3-(2-m-tolyl-thiophene-3-carbonyl)-3-aza-bicyclo[3.1.0]hex-2-ylmethyl]-amide | acidic | 1.10 1.14 | 488.4 |
| 290 | 3-Bromo-N-[(1S,2S,5R)-3-(2-m-tolyl-thiophene-3-carbonyl)-3-aza-bicyclo[3.1.0]hex-2-ylmethyl]-benzamide | acidic | 1.06 1.11 | 495.3 |
| 291 | 3-Chloro-N-[(1S,2S,5R)-3-(2-m-tolyl-thiophene-3-carbonyl)-3-aza-bicyclo[3.1.0]hex-2-ylmethyl]-benzamide | acidic | 1.06 1.10 | 451.3 |
| 292 | 3-Methyl-N-[(1S,2S,5R)-3-(2-m-tolyl-thiophene-3-carbonyl)-3-aza-bicyclo[3.1.0]hex-2-ylmethyl]-benzamide | acidic | 1.04 1.09 | 431.4 |
| 293 | Benzo[2,1,3]thiadiazole-4-carboxylic acid [(1S,2S,5R)-3-(2-m-tolyl-thiophene-3-carbonyl)-3-aza-bicyclo[3.1.0]hex-2-ylmethyl]-amide | acidic | 1.05 1.08 | 475.5 |
| 294 | Benzo[2,1,3]oxadiazole-4-carboxylic acid [(1S,2S,5R)-3-(2-m-tolyl-thiophene-3-carbonyl)-3-aza-bicyclo[3.1.0]hex-2-ylmethyl]-amide | acidic | 1.05 1.07 | 459.5 |
| 295 | 2,3-Dihydro-benzofuran-4-carboxylic acid [(1S,2S,5R)-3-(2-m-tolyl-thiophene-3-carbonyl)-3-aza-bicyclo[3.1.0]hex-2-ylmethyl]-amide | acidic | 1.02 1.06 | 459.5 |
| 296 | Benzothiazole-7-carboxylic acid [(1S,2S,5R)-3-(2-m-tolyl-thiophene-3-carbonyl)-3-aza-bicyclo[3.1.0]hex-2-ylmethyl]-amide | acidic | 1.03 1.09 | 474.5 |
| 297 | 2-Methyl-benzoxazole-4-carboxylic acid [(1S,2S,5R)-3-(2-m-tolyl-thiophene-3-carbonyl)-3-aza-bicyclo[3.1.0]hex-2-ylmethyl]-amide | acidic | 1.08 | 472.6 |
| 298 | 2-Methyl-benzoxazole-7-carboxylic acid [(1S,2S,5R)-3-(2-m-tolyl-thiophene-3-carbonyl)-3-aza-bicyclo[3.1.0]hex-2-ylmethyl]-amide | acidic | 0.99 1.03 | 472.5 |

B.5 Example 299

2-Chloro-benzothiazole-4-carboxylic Acid[(1S,2S,5R)-3-(2-methyl-5-m-tolyl-thiazole-4-carbonyl)-3-aza-bicyclo[3.1.0]hex-2-ylmethyl]-amide A solution of ((1S,2S,5R)-2-Aminomethyl-3-aza-bicyclo[3.1.0]hex-3-yl)-(2-methyl-5-m-tolyl-thiazol-4-yl)-methanone (0.24 mmol) in MeCN (1.0 mL) is treated successively with DIPEA (0.49 mmol) and 2-Chloro-benzothiazole-4-carbonyl chloride (0.24 mmol; U.S. Pat. No. 3,654,296). The mixture is stirred for 30 min and purified by prep. HPLC to give the desired amide. LC-MS: $t_R$=1.03 min; $[M+H]^+$=523.0.

B.6 Example 300

Benzothiazole-4-carboxylic Acid[(1S,2S,5R)-3-(2-methyl-5-m-tolyl-thiazole-4-carbonyl)-3-aza-bicyclo[3.1.0]hex-2-ylmethyl]-amide A solution of 2-Chloro-benzothiazole-4-carboxylic acid [(1S,2S,5R)-3-(2-methyl-5-m-tolyl-thiazole-4-carbonyl)-3-aza-bicyclo[3.1.0]hex-2-ylmethyl]-amide (0.04 mmol) in MeOH (2.0 mL) is treated with Pd/C (10%, 50 mg) and stirred under a hydrogen atmosphere (1 bar) for 3 h. After filtration through celite and removal of the solvents the desired product is obtained. LC-MS: $t_R$=0.98 min; $[M+H]^+$=489.1.

II. Biological Assays

In vitro assay

The orexin receptor antagonistic activity of the compounds of formula (I) is determined in accordance with one of the following experimental methods.

Experimental Method:
Intracellular Calcium Measurements:

Chinese hamster ovary (CHO) cells expressing the human orexin-1 receptor and the human orexin-2 receptor, respectively, are grown in culture medium (Ham F-12 with L-Glutamine) containing 300 µg/ml G418, 100 U/ml penicillin, 100 µg/ml streptomycin and 10% heat inactivated fetal calf serum (FCS). The cells are seeded at 20'000 cells/well into 384-well black clear bottom sterile plates (Greiner). The seeded plates are incubated overnight at 37° C. in 5% $CO_2$.

Human orexin-A as an agonist is prepared as 1 mM stock solution in MeOH:water (1:1), diluted in HBSS containing 0.1% bovine serum albumin (BSA), $NaHCO_3$:0.375 g/l and 20 mM HEPES for use in the assay at a final concentration of 3 nM.

Antagonists are prepared as 10 mM stock solution in DMSO, then diluted in 384-well plates, first in DMSO, then in HBSS containing 0.1% bovine serum albumin (BSA), $NaHCO_3$: 0.375 g/l and 20 mM HEPES.

On the day of the assay, 50 µl of staining buffer (HBSS containing 1% FCS, 20 mM HEPES, $NaHCO_3$: 0.375 g/l, 5 mM probenecid (Sigma) and 3 µM of the fluorescent calcium indicator fluo-4 AM (1 mM stock solution in DMSO, containing 10% pluronic) is added to each well.

The 384-well cell-plates are incubated for 50 min at 37° C. in 5% $CO_2$ followed by equilibration at RT for 30-120 min before measurement.

Within the Fluorescent Imaging Plate Reader (FLIPR2 or FLIPR Tetra, Molecular Devices), antagonists are added to the plate in a volume of 10 µl/well, incubated for 10 min and finally 10 µl/well of agonist is added. Fluorescence is measured for each well at 1 second intervals, and the height of each fluorescence peak is compared to the height of the fluorescence peak induced by 3 nM orexin-A with vehicle in place of antagonist. For each antagonist, the $IC_{50}$ value (the concentration of compound needed to inhibit 50% of the agonistic response) is determined. With the FLIPR Tetra, non-optimized and optimized conditions were used. Optimized conditions were achieved by adjustment of pipetting speed and cell splitting regime. The calculated $IC_{50}$ values of the compounds may fluctuate depending on the daily cellular assay performance. Fluctuations of this kind are known to those skilled in the art.

Antagonistic activities ($IC_{50}$ values) of 289 exemplified compounds are in the range of 2-8583 nM with respect to the OX1 receptor; 11 compounds have been measured with an $IC_{50}$ value >10000 nM in this assay. $IC_{50}$ values of all exemplified compounds are in the range of 1-5303 nM with respect to the OX2 receptor. Antagonistic activities of selected compounds are displayed in Table 1.

TABLE 1

| Compound of Example | $OX_1$ $IC_{50}$ (nM) | $OX_2$ $IC_{50}$ (nM) |
| --- | --- | --- |
| 2 | 34 | 102 |
| 11 | 14 | 66 |
| 19 | 22 | 174 |
| 23 | 35 | 338 |
| 24 | 102 | 647 |
| 29 | 4 | 27 |
| 31 | 960 | 167 |
| 32 | 15 | 55 |
| 37 | 85 | 35 |
| 42 | 49 | 12 |
| 43 | 26 | 19 |
| 45 | 110 | 61 |
| 51 | 81 | 41 |
| 52 | 155 | 228 |
| 54 | 26 | 18 |
| 58 | 37 | 57 |
| 73 | 21 | 9 |
| 74 | 84 | 48 |
| 80 | 29 | 10 |
| 112 | 115 | 12 |
| 115 | 178 | 48 |
| 117 | 80 | 8 |
| 118 | 225 | 41 |
| 124 | 7028 | 12 |
| 147 | 324 | 26 |
| 148 | 1075 | 102 |
| 169 | >10000 | 61 |
| 177 | 691 | 88 |
| 186 | 3263[1] | 296[1] |
| 201 | 673[1] | 349[1] |
| 220 | 115[1] | 48[1] |
| 222 | 96[2] | 79[2] |
| 237 | 29[2] | 38[2] |
| 244 | 51[1] | 639[1] |
| 252 | 79[1] | 350[1] |
| 256 | 64[2] | 55[2] |
| 260 | 16[2] | 31[2] |
| 266 | 65[2] | 19[2] |
| 274 | 58[2] | 55[2] |
| 282 | 117[2] | 32[2] |
| 297 | 83[2] | 16[2] |
| 299 | 28[2] | 14[2] |

Values in table 1 are measured using FLIPR2; or using
[1] FLIPR Tetra, non-optimized conditions; or
[2] FLIPR Tetra, optimized conditions.

The invention claimed is:
1. A compound of formula (I), wherein the stereogenic centers are in a (1S,2S,5R)-configuration

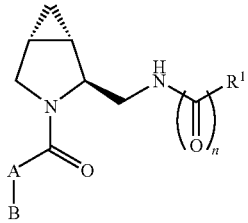

Formula (I)

wherein
- A represents aryl or heterocyclyl, wherein the aryl or heterocyclyl is unsubstituted or independently mono- or di-substituted, wherein the substituents are independently selected from the group consisting of $(C_{1-4})$alkyl, $(C_{3-6})$cycloalkyl, $(C_{1-4})$alkoxy, trifluoromethyl, —$NR^2R^3$ and halogen;
- B represents a hydrogen atom or an aryl- or heterocyclyl-group, wherein the aryl or heterocyclyl is unsubstituted or independently mono-, di-, or tri-substituted, wherein the substituents are independently selected from the group consisting of $(C_{1-4})$alkyl, $(C_{3-6})$cycloalkyl, $(C_{1-4})$alkoxy, trifluoromethyl, cyano, —$NR^2R^3$, —$NHSO_2$—$(C_{1-4})$alkyl, —$N(R^2)C(O)R^3$ and halogen;
- n represents the integer 1;
- $R^1$ represents aryl or heterocyclyl, wherein the aryl or heterocyclyl is unsubstituted or independently mono-, di-, or tri-substituted wherein the substituents are independently selected from the group consisting of $(C_{1-4})$alkyl, $(C_{3-6})$cycloalkyl, $(C_{1-4})$alkoxy, halogen, cyano, trifluoromethyl, trifluoromethoxy and —$NR^2R^3$; or $R^1$ represents a phenyl group which group is mono-substituted with a group selected from morpholin-4-yl and 4-methyl-piperazinyl; or $R^1$ represents a 2,3-dihydro-benzofuranyl-, a 2,3-dihydro-benzo[1,4]dioxinyl-, a 4H-benzo[1,3]dioxinyl-, a 2,3-dihydro-thieno[3,4-b][1,4]dioxinyl-, a 3-oxo-3,4-dihydro-2H-benzo[1,4]oxazinyl-, a 2H-chromenyl-, a 3,4-dihydro-2H-benzo[1,4]oxazinyl- or a chromanyl-group which groups are unsubstituted or independently mono- or di-substituted wherein the substituents are independently selected from the group consisting of $(C_{1-4})$alkyl, $(C_{1-4})$alkoxy and halogen;
- $R^2$ represents hydrogen or $(C_{1-4})$alkyl; and
- $R^3$ represents hydrogen or $(C_{1-4})$alkyl;
or a pharmaceutically acceptable salt thereof.

2. A compound according to claim 1, wherein A represents aryl or heterocyclyl, wherein the aryl or heterocyclyl is unsubstituted or independently mono- or di-substituted, wherein the substituents are independently selected from the group consisting of $(C_{1-4})$alkyl, $(C_{3-6})$cycloalkyl, $(C_{1-4})$alkoxy, trifluoromethyl, —$NR^2R^3$ and halogen;
- B represents a hydrogen atom or an aryl- or heterocyclyl-group, wherein the aryl or heterocyclyl is unsubstituted or independently mono-, di-, or tri-substituted, wherein the substituents are independently selected from the group consisting of $(C_{1-4})$alkyl, $(C_{3-6})$cycloalkyl, $(C_{1-4})$alkoxy, trifluoromethyl, —$NR^2R^3$ and halogen;
- $R^1$ represents aryl or heterocyclyl, wherein the aryl or heterocyclyl is unsubstituted or independently mono-, di-, or tri-substituted wherein the substituents are independently selected from the group consisting of $(C_{1-4})$alkyl, $(C_{3-6})$cycloalkyl, $(C_{1-4})$alkoxy, halogen, cyano, trifluoromethyl, trifluoromethoxy and —$NR^2R^3$; or $R^1$ represents a phenyl group which group is mono-substituted with a group selected from morpholin-4-yl and 4-methyl-piperazinyl; or $R^1$ represents a 2,3-dihydro-benzofuranyl-, a 2,3-dihydro-benzo[1,4]dioxinyl-, a 4H-benzo[1,3]dioxinyl-, a 2,3-dihydro-thieno[3,4-b][1,4]dioxinyl-, a 3-oxo-3,4-dihydro-2H-benzo[1,4]oxazinyl-, a 2H-chromenyl-, a 3,4-dihydro-2H-benzo[1,4]oxazinyl- or a chromanyl-group which groups are unsubstituted or independently mono- or di-substituted wherein the substituents are independently selected from the group consisting of $(C_{1-4})$alkyl, $(C_{1-4})$alkoxy and halogen;
- $R^2$ represents hydrogen or $(C_{1-4})$alkyl; and
- $R^3$ represents hydrogen or $(C_{1-4})$alkyl;
or a pharmaceutically acceptable salt thereof.

3. A compound according to claim 1, wherein
A represents aryl or heterocyclyl, wherein the aryl or heterocyclyl is unsubstituted or mono-substituted, wherein the substituent is selected from the group consisting of $(C_{1-4})$alkyl, $(C_{3-6})$cycloalkyl, $(C_{1-4})$alkoxy, —$NR^2R^3$ and halogen;
or a pharmaceutically acceptable salt thereof.

4. A compound according to claim 1, wherein
$R^1$ represents aryl or heterocyclyl, wherein the aryl or heterocyclyl is unsubstituted or independently mono-, di-, or tri-substituted wherein the substituents are independently selected from the group consisting of $(C_{1-4})$alkyl, $(C_{1-4})$alkoxy, halogen, cyano and trifluoromethyl; or $R^1$ represents a 2,3-dihydro-benzofuranyl-, a 2,3-dihydro-benzo[1,4]dioxinyl-, a 4H-benzo[1,3]dioxinyl-, a 2,3-dihydro-thieno[3,4-b][1,4]dioxinyl-, a 3-oxo-3,4-dihydro-2H-benzo[1,4]oxazinyl-, a 2H-chromenyl-, a 3,4-dihydro-2H-benzo[1,4]oxazinyl- or a chromanyl-group which groups are unsubstituted or independently mono- or di-substituted wherein the substituents are independently selected from the group consisting of $(C_{1-4})$alkyl and halogen;
or a pharmaceutically acceptable salt thereof.

5. A compound according to claim 1, wherein
A represents a phenyl-, a thienyl-, a thiazolyl-, a pyrimidyl-, a [1,6]naphthyridinyl or a imidazo[1,2-a]pyridyl-group, which group is unsubstituted or mono-substituted, wherein the substituent is selected from the group consisting of $(C_{1-4})$alkyl, $(C_{3-6})$cycloalkyl, $(C_{1-4})$alkoxy, —$NR^2R^3$ and halogen;
or a pharmaceutically acceptable salt thereof.

6. A compound according claim 1, wherein
A represents a phenyl- or a thiazolyl-group, which group is unsubstituted or mono-substituted, wherein the substituent is selected from the group consisting of $(C_{1-4})$alkyl and —$NR^2R^3$;
or a pharmaceutically acceptable salt thereof.

7. A compound according to claim 1, wherein
B represents a phenyl-group, which group is unsubstituted or mono- or di-substituted, wherein the substituents are independently selected from the group consisting of $(C_{1-4})$alkyl, $(C_{1-4})$alkoxy, trifluoromethyl, and halogen;
or a pharmaceutically acceptable salt thereof.

8. A compound according to claim 1, wherein
$R^1$ represents a phenyl-, isoxazolyl-, pyrazolyl-, indolyl-, benzofuranyl-, indazolyl-, benzo[d]isoxazolyl-, quinolinyl-, isoquinolinyl-, benzoxazolyl-, benzothiazolyl-, benzo[2,1,3]thiadiazolyl-, benzo[2,1,3]oxadiazolyl-, 4H-furo[3,2-b]pyrrolyl-, pyrrolo[2,1-b]thiazolyl-, pyrazolo[1,5-a]pyridyl-, imidazo[1,2-a]pyridyl- or imidazo[2,1-b]thiazolyl-group, which group is unsubstituted or independently mono- or di-substituted wherein the substituents are independently selected from the group consisting of $(C_{1-4})$ alkyl, $(C_{1-4})$alkoxy, halogen and trifluoromethyl; or $R^1$ represents a 2,3-dihydro-benzofuranyl-, a 2,3-dihydro-benzo[1,4]dioxinyl-, a 4H-benzo[1,3]dioxinyl-, a 2,3-dihydro-thieno[3,4-b][1,4]dioxinyl- or a chromanyl-group which groups are unsubstituted or independently mono- or di-substituted wherein the substituents are independently selected from the group consisting of $(C_{1-4}$alkyl and halogen;
or a pharmaceutically acceptable salt thereof.

9. A compound according to claim 1, wherein
$R^1$ represents a phenyl-, isoxazolyl-, pyrazolyl-, indolyl-, benzofuranyl-, indazolyl-, benzo[d]isoxazolyl-, quinolinyl-, isoquinolinyl-, benzoxazolyl-, benzothiazolyl-, benzo[2,1,3]thiadiazolyl-, benzo[2,1,3]oxadiazolyl-, 4H-furo[3,2-b]pyrrolyl-, pyrrolo[2,1-b]thiazolyl-, pyrazolo[1,5-a]pyridyl-, imidazo[1,2-a]pyridyl- or imidazo[2,1-b]thiazolyl-group, which group is unsubstituted or independently mono- or di-substituted wherein the substituents are independently selected from the group consisting of $(C_{1-4})$alkyl, $(C_{1-4})$alkoxy, halogen and trifluoromethyl; or a pharmaceutically acceptable salt thereof.

10. A compound according to claim 1, wherein
$R^1$ represents a 2,3-dihydro-benzofuranyl-, a 2,3-dihydro-benzo[1,4]dioxinyl-, a 4H-benzo[1,3]dioxinyl-, a 2,3-dihydro-thieno[3,4-b][1,4]dioxinyl- or a chromanyl-group which groups are unsubstituted or independently mono- or di-substituted wherein the substituents are independently selected from the group consisting of $(C_{1-4})$alkyl and halogen; or a pharmaceutically acceptable salt thereof.

11. A compound of formula (I) according to claim 1 selected from the group consisting of:

Benzofuran-4-carboxylic acid [(1S,2S,5R)-3-(biphenyl-2-carbonyl)-3-aza-bicyclo[3.1.0]hex-2-ylmethyl]-amide;
Benzofuran-4-carboxylic acid [(1S,2S,5R)-3-(2-methyl-5-p-tolyl-thiazole-4-carbonyl)-3-aza-bicyclo[3.1.0]hex-2-ylmethyl]-amide;
Benzofuran-4-carboxylic acid {(1S,2S,5R)-3-[5-(4-ethyl-phenyl)-2-methyl-thiazole-4-carbonyl]-3-aza-bicyclo[3.1.0]hex-2-ylmethyl}-amide;
Benzofuran-4-carboxylic acid {(1S,2S,5R)-3-[5-(4-fluoro-phenyl)-2-methyl-thiazole-4-carbonyl]-3-aza-bicyclo[3.1.0]hex-2-ylmethyl}-amide;
Benzofuran-4-carboxylic acid [(1S,2S,5R)-3-(2-methyl-5-m-tolyl-thiazole-4-carbonyl)-3-aza-bicyclo[3.1.0]hex-2-ylmethyl]-amide;
Benzofuran-4-carboxylic acid {(1S,2S,5R)-3-[5-(3-fluoro-phenyl)-2-methyl-thiazole-4-carbonyl]-3-aza-bicyclo[3.1.0]hex-2-ylmethyl}-amide;
6-Methyl-imidazo[2,1-b]thiazole-5-carboxylic acid {(1S,2S,5R)-3-[5-(2-fluoro-phenyl)-2-methyl-thiazole-4-carbonyl]-3-aza-bicyclo[3.1.0]hex-2-ylmethyl}-amide;
6-Methyl-imidazo[2,1-b]thiazole-5-carboxylic acid [(1S,2S,5R)-3-(2-methyl-5-o-tolyl-thiazole-4-carbonyl)-3-aza-bicyclo[3.1.0]hex-2-ylmethyl]-amide;
6-Methyl-imidazo[2,1-b]thiazole-5-carboxylic acid {(1S,2S,5R)-3-[5-(3-fluoro-phenyl)-2-methyl-thiazole-4-carbonyl]-3-aza-bicyclo[3.1.0]hex-2-ylmethyl}-amide;
6-Methyl-imidazo[2,1-b]thiazole-5-carboxylic acid {(1S,2S,5R)-3-[5-(3-chloro-phenyl)-2-methyl-thiazole-4-carbonyl]-3-aza-bicyclo[3.1.0]hex-2-ylmethyl}-amide;
6-Methyl-imidazo[2,1-b]thiazole-5-carboxylic acid {(1S,2S,5R)-3-[5-(4-fluoro-phenyl)-2-methyl-thiazole-4-carbonyl]-3-aza-bicyclo[3.1.0]hex-2-ylmethyl}-amide;
6-Methyl-imidazo[2,1-b]thiazole-5-carboxylic acid {(1S,2S,5R)-3-[5-(4-ethyl-phenyl)-2-methyl-thiazole-4-carbonyl]-3-aza-bicyclo[3.1.0]hex-2-ylmethyl}-amide;
6-Methyl-imidazo[2,1-b]thiazole-5-carboxylic acid [(1S,2S,5R)-3-(2-amino-5-m-tolyl-thiazole-4-carbonyl)-3-aza-bicyclo[3.1.0]hex-2-ylmethyl]-amide;
6-Methyl-imidazo[2,1-b]thiazole-5-carboxylic acid {(1S,2S,5R)-3-[2-amino-5-(3-fluoro-phenyl)-thiazole-4-carbonyl]-3-aza-bicyclo[3.1.0]hex-2-ylmethyl}-amide;
6-Methyl-imidazo[2,1-b]thiazole-5-carboxylic acid [(1S,2S,5R)-3-(biphenyl-2-carbonyl)-3-aza-bicyclo[3.1.0]hex-2-ylmethyl]-amide;
6-Methyl-imidazo[2,1-b]thiazole-5-carboxylic acid [(1S,2S,5R)-3-(2'-fluoro-biphenyl-2-carbonyl)-3-aza-bicyclo[3.1.0]hex-2-ylmethyl]-amide;
6-Methyl-imidazo[2,1-b]thiazole-5-carboxylic acid [(1S,2S,5R)-3-(3'-methyl-biphenyl-2-carbonyl)-3-aza-bicyclo[3.1.0]hex-2-ylmethyl]-amide;
6-Methyl-imidazo[2,1-b]thiazole-5-carboxylic acid [(1S,2S,5R)-3-(3'-chloro-biphenyl-2-carbonyl)-3-aza-bicyclo[3.1.0]hex-2-ylmethyl]-amide;
6-Methyl-imidazo[2,1-b]thiazole-5-carboxylic acid [(1S,2S,5R)-3-(3',4'-dimethyl-biphenyl-2-carbonyl)-3-aza-bicyclo[3.1.0]hex-2-ylmethyl]-amide;
6-Methyl-imidazo[2,1-b]thiazole-5-carboxylic acid [(1S,2S,5R)-3-(2-methyl-4-phenyl-pyrimidine-5-carbonyl)-3-aza-bicyclo[3.1.0]hex-2-ylmethyl]amide;
6-Methyl-imidazo[2,1-b]thiazole-5-carboxylic acid [(1S,2S,5R)-3-(2-methoxy-5-m-tolyl-thiazole-4-carbonyl)-3-aza-bicyclo[3.1.0]hex-2-ylmethyl]-amide;
6-Methyl-imidazo[2,1-b]thiazole-5-carboxylic acid [(1S,2S,5R)-3-(2-bromo-5-m-tolyl-thiazole-4-carbonyl)-3-aza-bicyclo[3.1.0]hex-2-ylmethyl]-amide;
6-Methyl-imidazo[2,1-b]thiazole-5-carboxylic acid [(1S,2S,5R)-3-(5-m-tolyl-thiazole-4-carbonyl)-3-aza-bicyclo[3.1.0]hex-2-ylmethyl]-amide;
6-Methyl-imidazo[2,1-b]thiazole-5-carboxylic acid [(1S,2S,5R)-3-(2-thiophen-2-yl-benzoyl)-3-aza-bicyclo[3.1.0]hex-2-ylmethyl]-amide;
6-Methyl-imidazo[2,1-b]thiazole-5-carboxylic acid [(1S,2S,5R)-3-(2-phenyl-[1,6]naphthyridine-3-carbonyl)-3-aza-bicyclo[3.1.0]hex-2-ylmethyl]-amide;
6-Methyl-imidazo[2,1-b]thiazole-5-carboxylic acid [(1S,2S,5R)-3-(6-chloro-2-phenyl-imidazo[1,2-a]pyridine-3-carbonyl)-3-aza-bicyclo[3.1.0]hex-2-ylmethyl]-amide;
6-Methyl-imidazo[2,1-b]thiazole-5-carboxylic acid {(1S,2S,5R)-3-[4-(3-fluoro-phenyl)-2-methyl-thiazole-5-carbonyl]-3-aza-bicyclo[3.1.0]hex-2-ylmethyl}-amide;
2,3-Dihydro-benzo[1,4]dioxine-5-carboxylic acid [(1S,2S,5R)-3-(2-methyl-5-m-tolyl-thiazole-4-carbonyl)-3-aza-bicyclo[3.1.0]hex-2-ylmethyl]-amide;
2,3-Dihydro-benzofuran-4-carboxylic acid [(1S,2S,5R)-3-(2-methyl-5-m-tolyl-thiazole-4-carbonyl)-3-aza-bicyclo[3.1.0]hex-2-ylmethyl]-amide;
2,3-Dihydro-benzofuran-7-carboxylic acid [(1S,2S,5R)-3-(2-methyl-5-m-tolyl-thiazole-4-carbonyl)-3-aza-bicyclo[3.1.0]hex-2-ylmethyl]-amide;
6-Fluoro-4H-benzo[1,3]dioxine-8-carboxylic acid [(1S,2S,5R)-3-(2-methyl-5-m-tolyl-thiazole-4-carbonyl)-3-aza-bicyclo[3.1.0]hex-2-ylmethyl]-amide;
2,2-Dimethyl-2,3-dihydro-benzofuran-7-carboxylic acid [(1S,2S,5R)-3-(2-methyl-5-m-tolyl-thiazole-4-carbonyl)-3-aza-bicyclo[3.1.0]hex-2-ylmethyl]-amide;

3-Bromo-N-[(1S,2S,5R)-3-(2-methyl-5-m-tolyl-thiazole-4-carbonyl)-3-aza-bicyclo[3.1.0]hex-2-ylmethyl]-benzamide;
N-[(1S,2S,5R)-3-(2-Methyl-5-m-tolyl-thiazole-4-carbonyl)-3-aza-bicyclo[3.1.0]hex-2-ylmethyl]-3-trifluoromethyl-benzamide;
3-Chloro-N-[(1S,2S,5R)-3-(2-methyl-5-m-tolyl-thiazole-4-carbonyl)-3-aza-bicyclo[3.1.0]hex-2-ylmethyl]-benzamide;
3,5-Dimethoxy-N-[(1S,2S,5R)-3-(2-methyl-5-m-tolyl-thiazole-4-carbonyl)-3-aza-bicyclo[3.1.0]hex-2-ylmethyl]-benzamide;
2,5-Dimethyl-2H-pyrazole-3-carboxylic acid [(1S,2S,5R)-3-(2-methyl-5-m-tolyl-thiazole-4-carbonyl)-3-aza-bicyclo[3.1.0]hex-2-ylmethyl]-amide;
1,3-Dimethyl-1H-pyrazole-4-carboxylic acid [(1S,2S,5R)-3-(2-methyl-5-m-tolyl-thiazole-4-carbonyl)-3-aza-bicyclo[3.1.0]hex-2-ylmethyl]-amide;
2-Ethyl-5-methyl-2H-pyrazole-3-carboxylic acid [(1S,2S,5R)-3-(2-methyl-5-m-tolyl-thiazole-4-carbonyl)-3-aza-bicyclo[3.1.0]hex-2-ylmethyl]-amide;
3,5-Dimethyl-isoxazole-4-carboxylic acid [(1S,2S,5R)-3-(2-methyl-5-m-tolyl-thiazole-4-carbonyl)-3-aza-bicyclo[3.1.0]hex-2-ylmethyl]-amide;
Quinoline-8-carboxylic acid [(1S,2S,5R)-3-(2-methyl-5-m-tolyl-thiazole-4-carbonyl)-3-aza-bicyclo[3.1.0]hex-2-ylmethyl]-amide;
Isoquinoline-1-carboxylic acid [(1S,2S,5R)-3-(2-methyl-5-m-tolyl-thiazole-4-carbonyl)-3-aza-bicyclo[3.1.0]hex-2-ylmethyl]-amide;
Quinoline-2-carboxylic acid [(1S,2S,5R)-3-(2-methyl-5-m-tolyl-thiazole-4-carbonyl)-3-aza-bicyclo[3.1.0]hex-2-ylmethyl]-amide;
1H-Indole-3-carboxylic acid [(1S,2S,5R)-3-(2-methyl-5-m-tolyl-thiazole-4-carbonyl)-3-aza-bicyclo[3.1.0]hex-2-ylmethyl]-amide;
1-Methyl-1H-indole-3-carboxylic acid [(1S,2S,5R)-3-(2-methyl-5-m-tolyl-thiazole-4-carbonyl)-3-aza-bicyclo[3.1.0]hex-2-ylmethyl]-amide;
1H-Indazole-3-carboxylic acid [(1S,2S,5R)-3-(2-methyl-5-m-tolyl-thiazole-4-carbonyl)-3-aza-bicyclo[3.1.0]hex-2-ylmethyl]-amide;
1-Methyl-1H-indazole-3-carboxylic acid [(1S,2S,5R)-3-(2-methyl-5-m-tolyl-thiazole-4-carbonyl)-3-aza-bicyclo[3.1.0]hex-2-ylmethyl]-amide;
1,2-Dimethyl-1H-indole-3-carboxylic acid [(1S,2S,5R)-3-(2-methyl-5-m-tolyl-thiazole-4-carbonyl)-3-aza-bicyclo[3.1.0]hex-2-ylmethyl]-amide;
Benzo[d]isoxazole-3-carboxylic acid [(1S,2S,5R)-3-(2-methyl-5-m-tolyl-thiazole-4-carbonyl)-3-aza-bicyclo[3.1.0]hex-2-ylmethyl]-amide;
Imidazo[1,2-a]pyridine-3-carboxylic acid [(1S,2S,5R)-3-(2-methyl-5-m-tolyl-thiazole-4-carbonyl)-3-aza-bicyclo[3.1.0]hex-2-ylmethyl]-amide;
Pyrazolo[1,5-a]pyridine-3-carboxylic acid [(1S,2S,5R)-3-(2-methyl-5-m-tolyl-thiazole-4-carbonyl)-3-aza-bicyclo[3.1.0]hex-2-ylmethyl]-amide;
2,3-Dihydro-thieno[3,4-b][1,4]dioxine-5-carboxylic acid [(1S,2S,5R)-3-(2-methyl-5-m-tolyl-thiazole-4-carbonyl)-3-aza-bicyclo[3.1.0]hex-2-ylmethyl]-amide;
5-Fluoro-1-methyl-1H-indole-2-carboxylic acid [(1S,2S,5R)-3-(2-methyl-5-m-tolyl-thiazole-4-carbonyl)-3-aza-bicyclo[3.1.0]hex-2-ylmethyl]-amide;
Imidazo[2,1-b]thiazole-5-carboxylic acid [(1S,2S,5R)-3-(2-methyl-5-m-tolyl-thiazole-4-carbonyl)-3-aza-bicyclo[3.1.0]hex-2-ylmethyl]-amide;
3-Methyl-imidazo[2,1-b]thiazole-2-carboxylic acid [(1S,2S,5R)-3-(2-methyl-5-m-tolyl-thiazole-4-carbonyl)-3-aza-bicyclo[3.1.0]hex-2-ylmethyl]-amide;
Imidazo[2,1-b]thiazole-6-carboxylic acid [(1S,2S,5R)-3-(2-methyl-5-m-tolyl-thiazole-4-carbonyl)-3-aza-bicyclo[3.1.0]hex-2-ylmethyl]-amide;
2,3-Dihydro-benzo[1,4]dioxine-5-carboxylic acid {(1S,2S,5R)-3-[5-(3-chloro-phenyl)-2-methyl-thiazole-4-carbonyl]-3-aza-bicyclo[3.1.0]hex-2-ylmethyl}-amide;
2,3-Dihydro-benzofuran-4-carboxylic acid {(1S,2S,5R)-3-[5-(3-chloro-phenyl)-2-methyl-thiazole-4-carbonyl]-3-aza-bicyclo[3.1.0]hex-2-ylmethyl}-amide;
2,3-Dihydro-benzofuran-7-carboxylic acid {(1S,2S,5R)-3-[5-(3-chloro-phenyl)-2-methyl-thiazole-4-carbonyl]-3-aza-bicyclo[3.1.0]hex-2-ylmethyl}-amide;
6-Fluoro-4H-benzo[1,3]dioxine-8-carboxylic acid {(1S,2S,5R)-3-[5-(3-chloro-phenyl)-2-methyl-thiazole-4-carbonyl]-3-aza-bicyclo[3.1.0]hex-2-ylmethyl}-amide;
2,2-Dimethyl-2,3-dihydro-benzofuran-7-carboxylic acid {(1S,2S,5R)-3-[5-(3-chloro-phenyl)-2-methyl-thiazole-4-carbonyl]-3-aza-bicyclo[3.1.0]hex-2-ylmethyl}-amide;
3-Bromo-N-{(1S,2S,5R)-3-[5-(3-chloro-phenyl)-2-methyl-thiazole-4-carbonyl]-3-aza-bicyclo[3.1.0]hex-2-ylmethyl}-benzamide;
N-{(1S,2S,5R)-3-[5-(3-Chloro-phenyl)-2-methyl-thiazole-4-carbonyl]-3-aza-bicyclo[3.1.0]hex-2-ylmethyl}-3-trifluoromethyl-benzamide;
3-Chloro-N-{(1S,2S,5R)-3-[5-(3-chloro-phenyl)-2-methyl-thiazole-4-carbonyl]-3-aza-bicyclo[3.1.0]hex-2-ylmethyl}-benzamide;
N-{(1S,2S,5R)-3-[5-(3-Chloro-phenyl)-2-methyl-thiazole-4-carbonyl]-3-aza-bicyclo[3.1.0]hex-2-ylmethyl}-3,5-dimethoxy-benzamide;
2,5-Dimethyl-2H-pyrazole-3-carboxylic acid {(1S,2S,5R)-3-[5-(3-chloro-phenyl)-2-methyl-thiazole-4-carbonyl]-3-aza-bicyclo[3.1.0]hex-2-ylmethyl}-amide;
1,3-Dimethyl-1H-pyrazole-4-carboxylic acid {(1S,2S,5R)-3-[5-(3-chloro-phenyl)-2-methyl-thiazole-4-carbonyl]-3-aza-bicyclo[3.1.0]hex-2-ylmethyl}-amide;
2-Ethyl-5-methyl-2H-pyrazole-3-carboxylic acid {(1S,2S,5R)-3-[5-(3-chloro-phenyl)-2-methyl-thiazole-4-carbonyl]-3-aza-bicyclo[3.1.0]hex-2-ylmethyl}-amide;
3,5-Dimethyl-isoxazole-4-carboxylic acid {(1S,2S,5R)-3-[5-(3-chloro-phenyl)-2-methyl-thiazole-4-carbonyl]-3-aza-bicyclo[3.1.0]hex-2-ylmethyl}-amide;
Quinoline-8-carboxylic acid {(1S,2S,5R)-3-[5-(3-chloro-phenyl)-2-methyl-thiazole-4-carbonyl]-3-aza-bicyclo[3.1.0]hex-2-ylmethyl}-amide;
Isoquinoline-1-carboxylic acid {(1S,2S,5R)-3-[5-(3-chloro-phenyl)-2-methyl-thiazole-4-carbonyl]-3-aza-bicyclo[3.1.0]hex-2-ylmethyl}-amide;
Quinoline-2-carboxylic acid {(1S,2S,5R)-3-[5-(3-chloro-phenyl)-2-methyl-thiazole-4-carbonyl]-3-aza-bicyclo[3.1.0]hex-2-ylmethyl}-amide;
1H-Indole-3-carboxylic acid {(1S,2S,5R)-3-[5-(3-chloro-phenyl)-2-methyl-thiazole-4-carbonyl]-3-aza-bicyclo[3.1.0]hex-2-ylmethyl}-amide;
1-Methyl-1H-indole-3-carboxylic acid {(1S,2S,5R)-3-[5-(3-chloro-phenyl)-2-methyl-thiazole-4-carbonyl]-3-aza-bicyclo[3.1.0]hex-2-ylmethyl}-amide;
1H-Indazole-3-carboxylic acid {(1S,2S,5R)-3-[5-(3-chloro-phenyl)-2-methyl-thiazole-4-carbonyl]-3-aza-bicyclo[3.1.0]hex-2-ylmethyl}-amide;
1-Methyl-1H-indazole-3-carboxylic acid {(1S,2S,5R)-3-[5-(3-chloro-phenyl)-2-methyl-thiazole-4-carbonyl]-3-aza-bicyclo[3.1.0]hex-2-ylmethyl}-amide;

1,2-Dimethyl-1H-indole-3-carboxylic acid {(1S,2S,5R)-3-[5-(3-chloro-phenyl)-2-methyl-thiazole-4-carbonyl]-3-aza-bicyclo[3.1.0]hex-2-ylmethyl}-amide;
Imidazo[1,2-a]pyridine-3-carboxylic acid {(1S,2S,5R)-3-[5-(3-chloro-phenyl)-2-methyl-thiazole-4-carbonyl]-3-aza-bicyclo[3.1.0]hex-2-ylmethyl}-amide;
Pyrazolo[1,5-a]pyridine-3-carboxylic acid {(1S,2S,5R)-3-[5-(3-chloro-phenyl)-2-methyl-thiazole-4-carbonyl]-3-aza-bicyclo[3.1.0]hex-2-ylmethyl}-amide;
2,3-Dihydro-thieno[3,4-b][1,4]dioxine-5-carboxylic acid {(1S,2S,5R)-3-[5-(3-chloro-phenyl)-2-methyl-thiazole-4-carbonyl]-3-aza-bicyclo[3.1.0]hex-2-ylmethyl}-amide;
5-Fluoro-1-methyl-1H-indole-2-carboxylic acid {(1S,2S,5R)-3-[5-(3-chloro-phenyl)-2-methyl-thiazole-4-carbonyl]-3-aza-bicyclo[3.1.0]hex-2-ylmethyl}-amide;
Imidazo[2,1-b]thiazole-5-carboxylic acid {(1S,2S,5R)-3-[5-(3-chloro-phenyl)-2-methyl-thiazole-4-carbonyl]-3-aza-bicyclo[3.1.0]hex-2-ylmethyl}-amide;
3-Methyl-imidazo[2,1-b]thiazole-2-carboxylic acid {(1S,2S,5R)-3-[5-(3-chloro-phenyl)-2-methyl-thiazole-4-carbonyl]-3-aza-bicyclo[3.1.0]hex-2-ylmethyl}-amide;
2,3-Dihydro-benzo[1,4]dioxine-5-carboxylic acid {(1S,2S,5R)-3-[2-amino-5-(3-fluoro-phenyl)-thiazole-4-carbonyl]-3-aza-bicyclo[3.1.0]hex-2-ylmethyl}-amide;
2,3-Dihydro-benzofuran-4-carboxylic acid {(1S,2S,5R)-3-[2-amino-5-(3-fluoro-phenyl)-thiazole-4-carbonyl]-3-aza-bicyclo[3.1.0]hex-2-ylmethyl}-amide;
2,3-Dihydro-benzofuran-7-carboxylic acid {(1S,2S,5R)-3-[2-amino-5-(3-fluoro-phenyl)-thiazole-4-carbonyl]-3-aza-bicyclo[3.1.0]hex-2-ylmethyl}-amide;
6-Fluoro-4H-benzo[1,3]dioxine-8-carboxylic acid {(1S,2S,5R)-3-[2-amino-5-(3-fluoro-phenyl)-thiazole-4-carbonyl]-3-aza-bicyclo[3.1.0]hex-2-ylmethyl}-amide;
2,2-Dimethyl-2,3-dihydro-benzofuran-7-carboxylic acid {(1S,2S,5R)-3-[2-amino-5-(3-fluoro-phenyl)-thiazole-4-carbonyl]-3-aza-bicyclo[3.1.0]hex-2-ylmethyl}-amide;
N-{(1S,2S,5R)-3-[2-Amino-5-(3-fluoro-phenyl)-thiazole-4-carbonyl]-3-aza-bicyclo[3.1.0]hex-2-ylmethyl}-3-trifluoromethyl-benzamide;
N-{(1S,2S,5R)-3-[2-Amino-5-(3-fluoro-phenyl)-thiazole-4-carbonyl]-3-aza-bicyclo[3.1.0]hex-2-ylmethyl}-3-chloro-benzamide;
N-{(1S,2S,5R)-3-[2-Amino-5-(3-fluoro-phenyl)-thiazole-4-carbonyl]-3-aza-bicyclo[3.1.0]hex-2-ylmethyl}-3,5-dimethoxy-benzamide;
2,5-Dimethyl-2H-pyrazole-3-carboxylic acid {(1S,2S,5R)-3-[2-amino-5-(3-fluoro-phenyl)-thiazole-4-carbonyl]-3-aza-bicyclo[3.1.0]hex-2-ylmethyl}-amide;
2-Ethyl-5-methyl-2H-pyrazole-3-carboxylic acid {(1S,2S,5R)-3-[2-amino-5-(3-fluoro-phenyl)-thiazole-4-carbonyl]-3-aza-bicyclo[3.1.0]hex-2-ylmethyl}-amide;
3,5-Dimethyl-isoxazole-4-carboxylic acid {(1S,2S,5R)-3-[2-amino-5-(3-fluoro-phenyl)-thiazole-4-carbonyl]-3-aza-bicyclo[3.1.0]hex-2-ylmethyl}-amide;
Quinoline-8-carboxylic acid {(1S,2S,5R)-3-[2-amino-5-(3-fluoro-phenyl)-thiazole-4-carbonyl]-3-aza-bicyclo[3.1.0]hex-2-ylmethyl}-amide;
Isoquinoline-1-carboxylic acid {(1S,2S,5R)-3-[2-amino-5-(3-fluoro-phenyl)-thiazole-4-carbonyl]-3-aza-bicyclo[3.1.0]hex-2-ylmethyl}-amide;
1-Methyl-1H-indole-3-carboxylic acid {(1S,2S,5R)-3-[2-amino-5-(3-fluoro-phenyl)-thiazole-4-carbonyl]-3-aza-bicyclo[3.1.0]hex-2-ylmethyl}-amide;
1H-Indazole-3-carboxylic acid {(1S,2S,5R)-3-[2-amino-5-(3-fluoro-phenyl)-thiazole-4-carbonyl]-3-aza-bicyclo[3.1.0]hex-2-ylmethyl}-amide;
1-Methyl-1H-indazole-3-carboxylic acid {(1S,2S,5R)-3-[2-amino-5-(3-fluoro-phenyl)-thiazole-4-carbonyl]-3-aza-bicyclo[3.1.0]hex-2-ylmethyl}-amide;
Imidazo[1,2-a]pyridine-3-carboxylic acid {(1S,2S,5R)-3-[2-amino-5-(3-fluoro-phenyl)-thiazole-4-carbonyl]-3-aza-bicyclo[3.1.0]hex-2-ylmethyl}-amide;
2,3-Dihydro-thieno[3,4-b][1,4]dioxine-5-carboxylic acid {(1S,2S,5R)-3-[2-amino-5-(3-fluoro-phenyl)-thiazole-4-carbonyl]-3-aza-bicyclo[3.1.0]hex-2-ylmethyl}-amide;
5-Fluoro-1-methyl-1H-indole-2-carboxylic acid {(1S,2S,5R)-3-[2-amino-5-(3-fluoro-phenyl)-thiazole-4-carbonyl]-3-aza-bicyclo[3.1.0]hex-2-ylmethyl}-amide;
Imidazo[2,1-b]thiazole-5-carboxylic acid {(1S,2S,5R)-3-[2-amino-5-(3-fluoro-phenyl)-thiazole-4-carbonyl]-3-aza-bicyclo[3.1.0]hex-2-ylmethyl}-amide;
3-Methyl-imidazo[2,1-b]thiazole-2-carboxylic acid {(1S,2S,5R)-3-[2-amino-5-(3-fluoro-phenyl)-thiazole-4-carbonyl]-3-aza-bicyclo[3.1.0]hex-2-ylmethyl}-amide;
1,2-Dimethyl-1H-indole-3-carboxylic acid {(1S,2S,5R)-3-[2-amino-5-(3-fluoro-phenyl)-thiazole-4-carbonyl]-3-aza-bicyclo[3.1.0]hex-2-ylmethyl}-amide;
2-Methoxy-N-[(1S,2S,5R)-3-(2-methyl-5-m-tolyl-thiazole-4-carbonyl)-3-aza-bicyclo[3.1.0]hex-2-ylmethyl]-benzamide;
4-Chloro-2-methoxy-N-[(1S,2S,5R)-3-(2-methyl-5-m-tolyl-thiazole-4-carbonyl)-3-aza-bicyclo[3.1.0]hex-2-ylmethyl]-benzamide;
3,4-Dichloro-N-[(1S,2S,5R)-3-(2-methyl-5-m-tolyl-thiazole-4-carbonyl)-3-aza-bicyclo[3.1.0]hex-2-ylmethyl]-benzamide;
2-Chloro-4,5-difluoro-N-[(1S,2S,5R)-3-(2-methyl-5-m-tolyl-thiazole-4-carbonyl)-3-aza-bicyclo[3.1.0]hex-2-ylmethyl]-benzamide;
3-Fluoro-2-methyl-N-[(1S,2S,5R)-3-(2-methyl-5-m-tolyl-thiazole-4-carbonyl)-3-aza-bicyclo[3.1.0]hex-2-ylmethyl]-benzamide;
5-Fluoro-2-methoxy-N-[(1S,2S,5R)-3-(2-methyl-5-m-tolyl-thiazole-4-carbonyl)-3-aza-bicyclo[3.1.0]hex-2-ylmethyl]-benzamide;
2,5-Dimethyl-N-[(1S,2S,5R)-3-(2-methyl-5-m-tolyl-thiazole-4-carbonyl)-3-aza-bicyclo[3.1.0]hex-2-ylmethyl]-benzamide;
2-Chloro-4-fluoro-N-[(1S,2S,5R)-3-(2-methyl-5-m-tolyl-thiazole-4-carbonyl)-3-aza-bicyclo[3.1.0]hex-2-ylmethyl]-benzamide;
3,5-Dimethyl-N-[(1S,2S,5R)-3-(2-methyl-5-m-tolyl-thiazole-4-carbonyl)-3-aza-bicyclo[3.1.0]hex-2-ylmethyl]-benzamide;
3-Cyano-N-[(1S,2S,5R)-3-(2-methyl-5-m-tolyl-thiazole-4-carbonyl)-3-aza-bicyclo[3.1.0]hex-2-ylmethyl]-benzamide;
N-[(1S,2S,5R)-3-(2-Methyl-5-m-tolyl-thiazole-4-carbonyl)-3-aza-bicyclo[3.1.0]hex-2-ylmethyl]-2-morpholin-4-yl-benzamide;
4-Chloro-N-[(1S,2S,5R)-3-(2-methyl-5-m-tolyl-thiazole-4-carbonyl)-3-aza-bicyclo[3.1.0]hex-2-ylmethyl]-benzamide;
2,3-Dimethoxy-N-[(1S,2S,5R)-3-(2-methyl-5-m-tolyl-thiazole-4-carbonyl)-3-aza-bicyclo[3.1.0]hex-2-ylmethyl]-benzamide;
2-Methyl-imidazo[2,1-b]thiazole-5-carboxylic acid [(1S,2S,5R)-3-(2-methyl-5-m-tolyl-thiazole-4-carbonyl)-3-aza-bicyclo[3.1.0]hex-2-ylmethyl]-amide;

6-Trifluoromethyl-imidazo[2,1-b]thiazole-5-carboxylic acid [(1S,2S,5R)-3-(2-methyl-5-m-tolyl-thiazole-4-carbonyl)-3-aza-bicyclo[3.1.0]hex-2-ylmethyl]-amide;

3,6-Dimethyl-imidazo[2,1-b]thiazole-5-carboxylic acid [(1S,2S,5R)-3-(2-methyl-5-m-tolyl-thiazole-4-carbonyl)-3-aza-bicyclo[3.1.0]hex-2-ylmethyl]-amide;

3-Methyl-imidazo[2,1-b]thiazole-5-carboxylic acid [(1S,2S,5R)-3-(2-methyl-5-m-tolyl-thiazole-4-carbonyl)-3-aza-bicyclo[3.1.0]hex-2-ylmethyl]-amide;

6-Chloro-imidazo[2,1-b]thiazole-5-carboxylic acid [(1S,2S,5R)-3-(2-methyl-5-m-tolyl-thiazole-4-carbonyl)-3-aza-bicyclo[3.1.0]hex-2-ylmethyl]-amide;

3-Oxo-3,4-dihydro-2H-benzo[1,4]oxazine-8-carboxylic acid [(1S,2S,5R)-3-(2-methyl-5-m-tolyl-thiazole-4-carbonyl)-3-aza-bicyclo[3.1.0]hex-2-ylmethyl]-amide;

2H-Chromene-5-carboxylic acid [(1S,2S,5R)-3-(2-methyl-5-m-tolyl-thiazole-4-carbonyl)-3-aza-bicyclo[3.1.0]hex-2-ylmethyl]-amide;

4-Methyl-3,4-dihydro-2H-benzo[1,4]oxazine-8-carboxylic acid [(1S,2S,5R)-3-(2-methyl-5-m-tolyl-thiazole-4-carbonyl)-3-aza-bicyclo[3.1.0]hex-2-ylmethyl]-amide;

Chroman-8-carboxylic acid [(1S,2S,5R)-3-(2-methyl-5-m-tolyl-thiazole-4-carbonyl)-3-aza-bicyclo[3.1.0]hex-2-ylmethyl]-amide;

3,4-Dihydro-2H-benzo[1,4]oxazine-5-carboxylic acid [(1S,2S,5R)-3-(2-methyl-5-m-tolyl-thiazole-4-carbonyl)-3-aza-bicyclo[3.1.0]hex-2-ylmethyl]-amide;

4-Methyl-3-oxo-3,4-dihydro-2H-benzo[1,4]oxazine-8-carboxylic acid [(1S,2S,5R)-3-(2-methyl-5-m-tolyl-thiazole-4-carbonyl)-3-aza-bicyclo[3.1.0]hex-2-ylmethyl]-amide;

4-Methyl-3,4-dihydro-2H-benzo[1,4]oxazine-5-carboxylic acid [(1S,2S,5R)-3-(2-methyl-5-m-tolyl-thiazole-4-carbonyl)-3-aza-bicyclo[3.1.0]hex-2-ylmethyl]-amide;

Imidazo[1,2-a]pyridine-3-carboxylic acid {(1S,2S,5R)-3-[5-(2,3-dichloro-phenyl)-2-methyl-thiazole-4-carbonyl]-3-aza-bicyclo[3.1.0]hex-2-ylmethyl}-amide;

2,3-Dihydro-benzofuran-4-carboxylic acid {(1S,2S,5R)-3-[5-(3,4-dichloro-phenyl)-2-methyl-thiazole-4-carbonyl]-3-aza-bicyclo[3.1.0]hex-2-ylmethyl}-amide;

2,3-Dihydro-benzofuran-4-carboxylic acid {(1S,2S,5R)-3-[5-(3,4-dimethyl-phenyl)-2-methyl-thiazole-4-carbonyl]-3-aza-bicyclo[3.1.0]hex-2-ylmethyl}-amide;

2,3-Dihydro-benzofuran-4-carboxylic acid [(1S,2S,5R)-3-(2-methyl-5-phenyl-thiazole-4-carbonyl)-3-aza-bicyclo[3.1.0]hex-2-ylmethyl]-amide;

2,3-Dihydro-benzofuran-4-carboxylic acid [(1S,2S,5R)-3-(2-cyclopropyl-5-phenyl-thiazole-4-carbonyl)-3-aza-bicyclo[3.1.0]hex-2-ylmethyl]-amide;

2,3-Dihydro-benzofuran-4-carboxylic acid [(1S,2S,5R)-3-(2-dimethylamino-5-phenyl-thiazole-4-carbonyl)-3-aza-bicyclo[3.1.0]hex-2-ylmethyl]-amide;

2,3-Dihydro-benzofuran-4-carboxylic acid {(1S,2S,5R)-3-[2-dimethylamino-5-(3-fluoro-phenyl)-thiazole-4-carbonyl]-3-aza-bicyclo[3.1.0]hex-2-ylmethyl}-amide;

2,3-Dihydro-thieno[3,4-b][1,4]dioxine-5-carboxylic acid {(1S,2S,5R)-3-[2-dimethylamino-5-(3-fluoro-phenyl)-thiazole-4-carbonyl]-3-aza-bicyclo[3.1.0]hex-2-ylmethyl}-amide;

6-Methyl-imidazo[2,1-b]thiazole-5-carboxylic acid [(1S,2S,5R)-3-(3-m-tolyl-thiophene-2-carbonyl)-3-aza-bicyclo[3.1.0]hex-2-ylmethyl]-amide;

6-Methyl-imidazo[2,1-b]thiazole-5-carboxylic acid [(1S,2S,5R)-3-(3-p-tolyl-thiophene-2-carbonyl)-3-aza-bicyclo[3.1.0]hex-2-ylmethyl]-amide;

6-Methyl-imidazo[2,1-b]thiazole-5-carboxylic acid [(1S,2S,5R)-3-(2-m-tolyl-thiophene-3-carbonyl)-3-aza-bicyclo[3.1.0]hex-2-ylmethyl]-amide;

6-Methyl-imidazo[2,1-b]thiazole-5-carboxylic acid [(1S,2S,5R)-3-(2-p-tolyl-thiophene-3-carbonyl)-3-aza-bicyclo[3.1.0]hex-2-ylmethyl]-amide;

6-Methyl-imidazo[2,1-b]thiazole-5-carboxylic acid {(1S,2S,5R)-3-[2-(4-fluoro-phenyl)-thiophene-3-carbonyl]-3-aza-bicyclo[3.1.0]hex-2-ylmethyl}-amide;

2-Ethyl-5-methyl-2H-pyrazole-3-carboxylic acid [(1S,2S,5R)-3-(4'-fluoro-biphenyl-2-carbonyl)-3-aza-bicyclo[3.1.0]hex-2-ylmethyl]-amide;

2-Ethyl-5-methyl-2H-pyrazole-3-carboxylic acid [(1S,2S,5R)-3-(3'-fluoro-biphenyl-2-carbonyl)-3-aza-bicyclo[3.1.0]hex-2-ylmethyl]-amide;

2-Ethyl-5-methyl-2H-pyrazole-3-carboxylic acid [(1S,2S,5R)-3-(4'-methyl-biphenyl-2-carbonyl)-3-aza-bicyclo[3.1.0]hex-2-ylmethyl]-amide;

2-Ethyl-5-methyl-2H-pyrazole-3-carboxylic acid [(1S,2S,5R)-3-(3'-methyl-biphenyl-2-carbonyl)-3-aza-bicyclo[3.1.0]hex-2-ylmethyl]-amide;

2-Ethyl-5-methyl-2H-pyrazole-3-carboxylic acid {(1S,2S,5R)-3-[5-(4-fluoro-phenyl)-2-methyl-thiazole-4-carbonyl]-3-aza-bicyclo[3.1.0]hex-2-ylmethyl}-amide;

2-Ethyl-5-methyl-2H-pyrazole-3-carboxylic acid [(1S,2S,5R)-3-(2-methyl-5-p-tolyl-thiazole-4-carbonyl)-3-aza-bicyclo[3.1.0]hex-2-ylmethyl]-amide;

2-Ethyl-5-methyl-2H-pyrazole-3-carboxylic acid {(1S,2S,5R)-3-[5-(3-bromo-4-fluoro-phenyl)-2-methyl-thiazole-4-carbonyl]-3-aza-bicyclo[3.1.0]hex-2-ylmethyl}-amide;

2-Ethyl-5-methyl-2H-pyrazole-3-carboxylic acid [(1S,2S,5R)-3-(5-m-tolyl-thiazole-4-carbonyl)-3-aza-bicyclo[3.1.0]hex-2-ylmethyl]-amide;

2-Ethyl-5-methyl-2H-pyrazole-3-carboxylic acid [(1S,2S,5R)-3-(2-dimethylamino-5-m-tolyl-thiazole-4-carbonyl)-3-aza-bicyclo[3.1.0]hex-2-ylmethyl]-amide;

2-Ethyl-5-methyl-2H-pyrazole-3-carboxylic acid [(1S,2S,5R)-3-(2-amino-5-m-tolyl-thiazole-4-carbonyl)-3-aza-bicyclo[3.1.0]hex-2-ylmethyl]-amide;

2-Ethyl-5-methyl-2H-pyrazole-3-carboxylic acid [(1S,2S,5R)-3-(2-cyclopropyl-5-m-tolyl-thiazole-4-carbonyl)-3-aza-bicyclo[3.1.0]hex-2-ylmethyl]-amide;

2-Ethyl-5-methyl-2H-pyrazole-3-carboxylic acid {(1S,2S,5R)-3-[5-(3,4-dimethyl-phenyl)-2-methyl-thiazole-4-carbonyl]-3-aza-bicyclo[3.1.0]hex-2-ylmethyl}-amide;

2-Ethyl-5-methyl-2H-pyrazole-3-carboxylic acid [(1S,2S,5R)-3-(2-methyl-5-o-tolyl-thiazole-4-carbonyl)-3-aza-bicyclo[3.1.0]hex-2-ylmethyl]-amide;

2-Ethyl-5-methyl-2H-pyrazole-3-carboxylic acid {(1S,2S,5R)-3-[5-(3,5-dimethyl-phenyl)-2-methyl-thiazole-4-carbonyl]-3-aza-bicyclo[3.1.0]hex-2-ylmethyl}-amide;

Benzoxazole-7-carboxylic acid [(1S,2S,5R)-3-(2-methyl-5-m-tolyl-thiazole-4-carbonyl)-3-aza-bicyclo[3.1.0]hex-2-ylmethyl]-amide;

2-Methyl-benzoxazole-7-carboxylic acid [(1S,2S,5R)-3-(2-methyl-5-m-tolyl-thiazole-4-carbonyl)-3-aza-bicyclo[3.1.0]hex-2-ylmethyl]-amide;

Benzothiazole-7-carboxylic acid [(1S,2S,5R)-3-(2-methyl-5-m-tolyl-thiazole-4-carbonyl)-3-aza-bicyclo[3.1.0]hex-2-ylmethyl]-amide;

7-Chloro-benzofuran-4-carboxylic acid [(1S,2S,5R)-3-(2-methyl-5-m-tolyl-thiazole-4-carbonyl)-3-aza-bicyclo[3.1.0]hex-2-ylmethyl]-amide;

7-Fluoro-benzofuran-4-carboxylic acid [(1S,2S,5R)-3-(2-methyl-5-m-tolyl-thiazole-4-carbonyl)-3-aza-bicyclo[3.1.0]hex-2-ylmethyl]-amide;
Pyrrolo[2,1-b]thiazole-7-carboxylic acid [(1S,2S,5R)-3-(2-methyl-5-m-tolyl-thiazole-4-carbonyl)-3-aza-bicyclo[3.1.0]hex-2-ylmethyl]-amide;
6-Methyl-pyrrolo[2,1-b]thiazole-7-carboxylic acid [(1S,2S,5R)-3-(2-methyl-5-m-tolyl-thiazole-4-carbonyl)-3-aza-bicyclo[3.1.0]hex-2-ylmethyl]-amide;
7-Chloro-2-methoxy-2,3-dihydro-benzofuran-4-carboxylic acid [(1S,2S,5R)-3-(2-methyl-5-m-tolyl-thiazole-4-carbonyl)-3-aza-bicyclo[3.1.0]hex-2-ylmethyl]-amide;
1-Methyl-1H-indole-3-carboxylic acid [(1S,2S,5R)-3-(2-p-tolyl-thiophene-3-carbonyl)-3-aza-bicyclo[3.1.0]hex-2-ylmethyl]-amide;
Quinoline-8-carboxylic acid [(1S,2S,5R)-3-(2-p-tolyl-thiophene-3-carbonyl)-3-aza-bicyclo[3.1.0]hex-2-ylmethyl]-amide;
4-Methyl-4H-furo[3,2-b]pyrrole-5-carboxylic acid [(1S,2S,5R)-3-(2-p-tolyl-thiophene-3-carbonyl)-3-aza-bicyclo[3.1.0]hex-2-ylmethyl]-amide;
3,4-Dihydro-2H-benzo[1,4]oxazine-5-carboxylic acid [(1S,2S,5R)-3-(2-p-tolyl-thiophene-3-carbonyl)-3-aza-bicyclo[3.1.0]hex-2-ylmethyl]-amide;
2,3-Dihydro-thieno[3,4-b][1,4]dioxine-5-carboxylic acid [(1S,2S,5R)-3-(2-p-tolyl-thiophene-3-carbonyl)-3-aza-bicyclo[3.1.0]hex-2-ylmethyl]-amide;
2-Ethyl-5-methyl-2H-pyrazole-3-carboxylic acid [(1S,2S,5R)-3-(2-p-tolyl-thiophene-3-carbonyl)-3-aza-bicyclo[3.1.0]hex-2-ylmethyl]-amide;
2,5-Dimethyl-2H-pyrazole-3-carboxylic acid [(1S,2S,5R)-3-(2-p-tolyl-thiophene-3-carbonyl)-3-aza-bicyclo[3.1.0]hex-2-ylmethyl]-amide;
3-Bromo-N-[(1S,2S,5R)-3-(2-p-tolyl-thiophene-3-carbonyl)-3-aza-bicyclo[3.1.0]hex-2-ylmethyl]-benzamide;
3-Chloro-N-[(1S,2S,5R)-3-(2-p-tolyl-thiophene-3-carbonyl)-3-aza-bicyclo[3.1.0]hex-2-ylmethyl]-benzamide;
3-Methyl-N-[(1S,2S,5R)-3-(2-p-tolyl-thiophene-3-carbonyl)-3-aza-bicyclo[3.1.0]hex-2-ylmethyl]-benzamide;
Benzo[2,1,3]thiadiazole-4-carboxylic acid [(1S,2S,5R)-3-(2-p-tolyl-thiophene-3-carbonyl)-3-aza-bicyclo[3.1.0]hex-2-ylmethyl]-amide;
2,3-Dihydro-benzofuran-4-carboxylic acid [(1S,2S,5R)-3-(2-p-tolyl-thiophene-3-carbonyl)-3-aza-bicyclo[3.1.0]hex-2-ylmethyl]-amide;
Benzoxazole-4-carboxylic acid [(1S,2S,5R)-3-(2-p-tolyl-thiophene-3-carbonyl)-3-aza-bicyclo[3.1.0]hex-2-ylmethyl]-amide;
2-Methyl-benzoxazole-4-carboxylic acid [(1S,2S,5R)-3-(2-p-tolyl-thiophene-3-carbonyl)-3-aza-bicyclo[3.1.0]hex-2-ylmethyl]-amide;
1-Methyl-1H-indole-3-carboxylic acid [(1S,2S,5R)-3-(2-m-tolyl-thiophene-3-carbonyl)-3-aza-bicyclo[3.1.0]hex-2-ylmethyl]-amide;
Quinoline-8-carboxylic acid [(1S,2S,5R)-3-(2-m-tolyl-thiophene-3-carbonyl)-3-aza-bicyclo[3.1.0]hex-2-ylmethyl]-amide;
4-Methyl-4H-furo[3,2-b]pyrrole-5-carboxylic acid [(1S,2S,5R)-3-(2-m-tolyl-thiophene-3-carbonyl)-3-aza-bicyclo[3.1.0]hex-2-ylmethyl]-amide;
Pyrrolo[2,1-b]thiazole-7-carboxylic acid [(1S,2S,5R)-3-(2-m-tolyl-thiophene-3-carbonyl)-3-aza-bicyclo[3.1.0]hex-2-ylmethyl]-amide;
3,4-Dihydro-2H-benzo[1,4]oxazine-5-carboxylic acid [(1S,2S,5R)-3-(2-m-tolyl-thiophene-3-carbonyl)-3-aza-bicyclo[3.1.0]hex-2-ylmethyl]-amide;
2,3-Dihydro-thieno[3,4-b][1,4]dioxine-5-carboxylic acid [(1S,2S,5R)-3-(2-m-tolyl-thiophene-3-carbonyl)-3-aza-bicyclo[3.1.0]hex-2-ylmethyl]-amide;
2-Ethyl-5-methyl-2H-pyrazole-3-carboxylic acid [(1S,2S,5R)-3-(2-m-tolyl-thiophene-3-carbonyl)-3-aza-bicyclo[3.1.0]hex-2-ylmethyl]-amide;
2,5-Dimethyl-2H-pyrazole-3-carboxylic acid [(1S,2S,5R)-3-(2-m-tolyl-thiophene-3-carbonyl)-3-aza-bicyclo[3.1.0]hex-2-ylmethyl]-amide;
3-Bromo-N-[(1S,2S,5R)-3-(2-m-tolyl-thiophene-3-carbonyl)-3-aza-bicyclo[3.1.0]hex-2-ylmethyl]-benzamide;
3-Chloro-N-[(1S,2S,5R)-3-(2-m-tolyl-thiophene-3-carbonyl)-3-aza-bicyclo[3.1.0]hex-2-ylmethyl]-benzamide;
3-Methyl-N-[(1S,2S,5R)-3-(2-m-tolyl-thiophene-3-carbonyl)-3-aza-bicyclo[3.1.0]hex-2-ylmethyl]-benzamide;
Benzo[2,1,3]thiadiazole-4-carboxylic acid [(1S,2S,5R)-3-(2-m-tolyl-thiophene-3-carbonyl)-3-aza-bicyclo[3.1.0]hex-2-ylmethyl]-amide;
Benzo[2,1,3]oxadiazole-4-carboxylic acid [(1S,2S,5R)-3-(2-m-tolyl-thiophene-3-carbonyl)-3-aza-bicyclo[3.1.0]hex-2-ylmethyl]-amide;
2,3-Dihydro-benzofuran-4-carboxylic acid [(1S,2S,5R)-3-(2-m-tolyl-thiophene-3-carbonyl)-3-aza-bicyclo[3.1.0]hex-2-ylmethyl]-amide;
Benzothiazole-7-carboxylic acid [(1S,2S,5R)-3-(2-m-tolyl-thiophene-3-carbonyl)-3-aza-bicyclo[3.1.0]hex-2-ylmethyl]-amide;
2-Methyl-benzoxazole-4-carboxylic acid [(1S,2S,5R)-3-(2-m-tolyl-thiophene-3-carbonyl)-3-aza-bicyclo[3.1.0]hex-2-ylmethyl]-amide;
2-Methyl-benzoxazole-7-carboxylic acid [(1S,2S,5R)-3-(2-m-tolyl-thiophene-3-carbonyl)-3-aza-bicyclo[3.1.0]hex-2-ylmethyl]-amide;
2-Chloro-benzothiazole-4-carboxylic acid [(1S,2S,5R)-3-(2-methyl-5-m-tolyl-thiazole-4-carbonyl)-3-aza-bicyclo[3.1.0]hex-2-ylmethyl]-amide; and
Benzothiazole-4-carboxylic acid [(1S,2S,5R)-3-(2-methyl-5-m-tolyl-thiazole-4-carbonyl)-3-aza-bicyclo[3.1.0]hex-2-ylmethyl]-amide;
or a pharmaceutically acceptable salt thereof.

12. A pharmaceutical composition comprising a compound of formula (I) according to claim 1, or a pharmaceutically acceptable salt thereof, and at least one therapeutically inert excipient.

13. A method for the treatment of an insomnia comprising administering to a subject in need thereof a pharmaceutically effective amount of a compound according to claim 1, in a free or pharmaceutically acceptable salt form.

14. A pharmaceutical composition according to claim 12 for the treatment of an insomnia.

15. A compound according to claim 6, wherein
B represents a phenyl-group, which group is unsubstituted or mono- or di-substituted, wherein the substituents are independently selected from the group consisting of $(C_{1-4})$alkyl, $(C_{1-4})$alkoxy, trifluoromethyl, and halogen;
or a pharmaceutically acceptable salt thereof.

16. A compound according to claim 6, wherein
$R^1$ represents a phenyl-, isoxazolyl-, pyrazolyl-, indolyl-, benzofuranyl-, indazolyl-, benzo[d]isoxazolyl-, quinolinyl-, isoquinolinyl-, benzoxazolyl-, benzothiazolyl-, benzo[2,1,3]thiadiazolyl-, benzo[2,1,3]oxadiazolyl-, 4H-furo[3,2-b]pyrrolyl-, pyrrolo[2,1-b]thiazolyl-, pyrazolo[1,5-a]pyridyl-, imidazo[1,2-a]pyridyl- or imidazo[2,1-b]thiazolyl-group, which group is unsubstituted or independently mono- or di-substituted wherein the substituents are independently selected from the group consisting of $(C_{1-4})$alkyl, $(C_{1-4})$alkoxy, halogen and trifluoromethyl;

or a pharmaceutically acceptable salt thereof.

17. A compound according to claim 15, wherein
$R^1$ represents a phenyl-, isoxazolyl-, pyrazolyl-, indolyl-, benzofuranyl-, indazolyl-, benzo[d]isoxazolyl-, quinolinyl-, isoquinolinyl-, benzoxazolyl-, benzothiazolyl-, benzo[2,1,3]thiadiazolyl-, benzo[2,1,3]oxadiazolyl-, 4H-furo[3,2-b]pyrrolyl-, pyrrolo[2,1-b]thiazolyl-, pyrazolo[1,5-a]pyridyl-, imidazo[1,2-a]pyridyl- or imidazo[2,1-b]thiazolyl-group, which group is unsubstituted or independently mono- or di-substituted wherein the substituents are independently selected from the group consisting of $(C_{1-4})$alkyl, $(C_{1-4})$alkoxy, halogen and trifluoromethyl;

or a pharmaceutically acceptable salt thereof.

\* \* \* \* \*